US011124796B2

(12) United States Patent
Sharp et al.

(10) Patent No.: US 11,124,796 B2
(45) Date of Patent: Sep. 21, 2021

(54) DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO

(71) Applicants: The Broad Institute, Inc., Cambridge, MA (US); Massachusetts Institute of Technology, Cambridge, MA (US)

(72) Inventors: Phillip A. Sharp, Newton, MA (US); Feng Zhang, Cambridge, MA (US); Randall Jeffrey Platt, Basel (CH); Sidi Chen, Milford, CT (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/467,888

(22) Filed: Mar. 23, 2017

(65) Prior Publication Data
US 2018/0010134 A1 Jan. 11, 2018

Related U.S. Application Data

(63) Continuation-in-part of application No. PCT/US2015/051446, filed on Sep. 22, 2015.

(60) Provisional application No. 62/067,886, filed on Oct. 23, 2014, provisional application No. 62/054,651, filed on Sep. 24, 2014.

(51) Int. Cl.
| | |
|---|---|
| *C12N 15/63* | (2006.01) |
| *A01K 67/027* | (2006.01) |
| *C12N 15/85* | (2006.01) |
| *C12N 15/11* | (2006.01) |
| *C12N 9/22* | (2006.01) |
| *C12N 15/10* | (2006.01) |
| *C12N 15/90* | (2006.01) |

(52) U.S. Cl.
CPC .......... *C12N 15/63* (2013.01); *A01K 67/0275* (2013.01); *C12N 9/22* (2013.01); *C12N 15/102* (2013.01); *C12N 15/111* (2013.01); *C12N 15/85* (2013.01); *C12N 15/8509* (2013.01); *C12N 15/907* (2013.01); *A01K 2217/00* (2013.01); *A01K 2227/105* (2013.01); *A01K 2267/0306* (2013.01); *A01K 2267/0331* (2013.01); *C12N 2310/20* (2017.05); *C12N 2310/3519* (2013.01); *C12N 2310/531* (2013.01); *C12N 2320/10* (2013.01); *C12N 2320/32* (2013.01); *C12N 2750/14143* (2013.01); *C12N 2830/48* (2013.01)

(58) Field of Classification Search
None
See application file for complete search history.

(56) References Cited

U.S. PATENT DOCUMENTS

| | | |
|---|---|---|
| 4,186,183 A | 1/1980 | Alving et al. |
| 4,217,344 A | 8/1980 | Handjani et al. |
| 4,234,871 A | 11/1980 | Guglielmi et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,846,946 A | 12/1998 | Huebner et al. |
| 6,750,059 B1 | 6/2004 | Blakesley et al. |
| 7,776,321 B2 | 8/2010 | Cascalho et al. |
| 8,404,658 B2 | 3/2013 | Hajjar et al. |

(Continued)

FOREIGN PATENT DOCUMENTS

| | | |
|---|---|---|
| WO | 1991016024 | 10/1991 |
| WO | 1991017424 | 11/1991 |

(Continued)

OTHER PUBLICATIONS

Khaled et al., "Cancer mouse models: Past, present and future" 27 Seminars in Cell & Developmental Biology 54-60 (Apr. 6, 2014).*
Mashiko et al., "Generation of mutant mice by pronuclear injection of circular plasmid expressing Cas9 and single guided RNA" 3: 3355 1-6 (Nov. 27, 2013).*
International Search Report dated Mar. 31, 2016, which issued during prosecution of International Application No. PCT/US2015/051446.
Auer, et al., "Highly efficient CRISPR/Cas9-mediated knock-in in zebrafish by homology-independent DNA repair" Genome Research, 2013, 24:142-153.

(Continued)

*Primary Examiner* — Nancy J Leith
(74) *Attorney, Agent, or Firm* — Johnson, Marcou, Isaacs & Nix, LLC; F. Brent Nix, Esq.; Rachel D. Rutledge, Esq.

(57) ABSTRACT

The invention involves inducing 3-50 or more mutations (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector) in transgenic Cas9 eukaryotes to model genetic disease, e.g. cancer. The invention comprehends testing putative treatments with such models, e.g., testing putative chemical compounds that may be pharmaceutically relevant for treatment or gene therapy that may be relevant for treatment, or combinations thereof. The invention allows for the study of genetic diseases and putative treatments to better understand and alleviate a genetic disease or a condition, e.g., cancer.

11 Claims, 43 Drawing Sheets

Specification includes a Sequence Listing.

(56) References Cited

U.S. PATENT DOCUMENTS

| | | | |
|---|---|---|---|
| 8,454,972 | B2 | 6/2013 | Nabel et al. |
| 8,697,359 | B1 | 4/2014 | Zhang |
| 8,771,945 | B1 | 7/2014 | Zhang |
| 8,795,965 | B2 | 8/2014 | Zhang |
| 8,871,445 | B2 | 10/2014 | Cong et al. |
| 2004/0171156 | A1 | 9/2004 | Hartley et al. |
| 2011/0059502 | A1 | 3/2011 | Chalasani |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0194361 | A1 | 7/2014 | Nicholas et al. |
| 2014/0287938 | A1 | 9/2014 | Zhang et al. |
| 2018/0355375 | A1 | 12/2018 | Zhang et al. |

FOREIGN PATENT DOCUMENTS

| | | | |
|---|---|---|---|
| WO | 1993024641 | | 12/1993 |
| WO | 1994026877 | | 11/1994 |
| WO | 199639154 | | 12/1996 |
| WO | 199703211 | | 1/1997 |
| WO | 2011014388 | A1 | 2/2011 |
| WO | 2011028929 | A3 | 10/2011 |
| WO | 2013138585 | A1 | 9/2013 |
| WO | WO 2013/176772 | A1 * | 11/2013 ............... C12N 9/22 |
| WO | 2014018423 | A2 | 1/2014 |
| WO | 2014093595 | | 6/2014 |
| WO | 2014093622 | | 6/2014 |
| WO | 2014093635 | A1 | 6/2014 |
| WO | 2014093655 | A2 | 6/2014 |
| WO | 2014093661 | A2 | 6/2014 |
| WO | 2014093694 | A1 | 6/2014 |
| WO | 2014093701 | A1 | 6/2014 |
| WO | 2014093709 | A1 | 6/2014 |
| WO | 2014093712 | A1 | 6/2014 |
| WO | 2014093718 | A1 | 6/2014 |
| WO | 2014197748 | | 12/2014 |

OTHER PUBLICATIONS

Cong, et al. "Multiplex Genome Engineering Using CRISPR/Cas Systems", Science, 2013, 819-823.

Yang, et al. "One-Step Generation of Mice Carrying Reporter and Confidintial Alleles by CRISPR/Cas-Mediated Genome Engineering", Cell, 2013, 154:1370-1379.

Platt, et al. "CRISPR-Cas9 Knocking Mice for Genome Editing and Cancer Modeling", Cell, 2014, 159:440-455.

Wang, et al. "One-Step Generation of Mice Carrying Mutations in Multiple Genes by CRISPR/Cas-Mediated Genome Engineering", Cell, 153:910-918, 2013.

Kotin, "Prospects for the Use of Adeno-Associated Virus as a Vector for Human Gene Therapy", Human Gene Therapy, vol. 5, 1994, 793-801.

Kremer, et al., "Adenovirus and Adeno-Associated Virus Mediated Gene Transfer", British Medical Bulletin, vol. 51, No. 1, 1995, 31-44.

Lawrence, et al., "Discovery and Saturation Analysis of Cancer Genes Across 21 Tumor Types", Nature, vol. 505, No. 7484, Jan. 23, 2014, 495-501.

Lawrence, et al., "Mutational Heterogeneity in Cancer and the Search for New Cancer Genes", Nature, vol. 499, No. 7457, Jul. 11, 2013, 214-218.

Lee, et al., "Molecularly Self-Assembled Nucleic Acid Nanoparticles for Targeted in Vivo siRNA Delivery", Nature Nanotechnology, vol. 7, No. 6, Jan. 22, 2014, 389-393.

Limberis, et al., "Adeno-Associated Virus Serotype 9 Vectors Transduce Murine Alveolar and Nasal Epithelia and can be Readministered", PNAS, vol. 103, No. 44, Aug. 29, 2006, 12993-12998.

Mali, et al., "RNA-Guided Human Genome Engineering via Cas9", Science, vol. 339, No. 6121, Feb. 15, 2013, 823-826.

Masepohl, et al., "Long Tandemly Repeated Repetitive (LTRR) Sequences in the Filamentous Cyanobacterium *Anabaena* sp. PCC 7120", Biochimica et Biophysica Acta (BBA)—Gene Structure and Expression, vol. 1307, Issue 1, Jun. 3, 1996, 26-30.

Miller, et al., "Construction and Properties of Retrovirus Packaging Cells Based on Gibbon Ape Leukemia Virus", Journal of Virology, vol. 65, No. 5, May 1991, 2220-2224.

Miller, "Human Gene Therapy Comes of Age", Nature, vol. 357, Jun. 11, 1992, 455-460.

Mitani, et al., "Delivering Therapeutic Genes—Matching Approach and Application", Tibtech, vol. 11, May 1992, 162-166.

Mojica, et al., "Intervening Sequences of Regularly Spaced Prokaryotic Repeats Derive from Foreign Genetic Elements", Journal of Molecular Evolution, vol. 60, No. 2, Mar. 2005, 174-182.

Mojica, et al., "MicroCorrespondence", Molecular Microbiology, vol. 36, 2000, 244-246.

Muzyczka, "Adeno-Associated Virus (AAV) Vectors: Will They Work?", Journal of Clinical Investigation, vol. 94, Oct. 1994, 1351.

Nabel, et al., "Direct Gene Transfer for Immunotherapy and Immunization", Trends In Biotechnology, vol. 11, No. 5, May 1993, 211-217.

Nishimasu, et al., "Crystal Structure of Cas9 in Complex with Guide RNA and Target DNA", Cell, vol. 156, No. 5, Feb. 27, 2014, 935-949.

O'Hare, et al., "Transformation of Mouse Fibroblasts to Methotrexate Resistance by A Recombinant Plasmid Expressing A Prokaryotic Dihydrofolate Reductase", Proceedings of the National Academy of Sciences, vol. 78, No. 3, Mar. 1981, 1527-1531.

Park, et al., "Ciliated Adenocarcinomas of the Lung: A tumor of Non-Terminal Respiratory Unit Origin", Modern Pathology, vol. 25, May 4, 2012, 1265-1274.

Pinkert, et al., "An Albumin Enhancer Located 10 kb Upstream Functions Along with its Promoter to Direct Efficient, Liver-Specific Expression in Transgenic Mice", Genes and Development, vol. 1, Issue 3, May 1987, 268-277.

Pylayeva-Gupta, et al., "RAS Oncogenes: Weaving a Tumorigenic Web", Nat. Rev. Cancer, vol. 11, No. 11, Oct. 13, 2011, 761-774.

Ran, et al., "Double Nicking by RNA-Guided CRISPR Cas9 for Enhanced Genome Editing Specificity", Cell, vol. 154, No. 6, Sep. 12, 2013, 1380-1389.

Ran, et al., "Genome Engineering using the CRISPR-Cas9 System", Nature Protocols, vol. 8, No. 11, Nov. 2013, 2281-2308.

Remy, et al., "Gene Transfer ith a Series Lipophilic DNA-Binding Molecules", Bioconjugate Chemistry, vol. 5, 1994, 647-654.

Samulski, et al., "Helper-Free Stocks of Recombinant Adeno-Associated Viruses: Normal Integration Does Not Require Viral Gene Expression", Journal of Virology, vol. 63, No. 9, Sep. 1989, 3822-3828.

Shackelford, et al., "The LKB1-AMPK Pathway: Metobolism and Growth Control in Tumor Suppression", Nat. Rev. Cancer, vol. 9, No. 8, Aug. 2009, 563-575.

Shalem, et al., "Genome-Scale CRISPR-Cas9 Knockout Screening in Human Cells", Science, vol. 343, No. 6166, Dec. 12, 2013, 84-87.

Takebe, et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, Jan. 1988, 466-472.

Tratschin, et al., "A Human Parvovirus, Adeno-Associated Virus, as a Eukaryotic Vector: Transient Expression and Encapsidation of the Procaryotic Gene for Chloramphenical Acetyltansferase", Mol. Cell Biol., vol. 4, No. 10, Oct. 1984, 2072-2081.

Tratschin, et al., "Adeno-Associated Virus Vector for High-Frequency Integration, Expression, and Rescue of Genes in Mammalian Cells", Molecular and Cellular Biology, vol. 5, No. 11, Nov. 1985, 3251-3260.

Van Brunt, "Molecular Farming: Transgenic Animals as Bioreactors", Biotechnology, vol. 6, No. 10, 1988, 1149-1154.

Van Embden, et al., "Genetic Variation and Evolutionary Origin of the Direct Repeat Locus of Mycobacterium tuberculosis Complex Bacteria", J. Bacteriology, vol. 182, No. 9, May 2000, 2393-2401.

(56) References Cited

OTHER PUBLICATIONS

Vigne, et al., "Third-Generation Adenovectors for Gene Therapy", Restorative Neurology and Neuroscience, vol. 8, 1995, 35-36.
Whitehead, et al., "The in-Vitro-In Vivo Translation of Lipid-Nanoparticles for Hepatocellular siRNA Delivery", ACS Nano, vol. 6, No. 8, Aug. 28, 2012, 6922-6929.
Wilson, et al., "Formation of Infecdtious Hybrid Virions with Gibbon Ape Leukemia Virus and Human T-cell Leukemia Virus Retroviral Envelope Glycoproteins and the gag and pol Proteins of Moloney Murine Leukemia Virus", Journal of Virology, vol. 63, No. 5, May 1989, 2374-2378.
Winoto, et al., "A Novel, Inducible and T Cell-Specific Enhancer Located at the 3' End of the T Cell Receptor α Locus", The EMBO Journal, vol. 8, No. 3, 1989, 729-733.
Wu, et al., "Genome-Wide Binding of the CRISPR Endonuclease Cas9 in Mammalian Cells", Nature Biotechnology, vol. 32, No. 7, Jul. 2014, 670-676.
Xue, et al., "CRISPR-Mediated Direct Mutation of Cancer Genes in the Mouse Liver", Nature, vol. 514, No. 7522, Oct. 16, 2014, 380-384.
Zhang, et al., "Lipid-Modified Aminoglycoside Derivatives for in vivo siRNA Delivery", Advanced Materials, vol. 25, No. 33, Sep. 6, 2013, 4641-4645.
Zuker, et al., "Optimal Computer Folding of Large RNA Sequences Using Thermodynamics and Auxiliary Information", Nucleic Acids Research, vol. 9, No. 1, 1981, 133-148.
"Comprehensive Molecular Profiling of Lung Adenocarcinoma", The Cancer Genome Atlas Research Network, Nature, vol. 511, No. 7511, Jul. 31, 2014, 543-550.
Ahmed, et al., "IL-17 in Obesity and Adipogenesis", Cytokine & Growth Factor Reviews, vol. 21, No. 6, Dec. 2010, 449-453.
Alabi, et al., "Multiparametric Approach for the Evaluation of Lipid Nanoparticles for siRNA Delivery", Proceedings of the National Academy of Sciences, vol. 110, No. 32, Jul. 23, 2013, 12881-12886.
Anderson, "Human Gene Therapy", Science, vol. 256, May 8, 1992, 808-813.
Balaggan, et al., "Stable and Efficient Intraoccular Gene Transfer Using Pseudotyped EIAV Lentivirus Vectors", The Journal of Gene Medicine, vol. 8, Nov. 21, 2005, 275-285.
Banerji, et al., "A Lymphocyte-Specific Cellular Enhancer is Located Downstream of the Joining Region in Immunoglobulin Heavy Chain Genes", Cell, vol. 33, Issue 3, Jul. 1983, 729-740.
Behr, "Gene Transfer with Synthetic Cationic Amphiphiles: Prospects for Gene Therapy", Bioconjugate Chemistry, vol. 5, 1994, 382-389.
Bell, et al., "The AAV9 Receptor and its Modification to Improve in Vivo Lung Gene Transfer in Mice", The Journal of Clinical Investigation, vol. 121, No. 6, Jun. 2011, 2427-2435.
Binley, et al., "Safety and Biodistribution of an Equine Infectious Anemai Virus-Based Gene Therapy, RetinoStat, for Age-Related Macular Degeneration", Human Gene Therapy, vol. 23, Sep. 2012, 980-991.
Buchschacher, et al., "Human Immunodeficiency Virus Vectors for Inducible Expression of Foreign Genes", Journal of Virology, vol. 66, No. 5, May, 1992, 2731-2739.
Byrne, et al., "Multiplex Gene Regulation: A Two-Tiered Approach to Transgene Regulation in Transgenic Mice", Proceedings of the National Academy of Sciences, vol. 86, Jul. 1989, 5473-5477.
Camper, et al., "Postnatal Repression of the Alpha-Fetoprotein Gene is Enhancer Independent", Genes and Development, vol. 3, 1989, 537-546.
Campochiaro, et al., "Adenoviral Vector-Delivered Pigment Epithelium-Derived Factor for Neovascular Age-Related Macular Degeneration: Results of Phase I Clinical Trial", Human Gene Therapy, vol. 17, Feb. 2006, 167-176.
Chen, et al., "Global microRNA Depletion Suppresses Tumor Angiogenesis", Genes & Development, vol. 28, May 15, 2014, 1054-1067.

Chung, et al., "Polycistronic RNA polymerase II Expression Vectors for RNA Interference Based on BIC/miR-155", Nucleic Acids Research, vol. 34, No. 7, e53, Apr. 13, 2006, 1-14.
Crystal, "Transfer of Genes to Humans: 20, 1995, 404-410. Early Lessons and Obstacles to Success", Science, vol. 270, Oct. 20, 1995, 404-410.
Dahlman, et al., "In Vivo Endothelial siRNA Delivery Using Polymeric Nanoparticles wiht Low Molecular Weight", Nature Nanotechnology, vol. 9, No. 8, Aug. 2014, 648-655.
Deltcheva, et al., "CRISPR RNA Maturation by Trans-Encoded Small RNA and Host Factor Rnase III", Nature, vol. 471, No. 7340, Mar. 31, 2011, 602-607.
Dillon, "Regulating Gene Expression in Gene Therapy", Tibtech, vol. 11, May 1993, 167-175.
Dull, et al., "A Third_Generation Lentivirus Vector with a Conditional Packaging System", Journal of Virology, vol. 72, No. 11, Nov. 1998, 8463-8471.
Dupage, et al., "Conditional Mouse Lung Cancer Models using Adenoviral or Lentiviral Delivery of Cre Recomibinase", Nature Protocols, vol. 4, No. 7, Jun. 2009, 1064-1072.
Edlund, et al., "Cell-Specific Expression of the Rat Insulin Gene: Evidence for Role of Two Distinct 5' Flanking Elements", Science. vol. 230, Issue 4728, Nov. 22, 1985, 912-916.
Frese, et al., "Maximizing Mouse Cancer Models", Nature Reviews/Cancer, vol. 7, Sep. 2007, 645-658.
Garraway, et al., "Lessons from the Cancer Genome", Cell, vol. 153, Mar. 28, 2013, 17-37.
Gasiunas, et al., "Cas9-CrRna Ribonucleoprotein Complex Mediates Specific DNA Cleavage for Adaptive Immunity in Bacteria", Proceedings of the National Academy of Sciences, vol. 109, No. 39, Sep. 25, 2012, E2579-E2586.
Govindan, et al., "Genomic Landscape of Non-Small Cell Lung Cancer in Smokers and Never Smokers", Cell, vol. 150, No. 6, Sep. 14, 2012, 1121-1134.
Grimm, et al., "In Vitro and In Vivo Gene Therapy Vector Evolution via Multispecies Interbreeding and Retargeting of Adeno-Associated Viruses", Journal of Virology, vol. 82, No. 12, Jun. 2008, 5887-5911.
Groenen, et al., "Nature of DNA Polymorphism in the Direct Repeat Cluster of Mycobacterium Tuberculosis; Application for Strain Differentiation by a Novel Typing Method", Molecular Microbiology, vol. 10, No. 5, Jan. 1994, 1057-1065.
Halbert, et al., "Efficient Mouse Airway Transduction Following Recombination Between AAV Vectors Carrying Parts of a Larger Gene", Nature Biotechnology, vol. 20, Jul. 2002, 697-701.
herbst, et al., "Molecular Origins of Cancer—Lung Cancer", New England Journal of Medicine, vol. 39, No. 13, Sep. 25, 2008, 1367-1380.
hermonat, et al., "Use of Adeno-Associated Virus as a Mammalian DNA Cloning Vector: Transduction of Neomycin Resistance into Mammalian Tissue Culture Cells", PNAS, vol. 81, Oct. 1984, 6466-6470.
Hoe, et al. "Rapid Molecular Genetic Subtyping of Serotype M1 Group A *Streptococcus* Strains", Emerging Infectious Diseases, vol. 5, No. 2, Marc∗ Apr. 1999, 254-263.
Hsu, et al., "Development and Applications of CRISPR-Cas9 for Genome Engineering", Cell, vol. 157, No. 6 Jun. 5, 2014, 1262-1278.
Hsu, et al., "DNA Targeting Specificity of RNA-Guided Cas9 Nucleases", Nat. Biotechnol. vol. 31, No. 9, Sep. 3, 2013, 827-832.
Ioannidis, et al., "A Compendium of Genome-Wide Associations for Cancer: Critical Synopsis and Reappraisal", Journal of the National Cancer Institute, vol. 102, No. 12, Jun. 16, 2010, 846-858.
Ishino, et al., "Nucleotide Sequence of the iap Gene, Responsible for Alkaline Phosphatase Isozyme Conversion in *Escherichia coli*, and Identification of the Gene Product", Journal of Bacteriology, vol. 169, No. 12, Dec. 1987, 5429-5433.
Jackson, et al., "Analysis of Lung Tumor Initiation and Progression using Conditional Expression of Oncogenic K-ras", Genes & Development, vol. 15, Dec. 14, 2001, 3243-3248.

(56) References Cited

OTHER PUBLICATIONS

Jansen, et al., "Identification of a Novel Family of Sequence Repeats among Prokaryotes", OMICS: A Journal of Integrative Biology, vol. 6, No. 1, Feb. 2002, 23-33.

Jansen, et al. "Identification of Genes that are Associated with DNA Repeats in Prokaryotes", Molecular Microbiology, vol. 46, No. 6, Apr. 2002, 1565-1575.

Ji, et al., "LKB1 Modulates Lung Cancer Differentiation and Metastasis", Nature, vol. 448, Aug. 2007, 807-811.

Jiang, et al., "CRISPR-assisted Editing of Bacterial Genomes", Nature Biotechnology, vol. 31, No. 3, Mar. 2013, 233-239.

Jiang, et al., "Lipidoid-coated Iron Oxide Nanoparticles for Efficient DNA and siRNA Delivery", Nano. Lett., vol. 13, No. 3, Mar. 13, 2013, 1059-1064.

Jinek, et al., "A Programmable Dual-RNA-Guided DNA Endonuclease in Adaptive Bacterial Immunity", Science, vol. 337, No. 6096,, Aug. 17, 2012, 816-821.

Johann, et al., "GLVR1, a Receptor for Gibbon Ape Leukemia Virus, is Homologous to a Phosphaate Permease of Neurospora crassa and is Expresssed at High Levels in the Brain and Thymus", Journal of Virology, vol. 66, No. 3, Mar. 1992, 1635-1640.

Johnson, et al., "Somatic Activation of K-ras Oncogene Causes Early Onset Lung Cancer in Mice", Nature, vol. 410, Apr. 26, 2001, 1111-1116.

Kandoth, et al., "Mutational Landscape and Significance across 12 Major Cancer Types", Nature, vol. 502, No. 7471, Oct. 17, 2013, 333-339.

Karagiannis, et al., "Rationally Designed Tumor-Penetrating Nanocomplexes", AC Nano, vol. 6, No. 10, 2012, 8484-8487.

Kessel, et al., "Murine Developmental Control Genes", Science, vol. 249, No. 4967, Jul. 27, 1990, 374-379.

Koboldt, et al., "VarScan 2: Somatic Mutation and Copy Number Alteration Discovery in Cancer by Exome Sequencing", Genome Research, vol. 22, Mar. 2012, 568-576.

Konermann, et al., "Optical Control of Mammalian Endogenous Transcription and Epigenetic States", Nature, vol. 500, No. 7463, Aug. 22, 2013, 472-476.

\* cited by examiner

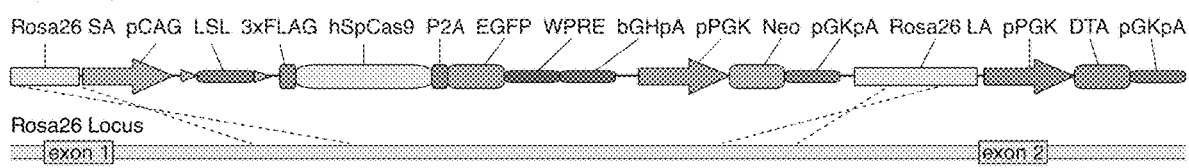
FIG. 1A
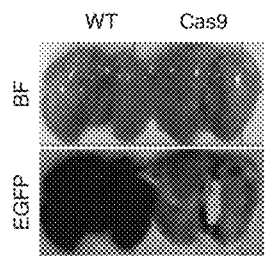
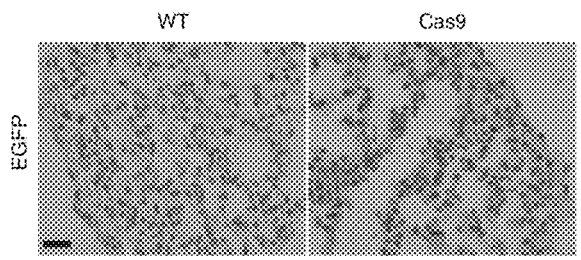
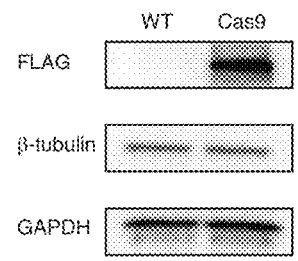
FIG. 1B    FIG. 1C    FIG. 1D

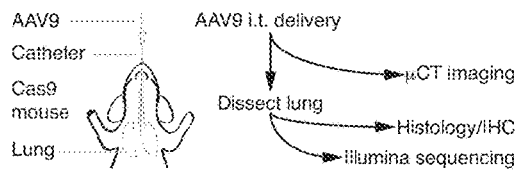
FIG. 2A
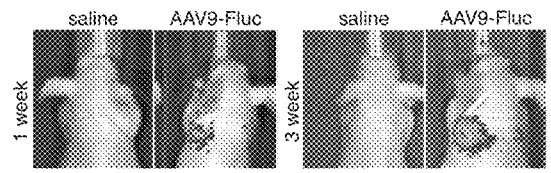
FIG. 2B
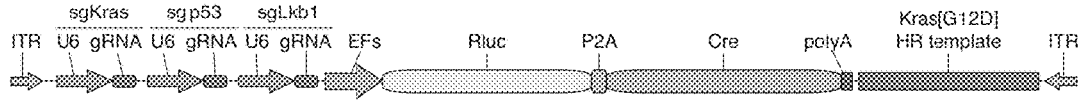
FIG. 2C
FIG. 2D
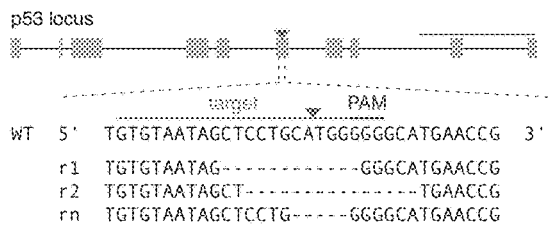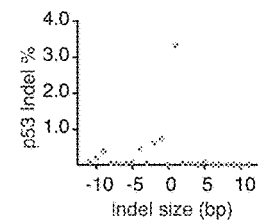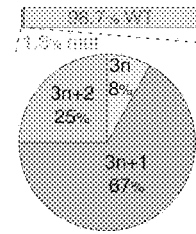
FIG. 2E
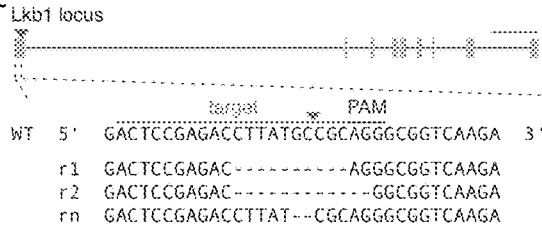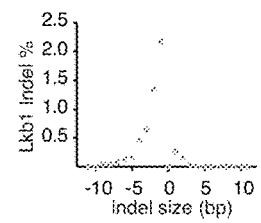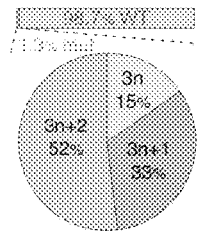
FIG. 2F
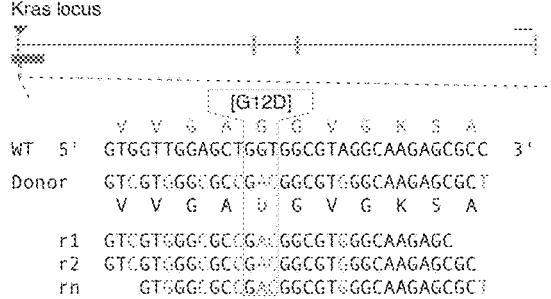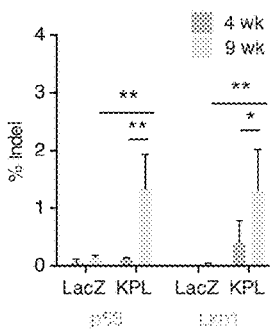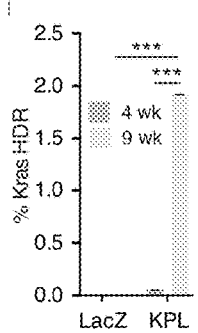
FIG. 2G  FIG. 2H FIG. 3A
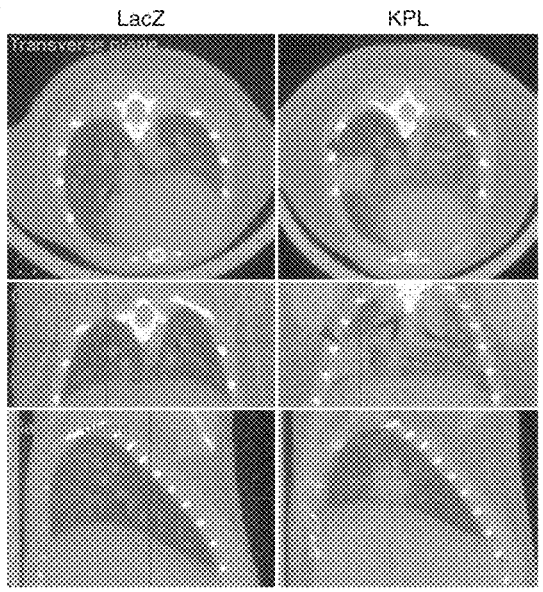
FIG. 3B
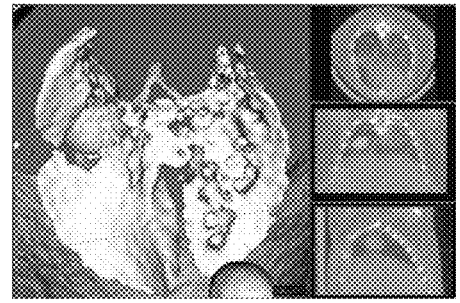
FIG. 3C
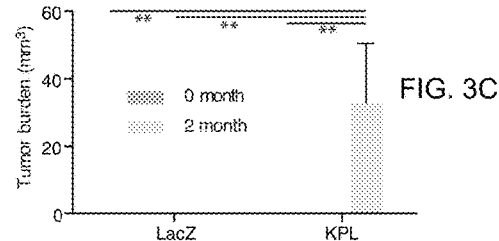
FIG. 3D
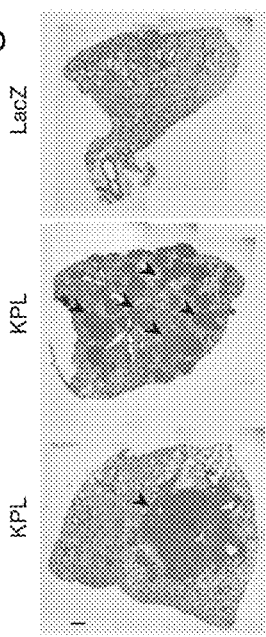
FIG. 3E
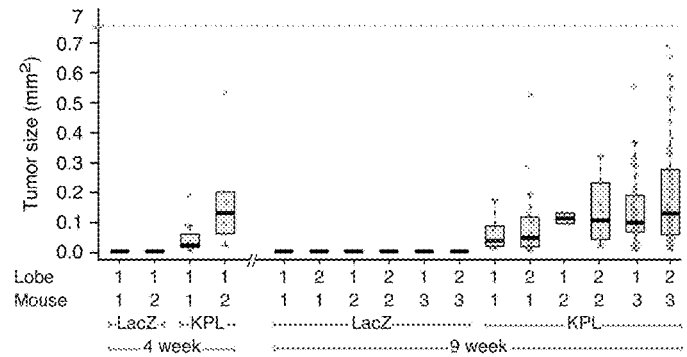
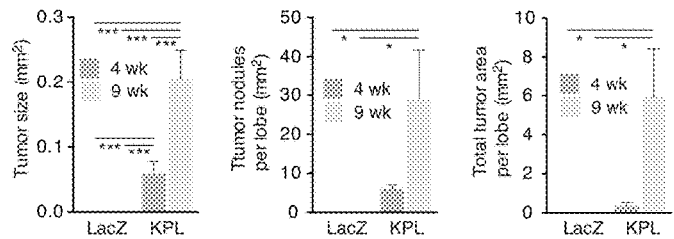
FIG. 3F     FIG. 3G     FIG. 3H

FIG. 8A

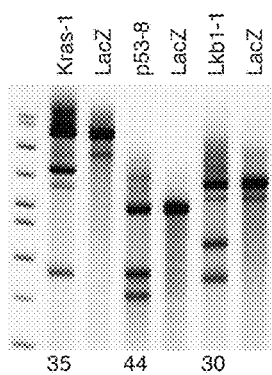

FIG. 8B

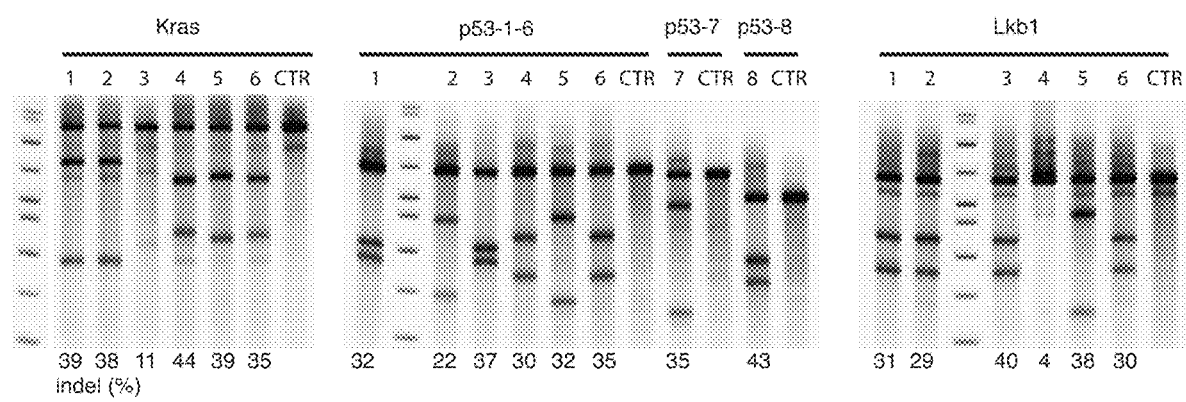

FIG. 8C

| Gene | sgRNA | Genomic target (5'-3') | PAM |
|---|---|---|---|
| KRAS | sgRNA-1 | GCAGCGTTACCTCTATCGTA | GGG |
| | sgRNA-2 | TGAGTATGACCCTACGATAG | AGG |
| | sgRNA-3 | CTGAATTAGCTGTATCGTCA | AGG |
| | sgRNA-4 | GACTGAGTATAAACTTGTGG | TGG |
| | sgRNA-5 | GTGGTTGGAGCTGGTGGCGT | AGG |
| | sgRNA-6 | AAACTTGTGGTGGTTGGAGC | TGG |
| p53 | sgRNA-1 | GTACCTCTCTTTGCGCTCCC | TGG |
| | sgRNA-2 | CCGGATAGTGGGAACCTTCT | GGG |
| | sgRNA-3 | TACCTCTCTTTGCGCTCCCT | GGG |
| | sgRNA-4 | TCTGTACGGCGGTCTCTCCC | AGG |
| | sgRNA-5 | CCCAGAAGGTTCCCACTATC | CGG |
| | sgRNA-6 | CTGTACGGCGGTCTCTCCCA | GGG |
| | sgRNA-7 | CCTCGAGCTCCCTCTGAGCC | AGG |
| | sgRNA-8 | GTGTAATAGCTCCTGCATGG | GGG |
| LKB1 | sgRNA-1 | ACTCCGAGACCTTATGCCGC | AGG |
| | sgRNA-2 | AGCTTGGCGCGTTTGCGGCG | CGG |
| | sgRNA-3 | CTTGACCGCCCTGCGGCATA | AGG |
| | sgRNA-4 | GTGGCGGACCCCGAGCCGTT | GGG |
| | sgRNA-5 | CGTGGCGGACCCCGAGCCGT | TGG |
| | sgRNA-6 | CGATGAGCTTGGCGCGTTTG | CGG |

Kras locus

```
        WT  5'  GTGGTGGTTGGAGCTGGTGGCGTAGGCAAGAGCGCCTTG  3' r1      GTGGTCGTGGGCGCCGACGGCGTGGGCAAGAGCGCTTTG
HR reads r2     GTGGTCGTGGGCGCCGACGGCGTGGGCAAGAGCGCTTTG
         r3     GTGGTCGTGGGCGCCGACGGCGTGGGCAAGAGCGCTTTG
         r4     GTGGTCGTGGGCGCCGACGGCGTGGGCAAGAGCGCTTTG
         r5     GTGGTCGTGGGCGCCGACGGCGTGGGCAAGAGCGCTTTG
         rn                 GCCGACGGCGTGGGCAAGAGCGCTTTG

WT  5'  GTGGTGGTTGGAGCTGGTGGCGTAGGCAAGAGCGCCTTG  3' wt reads r1     GTGGTGGTTGGAGCTGGTGGCGTAGGCAAGAGCGCCTTG
         r2      TGGTGGTTGGAGCTGGTGGCGTAGGCAAGAGCGCCTTG
         rn           TGGAGCTGGTGGCGTAGGCAAGAGCGCCTTG
```

FIG. 9

FIG. 12A 1.1 Rosa26 Cas9 targeting vector

CAGGCCCTCCGAGCGTGGTGGAGCCGTTCTGTGAGACAGCCGGGTACGAGTCGTGACGC
TGGAAGGGGCAAGCGGGTGGTGGGCAGGAATGCGGTCCGCCCTGCAGCAACCGGAGGGG
GAGGGAGAAGGGAGCGGAAAAGTCTCCACCGGACGCGGCCATGGCTCGGGGGGGGGGGG
GCAGCGGAGGAGCGCTTCCGGCCGACGTCTCGTCGCTGATTGGCTTCTTTTCCTCCCGC
CGTGTGTGAAAACACAAATGGCGTGTTTTGGTTGGCGTAAGGCGCCTGTCAGTTAACGG
CAGCCGGAGTGCGCAGCCGCCGGCAGCCTCGCTCTGCCCACTGGGTGGGCGGGAGGTA
GGTGGGGTGAGGCGAGCTGGACGTGCGGGCGCGGTCGGCCTCTGGCGGGGCGGGGGAGG
GGAGGGAGGGTCAGCGAAAGTAGCTCGCGCGCGAGCGGCCGCCCACCCTCCCCTTCCTC
TGGGGGAGTCGTTTTACCCGCCGCCGGCCGGGCCTCGTCGTCTGATTGGCTCTCGGGGC
CCAGAAAACTGGCCCTTGCCATTGGCTCGTGTTCGTGCAAGTTGAGTCCATCCGCCGGC
CAGCGGGGCGGCGAGGAGGCGCTCCCAGGTTCCGGCCCTCCCTCGGCCCCGCGCCGC
AGAGTCTGGCCGCGCGCCCTGCGCAACGTGGCAGGAAGCGCGCGCTGGGGGCGGGGAC
GGGCAGTAGGGCTGAGCGGCTGCGGGGCGGGTGCAAGCACGTTTCCGACTTGAGTTGCC
TCAAGAGGGGCGTGCTGAGCCAGACCTCCATCGCGCACTCCGGGGAGTGGAGGGAAGGA
GCGAGGGCTCAGTTGGGCTGTTTTGGAGGCAGGAAGCACTTGCTCTCCCAAAGTCGCTC
TGAGTTGTTATCAGTAAGGGAGCTGCAGTGGAGTAGGCGGGGAGAAGGCCGCACCCTTC
TCCGGAGGGGGAGGGGAGTGTTGCAATACCTTTCTGGGAGTTCTCTGCTGCCTCCTGG
CTTCTGAGGACCGCCCTGGGCCTGGGAGAATCCCTTCCCCCTCTTCCCTCGTGATCTGC
AACTCCAGTCTTTCTAGCCTTAATTAACCGTTTAAACAATTCTGCAGGAATCTAGTTAT
TAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGT
CAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTACA
TGACCTTATGGGACTTTCCTACTTGGCAGTACATCTACGTATTAGTCATCGCTATTACC
ATGGTCGAGGTGAGCCCCACGTTCTGCTTCACTCTCCCCATCTCCCCCCCTCCCCACC
CCCAATTTTGTATTTATTTATTTTTAATTATTTTGTGCAGCGATGGGGGCGGGGGGGG
GGGGGGGCGCGCGCCAGGCGGGGCGGGGCGGGGCGAGGGGCGGGGCGGGGCGAGGCGG
AGAGGTGCGGCGGCAGCCAATCAGAGCGGCGCGCTCCGAAAGTTTCCTTTTATGGCGAG
GCGGCGGCGGCGGCGGCCCTATAAAAGCGAAGCGCGCGGCGGGCGGAAGTCGCTGCGC
GCTGCCTTCGCCCCGTGCCCCGCTCCGCCGCCGCCTCGCGCCGCCCGCCCGGCTCTGA
CTGACCGCGTTACTCCCACAGGTGAGCGGGCGGGACGGCCCTTCTCCTCCGGGCTGTAA
TTAGCGCTTGGTTTAATGACGGCTTGTTTCTTTTCTGTGGCTGCGTGAAAGCCTTGAGG

FIG. 12B

```
GGCTCCGGGAGGGCCCTTTGTGCGGGGGGAGCGGCTCGGGGGGTGCGTGCGTGTGTG
TGCGTGGGGAGCGCCGCGTGCGGCTCCGCGCTGCCCGGCGGCTGTGAGCGCTGCGGGCG
CGGCGCGGGGCTTTGTGCGCTCCGCAGTGTGCGCGAGGGGAGCGCGGCCGGGGCGGTG
CCCCGCGGTGCGGGGGGGGCTGCGAGGGGAACAAAGGCTGCGTGCGGGGTGTGTGCGTG
GGGGGGTGAGCAGGGGGTGTGGGCGCGTCGGTCGGGCTGCAACCCCCCTGCACCCCCC
TCCCCGAGTTGCTGAGCACGGCCCGGCTTCGGGTGCGGGGCTCCGTACGGGCGTGGCG
CGGGGCTCGCCGTGCCGGGCGGGGGTGGCGGCAGGTGGGGGTGCCGGGCGGGGCGGGG
CCGCCTCGGGCCGGGGAGGGCTCGGGGGAGGGGCGCGGCGGCCCCGGAGCGCCGGCGG
CTGTCGAGGCGCGGCGAGCCGCAGCCATTGCCTTTTATGGTAATCGTGCGAGAGGGCGC
AGGGACTTCCTTTGTCCCAAATCTGTGCGGAGCCGAAATCTGGGAGGCGCCGCCGCACC
CCCTCTAGCGGGCGCGGGCGAAGCGGTGCGGCGCCGGCAGGAAGGAAATGGGCGGGGA
GGGCCTTCGTGCGTCGCCGCGCCGCCGTCCCCTTCTCCCTCTCCAGCCTCGGGGCTGTC
CGCGGGGGGACGGCTGCCTTCGGGGGGACGGGGCAGGGCGGGGTTCGGCTTCTGGCGT
GTGACCGGCGGCTCTAGAGCCTCTGCTAACCATGTTCATGCCTTCTTCTTTTCCTACA
GCTCCTGGGCAACGTGCTGGTTATTGTGCTGTCTCATCATTTTGGCAAAGAATTGATTT
GATACCGCGGGCCCTAAGAAGTTCCTATTCTCTAGAAAGTATAGGAACTTCGTCGACAT
TTAAATCATTTAAATATAACTTCGTATAATGTATGCTATACGAAGTTATTCGCGATGAA
TAAATGAAAGCTTGCAGATCTGCGACTCTAGAGGATCTGCGACTCTAGAGGATCATAAT
CAGCCNTACCACATTTGTAGAGGTTTTACTNGCTTTAAAAAACCTCCCACACCTCCCC
CTGAACCTGAAACATAAAATGAATGCAATTGTTGTTGTTAACTTGTTTATTGCAGCTTA
TAATGGTTACAAATAAAGCAATAGCATCACAAATTTCACAATAAAGCATTTTTTTCAC
TGCATTCTAGTTGTGGTTTGTCCAAACTCATCAATGTATCTTATCATGTCTGGATCTGC
GACTCTAGAGGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAA
CTTGTTTATTGCAGCTTATAATGGTTACAAATAAAGCAATAGCATCACAAATTTCACAA
ATAAAGCATTTTTTTCACTGCATTCTAGTTGTGGTTTGTCCAAACTCATCAATGTATCT
TATCATGTCTGGATCTGCGACTCTAGAGGATCATAATCAGCCATACCACATTTGTAGAG
GTTTTACTTGCTTTAAAAAACCTCCCACACCTCCCCCTGAACCTGAAACATAAAATGAA
TGCAATTGTTGTTGTTAACTTGTTTATTGCAGCTTATAATGGTTACAAATAAAGCAATA
GCATCACAAATTTCACAATAAAGCATTTTTTTCACTGCATTCTAGTTGTGGTTTGTCC
AAACTCATCAATGTATCTTATCATGTCTGGATCCCCATCAAGCTGATCCGGAACCCTTA
ATATAACTTCGTATAATGTATGCTATACGAAGTTATTAGGTCCCTCGACCTGCAGCCCA
AGCTAGATCGAATTCGGCCGGCCTTCGAACACGTGCCACCATGGACTATAAGGACCACG
ACGGAGACTACAAGGATCATGATATTGATTACAAAGACGATGACGATAAGATGGCCCCA
AAGAAGAAGCGGAAGGTCGGTATCCACGGAGTCCCAGCAGCCGACAAGAAGTACAGCAT
CGGCCTGGACATCGGCACCAACTCTGTGGGCTGGGCCGTGATCACCGACGAGTACAAGG
TGCCCAGCAAGAAATTCAAGGTGCTGGGCAACACCGACCGGCACAGCATCAAGAAGAAC
CTGATCGGAGCCCTGCTGTTCGACAGCGGCGAAACAGCCGAGGCCACCCGGCTGAAGAG
AACCGCCAGAAGAAGATACACCAGACGGAAGAACCGGATCTGCTATCTGCAAGAGATCT
TCAGCAACGAGATGGCCAAGGTGGACGACAGCTTCTTCCACAGACTGGAAGAGTCCTTC
CTGGTGGAAGAGGATAAGAAGCACGAGCGGCACCCCATCTTCGGCAACATCGTGGACGA
```

FIG. 12C

```
GGTGGCCTACCACGAGAAGTACCCCACCATCTACCACCTGAGAAAGAAACTGGTGGACA
GCACCGACAAGGCCGACCTGCGGCTGATCTATCTGGCCCTGGCCCACATGATCAAGTTC
CGGGGCCACTTCCTGATCGAGGGCGACCTGAACCCCGACAACAGCGACGTGGACAAGCT
GTTCATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTGGAA
AATCTGATCGCCCAGCTGCCCGGCGAGAAGAAGAATGGCCTGTTCGGAAACCTGATTGC
CCTGAGCCTGGGCCTGACCCCAACTTCAAGAGCAACTTCGACCTGGCCGAGGATGCCA
AACTGCAGCTGAGCAAGGACACCTACGACGACGACCTGGACAACCTGCTGGCCCAGATC
GGCGACCAGTACGCCGACCTGTTTCTGGCCGCCAAGAACCTGTCCGACGCCATCCTGCT
GAGCGACATCCTGAGAGTGAACACCGAGATCACCAAGGCCCCCCTGAGCGCCTCTATGA
TCAAGAGATACGACGAGCACCACCAGGACCTGACCCTGCTGAAAGCTCTCGTGCGGCAG
CAGCTGCCTGAGAAGTACAAAGAGATTTTCTTCGACCAGAGCAAGAACGGCTACGCCGG
CTACATTGACGGCGGAGCCAGCCAGGAAGAGTTCTACAAGTTCATCAAGCCCATCCTGG
AAAAGATGGACGGCACCGAGGAACTGCTCGTGAAGCTGAACAGAGAGGACCTGCTGCGG
AAGCAGCGGACCTTCGACAACGGCAGCATCCCCCACCAGATCCACCTGGGAGAGCTGCA
CGCCATTCTGCGGCGGCAGGAAGATTTTTACCCATTCCTGAAGGACAACCGGGAAAAGA
TCGAGAAGATCCTGACCTTCCGCATCCCCTACTACGTGGGCCCTCTGGCCAGGGGAAAC
AGCAGATTCGCCTGGATGACCAGAAAGAGCGAGGAAACCATCACCCCCTGGAACTTCGA
GGAAGTGGTGGACAAGGGCGCTTCCGCCCAGAGCTTCATCGAGCGGATGACCAACTTCG
ATAAGAACCTGCCCAACGAGAAGGTGCTGCCCAAGCACAGCCTGCTGTACGAGTACTTC
ACCGTGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACCGGA
AAGTGACCGTGAAGCAGCTGAAAGAGGACTACTTCAAGAAAATCGAGTGCTTCGACTCC
GTGGAAATCTCCGGCGTGGAAGATCGGTTCAACGCCTCCCTGGGCACATACCACGATCT
GCTGAAAATTATCAAGGACAAGGACTTCCTGGACAATGAGGAAAACGAGGACATTCTGG
AAGATATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGGAGATA
CACCGGCTGGGGCAGGCTGAGCCGGAAGCTGATCAACGGCATCCGGGACAAGCAGTCCG
GCAAGACAATCCTGGATTTCCTGAAGTCCGACGGCTTCGCCAACAGAAACTTCATGCAG
CTGATCCACGACGACAGCCTGACCTTTAAAGAGGACATCCAGAAAGCCCAGGTGTCCGG
CCAGGGCGATAGCCTGCACGAGCACATTGCCAATCTGGCCGGCAGCCCCGCCATTAAGA
AGGGCATCCTGCAGACAGTGAAGGTGGTGGACGAGCTCGTGAAAGTGATGGGCCGGCAC
AAGCCCGAGAACATCGTGATCGAAATGGCCAGAGAGAACCAGACCACCCAGAAGGGACA
GAAGAACAGCCGCGAGAGAATGAAGCGGATCGAAGAGGGCATCAAAGAGCTGGGCAGCC
AGATCCTGAAAGAACACCCCGTGGAAAACACCCAGCTGCAGAACGAGAAGCTGTACCTG
TACTACCTGCAGAATGGGCGGGATATGTACGTGGACCAGGAACTGGACATCAACCGGCT
GTCCGACTACGATGTGGACCATATCGTGCCTCAGAGCTTTCTGAAGGACGACTCCATCG
ACAACAAGGTGCTGACCAGAAGCGACAAGAACCGGGGCAAGAGCGACAACGTGCCCTCC
GAAGAGGTCGTGAAGAAGATGAAGAACTACTGGCGGCAGCTGCTGAACGCCAAGCTGAT
TACCCAGAGAAAGTTCGACAATCTGACCAAGGCCGAGAGAGGCGGCCTGAGCGAACTGG
ATAAGGCCGGCTTCATCAAGAGACAGCTGGTGGAAACCCGGCAGATCACAAAGCACGTG
```

FIG. 12D

```
GCACAGATCCTGGACTCCCGGATGAACACTAAGTACGACGAGAATGACAAGCTGATCCG
GGAAGTGAAAGTGATCACCCTGAAGTCCAAGCTGGTGTCCGATTTCCGGAAGGATTTCC
AGTTTTACAAAGTGCGCGAGATCAACAACTACCACCACGCCCACGACGCCTACCTGAAC
GCCGTCGTGGGAACCGCCCTGATCAAAAAGTACCCTAAGCTGGAAAGCGAGTTCGTGTA
CGGCGACTACAAGGTGTACGACGTGCGGAAGATGATCGCCAAGAGCGAGCAGGAAATCG
GCAAGGCTACCGCCAAGTACTTCTTCTACAGCAACATCATGAACTTTTTCAAGACCGAG
ATTACCCTGGCCAACGGCGAGATCCGGAAGCGGCCTCTGATCGAGACAAACGGCGAAAC
CGGGGAGATCGTGTGGGATAAGGGCCGGGATTTTGCCACCGTGCGGAAAGTGCTGAGCA
TGCCCCAAGTGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGACTGGGACCC
TAAGAAGTACGGCGGCTTCGACAGCCCCACCGTGGCCTATTCTGTGCTGGTGGTGGCCA
AAGTGGAAAAGGGCAAGTCCAAGAAACTGAAGAGTGTGAAAGAGCTGCTGGGGATCACC
ATCATGGAAGAAGCAGCTTCGAGAAGAATCCCATCGACTTTCTGGAAGCCAAGGGCTA
CAAAGAAGTGAAAAAGGACCTGATCATCAAGCTGCCTAAGTACTCCCTGTTCGAGCTGG
AAAACGGCCGGAAGAGAATGCTGGCCTCTGCCGGCGAACTGCAGAAGGGAAACGAACTG
GCCCTGCCCTCCAAATATGTGAACTTCCTGTACCTGGCCAGCCACTATGAGAAGCTGAA
GGGCTCCCCCGAGGATAATGAGCAGAAACAGCTGTTTGTGGAACAGCACAAGCACTACC
TGGACGAGATCATCGAGCAGATCAGCGAGTTCTCCAAGAGAGTGATCCTGGCCGACGCT
AATCTGGACAAAGTGCTGTCCGCCTACAACAAGCACCGGGATAAGCCCATCAGAGAGCA
GGCCGAGAATATCATCCACCTGTTTACCCTGACCAATCTGGGAGCCCCTGCCGCCTTCA
AGTACTTTGACACCACCATCGACCGGAAGAGGTACACCAGCACCAAAGAGGTGCTGGAC
GCCACCCTGATCCACCAGAGCATCACCGGCCTGTACGAGACACGGATCGACCTGTCTCA
GCTGGGAGGCGACAAAAGGCCGGCGGCCACGAAAAAGGCCGGCCAGGCAAAAAAGAAAA
AGGGAAGCGGAGCCACTAACTTCTCCCTGTTGAAACAAGCAGGGGATGTCGAAGAGAAT
CCCGGGCCAGTGAGCAAGGGCGAGGAGCTGTTCACCGGGGTGGTGCCCATCCTGGTCGA
GCTGGACGGCGACGTAAACGGCCACAAGTTCAGCGTGTCCGGCGAGGGCGAGGGCGATG
CCACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCCGA
CCACATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCAA
CATCCTGGGGCACAAGCTGGAGTACAACTACAACAGCCACAACGTCTATATCATGGCCG
ACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCT
GCTGCCCGACAACCACTACCTGAGCACCCAGTCCGCCCTGAGCAAAGACCCCAACGAGA
AGCGCGATCACATGGTCCTGCTGGAGTTCGTGACCGCCGCGGGATCACTCTCGGCATG
GACGAGCTGTACAAGTAAACGCGTATGCATGGCCGGCCTGCAGGAATTCGATATCAAG
CTTATCGATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTGCTGTCTCTT
TATGAGGAGTTGTGGCCCGTTGTCAGGCAACGTGGCGTGGTGTGCACTGTGTTTGCTGA
```

FIG. 12E

```
CGCAACCCCCACTGGTTGGGGCATTGCCACCACCTGTCAGCTCCTTTCCGGGACTTTCG
CTTTCCCCCTCCCTATTGCCACGGCGGAACTCATCGCCGCCTGCCTTGCCCGCTGCTGG
ACAGGGGCTCGGCTGTTGGGCACTGACAATTCCGTGGTGTTGTCGGGGAAATCATCGTC
CTTTCCTTGGCTGCTCGCCTGTGTTGCCACCTGGATTCTGCGCGGGACGTCCTTCTGCT
ACGTCCCTTCGGCCCTCAATCCAGCGGACCTTCCTTCCCGCGGCCTGCTGCCGGCTCTG
CGGCCTCTTCCGCGTCTTCGCCTTCGCCCTCAGACGAGTCGGATCTCCCTTTGGGCCGC
CTCCCCGCATCGATACCGTCGACCTCGACCTCGACTGTGCCTTCTAGTTGCCAGCCATC
TGTTGTTTGCCCCTCCCCGTGCCTTCCTTGACCCTGGAAGGTGCCACTCCCACTGTCC
TTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATGGCAGGCATGC
TGGGGAACTAGTGGTGCCAGGGCGTGCCCTTGGGCTCCCCGGGCGCGGCGGCCGCATCG
AATTCTACCGGGTAGGGGAGGCGCTTTTCCCAAGGCAGTCTGGAGCATGCGCTTTAGCA
GCCCCGCTGGGCACTTGGCGCTACACAAGTGGCCTCTGGCCTCGCACACATTCCACATC
CACCGGTAGGCGCCAACCGGCTCCGTTCTTTGGTGGCCCCTTCGCGCCACCTTCTACTC
CTCCCCTAGTCAGGAAGTTCCCCCCCGCCCCGCAGCTCGCGTCGTGCAGGACGTGACAA
ATGGAAGTAGCACGTCTCACTAGTCTCGTGCAGATGGACAGCACCGCTGAGCAATGGAA
GCGGGTAGGCCTTTGGGGCAGCGGCCAATAGCAGCTTTGCTCCTTCGCTTTCTGGGCTC
AGAGGCTGGGAAGGGGTGGGTCCGGGGCGGGCTCAGGGGCGGGCTCAGGGGCGGGGCG
GGCGCCCGAAGGTCCTCCGGAGGCCCGGCATTCTGCACGCTTCAAAAGCGCACGTCTGC
CGCGCTGTTCTCCTCTTCCTCATCTCCGGGCCTTTCGACCTGCAATCGCCGCTAGCGAA
GTTCCTATTCTCTAGAAAGTATAGGAACTTCGCCACCATGGGATCGGCCATTGAACAAG
ATGGATTGCACGCAGGTTCTCCGGCCGCTTGGGTGGAGAGGCTATTCGGCTATGACTGG
GCACAACAGACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGCAGGACGAGG
CAGCGCGGCTATCGTGGCTGGCCACGACGGGCGTTCCTTGCGCAGCTGTGCTCGACGTT
GTCACTGAAGCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAATGCGGCGGC
TGCATACGCTTGATCCGGCTACCTGCCCATTCGACCACCAAGCGAAACATCGCATCGAG
CGAGCACGTACTCGGATGGAAGCCGGTCTTGTCGATCAGGATGATCTGGACGAAGAGCA
TCAGGGGCTCGCGCCAGCCGAACTGTTCGCCAGGCTCAAGGCGCGCATGCCCGACGGCG
ATGATCTCGTCGTGACCCATGGCGATGCCTGCTTGCCGAATATCATGGTGGAAAATGGC
CGCTTTTCTGGATTCATCGACTGTGGCCGGCTGGGTGTGGCGGACCGCTATCAGGACAT
AGCGTTGGCTACCCGTGATATTGCTGAAGAGCTTGGCGGCGAATGGGCTGACCGCTTCC
TCGTGCTTTACGGTATCGCCGCTCCCGATTCGCAGCGCATCGCCTTCTATCGCCTTCTT
GACGAGTTCTTCTGAGGGGATCCGCTGTAAGTCTGCAGAAATTGATGATCTATTAAACA
ATAAAGATGTCCACTAAAATGGAAGTTTTTCCTGTCATACTTTGTTAAGAAGGGTGAGA
ACAGAGTACCTACATTTTGAATGGAAGGATTGGAGCTACGGGGGTGGGGTGGGGTGGG
ATTAGATAAATGCCTGCTCTTTACTGAAGGCTCTTTACTATTGCTTTATGATAATGTTT
CATAGTTGGATATCATAATTTAAACAAGCAAAACCAAATTAAGGGCCAGCTCATTCCTC
CCACTCATGATCTATAGATCTATAGATCTCTCGTGGGATCATTGTTTTTCTCTTGATTC
CCACTTTGTGGTTCTAAGTACTGTGGTTTCCAAATGTGTCAGTTTCATAGCCTGAAGAA
```

FIG. 12F

```
CGAGATCAGCAGCCTCTGTTCCACATACACTTCATTCTCAGTATTGTTTTGCCAAGTTC
TAATTCCATCAGAAAGCTTGCAGAAGATCTCCCCAACTGGGGTAACCTTTGAGTTCTCT
CAGTTGGGGGGGCGCGCCGGCTAGAAGATGGGCGGGAGTCTTCTGGGCAGGCTTAAAGG
CTAACCTGGTGTGTGGGCGTTGTCCTGCAGGGGAATTGAACAGGTGTAAAATTGGAGGG
ACAAGACTTCCCACAGATTTCGGTTTTGTCGGGAAGTTTTTAATAGGGGCAAATAAG
GAAAATGGGAGGATAGGTAGTCATCTGGGGTTTTATGCAGCAAAACTACAGGTTATTAT
TGCTTGTGATCCGCCTCGGAGTATTTTCCATCGAGGTAGATTAAAGACATGCTCACCCG
AGTTTTATACTCCTGCTTGAGATCCTTACTACAGTATGAAATTACAGTGTCGCGAGT
TAGACTATGTAAGCAGAATTTTAATCATTTTAAAGAGCCCAGTACTTCATATCCATTT
CTCCCGCTCCTTCTGCAGCCTTATCAAAAGGTATTTAGAACACTCATTTAGCCCCAT
TTTCATTTATTATACTGGCTTATCCAACCCTAGACAGAGCATTGGCATTTTCCCTTTC
CTGATCTTAGAAGTCTGATGACTCATGAAACCAGACAGATTAGTTACATACACCACAAA
TCGAGGCTGTAGCTGGGGCCTCAACACTGCAGTTCTTTTATAACTCCTTAGTACACTTT
TTGTTGATCCTTTGCCTTGATCCTTAATTTTCAGTGTCTATCACCTCTCCCGTCAGGTG
GTGTTCCACATTTGGGCCTATTCTCAGTCCAGGGAGTTTTACAACAATAGATGTATTGA
GAATCCAACCTAAAGCTTAACTTTCCACTCCCATGAATGCCTCTCTCCTTTTCTCCAT
TTATAAACTGAGCTATTAACCATTAATGGTTTCCAGGTGGATGTCTCCTCCCCAATAT
TACCTGATGTATCTTACATATTGCCAGGCTGATATTTAAGACATTAAAAGGTATATTT
CATTATTGAGCCACATGGTATTGATTACTGCTTACTAAAATTTTGTCATTGTACACATC
TGTAAAAGGTGGTTCCTTTTGGAATGCAAAGTTCAGGTGTTTGTTGTCTTTCCTGACCT
AAGGTCTTGTGAGCTTGTATTTTTTCTATTTAAGCAGTGCTTTCTCTTGGACTGGCTTG
ACTCATGGCATTCTACACGTTATTGCTGGTCTAAATGTGATTTGCCAAGCTTCTTCAG
GACCTATAATTTTGCTTGACTTGTAGCCAAACACAAGTAAAATGATTAAGCAACAAATG
TATTTGTGAAGCTTGGTTTTTAGGTTGTTGTGTTGTGTGTGCTTGTGCTCTATAATAAT
ACTATCCAGGGGCTGGAGAGGTGGCTCGGAGTTCAAGAGCACAGACTGCTCTTCCAGAA
GTCCTGAGTTCAATTCCCAGCAACCACATGGTGGCTCACAACCATCTGTAATGGGATCT
GATGCCCTCTTCTGGTGTGTCTGAAGACCACAAGTGTATTCACATTAAATAAATAAATC
CTCCTTCTTCTTCTTTTTTTTTTTTTAAAGAGAATACTGTCTCCAGTAGAATTTACTG
AAGTAATGAAATACTTTGTGTTTGTTCCAATATGGTAGCCAATAATCAAATTACTCTTT
AAGCACTGGAAATGTTACCAAGGAACTAATTTTTATTTGAAGTGTAACTGTGGACAGAG
GAGCCATAACTGCAGACTTGTGGGATACAGAAGACCAATGCAGACTTTAATGTCTTTTC
TCTTACACTAAGCAATAAAGAAATAAAAATTGAACTTCTAGTATCCTATTTGTTTAAAC
TGCTAGCTTTACTTAACTTTTGTGCTTCATCTATACAAAGCTGAAAGCTAAGTCTGCAG
CCATTACTAAACATGAAAGCAAGTAATGATAATTTTGGATTTCAAAAATGTAGGGCCAG
AGTTTAGCCAGCCAGTGGTGGTGCTTGCCTTTATGCCTTTAATCCCAGCACTCTGGAGG
CAGAGACAGGCAGATCTCTGAGTTTGAGCCCAGCCTGGTCTACACATCAAGTTCTATCT
AGGATAGCCAGGAATACACACAGAAACCCTGTTGGGGAGGGGGCTCTGAGATTTCATA
AAATTATAATTGAAGCATTCCCTAATGAGCCACTATGGATGTGGCTAAATCCGTCTACC
TTTCTGATGAGATTTGGGTATTATTTTTCTGTCTCTGCTGTTGGTTGGGTCTTTTGAC
ACTGTGGGCTTTCTTTAAAGCCTCCTTCCTGCCATGTGGTCTCTTGTTTGCTACTAACT
TCCCATGGCTTAAATGGCATGGCTTTTGCCTTCTAAGGGCAGCTGCTGAGATTTGCAG
```

FIG. 12G

```
CCTGATTTCCAGGGTGGGGTTGGGAAATCTTTCAAACACTAAAATTGTCCTTTAATTTT
TTTTTAAAAAATGGGTTATATAATAAACCTCATAAAATAGTTATGAGGAGTGAGGTGG
ACTAATATTAAATGAGTCCCTCCCCTATAAAGAGCTATTAAGGCTTTTTGTCTTATAC
TTAACTTTTTTTTAAATGTGGTATCTTAGAACCAAGGGTCTAGAGTTTTAGTATAC
AGAAACTGTTGCATCGCTTAATCAGATTTTCTAGTTTCAAATCCAGAGAATCCAAATTC
TTCACAGCCAAAGTCAAATTAAGAATTTCTGACTTTTAATGTTAATTTGCTTACTGTGA
ATATAAAATGATAGCTTTTCCTGAGGCAGGGTCTCACTATGTATCTCTGCCTGATCTG
CAACAAGATATGTAGACTAAAGTTCTGCCTGCTTTTGTCTCCTGAATACTAAGGTTAAA
ATGTAGTAATACTTTTGGAACTTGCAGGTCAGATTCTTTTATAGGGGACACACTAAGGG
AGCTTGGGTGATAGTTGGTAAATGTGTTTAAGTGATGAAAACTTGAATTATTATCACCG
CAACCTACTTTTTAAAAAAAAAGCCAGGCCTGTTAGAGCATGCTTAAGGGATCCCTAG
GACTTGCTGAGCACACAAGAGTAGTTACTTGGCAGGCTCCTGGTGAGAGCATATTTCAA
AAAACAAGGCAGACAACCAAGAAACTACAGTTAAGGTTACCTGTCTTTAAACCATCTGC
ATATACACAGGGATATTAAAATATTCCAAATAATATTTCATTCAAGTTTTCCCCATCA
AATTGGGACATGGATTTCTCCGGTGAATAGGCAGAGTTGGAAACTAAACAAATGTTGGT
TTTGTGATTTGTGAAATTGTTTTCAAGTGATAGTTAAAGCCCATGAGATACAGAACAAA
GCTGCTATTTCGAGGTCTCTTGGTTTATACTCAGAAGCACTTCTTTGGGTTTCCCTGCA
CTATCCTGATCATGTGCTAGGCCTACCTTAGGCTGATTGTTGTTCAAATAAACTTAAGT
TTCCTGTCAGGTGATGTCATATGATTTCATATATCAAGGCAAAACATGTTATATATGTT
AAACATTTGTACTTAATGTGAAAGTTAGGTCTTTGTGGGTTTGATTTTAATTTTCAAA
ACCTGAGCTAAATAAGTCATTTTTACATGTCTTACATTTGGTGGAATTGTATAATTGTG
GTTTGCAGGCAAGACTCTCTGACCTAGTAACCCTACCTATAGAGCACTTTGCTGGGTCA
CAAGTCTAGGAGTCAAGCATTTCACCTTGAAGTTGAGACGTTTTGTTAGTGTATACTAG
TTTATATGTTGGAGGACATGTTTATCCAGAAGATATTCAGGACTATTTTGACTGGGCT
AAGGAATTGATTCTGATTAGCACTGTTAGTGAGCATTGAGTGGCCTTTAGGCTTGAATT
GGAGTCACTTGTATATCTCAAATAATGCTGGCCTTTTTAAAAGCCCTTGTTCTTTATC
ACCCTGTTTCTACATAATTTTTGTTCAAAGAAATACTTGTTTGGATCTCCTTTTGACA
ACAATAGCATGTTTTCAAGCCATATTTTTTTCCTTTTTTTTTTTTTTTTTGGTTTTTC
GAGACAGGGTTTCTCTGTATAGCCCTGGCTGTCCTGGAACTCACTTTGTAGACCAGGCT
GGCCTCGAACTCAGAAATCCGCCTGCCTCTGCCTCCTGAGTGCCGGGATTAAAGGCGTG
CACCACCACGCCTGGCTAAGTTGGATATTTGTTATATAACTATAACCAATACTAACTC
CACTGGGTGGATTTTAATTCAGTCAGTAGTCTTAAGTGGTCTTTATTGGCCCTTCATT
AAAATCTACTGTTCACTCTAACAGAGGCTGTTGGTACTAGTGGCACTTAAGCAACTTCC
TACGGATATACTAGCAGATTAAGGGTCAGGGATAGAAACTAGTCTAGCGTTTTGTATAC
CTACCAGCTTTATACTACCTTGTTCTGATAGAAATATTTCAGGACATCTAGCTTATCGA
TACCGTCGACGGTATCGATAAGCTTGATATCGAATTCTACCGGGTAGGGGAGGCGCTTT
TCCCAAGGCAGTCTGGAGCATGCGCTTTAGCAGCCCGCTGGGCACTTGGCGCTACACA
AGTGGCCTCTGGCCTCGCACACATTCCACATCCACCGGTAGGCGCCAACCGGCTCCGTT
CTTTGGTGGCCCCTTCGCGCCACCTTCTACTCCTCCCCTAGTCAGGAAGTTCCCCCCG
CCCCGCAGCTCGCGTCGTGCAGGACGTGACAAATGGAAGTAGCACGTCTCACTAGTCTC
GTGCAGATGGACAGCACCGCTGAGCAATGGAAGCGGGTAGGCCTTTGGGGCAGCGGCCA
```

FIG. 12H

```
ATAGCAGCTTTGCTCCTTCGCTTTCTGGGCTCAGAGGCTGGGAAGGGGTGGGTCCGGGG
GCGGGCTCAGGGGCGGGCTCAGGGGCGGGGCGGGCGCCCGAAGGTCCTCCGGAGGCCCG
GCATTCTGCACGCTTCAAAAGCGCACGTCTGCCGCGCTGTTCTCCTCTTCCTCATCTCC
GGGCCTTTCGACCTGCAGGTCCTCGCCATGGATCCTGATGATGTTGTTGATTCTTCTAA
ATCTTTTGTGATGGAAAACTTTTCTTCGTACCACGGGACTAAACCTGGTTATGTAGATT
CCATTCAAAAGGTATACAAAAGCCAAAATCTGGTACACAAGGAAATTATGACGATGAT
TGGAAAGGGTTTTATAGTACCGACAATAAATACGACGCTGCGGGATACTCTGTAGATAA
TGAAAACCGCTCTCTGGAAAAGCTGGAGGCGTGGTCAAAGTGACGTATCCAGGACTGA
CGAAGGTTCTCGCACTAAAAGTGGATAATGCCGAAACTATTAAGAAAGAGTTAGGTTTA
AGTCTCACTGAACCGTTGATGGAGCAAGTCGGAACGGAAGAGTTTATCAAAAGGTTCGG
TGATGGTGCTTCGCGTGTAGTGCTCAGCCTTCCCTTCGCTGAGGGGAGTTCTAGCGTTG
AATATATTAATAACTGGGAACAGGCGAAAGCGTTAAGCGTAGAACTTGAGATTAATTTT
GAAACCCGTGGAAAACGTGGCCAAGATGCGATGTATGAGTATATGGCTCAAGCCTGTGC
AGGAAATCGTGTCAGGCGATCTCTTTGTGAAGGAACCTTACTTCTGTGGTGTGACATAA
TTGGACAAACTACCTACAGAGATTTAAAGCTCTAAGGTAAATATAAAATTTTTAAGTGT
ATAATGTGTTAAACTACTGATTCTAATTGTTTGTGTATTTTAGATTCCAACCTATGGAA
CTGATGAATGGGAGCAGTGGTGGAATGCAGATCCTAGAGCTCGCTGATCAGCCTCGACT
GTGCCTTCTAGTTGCCAGCCATCTGTTGTTTGCCCCTCCCCGTGCCTTCCTTGACCCT
GGAAGGTGCCACTCCCACTGTCCTTTCCTAATAAAATGAGGAAATTGCATCGCATTGTC
TGAGTAGGTGTCATTCTATTCTGGGGGGTGGGGTGGGCAGGACAGCAAGGGGGAGGAT
TGGGAAGACAATAGCAGGCATGCTGGGGATGCGGTGGCTCTATGGCTTCTGAGGCGGA
AAGAACCAGCTGGGGCTCGAGGGGGGCCCGGTACCCAGCTTTTGTTCCCTTTAGTGAGG
GTTAATTGCGCGCTTGGCGTAATCATGGTCATAGCTGTTTCCTGTGTGAAATTGTTATC
CGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGG
AAACCTGTCGTGCCAGCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTG
CGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCTGACGAGCATCACAAAAATCGA
CGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCGTTCAGCCCGA
CCGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTTGATCCGGCA
AACAAACCACCGCTGGTAGCGGTGGTTTTTTGTTTGCAAGCAGCAGATTACGCGCAGA
AAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGA
```

FIG. 12I

```
TCCTTTTAAATTAAAAATGAAGTTTTAAATCAATCTAAAGTATATATGAGTAAACTTGG
TCTGACAGTGGAGCTCCAATTCGCCCTATAGTGAGTCGTATTACGCGCGCTCACTGGCC
GTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTT
CCCAACAGTTGCGCAGCCTGAATGGCGAATGGGACGCGCCCTGTAGCGGCGCATTAAGC
GCGGCGGGTGTGGTGGTTACGCGCAGCGTGACCGCTACACTTGCCAGCGCCCTAGCGCC
CGCTCCTTTCGCTTTCTTCCCTTCCTTTCTCGCCACGTTCGCCGGCTTTCCCCGTCAAG
CTCTAAATCGGGGGCTCCCTTTAGGGTTCCGATTTAGTGCTTTACGGCACCTCGACCCC
AAAAAACTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAA
CAACACTCAACCCTATCTCGGTCTATTCTTTTGATTTATAAGGGATTTTGCCGATTTCG
GCCTATTGGTTAAAAAATGAGCTGATTTAACAAAAATTTAACGCGAATTTTAACAAAAT
ATTAACGCTTACAATTAGGTGGCACTTTTCGGGGAAATGTGCGCGGAACCCCTATTTG
TTTATTTTTCTAAATACATTCAAATATGTATCCGCTCATGAGACAATAACCCTGATAAA
TGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACT
TTTAAAGTTCTGCTATGTGGCGCGGTATTATCCCGTATTGACGCCGGGCAAGAGCAACT
CGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGT
GATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGA
ATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATCATTGCAGCA
CTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATT
GGTAACCGCGG
```

1.2 Rosa26 Cas9 targeting vector elements 1.2.1 Rosa26 short arm

```
CAGGCCCTCCGAGCGTGGTGGAGCCGTTCTGTGAGACAGCCGGGTACGAGTCGTGACGC
TGGAAGGGGCAAGCGGGTGGTGGGCAGGAATGCGGTCCGCCCTGCAGCAACCGGAGGGG
GAGGGAGAAGGGAGCGGAAAAGTCTCCACCGGACGCGGCCATGGCTCGGGGGGGGGGGG
GCAGCGGAGGAGCGCTTCCGGCCGACGTCTCGTCGCTGATTGGCTTCTTTTCCTCCCGC
```

FIG. 12J

```
CGTGTGTGAAAACACAAATGGCGTGTTTTGGTTGGCGTAAGGCGCCTGTCAGTTAACGG
CAGCCGGAGTGCGCAGCCGCCGGCAGCCTCGCTCTGCCCACTGGGTGGGGCGGGAGGTA
GGTGGGGTGAGGCGAGCTGGACGTGCGGGCGCGGTCGGCCTCTGGCGGGGCGGGGGAGG
GGAGGGAGGGTCAGCGAAAGTAGCTCGCGCGCGAGCGGCCGCCCACCCTCCCCTTCCTC
TGGGGGAGTCGTTTTACCCGCCGCCGGCCGGGCCTCGTCGTCTGATTGGCTCTCGGGGC
CCAGAAAACTGGCCCTTGCCATTGGCTCGTGTTCGTGCAAGTTGAGTCCATCCGCCGGC
CAGCGGGGCGGCGAGGAGGCGCTCCCAGGTTCCGGCCCTCCCCTCGGCCCCGCGCCGC
AGAGTCTGGCCGCGCGCCCTGCGCAACGTGGCAGGAAGCGCGCGCTGGGGGCGGGGAC
GGGCAGTAGGGCTGAGCGGCTGCGGGCGGGTGCAAGCACGTTTCCGACTTGAGTTGCC
TCAAGAGGGGCGTGCTGAGCCAGACCTCCATCGCGCACTCCGGGGAGTGGAGGGAAGGA
GCGAGGGCTCAGTTGGGCTGTTTTGGAGGCAGGAAGCACTTGCTCTCCAAAGTCGCTC
TGAGTTGTTATCAGTAAGGGAGCTGCAGTGGAGTAGGCGGGGAGAAGGCCGCACCCTTC
TCCGGAGGGGGAGGGGAGTGTTGCAATACCTTTCTGGGAGTTCTCTGCTGCCTCCTGG
CTTCTGAGGACCGCCCTGGGCCTGGGAGAATCCCTTCCCCCTCTTCCCTCGTGATCTGC
AACTCCAGTCTTTCTAG
```

1.2.2 CAG promoter

```
CCGTTTAAACAATTCTGCAGGAATCTAGTTATTAATAGTAATCAATTACGGGGTCATTA
GTTCATAGCCCATATATGGAGTTCCGCGTTACATAACTTACGGTAAATGGCCCGCCTGG
CTGACCGCCCAACGACCCCCGCCCATTGACGTCAATAATGACGTATGTTCCCATAGTAA
CGCCAATAGGGACTTTCCATTGACGTCAATGGGTGGAGTATTTACGGTAAACTGCCCAC
TTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGC
AGTACATCTACGTATTAGTCATCGCTATTACCATGGTCGAGGTGAGCCCCACGTTCTGC
TTCACTCTCCCCATCTCCCCCCCCTCCCCACCCCCAATTTTGTATTTATTTATTTTTTA
ATTATTTTGTGCAGCGATGGGGGCGGGGGGGGGGGGGGCGCGCGCCAGGCGGGGCGG
GGCGGGGCGAGGGGCGGGGCGGGGCGAGGCGGAGAGGTGCGGCGGCAGCCAATCAGAGC
GGCGCGCTCCGAAAGTTTCCTTTTATGGCGAGGCGGCGGCGGCGGCGGCCCTATAAAAA
GCGAAGCGCGCGGCGGGCGGAAGTCGCTGCGCGCTGCCTTCGCCCCGTGCCCCGCTCCG
CCGCCGCCTCGCGCCGCCCGCCCCGGCTCTGACTGACCGCGTTACTCCCACAGGTGAGC
GGGCGGGACGGCCCTTCTCCTCCGGGCTGTAATTAGCGCTTGGTTTAATGACGGCTTGT
TTCTTTTCTGTGGCTGCGTGAAAGCCTTGAGGGGCTCCGGGAGGGCCCTTTGTGCGGGG
GGAGCGGCTCGGGGGTGCGTGCGTGTGTGTGCGTGGGGAGCGCCGCGTGCGGCTCC
GCGCTGCCCGGCGGCTGTGAGCGCTGCGGGCGCGGCGCGGGCTTTGTGCGCTCCGCAG
TGTGCGCGAGGGGAGCGCGGCCGGGGCGGTGCCCGCGGTGCGGGGGGGCTGCGAGG
GGAACAAAGGCTGCGTGCGGGGTGTGTGCGTGGGGGGTGAGCAGGGGTGTGGGCGCG
TCGGTCGGGCTGCAACCCCCCCTGCACCCCCCTCCCCGAGTTGCTGAGCACGGCCCGGC
TTCGGGTGCGGGGCTCCGTACGGGGCGTGGCGCGGGGCTCGCCGTGCCGGGCGGGGGGT
```

FIG. 12K

```
GGCGGCAGGTGGGGGTGCCGGGCGGGGCGGGGCCGCCTCGGGCCGGGGAGGGCTCGGGG
GAGGGGCGCGGCGGCCCCCGGAGCGCCGGCGGCTGTCGAGGCGCGGCGAGCCGCAGCCA
TTGCCTTTTATGGTAATCGTGCGAGAGGGCGCAGGGACTTCCTTTGTCCCAAATCTGTG
CGGAGCCGAAATCTGGGAGGCGCCGCCGCACCCCTCTAGCGGGCGCGGGGCGAAGCGG
TGCGGCGCCGGCAGGAAGGAAATGGGCGGGGAGGGCCTTCGTGCGTCGCCGCGCCGCCG
TCCCCTTCTCCCTCTCCAGCCTCGGGGCTGTCCGCGGGGGGACGGCTGCCTTCGGGGGG
GACGGGGCAGGGCGGGGTTCGGCTTCTGGCGTGTGACCGGCGGCTCTAGAGCCTCTGCT
AACCATGTTCATGCCTTCTTCTTTTTCCTACAGCTCCTGGGCAACGTGCTGGTTATTGT
GCTGTCTCATCATTTTGGCAAA
```

1.2.3 loxP-SV40pA x3-loxP

```
ATAACTTCGTATAATGTATGCTATACGAAGTTATTCGCGATGAATAAATGAAAGCTTGC
AGATCTGCGACTCTAGAGGATCTGCGACTCTAGAGGATCATAATCAGCCNTACCACATT
TTGTAGAGGTTTTACTNGCTTTAAAAAACCTCCCACACCTCCCCCTGAACCTGAAACAT
AAAATGAATGCAATTGTTGTTGTTAACTTGTTTATTGCAGCTTATAATGGTTACAAATA
AAGCAATAGCATCACAAATTTCACAAATAAAGCATTTTTTTCACTGCATTCTAGTTGTG
GTTTGTCCAAACTCATCAATGTATCTTATCATGTCTGGATCTGCGACTCTAGAGGATCA
TAATCAGCCATACCACATTTGTAGAGGTTTTACTTGCTTTAAAAAACCTCCCACACCTC
CCCCTGAACCTGAAACATAAAATGAATGCAATTGTTGTTGTTAACTTGTTTATTGCAGC
TTATAATGGTTACAAATAAAGCAATAGCATCACAAATTTCACAAATAAAGCATTTTTTT
CACTGCATTCTAGTTGTGGTTTGTCCAAACTCATCAATGTATCTTATCATGTCTGGATC
TGCGACTCTAGAGGATCATAATCAGCCATACCACATTTGTAGAGGTTTTACTTGCTTTA
AAAAACCTCCCACACCTCCCCCTGAACCTGAAACATAAAATGAATGCAATTGTTGTTGT
TAACTTGTTTATTGCAGCTTATAATGGTTACAAATAAAGCAATAGCATCACAAATTTCA
CAAATAAAGCATTTTTTTCACTGCATTCTAGTTGTGGTTTGTCCAAACTCATCAATGTA
TCTTATCATGTCTGGATCCCATCAAGCTGATCCGGAACCCTTAATATAACTTCGTATA
ATGTATGCTATACGAAGTTAT
```

1.2.4 3xFLAG

```
GACTATAAGGACCACGACGGAGACTACAAGGATCATGATATTGATTACAAAGACGATGA
CGATAAG
```

1.2.5 NLS

FIG. 12L

ATGGCCCCAAAGAAGAAGCGGAAGGTCGGTATCCACGGAGTCCCAGCAGCC 1.2.6 Cas9

GACAAGAAGTACAGCATCGGCCTGGACATCGGCACCAACTCTGTGGGCTGGGCCGTGAT
CACCGACGAGTACAAGGTGCCCAGCAAGAAATTCAAGGTGCTGGGCAACACCGACCGGC
ACAGCATCAAGAAGAACCTGATCGGAGCCCTGCTGTTCGACAGCGGCGAAACAGCCGAG
GCCACCCGGCTGAAGAGAACCGCCAGAAGAAGATACACCAGACGGAAGAACCGGATCTG
CTATCTGCAAGAGATCTTCAGCAACGAGATGGCCAAGGTGGACGACAGCTTCTTCCACA
GACTGGAAGAGTCCTTCCTGGTGGAAGAGGATAAGAAGCACGAGCGGCACCCCATCTTC
GGCAACATCGTGGACGAGGTGGCCTACCACGAGAAGTACCCCACCATCTACCACCTGAG
AAAGAAACTGGTGGACAGCACCGACAAGGCCGACCTGCGGCTGATCTATCTGGCCCTGG
CCCACATGATCAAGTTCCGGGGCCACTTCCTGATCGAGGGCGACCTGAACCCCGACAAC
AGCGACGTGGACAAGCTGTTCATCCAGCTGGTGCAGACCTACAACCAGCTGTTCGAGGA
AAACCCCATCAACGCCAGCGGCGTGGACGCCAAGGCCATCCTGTCTGCCAGACTGAGCA
AGAGCAGACGGCTGGAAAATCTGATCGCCCAGCTGCCCGGCGAGAAGAAGAATGGCCTG
TTCGGAAACCTGATTGCCCTGAGCCTGGGCCTGACCCCCAACTTCAAGAGCAACTTCGA
CCTGGCCGAGGATGCCAAACTGCAGCTGAGCAAGGACACCTACGACGACGACCTGGACA
ACCTGCTGGCCCAGATCGGCGACCAGTACGCCGACCTGTTTCTGGCCGCCAAGAACCTG
TCCGACGCCATCCTGCTGAGCGACATCCTGAGAGTGAACACCGAGATCACCAAGGCCCC
CCTGAGCGCCTCTATGATCAAGAGATACGACGAGCACCACCAGGACCTGACCCTGCTGA
AAGCTCTCGTGCGGCAGCAGCTGCCTGAGAAGTACAAAGAGATTTTCTTCGACCAGAGC
AAGAACGGCTACGCCGGCTACATTGACGGCGGAGCCAGCCAGGAAGAGTTCTACAAGTT
CATCAAGCCCATCCTGGAAAAGATGGACGGCACCGAGGAACTGCTCGTGAAGCTGAACA
GAGAGGACCTGCTGCGGAAGCAGCGGACCTTCGACAACGGCAGCATCCCCCACCAGATC
CACCTGGGAGAGCTGCACGCCATTCTGCGGCGGCAGGAAGATTTTTACCCATTCCTGAA
GGACAACCGGGAAAAGATCGAGAAGATCCTGACCTTCCGCATCCCCTACTACGTGGGCC
CTCTGGCCAGGGGAAACAGCAGATTCGCCTGGATGACCAGAAAGAGCGAGGAAACCATC
ACCCCCTGGAACTTCGAGGAAGTGGTGGACAAGGGCGCTTCCGCCCAGAGCTTCATCGA
GCGGATGACCAACTTCGATAAGAACCTGCCCAACGAGAAGGTGCTGCCCAAGCACAGCC
TGCTGTACGAGTACTTCACCGTGTATAACGAGCTGACCAAAGTGAAATACGTGACCGAG
GGAATGAGAAAGCCCGCCTTCCTGAGCGGCGAGCAGAAAAAGGCCATCGTGGACCTGCT
GTTCAAGACCAACCGGAAAGTGACCGTGAAGCAGCTGAAAGAGGACTACTTCAAGAAAA
TCGAGTGCTTCGACTCCGTGGAAATCTCCGGCGTGGAAGATCGGTTCAACGCCTCCCTG
GGCACATACCACGATCTGCTGAAAATTATCAAGGACAAGGACTTCCTGGACAATGAGGA
AAACGAGGACATTCTGGAAGATATCGTGCTGACCCTGACACTGTTTGAGGACAGAGAGA
TGATCGAGGAACGGCTGAAAACCTATGCCCACCTGTTCGACGACAAAGTGATGAAGCAG
CTGAAGCGGCGGAGATACACCGGCTGGGGCAGGCTGAGCCGGAAGCTGATCAACGGCAT
CCGGGACAAGCAGTCCGGCAAGACAATCCTGGATTTCCTGAAGTCCGACGGCTTCGCCA

FIG. 12M

```
ACAGAAACTTCATGCAGCTGATCCACGACGACAGCCTGACCTTTAAAGAGGACATCCAG
AAAGCCCAGGTGTCCGGCCAGGGCGATAGCCTGCACGAGCACATTGCCAATCTGGCCGG
CAGCCCCGCCATTAAGAAGGGCATCCTGCAGACAGTGAAGGTGGTGGACGAGCTCGTGA
AGTGATGGGCCGGCACAAGCCCGAGAACATCGTGATCGAAATGGCCAGAGAGAACCAG
ACCACCCAGAAGGGACAGAAGAACAGCCGCGAGAGAATGAAGCGGATCGAAGAGGGCAT
CAAAGAGCTGGGCAGCCAGATCCTGAAAGAACACCCCGTGGAAAACACCCAGCTGCAGA
ACGAGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTTCT
GAAGGACGACTCCATCGACAACAAGGTGCTGACCAGAAGCGACAAGAACCGGGCAAGA
GCGACAACGTGCCCTCCGAAGAGGTCGTGAAGAAGATGAAGAACTACTGGCGGCAGCTG
CTGAACGCCAAGCTGATTACCCAGAGAAAGTTCGACAATCTGACCAAGGCCGAGAGAGG
CGGCCTGAGCGAACTGGATAAGGCCGGCTTCATCAAGAGACAGCTGGTGGAAACCCGGC
AGATCACAAAGCACGTGGCACAGATCCTGGACTCCCGGATGAACACTAAGTACGACGAG
AATGACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACGCCC
ACGACGCCTACCTGAACGCCGTCGTGGGAACCGCCCTGATCAAAAAGTACCCTAAGCTG
GAAAGCGAGTTCGTGTACGGCGACTACAAGGTGTACGACGTGCGGAAGATGATCGCCAA
GAGCGAGCAGGAAATCGGCAAGGCTACCGCCAAGTACTTCTTCTACAGCAACATCATGA
ACTTTTTCAAGACCGAGATTACCCTGGCCAACGGCGAGATCCGGAAGCGGCCTCTGATC
GAGACAAACGGCGAAACCGGGGAGATCGTGTGGGATAAGGGCCGGGATTTTGCCACCGT
GCGGAAAGTGCTGAGCATGCCCCAAGTGAATATCGTGAAAAAGACCGAGGTGCAGACAG
GCGGCTTCAGCAAAGAGTCTATCCTGCCCAAGAGGAACAGCGATAAGCTGATCGCCAGA
AAGAAGGACTGGGACCCTAAGAAGTACGGCGGCTTCGACAGCCCCACCGTGGCCTATTC
TGTGCTGGTGGTGGCCAAAGTGGAAAAGGGCAAGTCCAAGAAACTGAAGAGTGTGAAAG
AGCTGCTGGGGATCACCATCATGGAAGAAGCAGCTTCGAGAAGAATCCCATCGACTTT
CTGGAAGCCAAGGGCTACAAGAAGTGAAAAAGGACCTGATCATCAAGCTGCCTAAGTA
CTCCCTGTTCGAGCTGGAAAACGGCCGGAAGAGAATGCTGGCCTCTGCCGGCGAACTGC
AGAAGGGAAACGAACTGGCCCTGCCCTCCAAATATGTGAACTTCCTGTACCTGGCCAGC
CACTATGAGAAGCTGAAGGGCTCCCCGAGGATAATGAGCAGAAACAGCTGTTTGTGGA
ACAGCACAAGCACTACCTGGACGAGATCATCGAGCAGATCAGCGAGTTCTCCAAGAGAG
TGATCCTGGCCGACGCTAATCTGGACAAAGTGCTGTCCGCCTACAACAAGCACCGGGAT
AAGCCCATCAGAGAGCAGGCCGAGAATATCATCCACCTGTTTACCCTGACCAATCTGGG
AGCCCCTGCCGCCTTCAAGTACTTTGACACCACCATCGACCGGAAGAGGTACACCAGCA
CCAAAGAGGTGCTGGACGCCACCCTGATCCACCAGAGCATCACCGGCCTGTACGAGACA
CGGATCGACCTGTCTCAGCTGGGAGGCGAC
```

1.2.7 NLS

```
AAAAGGCCGGCGGCCACGAAAAAGGCCGGCCAGGCAAAAAAGAAAAAG
```

FIG. 12N 1.2.8 P2A

GGAAGCGGAGCCACTAACTTCTCCCTGTTGAAACAAGCAGGGGATGTCGAAGAGAATCC
CGGGCCA 1.2.9 EGFP

GTGAGCAAGGGCGAGGAGCTGTTCACCGGGGTGGTGCCCATCCTGGTCGAGCTGGACGG
CGACGTAAACGGCCACAAGTTCAGCGTGTCCGGCGAGGGCGAGGGCGATGCCACCTACG
GCAAGCTGACCCTGAAGTTCATCTGCACCACCGGCAAGCTGCCCGTGCCCTGGCCCACC
CTCGTGACCACCCTGACCTACGGCGTGCAGTGCTTCAGCCGCTACCCCGACCACATGAA
GCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGA
AGAACGGCATCAAGGTGAACTTCAAGATCCGCCACAACATCGAGGACGGCAGCGTGCAG
CTCGCCGACCACTACCAGCAGAACACCCCCATCGGCGACGGCCCCGTGCTGCTGCCCGA
CAACCACTACCTGAGCACCCAGTCCGCCCTGAGCAAAGACCCCAACGAGAAGCGCGATC
ACATGGTCCTGCTGGAGTTCGTGACCGCCGCCGGGATCACTCTCGGCATGGACGAGCTG
TACAAG 1.2.10 WPRE

CGATAATCAACCTCTGGATTACAAAATTTGTGAAAGATTGACTGGTATTCTTAACTATG
TTGCTCCTTTTACGCTATGTGGATACGCTGCTTTAATGCCTTTGTATCATGCTATTGCT
TCCCGTATGGCTTTCATTTTCTCCTCCTTGTATAAATCCTGGTTGCTGTCTCTTTATGA
GGAGTTGTGGCCCGTTGTCAGGCAACGTGGCGTGGTGTGCACTGTGTTTGCTGACGCAA
CCCCCACTGGTTGGGGCATTGCCACCACCTGTCAGCTCCTTTCCGGGACTTTCGCTTTC
CCCCTCCCTATTGCCACGGCGGAACTCATCGCCGCCTGCCTTGCCCGCTGCTGGACAGG
GGCTCGGCTGTTGGGCACTGACAATTCCGTGGTGTTGTCGGGGAAATCATCGTCCTTTC
CTTGGCTGCTCGCCTGTGTTGCCACCTGGATTCTGCGCGGGACGTCCTTCTGCTACGTC
CCTTCGGCCCTCAATCCAGCGGACCTTCCTTCCCGCGGCCTGCTGCCGGCTCTGCGGCC
TCTTCCGCGTCTTCGCCTTCGCCCTCAGACGAGTCGGATCTCCCTTTGGGCCGCCTCCC
CGCATCG

FIG. 12O 1.2.11 bGHpolyA

```
CGACCTCGACCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGG
ACAGCAAGGGGGAGGATTGGGAAGACAATGGCAGGCATG
```

1.2.12 pPGK

```
AATTCTACCGGGTAGGGGAGGCGCTTTTCCCAAGGCAGTCTGGAGCATGCGCTTTAGCA
GCCCCGCTGGGCACTTGGCGCTACACAAGTGGCCTCTGGCCTCGCACACATTCCACATC
CACCGGTAGGCGCCAACCGGCTCCGTTCTTTGGTGGCCCCTTCGCGCCACCTTCTACTC
CTCCCCTAGTCAGGAAGTTCCCCCCGCCCCGCAGCTCGCGTCGTGCAGGACGTGACAA
ATGGAAGTAGCACGTCTCACTAGTCTCGTGCAGATGGACAGCACCGCTGAGCAATGGAA
GCGGGTAGGCCTTTGGGGCAGCGGCCAATAGCAGCTTTGCTCCTTCGCTTTCTGGGCTC
AGAGGCTGGGAAGGGGTGGGTCCGGGGCGGGCTCAGGGGCGGGCTCAGGGGCGGGGCG
GGCGCCCGAAGGTCCTCCGGAGGCCCGGCATTCTGCACGCTTCAAAAGCGCACGTCTGC
CGCGCTGTTCTCCTCTTCCTCATCTCCGGGCCTTTCGA
```

1.2.13 Neo

```
ATGGGATCGGCCATTGAACAAGATGGATTGCACGCAGGTTCTCCGGCCGCTTGGGTGGA
GAGGCTATTCGGCTATGACTGGGCACAACAGACAATCGGCTGCTCTGATGCCGCCGTGT
TCCGGCTGTCAGCGCAGGGGCGCCCGGTTCTTTTTGTCAAGACCGACCTGTCCGGTGCC
CTGAATGAACTGCAGGACGAGGCAGCGCGGCTATCGTGGCTGGCCACGACGGGCGTTCC
TTGCGCAGCTGTGCTCGACGTTGTCACTGAAGCGGGAAGGGACTGGCTGCTATTGGGCG
AAGTGCCGGGGCAGGATCTCCTGTCATCTCACCTTGCTCCTGCCGAGAAAGTATCCATC
ATGGCTGATGCAATGCGGCGGCTGCATACGCTTGATCCGGCTACCTGCCCATTCGACCA
CCAAGCGAAACATCGCATCGAGCGAGCACGTACTCGGATGGAAGCCGGTCTTGTCGATC
AGGATGATCTGGACGAAGAGCATCAGGGGCTCGCGCCAGCCGAACTGTTCGCCAGGCTC
AAGGCGCGCATGCCCGACGGCGATGATCTCGTCGTGACCCATGGCGATGCCTGCTTGCC
GAATATCATGGTGGAAAATGGCCGCTTTTCTGGATTCATCGACTGTGGCCGGCTGGGTG
TGGCGGACCGCTATCAGGACATAGCGTTGGCTACCCGTGATATTGCTGAAGAGCTTGGC
GGCGAATGGGCTGACCGCTTCCTCGTGCTTTACGGTATCGCCGCTCCCGATTCGCAGCG
CATCGCCTTCTATCGCCTTCTTGACGAGTTCTTCTGA
```

FIG. 12P 1.2.14 pGKpA

CTGTAAGTCTGCAGAAATTGATGATCTATTAAACAATAAAGATGTCCACTAAAATGGAA
GTTTTCCTGTCATACTTTGTTAAGAAGGGTGAGAACAGAGTACCTACATTTTGAATGG
AAGGATTGGAGCTACGGGGGTGGGGGTGGGGTGGGATTAGATAAATGCCTGCTCTTTAC
TGAAGGCTCTTTACTATTGCTTTATGATAATGTTTCATAGTTGGATATCATAATTTAAA
CAAGCAAAACCAAATTAAGGGCCAGCTCATTCCTCCCACTCATGATCTATAGATCTATA
GATCTCTCGTGGGATCATTGTTTTCTCTTGATTCCCACTTTGTGGTTCTAAGTACTGT
GGTTTCCAAATGTGTCAGTTTCATAGCCTGAAGAACGAGATCAGCAGCCTCTGTTCCAC
ATACACTTCATTCTCAGTATTGTTTTGCCAAGTTCTAATTCCATCAGAAAGC 1.2.15 Rosa26 long arm AGATGGGCGGGAGTCTTCTGGGCAGGCTTAAAGGCTAACCTGGTGTGTGGGCGTTGTCC
TGCAGGGGAATTGAACAGGTGTAAAATTGGAGGGACAAGACTTCCCACAGATTTTCGGT
TTTGTCGGGAAGTTTTTTAATAGGGGCAAATAAGGAAAATGGGAGGATAGGTAGTCATC
TGGGGTTTTATGCAGCAAAACTACAGGTTATTATTGCTTGTGATCCGCCTCGGAGTATT
TTCCATCGAGGTAGATTAAAGACATGCTCACCCGAGTTTTATACTCTCCTGCTTGAGAT
CCTTACTACAGTATGAAATTACAGTGTCGCGAGTTAGACTATGTAAGCAGAATTTTAAT
CATTTTTAAAGAGCCCAGTACTTCATATCCATTTCTCCCGCTCCTTCTGCAGCCTTATC
AAAAGGTATTTTAGAACACTCATTTTAGCCCCATTTTCATTTATTATACTGGCTTATCC
AACCCCTAGACAGAGCATTGGCATTTTCCCTTTCCTGATCTTAGAAGTCTGATGACTCA
TGAAACCAGACAGATTAGTTACATACACCACAAATCGAGGCTGTAGCTGGGGCCTCAAC
ACTGCAGTTCTTTTATAACTCCTTAGTACACTTTTTGTTGATCCTTTGCCTTGATCCTT
AATTTTCAGTGTCTATCACCTCTCCCGTCAGGTGGTGTTCCACATTTGGGCCTATTCTC
AGTCCAGGGAGTTTTACAACAATAGATGTATTGAGAATCCAACCTAAAGCTTAACTTTC
CACTCCCATGAATGCCTCTCTCCTTTTCTCCATTTATAAACTGAGCTATTAACCATTA
ATGGTTTCCAGGTGGATGTCTCCTCCCCAATATTACCTGATGTATCTTACATATTGCC
AGGCTGATATTTAAGACATTAAAAGGTATATTTCATTATTGAGCCACATGGTATTGAT
TACTGCTTACTAAAATTTTGTCATTGTACACATCTGTAAAGGTGGTTCCTTTTGGAAT
GCAAAGTTCAGGTGTTTGTTGTCTTTCCTGACCTAAGGTCTTGTGAGCTTGTATTTTTT
CTATTTAAGCAGTGCTTTCTCTTGGACTGGCTTGACTCATGGCATTCTACACGTTATTG
CTGGTCTAAATGTGATTTTGCCAAGCTTCTTCAGGACCTATAATTTTGCTTGACTTGTA
GCCAAACACAAGTAAAATGATTAAGCAACAAATGTATTTGTGAAGCTTGGTTTTTAGGT
TGTTGTGTTGTGTGTGCTTGTGCTCTATAATAATACTATCCAGGGGCTGGAGAGGTGGC
TCGGAGTTCAAGAGCACAGACTGCTCTTCCAGAAGTCCTGAGTTCAATTCCCAGCAACC
ACATGGTGGCTCACAACCATCTGTAATGGGATCTGATGCCCTCTTCTGGTGTGTCTGAA

FIG. 12Q

```
GACCACAAGTGTATTCACATTAAATAAATAAATCCTCCTTCTTCTTCTTTTTTTTTTT
TTAAAGAGAATACTGTCTCCAGTAGAATTTACTGAAGTAATGAAATACTTTGTGTTTGT
TCCAATATGGTAGCCAATAATCAAATTACTCTTTAAGCACTGGAAATGTTACCAAGGAA
CTAATTTTTATTTGAAGTGTAACTGTGGACAGAGGAGCCATAACTGCAGACTTGTGGA
TACAGAAGACCAATGCAGACTTTAATGTCTTTTCTCTTACACTAAGCAATAAGAAATA
AAAATTGAACTTCTAGTATCCTATTTGTTTAAACTGCTAGCTTTACTTAACTTTTGTGC
TTCATCTATACAAAGCTGAAAGCTAAGTCTGCAGCCATTACTAAACATGAAAGCAAGTA
ATGATAATTTTGGATTTCAAAAATGTAGGGCCAGAGTTTAGCCAGCCAGTGGTGGTGCT
TGCCTTTATGCCTTTAATCCAGCACTCTGGAGGCAGAGACAGGCAGATCTCTGAGTTT
GAGCCCAGCCTGGTCTACACATCAAGTTCTATCTAGGATAGCCAGGAATACACACAGAA
ACCCTGTTGGGGAGGGGGCTCTGAGATTTCATAAAATTATAATTGAAGCATTCCCTAA
TGAGCCACTATGGATGTGGCTAAATCCGTCTACCTTTCTGATGAGATTTGGGTATTATT
TTTTCTGTCTCTGCTGTTGGTTGGTCTTTTGACACTGTGGGCTTTCTTTAAAGCCTCC
TTCCTGCCATGTGGTCTCTTGTTTGCTACTAACTTCCCATGGCTTAAATGGCATGGCTT
TTTGCCTTCTAAGGGCAGCTGCTGAGATTTGCAGCCTGATTTCCAGGGTGGGGTTGGGA
AATCTTTCAAACACTAAAATTGTCCTTTAATTTTTTTTTAAAAAATGGGTTATATAAT
AAACCTCATAAAATAGTTATGAGGAGTGAGGTGGACTAATATTAAATGAGTCCCTCCCC
TATAAAGAGCTATTAAGGCTTTTTGTCTTATACTTAACTTTTTTTTAAATGTGGTAT
CTTTAGAACCAAGGGTCTTAGAGTTTTAGTATACAGAAACTGTTGCATCGCTTAATCAG
ATTTTCTAGTTTCAAATCCAGAGAATCCAAATTCTTCACAGCCAAAGTCAAATTAAGAA
TTTCTGACTTTTAATGTTAATTTGCTTACTGTGAATATAAAAATGATAGCTTTTCCTGA
GGCAGGGTCTCACTATGTATCTCTGCCTGATCTGCAACAAGATATGTAGACTAAAGTTC
TGCCTGCTTTTGTCTCCTGAATACTAAGGTTAAAATGTAGTAATACTTTGGAACTTGC
AGGTCAGATTCTTTTATAGGGGACACACTAAGGGAGCTTGGGTGATAGTTGGTAAATGT
GTTAAGTGATGAAAACTTGAATTATTATCACCGCAACCTACTTTTAAAAAAAAAGC
CAGGCCTGTTAGAGCATGCTTAAGGGATCCCTAGGACTTGCTGAGCACACAAGAGTAGT
TACTTGGCAGGCTCCTGGTGAGAGCATATTTCAAAAAACAAGGCAGACAACCAAGAAAC
TACAGTTAAGGTTACCTGTCTTTAAACCATCTGCATATACAGGGATATTAAAATATT
CCAAATAATATTTCATTCAAGTTTTCCCCATCAAATTGGGACATGGATTTCTCCGGTG
AATAGGCAGAGTTGGAAACTAAACAAATGTTGGTTTTGTGATTTGTGAAATTGTTTTCA
AGTGATAGTTAAAGCCCATGAGATACAGAACAAAGCTGCTATTCGAGGTCTCTTGGTT
TATACTCAGAAGCACTTCTTTGGGTTTCCCTGCACTATCCTGATCATGTGCTAGGCCTA
CCTTAGGCTGATTGTTGTTCAAATAAACTTAAGTTTCCTGTCAGGTGATGTCATATGAT
TTCATATATCAAGGCAAAACATGTTATATATGTTAAACATTTGTACTTAATGTGAAAGT
TAGGTCTTTGTGGGTTTGATTTTAATTTTCAAAACCTGAGCTAAATAAGTCATTTTTA
CATGTCTTACATTTGGTGGAATTGTATAATTGTGGTTTGCAGGCAAGACTCTCTGACCT
AGTAACCCTACCTATAGAGCACTTTGCTGGGTCACAAGTCTAGGAGTCAAGCATTTCAC
CTTGAAGTTGAGACGTTTTGTTAGTGTATACTAGTTTATATGTTGGAGGACATGTTTAT
CCAGAAGATATTCAGGACTATTTTGACTGGGCTAAGGAATTGATTCTGATTAGCACTG
TTAGTGAGCATTGAGTGGCCTTTAGGCTTGAATTGGAGTCACTTGTATATCTCAAATAA
TGCTGGCCTTTTTTAAAAGCCCTTGTTCTTTATCACCCTGTTTCTACATAATTTTTGT
```

FIG. 12R

```
TCAAAGAAATACTTGTTTGGATCTCCTTTTGACAACAATAGCATGTTTTCAAGCCATAT
TTTTTTTCCTTTTTTTTTTTTTTTTTTGGTTTTTCGAGACAGGGTTTCTCTGTATAGCCC
TGGCTGTCCTGGAACTCACTTTGTAGACCAGGCTGGCCTCGAACTCAGAAATCCGCCTG
CCTCTGCCTCCTGAGTGCCGGGATTAAAGGCGTGCACCACCACGCCTGGCTAAGTTGGA
TATTTGTTATATAACTATAACCAATACTAACTCCACTGGGTGGATTTTTAATTCAGTC
AGTAGTCTTAAGTGGTCTTTATTGGCCCTTCATTAAATCTACTGTTCACTCTAACAGA
GGCTGTTGGTACTAGTGGCACTTAAGCAACTTCTACGGATATACTAGCAGATTAAGGG
TCAGGGATAGAAACTAGTCTAGCGTTTTGTATACCTACCAGCTTTATACTACCTTGTTC
TGATAGAAATATTTCAGGACATCTAGCTT
```

1.2.16 pPGK

```
AATTCTACCGGGTAGGGGAGGCGCTTTTCCCAAGGCAGTCTGGAGCATGCGCTTTAGCA
GCCCCGCTGGGCACTTGGCGCTACACAAGTGGCCTCTGGCCTCGCACACATTCCACATC
CACCGGTAGGCGCCAACCGGCTCCGTTCTTTGGTGGCCCCTTCGCGCCACCTTCTACTC
CTCCCCTAGTCAGGAAGTTCCCCCCCGCCCCGCAGCTCGCGTCGTGCAGGACGTGACAA
ATGGAAGTAGCACGTCTCACTAGTCTCGTGCAGATGGACAGCACCGCTGAGCAATGGAA
GCGGGTAGGCCTTTGGGGCAGCGGCCAATAGCAGCTTTGCTCCTTCGCTTTCTGGGCTC
AGAGGCTGGGAAGGGGTGGGTCCGGGGGCGGGCTCAGGGGCGGGCTCAGGGGCGGGGCG
GGCGCCCGAAGGTCCTCCGGAGGCCCGGCATTCTGCACGCTTCAAAAGCGCACGTCTGC
CGCGCTGTTCTCCTCTTCCTCATCTCCGGGCCTTTCGA
```

1.2.17 DTA

```
ATGGATCCTGATGATGTTGTTGATTCTTCTAAATCTTTTGTGATGGAAAACTTTTCTTC
GTACCACGGGACTAAACCTGGTTATGTAGATTCCATTCAAAAGGTATACAAAGCCAA
AATCTGGTACACAAGGAAATTATGACGATGATTGGAAAGGGTTTTATAGTACCGACAAT
AAATACGACGCTGCGGGATACTCTGTAGATAATGAAAACCCGCTCTCTGGAAAAGCTGG
AGGCGTGGTCAAAGTGACGTATCCAGGACTGACGAAGGTTCTCGCACTAAAAGTGGATA
ATGCCGAAACTATTAAGAAAGAGTTAGGTTTAAGTCTCACTGAACCGTTGATGGAGCAA
GTCGGAACGGAAGAGTTTATCAAAAGGTTCGGTGATGGTGCTTCGCGTGTAGTGCTCAG
CCTTCCCTTCGCTGAGGGGAGTTCTAGCGTTAATATATTAATAACTGGGAACAGGCGA
AAGCGTTAAGCGTAGAACTTGAGATTAATTTTGAAACCCGTGGAAAACGTGGCCAAGAT
GCGATGTATGAGTATATGGCTCAAGCCTGTGCAGGAAATCGTGTCAGGCGATCTCTTTG
TGAAGGAACCTTACTTCTGTGGTGTGACATAATTGGACAAACTACCTACAGAGATTTAA
AGCTCTAA
```

FIG. 12S 1.2.18 pGKpA

CGACTGTGCCTTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGGGG
AGGATTGGGAAGACAATAGCAGGCATG 2.1 KPL vector CCTGCAGGCAGCTGCGCGCTCGCTCGCTCACTGAGGCCGCCCGGGCAAAGCCCGGGCGT
CGGGCGACCTTTGGTCGCCCGGCCTCAGTGAGCGAGCGAGCGCGCAGAGAGGGAGTGGC
CAACTCCATCACTAGGGGTTCCTGCGGCCGCACGCGTGAGGGCCTATTTCCCATGATTC
CTTCATATTTGCATATACGATACAAGGCTGTTAGAGAGATAATTGGAATTAATTTGACT
GTAAACACAAAGATATTAGTACAAAATACGTGACGTAGAAAGTAATAATTTCTTGGGTA
GTTTGCAGTTTTAAAATTATGTTTTAAAATGGACTATCATATGCTTACCGTAACTTGAA
AGTATTTCGATTTCTTGGCTTTATATATCTTGTGGAAAGGACGAAACACCGCAGCGTTA
CCTCTATCGTAGTTTTAGAGCTAGAAATAGCAAGTTAAAATAAGGCTAGTCCGTTATCA
ACTTGAAAAGTGGCACCGAGTCGGTGCTTTTTGGATCCGAGGGCCTATTTCCCATGA
TTCCTTCATATTTGCATATACGATACAAGGCTGTTAGAGAGATAATTGGAATTAATTTG
ACTGTAAACACAAAGATATTAGTACAAAATACGTGACGTAGAAAGTAATAATTTCTTGG
GTAGTTTGCAGTTTTAAAATTATGTTTTAAAATGGACTATCATATGCTTACCGTAACTT
GAAAGTATTTCGATTTCTTGGCTTTATATATCTTGTGGAAAGGACGAAACACCGTGTAA
TAGCTCCTGCATGGGTTTTAGAGCTAGAAATAGCAAGTTAAAATAAGGCTAGTCCGTTA
TCAACTTGAAAAGTGGCACCGAGTCGGTGCTTTTTTCTAGAAGAGGGCCTATTTCCC
ATGATTCCTTCATATTTGCATATACGATACAAGGCTGTTAGAGAGATAATTGGAATTAA
TTTGACTGTAAACACAAAGATATTAGTACAAAATACGTGACGTAGAAAGTAATAATTTC
TTGGGTAGTTTGCAGTTTTAAAATTATGTTTTAAAATGGACTATCATATGCTTACCGTA
ACTTGAAAGTATTTCGATTTCTTGGCTTTATATATCTTGTGGAAAGGACGAAACACCAC
TCCGAGACCTTATGCCGCGTTTTAGAGCTAGAAATAGCAAGTTAAAATAAGGCTAGTCC
GTTATCAACTTGAAAAGTGGCACCGAGTCGGTGCTTTTTGGTACCAGGTCTTGAAAG
GAGTGGGAATTGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGGGGT
AAACTGGGAAAGTGATGTCGTGTACTGGCTCCGCCTTTTCCCGAGGGTGGGGGAGAAC
CGTATATAAGTGCAGTAGTCGCCGTGAACGTTCTTTTCGCAACGGGTTTGCCGCCAGA
ACACAGGCGTACGGCCACCATGACTTCGAAAGTTTATGATCCAGAACAAAGGAAACGGA
TGATAACTGGTCCGCAGTGGTGGGCCAGATGTAAACAAATGAATGTTCTTGATTCATTT
ATTAATTATTATGATTCAGAAAACATGCAGAAATGCTGTTATTTTTTTACATGGTAA
CGCGGCCTCTTCTTATTTATGGCGACATGTTGTGCCACATATTGAGCCAGTAGCGCGGT

FIG. 12T

```
GTATTATACCAGACCTTATTGGTATGGGCAAATCAGGCAAATCTGGTAATGGTTCTTAT
AGGTTACTTGATCATTACAAATATCTTACTGCATGGTTTGAACTTCTTAATTTACCAAA
GAAGATCATTTTTGTCGGCCATGATTGGGGTGCTTGTTTGGCATTTCATTATAGCTATG
AGCATCAAGATAAGATCAAAGCAATAGTTCACGCTGAAAGTGTAGTAGATGTGATTGAA
TCATGGGATGAATGGCCTGATATTGAAGAAGATATTGCGTTGATCAAATCTGAAGAAGG
AGAAAAATGGTTTTGGAGAATAACTTCTTCGTGGAAACCATGTTGCCATCAAAAATCA
TGAGAAAGTTAGAACCAGAAGAATTTGCAGCATATCTTGAACCATTCAAAGAGAAAGGT
GAAGTTCGTCGTCCAACATTATCATGGCCTCGTGAAATCCCGTTAGTAAAGGTGGTAA
ACCTGACGTTGTACAAATTGTTAGGAATTATAATGCTTATCTACGTGCAAGTGATGATT
TACCAAAAATGTTTATTGAATCGGACCCAGGATTCTTTTCCAATGCTATTGTTGAAGGT
GCCAAGAAGTTTCCTAATACTGAATTTGTCAAAGTAAAAGGTCTTCATTTTTCGCAAGA
AGATGCACCTGATGAAATGGGAAAATATATCAAATCGTTCGTTGAGCGAGTTCTCAAAA
ATGAACAAGCTAGCGGAAGCGGAGCCACTAACTTCTCCCTGTTGAAACAAGCAGGGGAT
GTCGAAGAGAATCCCGGGCCACCCAAGAAGAAGAGGAAGGTGTCCAATCTCCTGACTGT
TCACCAGAACCTCCCTGCGCTGCCAGTAGATGCCACTAGCGATGAGGTCAGGAAAAATC
TCATGGATATGTTTAGGGATAGACAGGCGTTTTCTGAACACACCTGGAAAATGCTGCTT
AGCGTGTGCCGATCCTGGGCAGCCTGGTGTAAGCTGAACAATCGCAAATGGTTCCCCGC
CGAGCCGGAGGACGTGCGCGATTACCTGCTGTATCTCCAGGCAAGAGGGCTGGCTGTCA
AGACTATCCAGCAGCACTTGGGCCAACTGAATATGCTGCATCGACGCAGCGGGCTCCCC
CGGCCTAGCGATTCAAACGCAGTCTCCCTTGTTATGAGGAGAATTAGAAAGGAAAACGT
AGATGCGGGTGAGAGGGCTAAGCAGGCTCTCGCTTTTGAGCGGACTGATTTCGACCAGG
TCAGATCCCTGATGGAGAACAGCGATCGGTGCCAGGACATCAGGAACCTCGCATTTCTG
GGAATTGCATATAACACACTTCTGCGCATAGCTGAGATCGCCCGGATCAGAGTGAAAGA
CATCAGTCGAACGGACGGCGGCCGGATGCTTATTCATATTGGACGCACAAAGACATTGG
TCAGCACCGCTGGCGTTGAAAAGGCCTTGTCCCTGGGCGTAACGAAGCTGGTGGAAAGA
TGGATCTCAGTGTCCGGCGTGGCTGACGACCCTAATAATTACTTGTTCTGTCGAGTGAG
AAAAAACGGAGTCGCCGCGCCCTCTGCCACCAGCCAATTGAGTACACGGGCCCTTGAAG
GGATCTTTGAGGCAACCCACCGACTCATATACGGAGCCAAGGATGACAGTGGCCAGAGG
TATCTCGCCTGGTCAGGTCATTCTGCTAGGGTGGGGGCCGCACGAGACATGGCGCGGGC
AGGAGTCTCCATACCAGAGATTATGCAAGCTGGAGGTTGGACAAATGTGAACATCGTTA
TGAACTATATCCGCAATCTTGACTCTGAAACCGGGGCCATGGTGAGACTGCTCGAAGAT
GGTGACTACCCATACGATGTTCCAGATTACGCTTAAAGCGCTAATAAAGATCTTTATT
TTCATTAGATCTGTGTGTTGGTTTTTGTGTAAGCTTTGGCTCCAACACAGATGTTCTT
AGGCTACCTAACTTCTAACTTTTAATATCCAGTCAACAAGAATACCGCAAGGGTAGGT
GTTGGGATAGCTGTCGACAAGCTCATGCGGGTGTGTCCACAGGGTATAGCGTACTATGC
AGAATATTTGTACTGAGTGAAGTCATGATACATTCCTTTGAGAGCCATTAGCTGCTACA
AAACAGTAATCTGGCTGTTTAGATCAACAAGCTAAATGATAGAAGATGAAAGTACTGGT
TTCCATGTATTTTTATTAAGTGTTGATGAGAAAGTTGTAAGTGACTTACAGGTTACTCT
GTACATCTGTAGTCACTGAATTCGGAATATCTTAGAGTTTTACACACAAAGGTGAGTGT
TAAAATATTGATAAAGTTTTTGATAATCTTGTGTGAGACATGTTCTAATTTAGTTGTAT
TTTATTATTTTTATTGTAAGGCCTGCTGAAAATGACTGAGTATAAACTTGTGGTCGTGG
```

FIG. 12U

```
GCGCCGACGGCGTGGGCAAGAGCGCTTTGACGATACAGCTAATTCAGAATCACTTTGTG
GATGAGTATGATCCAACCATCGAGGTAACGCTGCTCTACAGTCTGCGTGCGCTTGTAAA
GGACGGCAGCCAGCCGCTTTGAAAAGATATCATTTTTATATTTATTAGAAAATTATAT
TGAAAGTTATTTCAGTTATATGTGATGTCCTTTAGTTCCAAGGCTTTAAACTGGGTGTT
AGGGAACCATAGGTGCAAGAAAGTCCACTTCTCATGAGAGCTCACCACAGAGAAAGAAA
GTCCACTTCTCAGGTAACCACGTGCGGACCGAGCGGCCGCAGGAACCCCTAGTGATGGA
GTTGGCCACTCCCTCTCTGCGCGCTCGCTCGCTCACTGAGGCCGGGCGACCAAAGGTCG
CCCGACGCCCGGGCTTTGCCCGGGCGGCCTCAGTGAGCGAGCGAGCGCGCAGCTGCCTG
CAGGTATTTTCTCCTTACGCATCTGTGCGGTATTTCACACCGCATACGTCAAAGCAACC
ATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGCTCCCTTTAGGGTT
CCGATTTAGTGCTTTACGGCACCTCGACCCCAAAAAACTTGATTTGGGTGATGGTTCAC
GTAGTGGGCCATCGCCCTGATAGACGGTTTTTCGCCCTTTGACGTTGGAGTCCACGTTC
TTTAATAGTGGACTCTTGTTCCAAACTGGAACAACACTCAACCCTATCTCGGCTATTC
TTTTGATTTATAAGGGATTTTGCCGATTTCGGCCTATTGGTTAAAAAATGAGCTGATTT
AACAAAATTTAACGCGAATTTTAACAAAATATTAACGTTTACAATTTTATGGTGCACT
CTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGA
CCGTCTCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGGTTTC
TTAGACGTCAGGTGGCACTTTTCGGGGAAATGTGCGCGGAACCCCTATTTGTTTATTTT
TCTAAATACATTCAAATATGTATCCGCTCATGAGACAATAACCCTGATAAATGCTTCAA
TAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAG
ATGCTGAAGATCAGTTGGGTGCACGAGTGGGTTACATCGAACTGGATCTCAACAGCGGT
AAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGATAACAC
TGCGGCCAACTTACTTCTGACAACGATCGGAGGACCGAAGGAGCTAACCGCTTTTTGC
ACAACATGGGGGATCATGTAACTCGCCTTGATCGTTGGGAACCGGAGCTGAATGAAGCC
ATACCAAACGACGAGCGTGACACCACGATGCCTGTAGCAATGGCAACAACGTTGCGCAA
ACTATTAACTGGCGAACTACTTACTCTAGCTTCCCGGCAACAATTAATAGACTGGATGG
AGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGG
ATGAACGAAATAGACAGATCGCTGAGATAGGTGCCTCACTGATTAAGCATTGGTAACTG
TCAGACCAAGTTTACTCATATATACTTTAGATTGATTTAAAACTTCATTTTTAATTTAA
AAGGATCTAGGTGAAGATCCTTTTTGATAATCTCATGACCAAAATCCCTTAACGTGAGT
TTTCGTTCCACTGAGCGTCAGACCCCGTAGAAAGATCAAAGGATCTTCTTGAGATCCT
```

FIG. 12V

```
TTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAG
CGCAGATACCAAATACTGTCCTTCTAGTGTAGCCGTAGTTAGGCCACCACTTCAAGAAC
TCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGC
AGCGGTCGGGCTGAACGGGGGGTTCGTGCACACAGCCCAGCTTGGAGCGAACGACCTAC
ACCGAACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAGGGAGC
TTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAA
CGCGGCCTTTTACGGTTCCTGGCCTTTGCTGGCCTTTGCTCACATGT
```

2.2 KPL vector elements 2.2.1 ITR

```
CCTGCAGGCAGCTGCGCGCTCGCTCGCTCACTGAGGCCGCCCGGGCAAAGCCCGGGCGT
CGGGCGACCTTTGGTCGCCCGGCCTCAGTGAGCGAGCGAGCGCGCAGAGAGGGAGTGGC
CAACTCCATCACTAGGGGTTCCT
```

2.2.2 U6

```
GAGGGCCTATTTCCCATGATTCCTTCATATTTGCATATACGATACAAGGCTGTTAGAGA
GATAATTGGAATTAATTTGACTGTAAACACAAAGATATTAGTACAAAATACGTGACGTA
GAAAGTAATAATTTCTTGGGTAGTTTGCAGTTTTAAAATTATGTTTTAAAATGGACTAT
CATATGCTTACCGTAACTTGAAAGTATTTCGATTTCTTGGCTTTATATCTTGTGGAA
AGGACGAAACACC
```

2.2.3 Kras-1

```
GCAGCGTTACCTCTATCGTA
```

2.2.4 sgRNA

FIG. 12W

GTTTTAGAGCTAGAAATAGCAAGTTAAAATAAGGCTAGTCCGTTATCAACTTGAAAAAG
TGGCACCGAGTCGGTGCTTTTTT 2.2.5 U6

GAGGGCCTATTTCCCATGATTCCTTCATATTTGCATATACGATACAAGGCTGTTAGAGA
GATAATTGGAATTAATTTGACTGTAAACACAAAGATATTAGTACAAAATACGTGACGTA
GAAAGTAATAATTTCTTGGGTAGTTTGCAGTTTTAAAATTATGTTTTAAAATGGACTAT
CATATGCTTACCGTAACTTGAAAGTATTTCGATTTCTTGGCTTTATATATCTTGTGGAA
AGGACGAAACACC 2.2.6 P53-8

GTGTAATAGCTCCTGCATGG 2.2.7 sgRNA

GTTTTAGAGCTAGAAATAGCAAGTTAAAATAAGGCTAGTCCGTTATCAACTTGAAAAAG
TGGCACCGAGTCGGTGCTTTTTT 2.2.8 U6

GAGGGCCTATTTCCCATGATTCCTTCATATTTGCATATACGATACAAGGCTGTTAGAGA
GATAATTGGAATTAATTTGACTGTAAACACAAAGATATTAGTACAAAATACGTGACGTA
GAAAGTAATAATTTCTTGGGTAGTTTGCAGTTTTAAAATTATGTTTTAAAATGGACTAT
CATATGCTTACCGTAACTTGAAAGTATTTCGATTTCTTGGCTTTATATATCTTGTGGAA
AGGACGAAACACC 2.2.9 Lkb1-1

FIG. 12X

ACTCCGAGACCTTATGCCGC 2.2.10 sgRNA

GTTTTAGAGCTAGAAATAGCAAGTTAAAATAAGGCTAGTCCGTTATCAACTTGAAAAAG
TGGCACCGAGTCGGTGCTTTTTT 2.2.11 EFs

AGGTCTTGAAAGGAGTGGGAATTGGCTCCGGTGCCCGTCAGTGGGCAGAGCGCACATCG
CCCACAGTCCCCGAGAAGTTGGGGGGAGGGGTCGGCAATTGAACCGGTGCCTAGAGAAG
GTGGCGCGGGGTAAACTGGGAAAGTGATGTCGTGTACTGGCTCCGCCTTTTCCCGAGG
GTGGGGGAGAACCGTATATAAGTGCAGTAGTCGCCGTGAACGTTCTTTTTCGCAACGGG
TTTGCCGCCAGAACACAGG 2.2.12 Rluc ATGACTTCGAAAGTTTATGATCCAGAACAAAGGAAACGGATGATAACTGGTCCGCAGTG
GTGGGCCAGATGTAAACAAATGAATGTTCTTGATTCATTTATTAATTATTATGATTCAG
AAAAACATGCAGAAAATGCTGTTATTTTTTACATGGTAACGCGGCCTCTTCTTATTTA
TGGCGACATGTTGTGCCACATATTGAGCCAGTAGCGCGGTGTATTATACCAGACCTTAT
TGGTATGGGCAAATCAGGCAAATCTGGTAATGGTTCTTATAGGTTACTTGATCATTACA
AATATCTTACTGCATGGTTTGAACTTCTTAATTTACCAAAGAAGATCATTTTTGTCGGC
CATGATTGGGGTGCTTGTTTGGCATTTCATTATAGCTATGAGCATCAAGATAAGATCAA
AGCAATAGTTCACGCTGAAAGTGTAGTAGATGTGATTGAATCATGGGATGAATGGCCTG
ATATTGAAGAAGATATTGCGTTGATCAAATCTGAAGAAGGAGAAAAAATGGTTTTGGAG
AATAACTTCTTCGTGGAAACCATGTTGCCATCAAAAATCATGAGAAAGTTAGAACCAGA
AGAATTTGCAGCATATCTTGAACCATTCAAAGAGAAGGTGAAGTTCGTCGTCCAACAT
TATCATGGCCTCGTGAAATCCCGTTAGTAAAAGGTGGTAAACCTGACGTTGTACAAATT
GTTAGGAATTATAATGCTTATCTACGTGCAAGTGATGATTACCAAAAATGTTTATTGA
ATCGGACCCAGGATTCTTTTCCAATGCTATTGTTGAAGGTGCCAAGAAGTTTCCTAATA
CTGAATTTGTCAAAGTAAAAGGTCTTCATTTTCGCAAGAAGATGCACCTGATGAAATG
GGAAAATATATCAAATCGTTCGTTGAGCGAGTTCTCAAAAATGAACAA

FIG. 12Y 2.2.13 P2A

GGAAGCGGAGCCACTAACTTCTCCCTGTTGAAACAAGCAGGGGATGTCGAAGAGAATCC
CGGGCCA 2.2.14 Cre

CCCAAGAAGAAGAGGAAGGTGTCCAATCTCCTGACTGTTCACCAGAACCTCCCTGCGCT
GCCAGTAGATGCCACTAGCGATGAGGTCAGGAAAAATCTCATGGATATGTTTAGGGATA
GACAGGCGTTTTCTGAACACACCTGGAAAATGCTGCTTAGCGTGTGCCGATCCTGGGCA
GCCTGGTGTAAGCTGAACAATCGCAAATGGTTCCCCGCCGAGCCGGAGGACGTGCGCGA
TTACCTGCTGTATCTCCAGGCAAGAGGGCTGGCTGTCAAGACTATCCAGCAGCACTTGG
GCCAACTGAATATGCTGCATCGACGCAGCGGGCTCCCCGGCCTAGCGATTCAAACGCA
GTCTCCCTTGTTATGAGGAGAATTAGAAAGGAAAACGTAGATGCGGGTGAGAGGGCTAA
GCAGGCTCTCGCTTTTGAGCGGACTGATTTCGACCAGGTCAGATCCCTGATGGAGAACA
GCGATCGGTGCCAGGACATCAGGAACCTCGCATTTCTGGGAATTGCATATAACACACTT
CTGCGCATAGCTGAGATCGCCCGGATCAGAGTGAAAGACATCAGTCGAACGGACGGCGG
CCGGATGCTTATTCATATTGGACGCACAAAGACATTGGTCAGCACCGCTGGCGTTGAAA
AGGCCTTGTCCCTGGGCGTAACGAAGCTGGTGGAAAGATGGATCTCAGTGTCCGGCGTG
GCTGACGACCCTAATAATTACTTGTTCTGTCGAGTGAGAAAAAACGGAGTCGCCGCGCC
CTCTGCCACCAGCCAATTGAGTACACGGGCCCTTGAAGGGATCTTTGAGGCAACCCACC
GACTCATATACGGAGCCAAGGATGACAGTGGCCAGAGGTATCTCGCCTGGTCAGGTCAT
TCTGCTAGGGTGGGGCCGCACGAGACATGGCGCGGGCAGGAGTCTCCATACCAGAGAT
TATGCAAGCTGGAGGTTGGACAAATGTGAACATCGTTATGAACTATATCCGCAATCTTG
ACTCTGAAACCGGGGCCATGGTGAGACTGCTCGAAGATGGTGAC 2.2.15 HA

TACCCATACGATGTTCCAGATTACGCT 2.2.16 polyA

AATAAAAGATCTTTATTTTCATTAGATCTGTGTGTTGGTTTTTTGTGT

FIG. 12Z 2.2.17 HDR donor

```
GGCTCCAACACAGATGTTCTTAGGCTACCTAACTTCTAACTTTTAATATCCAGTCAACA
AAGAATACCGCAAGGGTAGGTGTTGGGATAGCTGTCGACAAGCTCATGCGGGTGTGTCC
ACAGGGTATAGCGTACTATGCAGAATATTTGTACTGAGTGAAGTCATGATACATTCCTT
TGAGAGCCATTAGCTGCTACAAAACAGTAATCTGGCTGTTTAGATCAACAAGCTAAATG
ATAGAAGATGAAAGTACTGGTTTCCATGTATTTTATTAAGTGTTGATGAGAAAGTTGT
AAGTGACTTACAGGTTACTCTGTACATCTGTAGTCACTGAATTCGGAATATCTTAGAGT
TTTACACACAAAGGTGAGTGTTAAAATATTGATAAAGTTTTTGATAATCTTGTGTGAGA
CATGTTCTAATTTAGTTGTATTTATTATTTTTATTGTAAGGCCTGCTGAAAATGACTG
AGTATAAACTTGTGGTCGTGGGCGCCGACGGCGTGGGCAAGAGCGCTTTGACGATACAG
CTAATTCAGAATCACTTTGTGGATGAGTATGATCCAACCATCGAGGTAACGCTGCTCTA
CAGTCTGCGTGCGCTTGTAAAGGACGGCAGCCAGCCGCTTTGAAAAGATATCATTTTT
ATATTTATTAGAAAATTATATTGAAAGTTATTTCAGTTATATGTGATGTCCTTTAGTTC
CAAGGCTTTAAACTGGGTGTTAGGGAACCATAGGTGCAAGAAAGTCCACTTCTCATGAG
AGCTCACCACAGAGAAAGAAAGTCCACTTCTCA
```

2.2.18 ITR

```
AGGAACCCCTAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTCAGTGAGCGA
GCGAGCGCGCAGCTGCCTGCAGG
```

3.1 sgLacZ (KPL control) vector

```
CCTGCAGGCAGCTGCGCGCTCGCTCGCTCACTGAGGCCGCCCGGGCAAAGCCCGGGCGT
CGGGCGACCTTTGGTCGCCCGGCCTCAGTGAGCGAGCGAGCGCGCAGAGAGGGAGTGGC
CAACTCCATCACTAGGGGTTCCTGCGGCCGCACGCGTGAGGGCCTATTTCCCATGATTC
CTTCATATTTGCATATACGATACAAGGCTGTTAGAGAGATAATTGGAATTAATTTGACT
GTAAACACAAGATATTAGTACAAAATACGTGACGTAGAAAGTAATAATTTCTTGGGTA
GTTTGCAGTTTTAAAATTATGTTTTAAAATGGACTATCATATGCTTACCGTAACTTGAA
AGTATTTCGATTTCTTGGCTTTATATATCTTGTGGAAAGGACGAAACACCGTGCGAATA
CGCCCACGCGATGTTTTAGAGCTAGAAATAGCAAGTTAAAATAAGGCTAGTCCGTTATC
AACTTGAAAAAGTGGCACCGAGTCGGTGCTTTTTGGTACCAGGTCTTGAAGGAGTGG
GAATTGGCTCCGGTGCCCGTCAGTGGGCAGAGCGCACATCGCCCACAGTCCCCGAGAAG
TTGGGGGGAGGGGTCGGCAATTGAACCGGTGCCTAGAGAAGGTGGCGCGGGGTAAACTG
```

FIG. 12AA

GGAAAGTGATGTCGTGTACTGGCTCCGCCTTTTTCCCGAGGGTGGGGGAGAACCGTATA
TAAGTGCAGTAGTCGCCGTGAACGTTCTTTTTCGCAACGGGTTTGCCGCCAGAACACAG
GCGTACGGCCACCATGACTTCGAAAGTTTATGATCCAGAACAAAGGAAACGGATGATAA
CTGGTCCGCAGTGGTGGGCCAGATGTAAACAAATGAATGTTCTTGATTCATTTATTAAT
TATTATGATTCAGAAAACATGCAGAAATGCTGTTATTTTTTACATGGTAACGCGGC
CTCTTCTTATTTATGGCGACATGTTGTGCCACATATTGAGCCAGTAGCGCGGTGTATTA
TACCAGACCTTATTGGTATGGGCAAATCAGGCAAATCTGGTAATGGTTCTTATAGGTTA
CTTGATCATTACAAATATCTTACTGCATGGTTTGAACTTCTTAATTTACCAAAGAAGAT
CATTTTGTCGGCCATGATTGGGGTGCTTGTTTGGCATTTCATTATAGCTATGAGCATC
AAGATAAGATCAAAGCAATAGTTCACGCTGAAAGTGTAGTAGATGTGATTGAATCATGG
GATGAATGGCCTGATATTGAAGAAGATATTGCGTTGATCAAATCTGAAGAAGGAGAAAA
AATGGTTTTGGAGAATAACTTCTTCGTGGAAACCATGTTGCCATCAAAAATCATGAGAA
AGTTAGAACCAGAAGAATTTGCAGCATATCTTGAACCATTCAAAGAGAAAGGTGAAGTT
CGTCGTCCAACATTATCATGGCCTCGTGAAATCCCGTTAGTAAAAGGTGGTAAACCTGA
CGTTGTACAAATTGTTAGGAATTATAATGCTTATCTACGTGCAAGTGATGATTTACCAA
AAATGTTTATTGAATCGGACCCAGGATTCTTTTCCAATGCTATTGTTGAAGGTGCCAAG
AAGTTTCCTAATACTGAATTTGTCAAAGTAAAAGGTCTTCATTTTTCGCAAGAAGATGC
ACCTGATGAAATGGGAAAATATATCAAATCGTTCGTTGAGCGAGTTCTCAAAAATGAAC
AAGCTAGCGGAAGCGGAGCCACTAACTTCTCCCTGTTGAAACAAGCAGGGGATGTCGAA
GAGAATCCCGGGCCACCCAAGAAGAAGAGGAAGGTGTCCAATCTCCTGACTGTTCACCA
GAACCTCCCTGCGCTGCCAGTAGATGCCACTAGCGATGAGGTCAGGAAAAATCTCATGG
ATATGTTTAGGGATAGACAGGCGTTTTCTGAACACACCTGGAAAATGCTGCTTAGCGTG
TGCCGATCCTGGGCAGCCTGGTGTAAGCTGAACAATCGCAAATGGTTCCCCGCCGAGCC
GGAGGACGTGCGCGATTACCTGCTGTATCTCCAGGCAAGAGGGCTGGCTGTCAAGACTA
TCCAGCAGCACTTGGGCCAACTGAATATGCTGCATCGACGCAGCGGGCTCCCCCGGCCT
AGCGATTCAAACGCAGTCTCCCTTGTTATGAGGAGAATTAGAAAGGAAAACGTAGATGC
GGGTGAGAGGGCTAAGCAGGCTCTCGCTTTTGAGCGGACTGATTTCGACCAGGTCAGAT
CCCTGATGGAGAACAGCGATCGGTGCCAGGACATCAGGAACCTCGCATTTCTGGGAATT
GCATATAACACACTTCTGCGCATAGCTGAGATCGCCCGGATCAGAGTGAAAGACATCAG
TCGAACGGACGGCGGCCGGATGCTTATTCATATTGGACGCACAAAGACATTGGTCAGCA
CCGCTGGCGTTGAAAAGGCCTTGTCCCTGGGCGTAACGAAGCTGGTGGAAAGATGGATC
TCAGTGTCCGGCGTGGCTGACGACCCTAATAATTACTTGTTCTGTCGAGTGAGAAAAAA
CGGAGTCGCCGCGCCCTCTGCCACCAGCCAATTGAGTACACGGGCCCTTGAAGGGATCT
TTGAGGCAACCCACCGACTCATATACGGAGCCAAGGATGACAGTGGCCAGAGGTATCTC
GCCTGGTCAGGTCATTCTGCTAGGGTGGGGCCGCACGAGACATGGCGCGGGCAGGAGT
CTCCATACCAGAGATTATGCAAGCTGGAGGTTGGACAAATGTGAACATCGTTATGAACT
ATATCCGCAATCTTGACTCTGAAACCGGGGCCATGGTGAGACTGCTCGAAGATGGTGAC
TACCCATACGATGTTCCAGATTACGCTTAAAGCGCTAATAAAGATCTTTATTTTCATT
AGATCTGTGTGTTGGTTTTTTGTGTAAGCTTTGGCTCCAACACAGATGTTCTTAGGCTA
CCTAACTTCTAACTTTTAATATCCAGTCAACAAGAATACCGCAAGGGTAGGTGTTGGG
ATAGCTGTCGACAAGCTCATGCGGGTGTGTCCACAGGGTATAGCGTACTATGCAGAATA

FIG. 12AB

```
TTTGTACTGAGTGAAGTCATGATACATTCCTTTGAGAGCCATTAGCTGCTACAAAACAG
TAATCTGGCTGTTTAGATCAACAAGCTAAATGATAGAAGATGAAAGTACTGGTTTCCAT
GTATTTTATTAAGTGTTGATGAGAAAGTTGTAAGTGACTTACAGGTTACTCTGTACAT
CTGTAGTCACTGAATTCGGAATATCTTAGAGTTTTACACACAAAGGTGAGTGTTAAAAT
ATTGATAAAGTTTTTGATAATCTTGTGTGAGACATGTTCTAATTTAGTTGTATTTTATT
ATTTTATTGTAAGGCCTGCTGAAAATGACTGAGTATAAACTTGTGGTCGTGGGCGCCG
ACGGCGTGGGCAAGAGCGCTTTGACGATACAGCTAATTCAGAATCACTTTGTGGATGAG
TATGATCCAACCATCGAGGTAACGCTGCTCTACAGTCTGCGTGCGCTTGTAAAGGACGG
CAGCCAGCCGCTTTGAAAAGATATCATTTTTATATTTATTAGAAAATTATATTGAAAG
TTATTTCAGTTATATGTGATGTCCTTTAGTTCCAAGGCTTTAAACTGGGTGTTAGGGAA
CCATAGGTGCAAGAAAGTCCACTTCTCATGAGAGCTCACCACAGAGAAAGAAAGTCCAC
TTCTCAGGTAACCACGTGCGGACCGAGCGGCCGCAGGAACCCCTAGTGATGGAGTTGGC
CACTCCCTCTCTGCGCGCTCGCTCGCTCACTGAGGCCGGGCGACCAAAGGTCGCCCGAC
GCCCGGGCTTTGCCCGGGCGGCCTCAGTGAGCGAGCGAGCGCGCAGCTGCCTGCAGGTA
TTTTCTCCTTACGCATCTGTGCGGTATTTCACACCGCATACGTCAAAGCAACCATAGTA
CGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATT
TAGTGCTTTACGGCACCTCGACCCCAAAAAACTTGATTTGGGTGATGGTTCACGTAGTG
GGCCATCGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTCTTTTGA
TTTATAAGGGATTTTGCCGATTTCGGCCTATTGGTTAAAAAATGAGCTGATTTAACAAA
AATTTAACGCGAATTTTAACAAAATATTAACGTTTACAATTTTATGGTGCACTCTCAGT
ACAATCTGCTCTGATGCCGCATAGTTAAGCCAGCCCCGACACCCGCCAACACCCGCTGA
CGCGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGACGAAAG
GGCCTCGTGATACGCCTATTTTTATAGGTTAATGTCATGATAATAATGGTTTCTTAGAC
GTCAGGTGGCACTTTTCGGGGAAATGTGCGCGGAACCCCTATTTGTTTATTTTTCTAAA
TACATTCAAATATGTATCCGCTCATGAGACAATAACCCTGATAAATGCTTCAATAATAT
TGAAAAAGGAAGAGTATGAGTATTCAACATTTCCGTGTCGCCCTTATTCCCTTTTTTGC
GGCATTTTGCCTTCCTGTTTTTGCTCACCCAGAAACGCTGGTGAAAGTAAAAGATGCTG
AAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCT
ATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGAT
GGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTGCACAACA
TGGGGGATCATGTAACTCGCCTTGATCGTTGGGAACCGGAGCTGAATGAAGCCATACCA
AACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGG
ATAAAGTTGCAGGACCACTTCTGCGCTCGGCCCTTCCGGCTGGCTGGTTTATTGCTGAT
```

FIG. 12AC

```
AAATCTGGAGCCGGTGAGCGTGGGTCTCGCGGTATCATTGCAGCACTGGGGCCAGATGG
TAAGCCCTCCCGTATCGTAGTTATCTACACGACGGGGAGTCAGGCAACTATGGATGAAC
GAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGAT
CTAGGTGAAGATCCTTTTTGATAATCTCATGACCAAAATCCCTTAACGTGAGTTTTCGT
TCCACTGAGCGTCAGACCCCGTAGAAAAGATCAAAGGATCTTCTTGAGATCCTTTTTT
CTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGA
TACCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAGCAACGCGGC
CTTTTTACGGTTCCTGGCCTTTTGCTGGCCTTTTGCTCACATGT
```

3.2 sgLacZ (KPL control) vector elements 3.2.1 ITR

```
CCTGCAGGCAGCTGCGCGCTCGCTCGCTCACTGAGGCCGCCCGGGCAAAGCCCGGGCGT
CGGGCGACCTTTGGTCGCCCGGCCTCAGTGAGCGAGCGAGCGCGCAGAGAGGGAGTGGC
CAACTCCATCACTAGGGGTTCCT
```

3.2.2 U6

```
GAGGGCCTATTTCCCATGATTCCTTCATATTTGCATATACGATACAAGGCTGTTAGAGA
GATAATTGGAATTAATTTGACTGTAAACACAAAGATATTAGTACAAAATACGTGACGTA
GAAAGTAATAATTTCTTGGGTAGTTTGCAGTTTTAAAATTATGTTTTAAAATGGACTAT
CATATGCTTACCGTAACTTGAAAGTATTTCGATTTCTTGGCTTTATATATCTTGTGGAA
AGGACGAAACACC
```

FIG. 12AD 3.2.3 LacZ

TGCGAATACGCCCACGCGAT 3.2.4 sgRNA

GTTTTAGAGCTAGAAATAGCAAGTTAAAATAAGGCTAGTCCGTTATCAACTTGAAAAAG
TGGCACCGAGTCGGTGCTTTTTT 3.2.5 EFs

AGGTCTTGAAAGGAGTGGGAATTGGCTCCGGTGCCCGTCAGTGGGCAGAGCGCACATCG
CCCACAGTCCCCGAGAAGTTGGGGGGAGGGGTCGGCAATTGAACCGGTGCCTAGAGAAG
GTGGCGCGGGGTAAACTGGGAAAGTGATGTCGTGTACTGGCTCCGCCTTTTTCCCGAGG
GTGGGGGAGAACCGTATATAAGTGCAGTAGTCGCCGTGAACGTTCTTTTCGCAACGGG
TTTGCCGCCAGAACACAGG 3.2.6 Rluc ATGACTTCGAAAGTTTATGATCCAGAACAAAGGAAACGGATGATAACTGGTCCGCAGTG
GTGGGCCAGATGTAAACAAATGAATGTTCTTGATTCATTTATTAATTATTATGATTCAG
AAAAACATGCAGAAAATGCTGTTATTTTTTTACATGGTAACGCGGCCTCTTCTTATTTA
TGGCGACATGTTGTGCCACATATTGAGCCAGTAGCGCGGTGTATTATACCAGACCTTAT
TGGTATGGGCAAATCAGGCAAATCTGGTAATGGTTCTTATAGGTTACTTGATCATTACA
AATATCTTACTGCATGGTTTGAACTTCTTAATTTACCAAAGAAGATCATTTTGTCGGC
CATGATTGGGGTGCTTGTTTGGCATTTCATTATAGCTATGAGCATCAAGATAAGATCAA
AGCAATAGTTCACGCTGAAAGTGTAGTAGATGTGATTGAATCATGGGATGAATGGCCTG
ATATTGAAGAAGATATTGCGTTGATCAAATCTGAAGAAGGAGAAAAATGGTTTTGGAG
AATAACTTCTTCGTGGAAACCATGTTGCCATCAAAAATCATGAGAAGTTAGAACCAGA
AGAATTTGCAGCATATCTTGAACCATTCAAAGAGAAAGGTGAAGTTCGTCGTCCAACAT
TATCATGGCCTCGTGAAATCCCGTTAGTAAAAGGTGGTAAACCTGACGTTGTACAATT
GTTAGGAATTATAATGCTTATCTACGTGCAAGTGATGATTTACCAAAAATGTTTATTGA
ATCGGACCCAGGATTCTTTTCCAATGCTATTGTTGAAGGTGCCAAGAAGTTTCCTAATA
CTGAATTTGTCAAAGTAAAAGGTCTTCATTTTTCGCAAGAAGATGCACCTGATGAAATG
GGAAAATATATCAAATCGTTCGTTGAGCGAGTTCTCAAAAATGAACAA

FIG. 12AE 3.2.7 P2A

GGAAGCGGAGCCACTAACTTCTCCCTGTTGAAACAAGCAGGGGATGTCGAAGAGAATCC
CGGGCCA 3.2.8 Cre

CCCAAGAAGAAGAGGAAGGTGTCCAATCTCCTGACTGTTCACCAGAACCTCCCTGCGCT
GCCAGTAGATGCCACTAGCGATGAGGTCAGGAAAAATCTCATGGATATGTTTAGGGATA
GACAGGCGTTTTCTGAACACACCTGGAAAATGCTGCTTAGCGTGTGCCGATCCTGGGCA
GCCTGGTGTAAGCTGAACAATCGCAAATGGTTCCCCGCCGAGCCGGAGGACGTGCGCGA
TTACCTGCTGTATCTCCAGGCAAGAGGGCTGGCTGTCAAGACTATCCAGCAGCACTTGG
GCCAACTGAATATGCTGCATCGACGCAGCGGGCTCCCCGGCCTAGCGATTCAAACGCA
GTCTCCTTGTTATGAGGAGAATTAGAAAGGAAAACGTAGATGCGGGTGAGAGGGCTAA
GCAGGCTCTCGCTTTTGAGCGGACTGATTTCGACCAGGTCAGATCCCTGATGGAGAACA
GCGATCGGTGCCAGGACATCAGGAACCTCGCATTTCTGGGAATTGCATATAACACACTT
CTGCGCATAGCTGAGATCGCCCGGATCAGAGTGAAAGACATCAGTCGAACGGACGGCGG
CCGGATGCTTATTCATATTGGACGCACAAAGACATTGGTCAGCACCGCTGGCGTTGAAA
AGGCCTTGTCCCTGGGCGTAACGAAGCTGGTGGAAAGATGGATCTCAGTGTCCGGCGTG
GCTGACGACCCTAATAATTACTTGTTCTGTCGAGTGAGAAAAACGGAGTCGCCGCGCC
CTCTGCCACCAGCCAATTGAGTACACGGGCCCTTGAAGGGATCTTTGAGGCAACCCACC
GACTCATATACGGAGCCAAGGATGACAGTGGCCAGAGGTATCTCGCCTGGTCAGGTCAT
TCTGCTAGGGTGGGGGCCGCACGAGACATGGCGCGGGCAGGAGTCTCCATACCAGAGAT
TATGCAAGCTGGAGGTTGGACAAATGTGAACATCGTTATGAACTATATCCGCAATCTTG
ACTCTGAAACCGGGGCCATGGTGAGACTGCTCGAAGATGGTGAC 3.2.9 HA

TACCCATACGATGTTCCAGATTACGCT 3.2.10 polyA

AATAAAGATCTTTATTTTCATTAGATCTGTGTGTTGGTTTTTTGTGT

FIG. 12AF 3.2.11 HDR donor

```
GGCTCCAACACAGATGTTCTTAGGCTACCTAACTTCTAACTTTTAATATCCAGTCAACA
AAGAATACCGCAAGGGTAGGTGTTGGGATAGCTGTCGACAAGCTCATGCGGGTGTGTCC
ACAGGGTATAGCGTACTATGCAGAATATTTGTACTGAGTGAAGTCATGATACATTCCTT
TGAGAGCCATTAGCTGCTACAAAACAGTAATCTGGCTGTTTAGATCAACAAGCTAAATG
ATAGAAGATGAAAGTACTGGTTTCCATGTATTTTATTAAGTGTTGATGAGAAAGTTGT
AAGTGACTTACAGGTTACTCTGTACATCTGTAGTCACTGAATTCGGAATATCTTAGAGT
TTTACACACAAGGTGAGTGTTAAAATATTGATAAAGTTTTGATAATCTTGTGTGAGA
CATGTTCTAATTTAGTTGTATTTATTATTTTATTGTAAGGCCTGCTGAAAATGACTG
AGTATAAACTTGTGGTCGTGGGCGCCGACGGCGTGGGCAAGAGCGCTTTGACGATACAG
CTAATTCAGAATCACTTTGTGGATGAGTATGATCCAACCATCGAGGTAACGCTGCTCTA
CAGTCTGCGTGCGCTTGTAAAGGACGGCAGCCAGCCGCTTTGAAAAGATATCATTTTT
ATATTTATTAGAAAATTATATTGAAAGTTATTTCAGTTATATGTGATGTCCTTTAGTTC
CAAGGCTTTAAACTGGGTGTTAGGGAACCATAGGTGCAAGAAAGTCCACTTCTCATGAG
AGCTCACCACAGAGAAAGAAAGTCCACTTCTCA
```

3.2.12 ITR

```
AGGAACCCCTAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTCAGTGAGCGA
GCGAGCGCGCAGCTGCCTGCAGG
```

US 11,124,796 B2

DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO

RELATED APPLICATIONS AND/OR INCORPORATION BY REFERENCE

This application is a Continuation-in-Part of International Application Number PCT/US15/51446 filed on Sep. 22, 2015, which published as WO2016/049024 on Mar. 31, 2016 and claims benefit of and priority to U.S. provisional patent application Ser. No. 62/054,651, filed Sep. 24, 2014 and U.S. provisional patent application Ser. No. 62/067,886, filed Oct. 23, 2014.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant numbers MH100706, CA133404, CA151884, CA14051 and CA42063 awarded by the National Institutes of Health. The government has certain rights in the invention.

PARTIES TO A JOINT RESEARCH AGREEMENT

The claimed invention was made by, on behalf of, and/or in connection with one or more of the following parties to a joint research agreement: The Broad Institute, Inc., Massachusetts Institute of Technology, and President and Fellows of Harvard College. The joint research agreement was in effect on and before the date the claimed invention was made, and the claimed invention was made as a result of activities undertaken within the scope of the joint research agreement.

SEQUENCE LISTING

The instant application contains a Sequence Listing which has been submitted electronically in ASCII format and is hereby incorporated by reference in its entirety. Said ASCII copy, created Mar. 21, 2017 is named 47627992078 SL.txt and is 114,990 bytes in size.

FIELD OF THE INVENTION

The present invention generally relates to the Clustered Regularly Interspaced Short Palindromic Repeats (CRISPR)-Cas System and components thereof. More specifically, the present invention relates to modeling competition of multiple cancer mutations ex vivo and/or in vivo using a transgenic CRISPR-Cas9 animal (e.g., mouse) model, including the model(s) and methods for generation and uses thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications.

The genomes of cancer cells encompass complex combinations of genetic lesions (Weinberg 2007). A major challenge facing the continued study of cancer genetics is distinguishing which mutations are driving the tumor ("drivers") from those that are not ("passengers") (Garraway and Lander, 2013; Lawrence et al. 2013). The difficulty of elucidating these distinctions in animal models lies in precisely generating such mutation(s) and measuring the influence of specific mutations throughout tumor evolution. These challenges apply to other areas of genetic and tissue-specific biological studies as well.

Citation or identification of any document in this application is not an admission that such document is available as prior art to the present invention.

SUMMARY OF THE INVENTION

There exists a pressing need for alternative and robust systems and techniques for experimental modeling of cancer mutations, especially multiple mutations, in animals to enable the study of the effects of specific, multiple mutagenic events. Mutagenic events can include knock out events. Aspects of this invention may address this need and provide related advantages. Aspects of the present invention may address herein discussed challenges and need in the art by advantageously providing methods, systems, compositions and models for ex vivo and in vivo modeling of multiple genetic, e.g., cancer or tissue-specific mutations. Aspects of the invention provide methods for enabling rapid and direct in vivo and ex vivo modeling of the dynamics of multiple genetic, e.g., cancer or tissue-specific mutations. Aspects of the present invention involve sequence targeting, such as genome perturbation or induction of multiple mutations using the Clustered Regularly Interspaced Short Palindromic Repeats (CRISPR) system or components thereof. The invention provides systematic reverse engineering of causal genetic variations, including through selective perturbation of individual, and moreover, multiple genetic elements. For instance, in non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken, insect, arthropod or plant, e.g., dicot (e.g., nightshade such as tobacco, tuber such as potato) or monocot (e.g., corn) models that constitutively or through induction or through administration or delivery, have cells that contain Cas9. The invention provides tools for studying genetic interaction between multiple individual genetic elements by allowing selective perturbation of e.g., one or more cancer-associated or correlated gene(s)/genetic element(s). In an aspect, the invention provides methods for using one or more elements/components of a CRISPR-Cas system via a vector and/or particle and/or nanoparticle delivery formulation or system as a means to modify a target polynucleotide. In preferred embodiments, the delivery is via a viral vector (e.g., AAV, adenovirus, lentivirus). The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types in various tissues and organs, e.g., endothelial cells, skin, heart, muscle or lung. As such the CRISPR complex of the invention has a broad spectrum of applications in modeling of multiple genetic, e.g., cancer or tissue-specific mutations, and hence gene therapy, drug discovery, drug screening, disease diagnosis, and prognosis.

It will be appreciated that in the present methods, where the non-human transgenic Cas9 organism is multicellular, e.g., an animal or plant, the modification may occur ex vivo or in vitro, for instance in a cell culture and in some instances not in vivo. In other embodiments, it may occur in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise: A) I. RNA(s) having polynucleotide sequence(s), e.g., a CRISPR-Cas system chimeric RNA (chiRNA) having polynucleotide a sequence, wherein the polynucleotide sequence comprises: (a) a guide sequence capable of hybridizing to a target sequence in a eukaryotic cell, (b) a tracr mate sequence, and (c) a tracr sequence; wherein (a), (b) and (c) are arranged in a 5' to 3' orientation. The composition can also comprise A) II. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridizable to the target sequence, and (2) the tracr mate sequence that is hybridizable to the tracr sequence. The polynucleotide sequence encoding a CRISPR enzyme is DNA or RNA. When the Cas9 is already present in the cell, e.g., through the cell having already been provided (A) II. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (A) I. is provided as the CRISPR complex is formed in situ or in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise (B) I. polynucleotides comprising: (a) a guide sequence capable of hybridizing to a target sequence in a eukaryotic cell, and (b) at least one or more tracr mate sequences. The composition can also comprise (B) II. a polynucleotide sequence comprising a tracr sequence. The composition can also comprise (B) III. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence. The CRISPR complex comprises the CRISPR enzyme complexed with (1) the guide sequence that is hybridizable to the target sequence, and (2) the tracr mate sequence that is hybridizable to the tracr sequence, and the polynucleotide sequence encoding a CRISPR enzyme is DNA or RNA. When the Cas9 is already present in the cell, e.g., through the cell having already been provided (B) III. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (B) I. and (B) II. are provided as the CRISPR complex is formed in situ or in vivo. Accordingly, components I and II or I, II and III or the foregoing embodiments can be delivered separately; for instance, in embodiments involving components I, II and III, components I and II can be delivered together, while component II can be delivered separately, e.g., prior to components I and II, so that the cell or eukaryote expresses Cas9. It will be further appreciated that heretofore it could not be expected that multiple, specific mutations, especially in the numbers herein discussed, e.g., 3-50 or more, or 3, 16, 32, 48 or 50 or more, could be able to be achieved. In undertaking embodiments of the invention, the Applicants have indeed divined that such multiple mutations are present in significant numbers of cells of the non-human eukaryote. For instance, it was surprising and unexpected that cells and tumors of the non-human transgenic organisms of the invention could have multiple mutations of the delivered RNA(s) (sgRNAs); indeed, all of the multiple mutations.

In some embodiments the invention comprehends delivering a CRISPR enzyme comprising delivering to a cell mRNA encoding the CRISPR enzyme, e.g., via nanoparticle complex(es). In some of these methods the CRISPR enzyme is a Cas9. In certain preferred embodiments the Cas9 enzyme is constitutively present, e.g., through knock-in. Thus, in a preferred embodiment of the invention, the Cas9 enzyme is constitutively present in vivo (e.g, a non-human transgenic eukaryote, animal, mammal, primate, rodent, etc) or ex vivo (cells comprising a vector containing nucleic acid molecule(s) for in vivo expression of the Cas9). The CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence. The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme. Thus, the Cas9 may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the CRISPR enzyme or has a mutation as otherwise as discussed herein. In one aspect of the invention, the Cas9 enzyme may be fused to a protein, e.g., a TAG, and/or an inducible/controllable domain such as a chemically inducible/controllable domain. The Cas9 in the invention may be a chimeric Cas9 proteins; e.g., a Cas9 having enhanced function by being a chimera. Chimeric Cas9 proteins may be new Cas9 containing fragments from more than one naturally occurring Cas9. These may comprise fusions of N-terminal fragment(s) of one Cas9 homolog with C-terminal fragment(s) of another Cas9 homolog. The Cas9 can be delivered into the cell in the form of mRNA. The expression of Cas9 can be under the control of an inducible promoter.

The tracrRNA and direct repeat sequences can be mutant sequences or the invention can encompass RNA of the CRISPR-Cas system that includes mutant chimeric guide sequences that allow for enhancing performance of these RNAs in cells. A suitable promoter, such as the Pol III promoter, such as a U6 promoter, can be added onto the guide RNA that is advantageously delivered via AAV or particle or nanoparticle. Aspects of the invention also relate to the guide RNA being transcribed in vitro or ordered from a synthesis company and directly transfected. Expression of RNA(s), e.g., guide RNAs or sgRNA under the control of the T7 promoter driven by the expression of T7 polymerase in the cell is also envisioned. In an advantageous embodiment, the cell is a eukaryotic cell. In a preferred embodiment the eukaryotic cell is a human cell. In a more preferred embodiment the cell is a patient-specific cell, e.g., a cell in which 3-50 or more mutations associated or correlated with a patient's genetic disease, e.g., cancer, are expressed in the cell, e.g., via Cas9 being present in the cell and RNA(s) for such mutations delivered to the cell (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), whereby the CRISPR-Cas complexes result in the cells having the mutations and the cells and the eukaryote, e.g., animal, containing the cells being a model for the patient's genetic disease. In an advantageous embodiment, AAV may package U6 tandem sgRNA targeting up to about 50 genes.

A codon optimized sequence can be a sequence optimized for a eukaryote, or for specific organs such as the lung. It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding. It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). Applicants envisage, inter alia, a single cell or a population of cells and these may preferably be modified ex vivo and then re-introduced, e.g., transplanted to make transgenic organisms that express Cas9 in certain cells. The invention in some embodiments comprehends a method of modifying a eukaryote, such as a Cas9 transgenic eukaryote comprising delivering, e.g., via vector(s) and/or particle(s) and/or nanoparticles a non-naturally occurring or engineered composition. The composition comprises: I. a first regulatory element operably linked to (a) a first guide sequence capable of hybridizing to a first target sequence, and (b) at least one or more tracr mate sequences, II. a second regulatory element operably linked to (a) a second guide sequence capable of hybridizing to a second target sequence, and (b) at least one or more tracr mate sequences, III. a third regulatory element operably linked to (a) a third guide sequence capable of hybridizing to a third target sequence, and (b) at least one or more tracr mate sequences, and IV. a fourth regulatory element operably linked to a tracr sequence. There can be additional regulatory element(s) operably linked to additional guide sequence(s). Optionally, the composition can involve V. a fifth regulatory element operably linked to an enzyme-coding sequence encoding a CRISPR enzyme (e.g., for establishing the Cas9 transgenic eukaryote). Components I, II, III and IV (as well as any other regulatory element(s) linked to additional guide sequence(s)) are located on the same or different vectors and/or particles and/or nanoparticles of the system. When transcribed, the tracr mate sequence hybridizes to the tracr sequence and the first, second and the third guide sequences direct sequence-specific binding of a first, second and a third CRISPR complexes to the first, second and third target sequences respectively, wherein the first CRISPR complex comprises the CRISPR enzyme complexed with (1) the first guide sequence that is hybridizable to the first target sequence, and (2) the tracr mate sequence that is hybridizable to the tracr sequence, wherein the second CRISPR complex comprises the CRISPR enzyme complexed with (1) the second guide sequence that is hybridizable to the second target sequence, and (2) the tracr mate sequence that is hybridizable to the tracr sequence, and wherein the third CRISPR complex comprises the CRISPR enzyme complexed with (1) the third guide sequence that is hybridizable to the third target sequence, and (2) the tracr mate sequence that is hybridizable to the tracr sequence, whereby in a Cas9 transgenic eukaryote or cell thereof, at least three (3) mutations may be induced, and advantageously the mutations are correlated or associated with a genetic disease condition, whereby the eukaryote or cell becomes a model of the disease, e.g., cancer. The invention also provides a vector system as described herein. The system may comprise one, two, three or four different vectors; and the system may comprise one, two, three or four different nanoparticle complex(es) delivering the component(s) of the system. Components I, II, III and IV may thus be located on one, two, three or four different vectors, and may be delivered by one, two, three or four different particle or nanoparticle complex(es) or AAVs or components I, II, III and IV can be located on same or different vector(s)/particle(s)/nanoparticle(s), with all combinations of locations envisaged. And complexes that target lung or lung tissue or cells are advantageous.

In some methods of the invention any or all of the polynucleotide sequence encoding the CRISPR enzyme, the first and the second guide sequence, the first and the second tracr mate sequence or the first and the second tracr sequence, is/are RNA; and advantageously delivered via nanoparticle complex(es). Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell or a human cell. The invention also comprehends an engineered, non-naturally occurring vector system. The system comprises one or more vectors comprising: (a) a first regulatory element operably linked to each of two or more e.g., three, CRISPR-Cas system guide RNAs that target a first target sequence, a second target sequence and a third target sequence respectively of a double stranded DNA molecule, wherein either strand of the double stranded DNA molecule may be targeted by each CRISPR-Cas system guide RNA. The system can also comprise (b) a second regulatory element operably linked to a Cas protein. Components (a) and (b) are located on same or different vectors of the system, but advantageously separate vectors as it is preferred that cells receiving (a) contain Cas9, e.g., via the cells being those of a transgenic Cas9 eukaryote (whereby (b) may have been administered to cells that gave rise to the eukaryote). The guide RNAs target DNA and at least three mutations are induced in the cells, e.g., mutations correlated to or associated with a genetic disorder such as cancer.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence; and advantageously the complex or a component thereof has been delivered via nanoparticle complex(es). In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. The mutation can be a mutation correlated to or associated with a genetic disease condition, such as cancer. In some embodiments, said mutation results in one or more amino acid changes in a protein expressed from a gene comprising the target sequence. In some embodiments, vectors are delivered to the eukaryotic cell in a transgenic Cas9 eukaryote. In some embodiments, said modifying takes place in said eukaryotic cell in a cell culture. In one aspect, the invention provides a method of generating a model eukaryotic cell or a model Cas9 transgenic eukaryote comprising mutated disease gene(s), e.g., having 3-50 mutations correlated to or associated with a genetic disease such as cancer (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector). In some embodiments, a disease gene is any gene associated with an increase in the risk of having or developing a disease.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In certain embodiments, the target sequence is flanked or followed, at its 3' end, by a PAM suitable for the CRISPR enzyme, typically a Cas and in particular a Cas9. For example, a suitable PAM is 5'-NRG or 5'-NNGRR for SpCas9 or SaCas9 enzymes (or derived enzymes), respectively.

Delivery can be in the form of a vector which may be a plasmid or other nucleic acid molecule form, especially when the delivery is via a nanoparticle complex; and the vector also can be viral vector, such as a herpes, e.g., herpes simplex virus, lenti- or baculo- or adeno-viral or adeno-associated viral vectors, but other means of delivery are known (such as yeast systems, microvesicles, gene guns/means of attaching vectors to gold nanoparticles) and are provided, especially as to those aspects of the complex not delivered via a nanoparticle complex. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell; and advantageously the complex or a component thereof is delivered via nanoparticle complex(es). Also envisaged is a method of delivering the present CRISPR enzyme comprising delivering to a cell mRNA encoding the CRISPR enzyme; and advantageously the complex or a component thereof has been delivered via nanoparticle complex(es). It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. When not delivering via a nanoparticle complex, AAV is a preferred vector. In certain embodiments, multiple RNA(s) or guide RNAs or sgRNAs formulated in one or more delivery vehicles (e.g., where some guide RNAs are provided in a vector and others are formulated in nanoparticles); and these may be provided alone (e.g., when Cas9 is already in a cell) or with a Cas9 delivery system. In certain embodiments, the Cas9 is also delivered in a nanoparticle formulation. In certain instances the RNA(s) or guide RNA or sgRNA-vector and/or particle and/or nanoparticle formulation(s) and the Cas9 vector and/or particle and/or nanoparticle formulation(s) may be delivered separately or may be delivered substantially contemporaneously (i.e., co-delivery). Sequential delivery could be done at separate points in time, separated by days, weeks or even months. And as Cas9 is advantageously present in a transgenic organism in the practice of the invention, e.g., through being constitutively or conditionally or inducibly present, sequential delivery can include initially administering or delivering the Cas9 vector and/or particle and/or nanoparticle formulation(s) to cells that give rise to the non-human Cas9 transgenic eukaryote, and thereafter, at a suitable time in the life of the transgenic eukaryote, administering the RNA(s) or guide RNA or sgRNA-vector and/or particle and/or nanoparticle formulation(s), e.g., so as to give rise to one or more, advantageously 3-50 mutations in the transgenic eukaryote (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), and advantageously the mutations are associated or correlated with a genetic disease, whereby the transgenic eukaryote is a model of the genetic disease, e.g., cancer. Multiple mutations may thus be introduced using any number of sgRNAs, e.g. the vector may comprise at least 3 sgRNAs, at least 8 sgRNAs, at least 16 sgRNAs, at least 32 sgRNAs, at least 48 sgRNAs, or at least 50 sgRNAs. Alternatively, the vector may comprise 1-2 sgRNAs, 1-3 sgRNAs, 1-4 sgRNAs, 1-5 sgRNAs, 3-6 sgRNAs, 3-7 sgRNAs, 3-8 sgRNAs, 3-9 sgRNAs, 3-10 sgRNAs, 3-16 sgRNAs, 3-30 sgRNAs, 3-32 sgRNAs, 3-48 sgRNAs or 3-50 sgRNAs. In certain embodiments, vector (e.g., AAV, adenovirus, lentivirus) and/or particle and/or nanoparticle formulations comprising one or more RNA(s) e.g. guide RNAs or sgRNA are adapted for delivery in vitro, ex vivo or in vivo in the context of the CRISPR-Cas system, e.g., so as to form CRISPR-Cas complexes in vitro, ex vivo or in vivo, to different target genes, different target cells or different target different tissues/organs, with different target genes and/or cells of the lung. Multiplexed gene targeting using nanoparticle formulations comprising one or more guide RNAs are also envisioned. In an embodiment, a nanoparticle formulation comprising one or more components of the CRISPR-Cas system is provided. In an embodiment, a RNA(s) or gRNA or sgRNA-nanoparticle formulation comprising one or more guide RNAs or sgRNA is provided. In certain embodiments, a composition comprising a nanoparticle formulation comprising one or more components of the CRISPR-Cas system is provided. In certain embodiments, a composition, e.g., a pharmaceutical or veterinary composition, comprising a vector (e.g., AAV, adenovirus, lentivirus) and/or particle and/or nanoparticle formulation comprising one or more components of the CRISPR-Cas system and/or nucleic acid molecule(s) coding therefor, advantageously with such nucleic acid molecule(s) operably linked to promoter(s) is provided. Accordingly, in certain embodiments, it may be useful to deliver the RNA(s) or guide RNA or sgRNA, e.g., vector and/or particle and/or nanoparticle formulations separately from the Cas9 or nucleic acid molecule(s) coding therefor. A dual-delivery system is envisaged such that the Cas 9 may be delivered via a vector and the RNA(s), e.g., guide RNAs or sgRNA are/is provided in a particle or nanoparticle formulation, for example, first Cas9 vector is delivered via a vector system followed by delivery of sgRNA-nanoparticle formulation. Vectors may be considered in the broadest light as simply any means of delivery, rather than specifically viral vectors.

In one aspect, the present invention provides a Cas9 transgenic eukaryote, e.g., mouse. In certain preferred embodiments, the Cas 9 transgenic eukaryote, e.g., mouse comprises a Cas9 transgene knocked into the Rosa26 locus. In one aspect, the present invention provides a Cas9 transgenic eukaryote, e.g., mouse wherein Cas9 transgene is driven by the ubiquitous CAG promoter thereby providing for constitutive expression of Cas9 in all tissues/cells/cell types of the mouse. In one aspect, the present invention provides a Cas9 transgenic eukaryote, e.g., mouse wherein the Cas9 transgene driven by the ubiquitous CAG promoter further comprises a Lox-Stop-polyA-Lox (LSL) cassette (Rosa26-LSL-Cas9 mouse) thereby rendering Cas9 expression inducible by the Cre recombinase. In one aspect, the present invention provides a constitutive Cas9 expressing eukaryote, e.g., mouse line obtained by crossing of the Rosa26-LSL-Cas9 mouse with a beta-actin-Cre eukaryote, e.g., mouse line. In certain embodiments, progeny (or progenies) derived from said Cas9 expressing eukaryote, e.g., mouse line, may be successfully bred over at least five generations without exhibiting increased levels of genome instability or cellular toxicity. In one aspect, the present invention provides a modular viral vector construct comprising a plurality of sgRNAs driven by a single RNA polymerase III promoter (e.g., U6), wherein the sgRNAs are in tandem, or where each of the sgRNAs is driven by one RNA polymerase III promoter. In one aspect, the present invention provides a modular viral vector construct comprising one or more cassettes expressing Cre recombinase, a plurality of sgRNAs to guide Cas9 cutting, and optionally including a Homology Directed Repair (HDR) template to model the dynamics of a complex pathological disease or disorder involving two or more genetic elements simultaneously using a single vector construct (in embodiments where the HDR template is not involved, the cutting creates the mutation to model the dynamics of a complex pathological disease or disorder (e.g., loss of function or gain of function). In certain non-limiting embodiments, the complex pathological disease or disorder is cancer. It can be appreciated that any kind of cancer of any tissue type are within the scope of the present invention. In a preferred embodiment, the present invention provides for modeling of lung cancer. In one aspect, the present invention provides a modular viral vector construct to model the dynamics of multiple cancer lesions simultaneously using a single vector. In certain embodiments, the modular viral vector construct comprises one or more cassettes expressing Cre recombinase, a plurality of sgRNAs to guide Cas9 cutting, and optionally one or more Homology Directed Repair (HDR) template(s) to introduce specific gain-of-function mutations or precise sequence substitution in target loci. In one aspect, the present invention provides a method for simultaneously introducing multiple mutations ex vivo in a tissue, organ or a cell line, or in vivo in the same animal comprising delivering a single viral vector construct, wherein the viral vector construct comprises one or more cassettes expressing Cre recombinase, a plurality of sgRNAs to guide Cas9 cutting, and optionally HDR template(s) for achieving targeted insertion or precise sequence substitution at specific target loci of interest. In one aspect, the present invention provides a method for generating loss-of-function mutations in two or more tumor suppressor genes and gain-of-function mutations in one or more proto-oncogenes using a modular viral vector construct which comprises one or more cassettes expressing Cre recombinase, a plurality of sgRNAs to guide Cas9 cutting, and optionally one or more HDR template(s). In certain non-limiting embodiments, tumor suppressor genes may include p53 and Lkb1 (serine/threonine kinase 11). In certain non-limiting embodiments, the proto-oncogene may include Kras. Heretofore, it had not been expected that multiple mutations wherein some mutations are loss of function (knock out) and some mutations are gain of function (knock in) could be achieved; and it had not been expected to achieve mutations in p53, Lkb1 and Kras and nor had there heretofore been any direction to select these particular genes for being mutated together. It can be readily appreciated that mutations in any cancer-associated gene is within the scope of the present invention. In one aspect, the present invention provides a method for delivering ex vivo or in vivo of any of the modular viral constructs disclosed herein using an AAV. Selection of the AAV serotype is based on its suitability and specificity for a tissue type. In certain preferred embodiments, AAV9 is used for delivery to lung tissue. In one aspect, the present invention provides a method for ex vivo and/or in vivo genome editing comprising delivering any of the above modular viral vector constructs, which comprise one or more cassettes expressing Cre recombinase, a plurality of sgRNAs to guide Cas9 cutting, and optionally one or more HDR template(s), into a Cas9 transgenic mouse (e.g., Rosa26-LSL-Cas9). In certain embodiments, the viral vector is AAV9. In one aspect, the present invention provides a Cas9 transgenic non-human eukaryote, e.g., animal model for lung cancer said model having loss-of-function mutations in p53 and/or Lkb1 and gain-of-function mutation in Kras. It can be appreciated that using the novel CRISPR-Cas9 tools disclosed herein, Cas9 transgenic non-human eukaryote, e.g., animal model with multiple mutations in any number of loci can be envisioned and are within the scope of the present invention. It will be appreciated that such a transgenic non-human eukaryote, e.g., animal model provides a valuable tool for research purposes, e.g., to delineate specific roles/contribution of individual mutations to cancer progression, to recapitulate specific combinations of mutations in a given cancer type, and opens the door for developing and testing new therapeutic interventions for cancers involving mutations at multiple loci. Such uses are within the scope of the present invention. In one aspect, the present invention provides a method of treating or inhibiting the development of a genetic disease in a subject in need thereof, comprising providing individualized or personalized treatment (or an individualized or personalized model or patient specific-modeling) comprising: delivering RNA(s), e.g., sgRNA, that targets a genetic locus correlated or associated with the genetic disease, e.g., cancer, to a Cas9 non-human transgenic eukaryote (e.g., animal, mammal, primate, rodent, fish etc as herein discussed), e.g., via vector such as AAV, adenovirus, lentivirus, or particle(s) or nanoparticle(s), whereby mutation(s), advantageously a plurality, e.g., 3-50 mutations (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), are induced in the eukaryote and the eukaryote is a model for the disease; and obtaining and/or extrapolating data from the Cas9 non-human transgenic eukaryote to humans to provide individualized or personalized treatment. The obtaining and/or extrapolating data can be subjecting the eukaryote to putative treatment(s) and/or therapy(ies), e.g., gene therapy, ascertaining whether such putative treatment(s) and/or therapy(ies) give rise to remission or treatment or alleviation or mitigation or stasis of the disease, and if so, then administering in dosing scaled to a 70 kg individual or subject, the putative treatment(s) and/or therapy(ies). The invention thus allows for one to ascertain whether a particular treatment and/or therapy may be effective as to a particular individual's disease.

In certain aspects the invention provides vector(s), particle(s) or nanoparticle(s) containing nucleic acid molecule(s), whereby in vivo in a eukaryotic cell containing or conditionally or inducibly expressing Cas9: the vector(s) express(es) a plurality of RNAs to guide the Cas9 and optionally delivers donor templates (e.g., HDR templates, and in certain embodiments advantageously includes and delivers such donor templates), and optionally in the event Cas9 is conditionally or inducibly expressed in the cell that which induces Cas9, e.g., Cre recombinase; whereby a plurality of specific mutations or precise sequence substitutions in a plurality of target loci are introduced. The vector(s) can be a viral vector such as lentivirus, adenovirus, or adeno-associated virus (AAV), e.g., AAV6 or AAV9. The Cas9 can be from S. thermophiles, *S. aureus*, or *S. pyogenes*. The eukaryotic cell can comprise a Cas9 transgene is functionally linked to a constitutive promoter, or a tissue specific promoter, or an inducible promoter; and, the eukaryotic cell can be part of a non-human transgenic eukaryote, e.g., a non-human mammal, primate, rodent, mouse, rat, rabbit, canine, dog, cow, bovine, sheep, ovine, goat, pig, fowl, poultry, chicken, fish, insect or arthropod; advantageously a mouse. The isolated eukaryotic cell or the non-human transgenic eukaryote can express an additional protein or enzyme, such as Cre; and, the expression of Cre can be driven by coding therefor functionally or operatively linked to a constitutive promoter, or a tissue specific promoter, or an inducible promoter.

The RNAs to guide Cas9 can comprise CRISPR RNA and transactivating (tracr) RNA. The tracr mate and the tracr sequence can be connected to form a transactivating (tracer) sequence. The tracr mate and the tracr sequence can optionally be designed to form a single guide RNA (sgRNA). Indeed, it is advantageous that the RNAs to guide Cas9 can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

The vector(s) can include the regulatory element(s), e.g., promoter(s). The vector(s) can comprise at least 3 or 8 or 16 or 32 or 48 or 50 RNA(s) (e.g., sgRNAs), such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53. short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The RNA(s), e.g., sgRNA(s), can be functionally or operatively linked to regulatory element(s) and hence the regulatory element(s) drive expression. The promoter(s) can be constitutive promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter U6.

Advantageously, each RNA (e.g., sgRNA) is specific to a different target sequence. Each different target sequence can be associated with or correlated to a form of cancer. Each RNA or sgRNA can be specific to a different target sequence but these RNA(s) or sgRNA(s) target specific gene sequences associated with or correlated to cancer, advantageously a particular type or form of cancer; for instance each RNA or sgRNA can be specific to a different target sequence but the target sequences of the RNA(s) or sgRNA(s) are associated with or correlated to the same type or form of cancer. The cancer selected from the group consisting of Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, and Urinary bladder cancer.

Advantageously, each sgRNA can be driven by an independent U6 promoter. The vector can be an AAV, e.g., an AAV9. Each of the sgRNAs can target a different genetic locus associated with a multigenic disease or disorder, e.g., a cancer, such as lung cancer. The sgRNAs can target one or more tumor suppressor genes so as to introduce loss-of-function mutations. The tumor suppressor genes can be p53 and/or Lkb1. The sgRNAs can target one or more proto-oncogenes or oncogenes so as to introduce a loss-of-function mutation. The proto-oncogenes or oncogenes can be Kras. The sgRNAs can target one or more of p53, Lkb1, or Kras loci. From 3 to 50 specific mutations or precise sequence substitutions in from 3 to 50 target loci can be introduced.

More generally, the sgRNAs can target one or more, e.g., 3 to 50 loci specific to a cancer, such as:

one or more loci specific to lung cancer such as one or more of Kras, p53, and Lkb1 specific to lung cancer (e.g., Kras, p53, and Lkb1 separately or in combination, wherein each is specific to lung cancer) or one or more, e.g., 3 or more, of Kras, p53, Lkb1, CHRNA3, CHRNA5, CHRNB4, PSMA4, LOC123688, CLPTM1L, BAT3, MSH5, TERT, and TRNAA-UGC specific to lung cancer;

one or more, e.g., 3 or more loci specific to lung adenocarcinoma, e.g., 3 or more, of TP53, KEAP1, STK11, CDKN2A, KRAS, U2AF1, SMARCA4, EGFR, MET, NF1, RIT1, BRAF, PIK3CA, RBM10, ERBB2, ARID1A, ATM, SLC4A5, NBPF1, STX2, MAP2K1, RB1, FAT1, APC, MLL3, NRAS, SMAD4, CDKN1B, CTNNB1, ARHGAP35, ARID2, and CDK12 specific to lung adenocarcinoma;

one or more, e.g., 3 or more loci specific to lung squamous cell carcinoma, such as one or more, e.g., 3 or more of TP53, CDKN2A, MLL2, KEAP1, PIK3CA, NFE2L2, RB1, HRAS, HLA-A, ARID1A, FBXW7, PTEN, EP300, EGFR, ARHGAP35, RASA1, FGFR3, NF1, NSD1, ASXL1, STK11, FAT1, NOTCH1, and ERPINB13 specific to lung squamous cell carcinoma;

one or more, e.g., 3 or more, loci specific to acute myeloid leukemia, such as one or more, e.g., 3 or more of FLT3, DNMT3A, NPM1, IDH2, IDH1, TET2, NRAS, RUNX1, WT1, U2AF1, TP53, KRAS, PTPN11, KIT, SMC3, STAG2, PHF6, RAD21, CEBPA, ASXL1, SFRS2, SMC1A, PAPD5, EZH2, PDSS2, XRA5, and KDM6A specific to acute myeloid leukemia;

one or more, e.g., 3 or more, loci specific to intergenic specific to basal cell (skin) carcinoma, such as one or more, e.g., 3 or more of RHOU, PADI4, PADI6, RCC2, ARHGEF10L, KRT5, and CDKN2A/B, intergenic specific to basal cell (skin) carcinoma;

one or more, e.g., 3 or more, loci specific to bladder cancer, such as one or more, e.g., 3 or more of TP53, KDM6A, RB1, PIK3CA, ARID1A, MLL2, CDKN1A, ERCC2, STAG2, RXRA, TBC1D12, NFE2L2, C3orf70, ERBB3, ELF3, FBXW7, FGFR3, FOXQ1, CREBBP, HRAS, SNX25, TSC1, MGA, EZR, DDX5, MLL, RHOA, PHF6, MLL3, BCLAF1, TGFBR2, EPHA2, SETD2, and CDKN2A specific to bladder cancer;

one or more, e.g., 3 or more, loci specific to breast cancer, such as one or more of PIK3CA, TP53, GATA3, MAP3K1, PTEN, AKT1, CTCF, CBFB, MLL3, MAP2K4, RUNX1, CDH1, SF3B1, PIK3R1, ARID1A, NCOR1, KRAS, SPEN, RB1, MLL, ERBB2, TBL1XR1, CDKN1B, HIST1H3B, FOXA1, CASP8, MED23, TBX3, CUL4B, STAG2, MYB, RAB40A, EP300, FGFR2, GNPTAB, ERBB3, ACVR1B, FGFR2, MAP3K1, Intergenic, LSP1, TNCR9, LOC643714, ECHDC1, RNF146, C6orf97, SLC4A7, NEK10, and COX11 specific to breast cancer;

one or more, e.g., 3 or more, loci specific to carcinoid cancer, e.g. CDKN1B specific to carcinoid cancer;

one or more, e.g., 3 or more, loci specific to specific to chronic lymphocytic leukemia, such as one or more, e.g., 3 or more of SF3B1, TP53, MYD88, XPO1, HIST1H1E, RPS15, RPS2, NRAS, DDX3X, SPEN, ATM, MED12, IDH1, SETDB1, and JAK1 specific to chronic lymphocytic leukemia;

one or more, e.g., 3 or more, loci specific to colorectal cancer, such as one or more, e.g., 3 or more of APC, TP53, FBXW7, SMAD4, NRAS, SMAD2, TCF7L2, BRAF, KRAS, PIK3CA, PCBP1, ARID1A, ACVR1B, ERBB3, CASP8, ELF3, TRIM23, CDC27, B2M, NTN4, AXIN2, SIRT4, GOT1, RBM10, BCLAF1, BCOR, MAP2K4, IDH2, PTEN, ERBB2, ARID2, CTNNB1, TRAF3, CNBD1, CD70, Intergenic, SMAD7, EIF3H, POU5FIP1, HsG57825, DQ515897, RHPN2, BMP4, and CDH1 specific to colorectal cancer;

one or more, e.g., 3 or more, loci specific to diffuse large B-cell lymphoma, such as one or more, e.g., 3 or more of TP53, MYD88, TNFRSF14, CD79B, MLL2, EZH2, CARD11, CREBBP, TNF, CD70, POU2F2, ITPKB, HLA-A, BRAF, GNA13, POU2AF1, HIST1H3B, KRAS, B2M, NOTCH1, PTEN, MAP2K1, and ZNF471 specific to diffuse large B-cell lymphoma;

one or more, e.g., 3 or more loci specific to endometrial cancer, such as one or more, e.g., 3 or more of PTEN, PIK3CA, PIK3R1, TP53, KRAS, FBXW7, CTCF, ARID1A, ARHGAP35, ZFHX3, FGFR2, CCND1, PPP2R1A, ING1, ZNF471, ERBB3, CTNNB1, BCOR, CUX1, SPOP, NRAS, FAT1, ARID5B, CCDC6, ZNF620, AKT1, SLC1A3, EIF2S2, TCP11L2, SGK1, DIAPH1, KLHL8, SOX17, GNPTAB, SLC44A3, ADNP, POLE, TTLL9, SELP, CHD4, PPM1D, RSBN1L, MICALCL, SACS, ANK3, TBL1XR1, SOS1, DNER, MORC4, MYCN, TXNDC8, INPPL1, ZRANB3, TAP1, EP300, TPX2, CAP2, ALKBH6, CASP8, RASA1, MGA, PBRM1, ERBB2, MLL4, ATM, CDKN1B, RB1, NFE2L2, TP53BP1, COL5A1, FLT3, MTOR, and TDRD10 specific to endometrial cancer;

one or more, e.g., 3 or more loci specific to esophageal cancer, such as one or more, e.g., 3 or more of ADH6, ADH1B, BRAP, and ALDH2 specific to esophageal cancer;

one or more, e.g., 3 or more, loci specific to esophageal adenocarcinoma, such as one or more, e.g., 3 or more of TP53, CDKN2A, FLG, SMARCA4, PIK3CA, SMARCB1, IL7R, COL5A1, SMAD4, KRAS, ARID1A, SETDB1, ERBB2, SACS, and PIK3R1 specific to esophageal adenocarcinoma;

one or more, e.g., 3 or more loci specific to glioblastoma multiforme, such as one or more, e.g., 3 or more of TP53, EGFR, PIK3R1, PIK3CA, IDH1, RB1, PTEN, NF1, STAG2, RPL5, SLC26A3, BRAF, MAP3K1, KEL, CD1D, CHD8, DDX5, MUC17, QKI, AZGP1, SETD2, NUP210L, SMC1A, BCOR, PTPN11, and EZR specific to glioblastoma multiforme;

one or more, such as 3 or more, loci specific to glioma, such as one or more, e.g., 3 or more of CDKN2A, CDKN2B, CCDC26, TERT, PHLDB1, RTEL1 (locus 1), CCDC26, RTEL1 (locus 2), and intergenic specific to glioma;

one or more, such as 3 or more, loci specific to head and neck cancer, such as 3 or more of TP53, CDKN2A, CASP8, FAT1, NFE2L2, NOTCH1, MLL2, NSD1, HRAS, EPHA2, PIK3CA, AJUBA, RAC1, ZNF750, RHOA, TGFBR2, PTEN, HLA-A, EP300, B2M, OTUD7A, HLA-B, CTCF, IPO7, RASA1, MAP4K3, RB1, KDM6A, SMAD4, ARID2, ASXL1, ARHGAP35, MLL3, NCOR1, and PBRM1 specific to head and neck cancer;

one or more, such as 3 or more, loci specific to kidney cell cancer such as kidney clear cell cancer, such as one or more, e.g., 3 or more of SETD2, BAP1, VHL, PBRM1, PTEN, KDM5C, TP53, MTOR, ARID1A, GUSB, RHEB, ATM, TCEB1, MPO, CCDC120, PIK3CA, EGFR, ARHGAP35, BRCA1, FGFR3, and COL5A3 specific to kidney clear cell cancer;

one or more, such as 3 or more, loci specific to medulloblastoma, such as one or more, e.g., 3 or more of DDX3X, CTNNB1, and TP53 specific to medulloblastoma;

one or more, such as 3 or more, loci, specific to melanoma, such as one or more, e.g., 3 or more of BRAF, NRAS, CDKN2A, TP53, BCLAF1, RAC1, PTEN, PPP6C, FRMD7, CDK4, STK19, ACO1, XIRP2, LCTL, OR52N1, ALPK2, WASF3, OR4A16, MYOCD, CTNNB1, ZNF750, KIT, MXRA5, ARID2, ANK3, RXRA, PIK3CA, NCOR1, CDC91L1, Intergenic, MC1R, TYR, and MC1R specific to melanoma;

one or more, such as 3 or more, loci specific to multiple myeloma such as one or more, e.g., 3 or more of KRAS, NRAS, TP53, DIS3, BRAF, FAM46C, INTS12, TRAF3, PRDM1, IRF4, IDH1, FGFR3, PTPN11, and EZR specific to multiple myeloma;

one or more, such as 3 or more, loci specific to nasopharyngeal cancer such as one or more of GABBR1, HLA-A, HLA-F, and HCG9 specific to nasopharyngeal cancer;

one or more, such as 3 or more, loci specific to neuroblastoma such as one or more, e.g., 3 or more of ALK, FLJ22536, FLJ44180, and BARD1 specific to neuroblastoma;

one or more, such as 3 or more, loci specific to ovarian cancer, such as one or more, e.g., 3 or more of TP53, BRCA1, RB1, CDK12, NF1, SMARCB1, KRAS, NRAS, CREBBP, ERBB2, and intergenic specific to ovarian cancer;

one or more, such as 3 or more, loci specific to prostate cancer, such as one or more, e.g., 3 or more of SPOP, TP53, ATM, MED12, FOXA1, COL5A1, Intergenic, TCF2, KLK3, SLC22A3, LMTK2, NUDT10, NUDT11, LOC340602, GSPT2, MAGED1, EHBP1, MSMB, THADA, ITGA6, PDLIM5, TET2, NKX3.1, IGF2, IGF2A, INS, TH, TTLL1, BIK, MCAT, and PACSIN2 specific to prostate cancer;

one or more, such as 3 or more, loci specific to rhadbdoid tumor, such as SMARCB1 gene specific to rhabdoid tumor;

one or more, such as 3 or more, loci specific to testicular germ cell tumor, such as one or more, e.g. 3 or more of KITLG, SPRY4, BAK1, and KITLG specific to testicular germ cell tumor;

one or more, such as 3 or more, loci specific to thyroid cancer such as one or more of FOXE1 and NKX2-1 specific to thyroid cancer; or one or more, such as 3 or more, loci specific to urinary bladder cancer, such as one or more, of MYC, BC042052, and PSAC specific to urinary bladder cancer.

The eukaryotic cell can be a mammalian cell, e.g., a mouse cell, such as a mouse cell that is part of a transgenic mouse having cells that express Cas9. The invention also comprehends a method for introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed. The method can comprise deliverying to cells of the transgenic non-human mammal, and the transgenic non-human mammal is a transgenic mouse having cells that express Cas9, e.g., a mouse that has had a Cas9 transgene knocked into the Rosa26 locus. The Cas9 transgene can further comprise a Lox-Stop-polyA-Lox (LSL) cassette thereby rendering Cas9 expression inducible by Cre recombinase. The invention additionally comprehends a method for modeling a genetic disease or cancer comprising introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed, wherein the specific mutations or precise sequence substitutions are or have been correlated to the genetic disease or cancer. This method can comprise delivering to cells of the transgenic non-human mammal the vector, and the transgenic non-human mammal is a transgenic mouse having cells that express Cas9, e.g., a mouse that has had a Cas9 transgene knocked into the Rosa26 locus; and, the Cas9 transgene can further comprise a Lox-Stop-polyA-Lox (LSL) cassette thereby rendering Cas9 expression inducible by Cre recombinase. The cancer can be lung cancer. The invention also envisions an individualized or personalized treatment of a genetic disease in a subject in need of such treatment comprising: (a) introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed, wherein the specific mutations or precise sequence substitutions are or have been correlated to the genetic disease; (b) testing treatment(s) for the genetic disease on the cells to which the vector has been delivered that have the specific mutations or precise sequence substitutions correlated to the genetic disease; and (c) treating the subject based on results from the testing of treatment(s) of step (b). The method can comprise delivering to cells of the transgenic non-human mammal the vector, and the transgenic non-human mammal is a transgenic mouse having cells that express Cas9, and the genetic disease is a cancer, e.g., lung cancer.

The invention comprehends a method of inducing one or more mutations in vitro or ex vivo in a eukaryotic cell as herein discussed comprising delivering to cell a vector as herein discussed. The invention further comprehends a method of inducing one or more mutations in vivo in the non-human transgenic eukaryote as herein discussed comprising delivering to said non-human transgenic eukaryote a vector as herein discussed. The delivery can be tissue specific delivery. The mutation(s) can include the introduction, deletion, or substitution of one or more nucleotides at each target sequence of cell(s) via the guide(s) or RNA(s) or sgRNA(s) resulting in loss-of-function and/or gain of function of the target(s). The mutations can include the introduction, deletion, or substitution of 1-75 nucleotides at each target sequence of said cell(s) via the guide(s) or RNA(s) sgRNA(s) resulting in loss-of-function or gain of function of the target(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 40, 45, 50, 75, 100, 200, 300, 400 or 500 nucleotides at each target sequence of said cell(s) via the guide(s) or RNA(s) or sgRNA(s) resulting in loss-of-function or gain of function of the target. The method or mutation(s) thereof can induce a cancer, e.g., Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, or Urinary bladder cancer.

The invention comprehends a method for identifying genes, mutations in genes or combinations thereof which are associated with or correlated to cancer comprising a method of inducing one or more mutations in vitro or ex vivo in a non-human eukaryotic cell as herein discussed or inducing one or more mutations in vivo in a non-human transgenic eukaryote as herein discussed, and identifying cancer resulting from such mutations(s). Cancer in this method and as herein discussed can be defined as abnormal growth as compared to controls. The method can include control cell(s) or eukaryote(s) that do not receive introduction of said mutation(s).

The invention also comprehends a method for modeling cancer comprising inducing one or more mutations in vivo in a non-human transgenic eukaryote as herein discussed, e.g., deliverying to a non-human transgenic eukaryote one or more vectors or RNA(s) guide(s) or sgRNA(s) as herein discussed. The cancer can be Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, or Urinary bladder cancer.

In embodiments of the invention cancer is advantageously Lung cancer, Lung adenocarcinoma, or Lung squamous cell carcinoma, e.g., Lung cancer.

In embodiments of the invention the target sequences are advantageously gene sequences of Kras, p53, and Lkb1 specific to lung cancer.

The invention additionally comprehends a method for generating cancerous non-human transgenic eukaryotes by introducing, as herein discussed, the one or more mutations as herein discussed. The invention additionally comprehends a cancerous non-human transgenic eukaryote; for instance, such a eukaryote produced by a method herein discussed. Such a non-human eukaryote contains or expresses or conditionally expresses Cas9 and has cancer.

The invention also comprehends a method for the identification of a treatment, e.g., chemical or gene therapy treatment, for cancer comprising applying, administering or delivering one or more treatments to the cancerous non-human transgenic eukaryote as herein discussed and identifying whether the cancer has improved; and, the cancer can be Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, or Urinary bladder cancer. The method can comprise applying, administering or delivering different doses of the treatment and/or employing different routes of administration and/or different carriers or excipients and/or applying, administering or delivering at different time intervals, e.g., applying, administering or delivering different does at different time intervals.

The invention also comprehends a method of treatment of cancer, e.g., a cancer identified in a method of identification or a cancer of a method of modeling, in a subject in need thereof, comprising treating the subject based on the results from the identification or modeling method.

The invention also comprehends kits; e.g., a comprising vector(s) as herein discussed or vector(s) as herein discussed and one or more eukaryotic cells or non-human transgenic eukaryotes as herein discussed; and advantageously the kit includes instructions for performing a method as herein discussed.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-D show generation of a Rosa26-LSL-Cas9 transgenic mouse (A) A schematic of the Rosa26-LSL-Cas9 knock-in cassette and targeting strategy; (B) Representative stereotactic images of lungs showing EGFP (Cas9-P2A-EGFP) expression in constitutively expressing R26C9-Cas9 (Rosa26-LSL-Cas9 mice crossed with beta-actin Cre mice) but not wild-type mice; (C) IHC imaging of lung sections stained with an anti-EGFP antibody showing EGFP (Cas9-P2A-EGFP) expression in constitutively expressing R26C9-Cas9 but not wild-type mice. Scale bar 20 µm; (D) Western blot of constitutively expressing R26C9-Cas9 and wild-type lung lysates showing FLAG staining at the predicted molecular weight for 3×FLAG-Cas9 protein (167 kDa). Anti-beta-tubulin and anti-GAPDH antibodies show equal loading of protein.

FIG. 2A-H show in vivo AAV9-KPL-HDR delivery and mutation analysis. (A) A schematic of intratracheal (i.t.) delivery of AAV9 into the lung of a Rosa26-LSL-Cas9 mouse and a workflow of experimental methodologies; (B) Delivery of constitutively active Firefly luciferase plasmid by AAV9 i.t. efficiently mediates transgene expression in the lung. (associated with FIG. 7); (C) A schematic of the single AAV9-KPL-HDR vector, which includes three U6-sgRNA cassettes, a truncated version of the constitutive EF1α promoter (EFs), *Renilla* luciferase (Rluc), P2A self-cleavage peptide, Cre recombinase, a short polyA sequence, and an 800 bp $Kras^{G12D}$ HDR donor template; (D-E) Left: p53 (SEQ ID NOS 59-62, respectively, in order of appearance) and Lkb1 (SEQ ID NOS 63-66, respectively, in order of appearance) targeting strategies and representative Illumina sequencing reads showing indel formation at the site of predicted cleavage. Middle: Size distribution of indels found at the target site. Right: Indel analysis showing efficiencies from whole lung (top) and the phase characteristics of the edited alleles (bottom). p53 and Lkb1 loci scale bars, 1 kb; (F) Kras (SEQ ID NOS 67-73, respectively, in order of appearance) targeting strategy for facilitating $Kras^{G12D}$ mutations. Representative Illumina sequencing reads showing G12D (green text) and synonymous (blue text) mutations. Kras locus scale bar, 1 kb; (G) p53 and Lkb1 mutation analysis. Quantification of indel frequencies found in AAV9-sgKPL-HDR and AAV9-sgLacZ injected mice. Data are plotted as mean±SEM. *p<0.05, p<0.005; (H) Kras HDR analysis. The percent $Kras^{G12D}$ HDR efficiency was quantified utilizing Illumina sequencing, whereby sequences matching the G12D and synonymous mutations were compared against adjacent sequence matching the wild-type Kras. Primers were designed outside of the HDR donor template such that AAV genomes were not amplified. The data are plotted as the mean±SEM. *p<0.0005.

FIG. 3A-H show tumor formation in AAV9-KPL-HDR injected mice. (A) Representative μCT images of AAV9-sgLacZ and AAV9-sgKPL-HDR injected mice, with transverse, coronal and sagittal plane views two months post transduction. Red arrows highlight tumors within the lungs of AAV9-sgKPL-HDR injected mice; (B) Representative μCT 3D rendering of AAV9-sgKPL-HDR injected mice showing the reconstructed lung where the location of a large tumor nodule is indicated in a yellow oval; (C) Major tumor burden quantification of AAV9-sgLacZ and AAV9-sgKPL-HDR injected mice. Data are plotted as mean±SEM. **p<0.005; (D) Representative HE stained lobes from AAV9-sgKPL-HDR and AAV9-sgLacZ injected mice. Black arrows highlight a representative subset of tumors within the lungs of AAV9-sgKPL-HDR injected mice. Scale bar, 500 μm; (E) Lung tumor size quantification of AAV9-sgLacZ and AAV9-sgKPL-HDR injected mice. Data are plotted per lobe as individual tumors (brown dots) and as mean (black line)±SEM; (F) Average tumor size, (G) nodules per lobe, and (H) total tumor area per lobe quantification of AAV9-sgLacZ and AAV9-sgKPL-HDR injected mice. Data are plotted as mean±SEM. *p<0.05, p<0.005, *p<0.0005.

FIG. 8A-C show design and validation of a single vector system to facilitate KrasG12D HDR and p53 and Lkb1 LOF in the lungs of Rosa26-LSL-Cas9 mice. (A) In vitro screen of sgRNAs targeted to Kras, p53, and Lkb1 in the N2a mouse cancer cell line by transient transfection and SURVEYOR nuclease assay; (B) In vitro validation of the single vector system (AAV9-KPL-HDR) in the N2a mouse cancer cell line by transient transfection and SURVEYOR nuclease assay; (C) Table of sgRNAs and genomic PCR primers used (SEQ ID NOS 74-93, respectively, in order of appearance).

FIG. 9 shows in vitro validation of KrasG12D HDR strategy. Representative sequencing reads from a mouse cancer cell line (N2a) transiently transfected with an AAV plasmid expressing Kras sgRNA and KrasG12D HDR donor template, plus constitutively active Cas9 plasmid, showing both wild-type and HDR reads (SEQ ID NOS 94, 95, 95, 95, 95, 95, 96, 94 and 97-99, respectively, in order of appearance).

FIG. 12A-12AF provides exemplary plasmid sequences (SEQ ID NOS:S 100-150, respectively, in order of appearance).

Figure 4A:
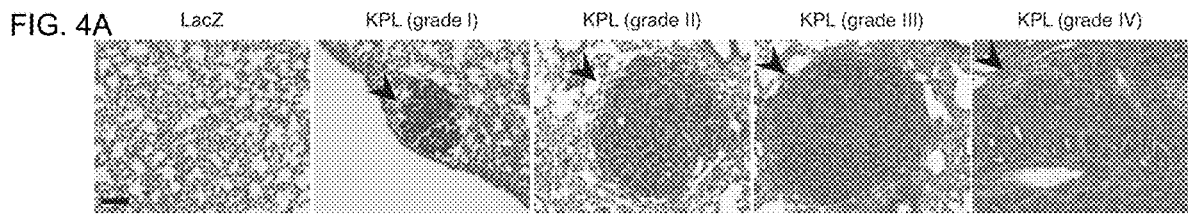
FIG. 4A-D show histopathology of tumors formed within AAV9-sgKPL-HDR injected mice. (A) Representative HE images of AAV9-sgLacZ and AAV9-sgKPL-HDR injected mice showing a spectrum of adenocarcinomas nine weeks post transduction. Black arrows highlight tumors found within AAV9-sgKPL-HDR injected mice. Scale bar, 100 μm; (B) HE image of an AAV9-sgKPL-HDR injected mouse showing grade IV adenocarcinoma with signs of invasion (black arrow) and aneuploidy (double black arrows). Scale bar, 100 μm; (C) Representative HE images showing a tumor nodule (black arrow) within the lung of an AAV9-sgKPL-HDR injected but not AAV9-sgLacZ injected mouse nine weeks post transduction. Clara cell secretory protein (CCSP) staining showing tumors adjacent to the clara cells (double black arrows) of a bronchial. Scale bar, 100 μm; (D) Representative IHC images of AAV9-sgLacZ and AAV9-sgKPL-HDR injected mice nine weeks post transduction. Ki67, a marker for proliferating cells (black arrow), staining showing extensive proliferation in tumors found within AAV9-sgKPL-HDR injected mice. CD31, a marker for endothelial cells (black arrow), staining showing embedded CD31-positive endothelial cells. Positive for pro-surfactant C (pSPC), a marker for type II pneumocytes, staining suggests tumors originate from this cell type. Scale bar, 200 μm.

The figures herein are for illustrative purposes only and are not necessarily drawn to scale.

DETAILED DESCRIPTION OF THE INVENTION

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, and 8,795,965; allowed U.S. application Ser. No. 14/259,420; US Patent Publications US 2014-0179006 A1 (U.S. application Ser. No. 14/183,486), US 2014-0189896 A1 (U.S. application Ser. No. 14/105,035), US 2014-0186843 A1 (U.S. application Ser. No. 14/104, 900), US 2014-0179770 A1 (U.S. application Ser. No. 14/104,837), US 2014-0186919 A1 (U.S. application Ser. No. 14/104,977), and US 2014-186958 A1 (U.S. application Ser. No. 14/105,017): PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), and WO2014/018423 (PCT/US2013/051418); U.S. provisional applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent applications 61/836,123, 61/847,537, 61/862,355 and 61/871,301, filed on Jun. 17, 2013; Jul. 17, 2013, Aug. 5, 2013 and Aug. 28, 2013 respectively. Reference is further made to U.S. provisional patent applications 61/736,527 and 61/748,427 filed on Dec. 12, 2012 and Jan. 2, 2013, respectively. Reference is additionally made to U.S. provisional patent application 61/791,409, filed on Mar. 15, 2013. Reference is also made to U.S. provisional patent application 61/799,800, filed Mar. 15, 2013. Reference is also made to U.S. provisional patent applications 61/835,931, 61/835, 936, 61/836,127, 61/836,101, 61/836,123, 61/836,080, and 61/835,973 each filed Jun. 17, 2013. Reference is made to U.S. provisional patent application 61/915,118, filed on Dec. 12, 2013 and U.S. provisional patent application 62/010,441 filed Jun. 10, 2014, each of which is incorporated herein by reference. Reference is also made to U.S. provisional patent applications 61/915,215 and 61/915,148, both filed on Dec. 12, 2013, each of which is incorporated herein by reference. Each of these applications, and all documents cited therein or during their prosecution ("appin cited documents") and all documents cited or referenced in the appin cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these applications and the appin cited documents) are incorporated herein by reference to the same extent as if each individual document was specifically and individually indicated to be incorporated by reference. Citations for documents cited herein may also be found in the foregoing herein-cited documents, as well as those hereinbelow cited.

Also with respect to general information on CRISPR-Cas Systems, mention is made of:

*Multiplex genome engineering using CRISPR/Cas systems.* Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

*RNA-guided editing of bacterial genomes using CRISPR-Cas systems.* Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering.* Wang H., Yang H., Shivalila C S., Dawlaty M M., Cheng A W., Zhang F., Jaenisch R. Cell May 9; 153(4): 910-8 (2013);

*Optical control of mammalian endogenous transcription and epigenetic states.* Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23;

*Double Nicking by RNA-Guided CRISPR Cas9 for Enhanced Genome Editing Specificity.* Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA guided Cas9 nucleases.* Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

*Genome engineering using the CRISPR-Cas9 system.* Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells.* Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

*Crystal structure of cas9 in complex with guide RNA and target DNA.* Nishimasu, H., Ran, F A., Hsu, P D., Konermann, S., Shehata, S I., Dohmae, N., Ishitani, R., Zhang, F., Nureki, O. Cell Feb. 27, 2014. 156(5):935-49;

*Genome-wide binding of the CRISPR endonuclease Cas9 in mammalian cells.* Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. 2014 Apr. 20. doi: 10.1038/nbt.2889, and

*Development and Applications of CRISPR-Cas9 for Genome Engineering,* Hsu et al, Cell 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus ther-* mophilus Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors reported that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspersed by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNN NNNNNNNNNN gttttgtact ctcaagattt aGAAAtaaat cttgcagaag ctacaaagat aaggcttcat gccgaaatca acaccctgtc attt- tatggc agggtgtttt cgttatttaa TTTTTT (SEQ ID NO: 1); (2) NNNNNNNNNN NNNNNNNNNN gttttgtac tctcaGAAAt gcagaagcta caaagataag gcttcatgcc gaaatcaaca ccctgtcatt ttatggcagg gtgttttcgt tatttaaTTT TTT (SEQ ID NO: 2); (3) NNNNNNNNNN NNNNNNNNNN gttttgtac tctcaGAAAt gcagaagcta caaagataag gcttcatgcc gaaatcaaca ccctgtcatt ttatggcagg gtgtTTTTTT (SEQ ID NO: 3); (4) NNNNNNNNNN NNNNNNNNNN gttttagagc taGAAAtagc aagttaaaat aaggctagtc cgttatcaac ttgaaaaagt ggcaccgagt cggtgcTTTT TT ((SEQ ID NO: 4); (5) NNNNNNNNNN NNNNNNNNNN gttttagagc taGAAATAGc aagttaaaat aaggctagtc cgttatcaac ttgaaaaagt gTTTTTTT (SEQ ID NO: 5); and (6) NNNNNNNNNN NNNNNNNNNN gttttagagc tagAAATAGc aagttaaaat aaggctagtc cgttatcaTT TTTTTT (SEQ ID NO: 6). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 7) in the EMX1 gene of the human genome, deep sequencing can be used to assess the level of modification at the following two off-target loci, 1: 5'-GAGTCCTAGCAGGAGAAGAA-3' (SEQ ID NO: 8) and 2: 5'-GAGTCTAAGCAGAAGAAGAA-3' (SEQ ID NO: 9). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9

(which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions. One can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 10); the NLS from nucleoplasmin (e.g. the nucleoplasmin bipartite NLS with the sequence KRPAATKKAGQAKKKK (SEQ ID NO: 11); the c-myc NLS having the amino acid sequence PAAKRVKLD (SEQ ID NO: 12) or RQRRNELKRSP (SEQ ID NO: 13); the hRNPA1 M9 NLS having the sequence NQSSNFGPMKGGNFG-GRSSGPYGGGGQYFAKPRNQGGY (SEQ ID NO: 14); the sequence RMRIZFKNKGKDTAELRRRRVEVS-VELRKAKKDEQILKRRNV (SEQ ID NO: 15) of the IBB domain from importin-alpha; the sequences VSRKRPRP (SEQ ID NO: 16) and PPKKARED (SEQ ID NO: 17) of the myoma T protein; the sequence PQPKKKPL (SEQ ID NO: 18) of human p53; the sequence SALIKKKKKMAP (SEQ ID NO: 19) of mouse c-abl IV; the sequences DRLRR (SEQ ID NO: 20) and PKQKKRK (SEQ ID NO: 21) of the influenza virus NS1; the sequence RKLKKKIKKL (SEQ ID NO: 22) of the Hepatitis virus delta antigen; the sequence REKKKFLKRR (SEQ ID NO: 23) of the mouse Mx1 protein; the sequence KRKGDEVDGVDEVAKKKSKK (SEQ ID NO: 24) of the human poly(ADP-ribose) polymerase; and the sequence RKCLQAGMNLEARKTKK (SEQ ID NO: 25) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

Transgenic non-human eukaryotic organisms, e.g., animals are also provided in an aspect of practice of the instant invention. Preferred examples include animals comprising Cas9, in terms of polynucleotides encoding Cas9 or the protein itself. In certain aspects, the invention involves a constitutive or conditional or inducible Cas9 non-human eukaryotic organism, such as an animal, e.g., a primate, rodent, e.g., mouse, rat and rabbit, are preferred; and can include a canine or dog, livestock (cow/bovine, sheep/ovine, goat or pig), fish, fowl or poultry, e.g., chicken, and an insect or arthropod, with it mentioned that it is advantageous if the animal is a model as to a human or animal genetic disease or condition, such as cancer, as use of the non-human eukaryotic organisms in genetic disease or condition modeling, e.g., via inducing a plurality, e.g., 3 to 50 mutations correlated or associated with a genetic disease or condition, are preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock ins are envisaged (alone or in combination). Example 1 provides a knockin Cas9 mouse and to generate a Cas9 knock in mice one may target the same constitutive and conditional constructs to the Rosa26 locus, reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. In a particular embodiment Applicants disclose herein a novel in vivo CRISPR approach with a combination of novel Cas9 reagents, as well as demonstrate application in modeling the dynamics of the top three cancer mutations in the lung; and, that this system can be used to model three and even more than three genetic mutations, such as any number between three (3) and fifty (50) or more. And, this can include modeling in post-mitotic cells. In 293 cells the Cas9 conditional expression construct can be activated by co-expression with Cre. Correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. The conditional Cas9 mouse can be crossed with a mouse that ubiquitously expresses Cre (ACTB-Cre line) and may arrive at a mouse that expresses Cas9 in every cell. The delivery of RNA(s) to guide Cas9, e.g. CRISPR RNA and transactivating (tracr) RNA or a single guide RNA (sgRNA) (chimeric RNA) can induce genome editing in embryonic or adult mice. Interestingly, when the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue. Further, the conditional Cas9 mouse is broadly applicable for many areas of biology and its uses as described herein provide many utilities. More generally, while Cas9 provides an effective way to model multiple genetic lesions, Cas9 delivery has challenges, including limitations due to the significant size of Cas9, and possible extra biosafety practices. The Cas9 transgenic eukaryote, e.g., mouse provides a most effective method for genetic, e.g., cancer modeling and other areas of tissues-specific biological studies. Applicants' approach provides a substantial packaging capacity for both sgRNAs as well as reporters and other modulators, etc. These features include efficient editing of cellular subtypes using Cre driver lines, hard to transfect/transduce primary cells, and delivery of sgRNA using non-viral, nanotechnology-based methods. Applicants used AAV in their study disclosed herein in Example 2. AAV is particularly advantageous in that it has the benefit of being DNA based and therefore there is no concern about recombination between repetitive sequences in the case of multiple U6-sgRNA expression cassettes. Further, AAV efficiently facilitates homology directed repair (HDR) expanding the capacity of Cas9-mediated genome engineering in vivo. To demonstrate the significant utility of this transgenic eukaryote, e.g., animal, e.g., mammal, e.g., mouse line, Applicants used this conditional Cas9 transgenic eukaryote, e.g., animal, e.g., mammal, e.g., mouse to study lung cancer, which is the top killer across all cancer types in both men and women in the US. Applicants constructed a modular viral construct to model the dynamics of multiple cancer lesions simultaneously. The construct encompasses cassettes expressing Cre recombinase, sgRNAs to guide Cas9 cutting, and HDR template to swap in specific gain-of-function mutations. Specifically, Applicants disclose herein in Example 2, the generation of a novel modular viral vector construct, AAV-Cre-sgp53-sgLkb1-sgKras-KrasG12D-HDR, which is capable of generating loss-of-function mutations in two tumor suppressor genes as well as gain-of-function mutations in a proto-oncogene, all in a single vector. Applicants have demonstrated that delivery of this novel vector construct by AAV9 intratracheally into the lung of Cas9 mice generated the targeted LOF mutations in both p53 and Lkb1, as well as HDR-mediated G12D mutations in Kras. These Cas9 mice rapidly developed lung cancer and their tumors developed within one month into adenomas and progressed into adenocarcinomas, with a full spectrum of grades I through IV pathologies that mimic the characteristics of human lung cancer, which is significantly faster and more cost-efficient than existing cancer models. These results underscore the enormous potential of this approach and the Cas9 mouse for cancer research. Further, the broad applicability of the novel conditional Cas9 mouse is for many areas of biology, particularly for study of complex pathologies involving multiple genetic loci can be envisioned.

Accordingly, the invention involves a non-human eukaryote, animal, mammal, primate, rodent, etc or cell thereof or tissue thereof that may be used as a disease model. As used herein, "disease" refers to a disease, disorder, or indication in a subject. For example, a method of the invention may be used to create a non-human eukaryote, e.g., an animal, mammal, primate, rodent or cell that comprises a modification, e.g., 3-50 modifications, in one or more nucleic acid sequences associated or correlated with a disease, e.g., cancer or cell or tissue of such. Such a mutated nucleic acid sequence be associated or correlated with a disease or cancer and may encode a disease associated protein sequence or may be a disease associated or correlated control sequence. The cell may be in vivo or ex vivo in the cases of multicellular organisms. In the instance where the cell is in cultured, a cell line may be established if appropriate culturing conditions are met and preferably if the cell is suitably adapted for this purpose (for instance a stem cell). Hence, cell lines are also envisaged. In some methods, the disease model can be used to study the effects of mutations on the animal or cell and development and/or progression of the disease using measures commonly used in the study of the disease. Alternatively, such a disease model is useful for studying the effect of a putatively pharmaceutically active compound or gene therapy on the disease. A disease-associated gene or polynucleotide can be modified to give rise to the disease in the model, and then putatively pharmaceutically active compound and/or gene therapy can be administered so as to observe whether disease development and/or progression is inhibited or reduced. In particular, the method comprises modifying so as to produce, one or more, advantageously 3-50 or more disease-associated or correlated gene(s) or polynucleotide(s). Accordingly, in some methods, a genetically modified animal may be compared with an animal predisposed to development of the disease, such that administering putative gene therapy, or pharmaceutically acceptable compound(s), or any combination thereof can be performed to assess how such putative therapy(ies) or treatment(s) may perform in a human. The invention can involve contacting a test compound with a cell or administering to a eukaryote a test compound, wherein the eukaryote or cell comprises one or more, e.g., 3-50 or more mutations from the CRISPR-Cas system, e.g., in an animal that expresses Cas9 and to which RNA(s) generating the mutations has/have been administered; and detecting a reduction or an augmentation of a cell signaling event associated with the mutation(s) or lack thereof. Screening of such putative pharmaceutically active compound(s) and/or gene therapy(ies) can be by cellular function change and/or intracellular signaling or extracellular signaling change. Such screening can involve evaluating for dosages or dose curves, as well as combinations of potential drugs and/or therapies. An altered expression of one or more genome sequences associated with a signaling biochemical pathway can be determined by assaying for a difference in the mRNA levels of the corresponding genes between the disease model eukaryote or animal or cell or tissue thereof and a normal eukaryote, animal, tissue or cell, and to ascertain whether when the disease model is administered or contacted with a candidate chemical agent or gene therapy it reverts to or towards normal. An assay can be for mutation(s)-induced alteration in the level of mRNA transcripts or corresponding polynucleotides in comparison with such level(s) in a normal eukaryote or animal and whether such level(s) are placed towards or to normal when a therapy or treatment or agent is employed. Screening can also involve evaluating whether the multiple mutations give rise to fibers. Accordingly, the invention comprehends delivery of multiple RNA (s), e.g., sgRNA(s), e.g., 3-50 or more, e.g., 3, 16, 32, 48, 50 or more to the transgenic Cas9 eukaryote and thereafter screening cells, tissue, tumors or the eukaryote for fibers or formation of fibers (with it understood that "eukaryote" is as herein discussed to include animal, mammal, etc). Inducing multiple mutations also enables the skilled person to divine new combinations of mutations that give rise to genetic disorders such as cancer. The ability to induce multiple mutations that accelerate or change the rate of a genetic disorder, e.g., cancer accordingly provides many advantages heretofore unknown in research and development of pharmaceuticals, therapies and treatments for such disorders.

In an aspect the invention can involve cells, e.g., non-human eukaryotic, e.g., animal, such as mammal, e.g., primate, rodent, mouse, rat, rabbit, etc., or even human cells, transformed to contain Cas9, e.g., such cells as to which a vector that contains nucleic acid molecule(s) encoding a Cas9, e.g., with nucleic acid(s) encoding a promoter and at least one NLS, advantageously two or more NLSs, or such cells that have had their genome altered, e.g., through the vector being an integrating virus or through such cells being stem cells or cells that give rise to a cell line or a living organism (but wherein such an organism is advantageously non-human), that contains and expresses nucleic acid molecule(s) encoding Cas9. Such cells are then transplanted into or onto an animal suitable for being a genetic disease, e.g., cancer, model, e.g., zebra fish (see, e.g., Haldi et al, "Human melanoma cells transplanted into zebrafish proliferate, migrate, produce melanin, form masses and stimulate angiogenesis in zebrafish," Angiogenesis. 2006; 9(3):139-51. Epub 2006 Oct. 19)), a rodent such as a mouse (see, e.g., literature on mouse transplantation cancer models, generally discussed at the NIH website; see emice.nci.nih.gov/aam/mouse/transplantation-mouse-models-1), chickens or chicken embryo or chicken embryo membrane (Kuzminien et al, "Evaluation of the Chicken Embryochorioallantoic membrane Model for Laryngeal Tumor Transplantation," Papers on Anthropology XX, 2011, pp. 229-240). The cells proliferate on or in the non-human eukaryote, e.g., animal model. The non-human eukaryote, e.g., animal model, having the proliferated heterologous transplanted Cas9-containing cells, is then administered RNA(s) or vector(s), e.g., AAV, adenovirus, lentivirus containing or providing RNA(s), e.g., under the control of a promoter such as a U6 promoter and/or particle(s) and/or nanoparticle(s) containing the RNA(s) and/or vector(s), whereby the RNA(s) direct the Cas9 in the cells to provide mutation, e.g., a plurality of mutation(s) such as from 3 to 50 mutations, advantageously mutation(s) associated or correlated with a genetic disease, e.g., cancer, whereby the non-human eukaryote, e.g., animal model is transformed into being a non-human eukaryote, e.g., animal model for the genetic disease, e.g., cancer. The non-human eukaryote, e.g., animal model can then be used for testing, e.g., as to potential therapy and/or putative treatment via a possibly pharmaceutically active compound. The administering can be at or to or for body delivery to the proliferated heterologous transplanted Cas9-containing cells, e.g., direct injection at or near such proliferated heterologous transplanted Cas9-containing cells, or injection or other administration in such a way that the RNA(s) are delivered into the proliferated heterologous transplanted Cas9-containing cells, e.g., injection into the bloodstream whereby bodily functions transport to the proliferated heterologous transplanted Cas9-containing cells. In an aspect of the invention, barcoding techniques of WO/2013/138585 A1 can be adapted or integrated into the practice of the invention. WO/2013/138585 A1 provides methods for simultaneously determining the effect of a test condition on viability or proliferation of each of a plurality of genetically heterogeneous cell types. The methods include: providing a unitary sample comprising a plurality of, e.g., five, ten, twenty, twenty-five, or more, genetically heterogeneous cell types (each individual cell type is genetically homogeneous within itself, but differs from the others in the plurality), wherein each cell type further comprises: (i) an exogenous nucleic acid tag stably integrated into the genome of the cells, e.g., a tag comprising a core sequence that is unique to each cell type, and flanking amplification primer binding sequences that are the same in all of the cells of the plurality, and (ii) optionally, a marker, e.g., a selectable or detectable marker; and a known number of cells of each cell type is present in the sample; exposing the sample to a test condition for a selected time; and detecting a level of the exogenous nucleic acid tag in each cell type, wherein the level of the exogenous nucleic acid tag is proportional to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. WO/2013/138585 A1 also provides methods for simultaneously determining the effect of a test condition on viability or proliferation of each of a plurality of genetically heterogeneous cell types, wherein the methods include providing a unitary sample comprising a plurality of, e.g., five, ten, twenty, twenty-five, or more, genetically heterogeneous cell types, wherein each cell type further comprises: (i) an exogenous nucleic acid tag stably integrated into the genome of the cells, e.g., comprising a core sequence that is unique to each cell type, and flanking amplification primer binding sequences that are the same in all of the cells of the plurality, and (ii) optionally, a selectable or detectable marker; and a known number of cells of each cell type is present in the sample; implanting the sample into a living animal; exposing the sample to a test condition for a selected time; harvesting the sample from the animal; and detecting a level of the exogenous nucleic acid tag in each cell type of the sample, wherein the level of the exogenous nucleic acid tag correlates to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. The tag can be Cas9 or another TAG or marker that is integrated into the genome of cells to be transplanted into or onto a non-human eukaryote, e.g., animal model, or that is integrated into the genome of the non-human transgenic eukaryote, e.g., animal, mammal, primate, rodent, mouse, rat, rabbit, etc (along with coding for Cas9). The test condition can be the administration or delivery of the RNA(s) to guide the Cas9 to induce one or more or a plurality, e.g., 3-50 or more, mutations. The test condition can be the administration, delivery or contacting with a putative chemical agent treatment and/or gene therapy treatment. The tag can also be the one or more or a plurality, e.g., 3-50 or more mutations, and the test condition can be the administration, delivery or contacting with a putative chemical agent treatment and/or gene therapy treatment.

The invention comprehends delivering the CRISPR-Cas system and/or component(s) thereof to the transgenic non-human eukaryote, e.g., mammal; for instance, to one or both lungs of a mammal, e.g., a non-human mammal. In general, delivery of the CRISPR-Cas system and/or component(s) thereof and/or coding for component(s) thereof can be as in WO 2014/093622 (PCT/US2013/074667), with AAV, lentivirus, and adenovirus vectors or particles or nanoparticles (including particle bombardment techniques that can include gold or other elemental, e.g., tungsten particles) preferred, and use thereof in the practice of the invention is within the ambit of the skilled artisan from this disclosure and the knowledge in the art, e.g., WO 2014/093622 (PCT/US2013/074667), incorporated herein by reference. The invention involves at least one component of the CRISPR complex, e.g., RNA, delivered via at least one vector or particle or nanoparticle complex. In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994). Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368;

WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells are typically used to form virus particles that are capable of infecting a host cell. Such cells include 293 cells, which package adenovirus, and w2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA. There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep. The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV. In addition to 293 cells, other cells that can be used in the practice of the invention and the relative infectivity of certain AAV serotypes in vitro as to these cells; see Grimm, D. et al, J. Virol. 82: 5887-5911 (2008) The invention provides rAAV that contains or consists essentially of an exogenous nucleic acid molecule encoding a CRISPR (Clustered Regularly Interspaced Short Palindromic Repeats) system or component(s) or coding therefor, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

If a Cas9-expressing model provided for herein is used, then only delivery of guide(s) is necessary. In some embodiments, one or more vectors described herein are used to produce a non-human transgenic Cas9 eukaryote, e.g., animal, mammal, primate, rodent, mouse, rat, rabbit. In some embodiments, the transgenic animal is a mammal, such as a mouse, rat, or rabbit. Guides or RNA(s) can be delivered via the same vector types as Cas9. When both guides or RNA(s) and Cas9 are being delivered a dual-vector system where the Cas9 is delivered via in vivo expression from an AAV vector and the guide(s) are delivered by a separate AAV vector. This can be done substantially contemporaneously (i.e., co-delivery), but it could also be done at separate points in time, separated even by weeks or months. Of course, the ultimate separation is where the transgenic Cas9 eukaryote is generated and thereafter the guide(s) or RNA(s) are delivered. Alternatively a first round of CRISPR-Cas9 systems can be delivered, and subsequently further guides or RNA(s) are delivered as the original Cas9 is still functional in the target cells may be re-used. If the Cas9 is under the control of an inducible promoter, then induction of transcription of new CAs9 in the target cells is preferred.

Aerosolized delivery is preferred for AAV or adenovirus delivery in general. An adenovirus or an AAV particle may be used for delivery. Suitable gene constructs, each operably linked to one or more regulatory sequences, may be cloned into the delivery vector. In this instance, Cbh or EF1α promoter for Cas9, U6 or H1 promoter for chimeric guide RNA may be advantageous. Cas9 and/or RNA(s) can be delivered using particles, adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The vectors can be injected into the tissue of interest. For cell-type specific genome modification, the expression of Cas9 can be driven by a cell-type specific promoter.

Among vectors that may be used in the practice of the invention, integration in the host genome is possible with the retrovirus, lentivirus, and adeno-associated virus gene transfer methods, often resulting in long term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors (and hence both lentiviral and retroviral vectors may be used in the practice of the invention).

Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Zou et al. administered about 10 µl of a recombinant lentivirus having a titer of $1 \times 10^9$ transducing units (TU)/ml by an intrathecal catheter. These sorts of dosages can be adapted or extrapolated to use of a retroviral or lentiviral vector in the present invention.

Also useful in the practice of the invention is a minimal non-primate lentiviral vector, such as a lentiviral vector based on the equine infectious anemia virus (EIAV) (see, e.g., Balagaan, J Gene Med 2006; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Intracameral, subretinal, intraocular and intravitreal injections are all within the ambit of the instant invention (see, e.g., Balagaan, J Gene Med 2006; 8: 275-285, Published online 21 Nov. 2005 in Wiley InterScience (www.interscience.wiley.com). DOI: 10.1002/jgm.845). In this regard, mention is made of RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for practice of the present invention. Dosing of RetinoStat® (e.g., $1.1 \times 10^5$ transducing units per eye (TU/eye) in a total volume of 100 µl) can be applied or extrapolated from in practicing the present invention with a lentivirus.

The invention also can be practiced with an adenovirus vector, e.g., an E1-, partial E3-, E4-deleted adenoviral vector may be used in the practice of the invention. Such vectors are safe as twenty-eight patients with advanced neovascular age-related macular degeneration (AMD) were given a single intravitreous injection of an E1-, partial E3-, E4-deleted adenoviral vector expressing human pigment epithelium-derived factor (AdPEDF.11) (see, e.g., Campochiaro et al., Human Gene Therapy 17:167-176 (February 2006)); and previous adenovirus doses ranging from $10^6$ to $10^{9.5}$ particle units (PU) can be adapted to or employed in the practice of the instant invention (see, e.g., Campochiaro et al., Human Gene Therapy 17:167-176 (February 2006)). Adenoviral vector-mediated RNA transfer appears to be a viable approach for delivery of RNA(S). For adenoviral vector injections into a rat, $2 \times 10^9$ infectious particles were injected in 3 ml of normal saline solution (NSS). This can be adapted to or extrapolated from in the practice of the present invention. For siRNA, a rat was injected into the great saphenous vein with 12.5 µg of a siRNA and a primate was injected into the great saphenous vein with 750 µg of a siRNA. This can be adapted to or extrapolated from in the practice of the present invention.

Accordingly, the invention contemplates amongst vector(s) useful in the practice of the invention: viral vectors, including retroviral vectors, lentiviral vectors, adenovirus vectors, or AAV vectors.

Several types of particle and nanoparticle delivery systems and/or formulations are known to be useful in a diverse spectrum of biomedical applications; and particle and nanoparticle delivery systems in the practice of the instant invention can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semi-conducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. Doses of about 5 mg/kg are contemplated, with single or multiple doses, depending on the target tissue. It is mentioned herein experiments involving mice involve 20 g mammals and that dosing can be scaled up to a 70 kg human. With regard to nanoparticles that can deliver RNA, see, e.g., Alabi et al., Proc Natl Acad Sci USA. 2013 Aug. 6; 110 (32):12881-6; Zhang et al., Adv Mater. 2013 Sep. 6; 25(33): 4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93. Lipid Nanoparticles, Spherical Nucleic Acid (SNA™) constructs, nanoplexes and other nanoparticles (particularly gold nanoparticles) are also contemplate as a means for delivery of CRISPR/Cas system or component(s) thereof or vector(s) to intended targets. Particles, nanoparticles, and the like and vectors are advantageous for delivering the RNA(s) of the CRISPR-Cas9 system and particles and nanoparticles and the like may be advantageous for delivery of vector containing nucleic acid(s) encoding or comprising RNA(s) of the invention. In certain instances, e.g., where Cas9 is constitutively or inducibly or conditionally expressed by an organism or cells thereof, it is useful to deliver the RNA(s) (also herein sometimes termed "guides") of the CRISPR-Cas9 system separately from the Cas9. It is considered as advantageous that the Cas9 may be delivered via a viral vector or be constitutively or inducibly or conditionally expressed and that guides specific to genomic targets are delivered separately. A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric nanoparticles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like nanoparticles, the nanoparticle formulation they used (termed 7C1), differed from traditional lipid-based nanoparticle formulations because it can deliver siRNA to lung endothelial cells at low doses without substantially reducing gene expression in pulmonary immune cells, hepatocytes or peritoneal immune cells. The study further demonstrated that that 7C1-mediated endothelial gene silencing affects function in vivo, by using the nanoformulation to modify mouse models of vascular permeability, emphysema, lung tumor growth and lung metastasis. To Applicants knowledge, the present studies are the first to describe successful in vivo use of a nanoparticle formulation in the context of CRISPR-Cas to achieve functional gene silencing. In the present studies, Applicants have formulated the 7C1 nanoparticle to mediate delivery of sgRNA to constitutively active Cas9 mouse. Synthesis of the 7C1 nanoparticle is described in Dahlman et al., 2014, Nature Nanotechnology.

Kits: In an aspect, the invention provides kits containing any one or more of the elements discussed herein. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow the provision of all elements of the systems of the invention. Kits can involve vector(s) and/or particle(s) and/or nanoparticle(s) containing or encoding RNA(s) for 3-50 or more mutations to be administered to a non-human transgenic Cas9 eukaryote, e.g., animal, mammal, primate, rodent, etc., with such a kit including instructions for administering to such a eukaryote; and such a kit can optionally include a transgenic Cas9 eukaryote, or when such a transgenic Cas9 eukaryote has Cas9 expression that is inducible or conditional, e.g., Cre-dependent, the kit may also include a mate that expresses the compound that induces or is the trigger or condition for Cas9 expression, e,g, Cre, either throughout all cells or in only certain cells or tissue, whereby offspring of the eukaryotes express of Cas9, e.g., in specific tissues or throughout most or all or nearly all cells, whereby the kit can include instructions for mating and then administering.

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$ allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4th Ed.—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table 1 below which describes a generally accepted Venn diagram grouping of amino acids.

TABLE 1

| Set | | Sub-set | |
|---|---|---|---|
| Hydro-phobic | F W Y H K M I L V A G | C Aromatic<br>Aliphatic | F W Y H<br>I L V |
| Polar | W Y H K R E D C S T N | Q Charged<br>Positively charged<br>Negatively charged | H K R E D<br>H K R<br>E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 26). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Banerji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the a-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena,* and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736, 465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Cas9 Transgenic and Knock in Mice

Reference is made to WO 2014/093622 (PCT/US13/74667), incorporated herein by reference. To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence. The conditional version has one additional stop cassette element, loxP-SV40 polyA x3-loxP, after the promoter and before NLS-Cas9-NLS (i.e. pCAG-loxP-SV40polyAx3-loxP-NLS-Cas9-NLS-P2A-EGFP-WPRE-bGHpolyA). The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 2: Modeling Competition of Multiple Cancer Mutations In Vivo Using a Conditional CRISPR-Cas9 Mouse The genomes of cancer cells encompass complex combinations of genetic lesions (Weinberg 2007). These genetic lesions usually include oncogenic gain-of function mutations, as well as loss-of-function (LOF) mutations that inactivate tumor suppressor genes (Garraway and Lander 2013). Large-scale cancer sequencing efforts have identified several common oncogenic mutations, such as Kirsten rat sarcoma viral oncogene (KRAS) and epithelial growth factor receptor (EGFR) (Govindan et al. 2012; Lawrence et al. 2013). Tumor suppressor genes that are significantly mutated in human cancers are on the order of dozens to hundreds in various patient cohorts, with the most common being tumor protein p53 (TP53 or P53), phosphatase and tensin homolog (PTEN), and serine/threonine kinase 11 (STK11, LKB1) (Govindan et al. 2012; Ji et al 2007; Lawrence et al. 2013). The genome of a sequenced tumor often encompasses different combinations of multiple mutations. Cells harboring these mutations might co-exist, cooperate or compete in a heterogeneous tumor (Weinberg 2007). A major challenge facing the continued study of cancer genetics is distinguishing which mutations are driving the tumor ("drivers") from those that are not ("passengers") (Garraway and Lander 2013; Lawrence et al. 2013). The difficulty of elucidating these distinctions in non-human eukaryote, e.g., animal models lies in precisely measuring the influence of specific mutations throughout tumor evolution.

The present invention relates to targeting genes and mutants thereof involved in, for example, signaling pathways as well as molecular characterization of varying cancers, by one or more guide RNAs. Genes (such as the gene encoding Nrf2) involved in malignant carcinomas that recur following therapy are typically de-differentiated and multidrug resistant (MDR) (see, e.g., Del Vecchio et al., PLoS Biol. 2014 Sep. 9; 12(9):e1001945) may be targeted by one or more guide RNAs. Genes involved in rescue of Her2-amplified breast cancer cells from HER2 inhibition or suppression that targeting of HER2 and the BCL-XL/BCL-2 anti-apoptotic pathway (see, e.g., Moody et al., Oncogene. 2014 Jun. 9; 0. doi: 10.1038/onc.2014.153) may be targeted by one or more guide RNAs. Genes (such as the gene encoding PARK2 tumor suppressor and CDK inhibitor p16) involved in regulating cyclin-CDK complexes and a master regulator of the stability of G1/S cyclins (see, e.g., Gong et al., Nat Genet. 2014 June; 46(6):588-94) may be targeted by one or more guide RNAs. Genes having nonrecurrent mutations at different nodes of the Wnt pathway which may contribute to leukemogenesis (see, e.g., Wang et al., Blood. 2014 Aug. 14; 124(7):1089-98) may be targeted by one or more guide RNAs. Genes having oncogenic BRAF(V600) mutations, which constitutively activate the MAPK pathway (see, e.g., Konieczkowski et al., Cancer Discov. 2014 July; 4(7):816-27) may be targeted by one or more guide RNAs. Genes involved in the mitochondrial oxidative phosphorylation (OXPHOS) pathway (see, e.g., Birsoy et al., Nature. 2014 Apr. 3; 508(7494):108-12) may be targeted by one or more guide RNAs. Genes (such as GRB2-associated binding protein 2 (GAB2)) having an ability to promote ovarian tumor formation (see, e.g., Dunn et al., Proc Natl Acad Sci USA. 2014 Jan. 21; 111(3):1102-7) may be targeted by one or more guide RNAs. Genes (such as KRAS, NRAS, BRAF, FAM46C, TP53, and DIS3) having significant mutations and copy number alterations in multiple myeloma (MM) patients (see, e.g., Lohr et al., Cancer Cell. 2014 Jan. 13; 25(1):91-101) may be targeted by one or more guide RNAs. Genes (such as serine/threonine-protein kinase BRAF) involved in RAF-MEK-ERK signaling in maglignant melanomas (see, e.g., Johannessen et al., Nature. 2013 Dec. 5; 504(7478): 138-42) may be targeted by one or more guide RNAs. Genes (such as genes encoding EGFR and PDGFRA) involved in glioblastoma tumor pathways (see, e.g., Brennan et al., Cell. 2013 Oct. 10; 155(2):462-77) may be targeted by one or more guide RNAs. Genes (such as genes encoding H3K36 methyltransferase SETD2) involved in the PI(3)K/AKT pathway, genes (such as PBRM1, ARID1A, SMARCA4) involved in the SWI/SNF chromatin remodelling complex, genes (such as AMPK and PTEN) involved in the TCA cycle, pentose phosphate pathway and the glutamine transporter genes, acetyl-CoA carboxylase protein and MIR21 and GBR10, all of which are implicated in clear cell renal cell carcinoma (see, e.g., Creighton et al., Nature. 2013 Jul. 4; 499(7456):43-9) may be targeted by one or more guide RNAs. Genes (such as the gene encoding Integrin Beta 3 (Itgb3)) involved in MLL-AF9 acute myeloid leukemia (AML) (see, e.g., Miler et al., Cancer Cell. 2013 Jul. 8; 24(1):45-58) may be targeted by one or more guide RNAs. Genes (such as genes encoding ribosomal S6 kinases RPS6KA2 (RSK3) and RPS6KA6 (RSK4)) involved in the PI3K signaling pathway in breast cancer (see, e.g., Serra et al., J Clin Invest. 2013 Jun. 3; 123(6):2551-63) may be targeted by one or more guide RNAs. Genes (such as genes encoding transcription factors (TFs) and ASCL1) involved in activation of developmental transcription factors (TFs) involved in gioblastoma (GBM), such as Wnt signaling, (see, e.g., Rheinbay et al., Cell Rep. 2013 May 30; 3(5): 1567-79) may be targeted by one or more guide RNAs.

Genes (such as genes having a TERT promoter region) involved in somatic genomic alterations of 66 chromophobe renal cell carcinomas (ChRCCs) (see, e.g., Davis et al., Cancer Cell, Volume 26, Issue 3, p319-330, 8 Sep. 2014) may be targeted by one or more guide RNAs. Genes identified in an integrative analysis using five genome-wide platforms and one proteomic platform on 3,527 specimens from 12 cancer types as described in Hoadley et al., Cell, Volume 158, Issue 4, p929-944, 14 Aug. 2014 may be targeted by one or more guide RNAs. Genes involved in molecularly classified gastric cancer, such as tumors positive for Epstein-Barr virus, which display recurrent PIK3CA mutations, extreme DNA hypermethylation, and amplification of JAK2, CD274 (also known as PD-L1) and PDCD1LG2 (also known as PD-L2); microsatellite unstable tumours, which show elevated mutation rates, including mutations of genes encoding targetable oncogenic signalling proteins; genomically stable tumours, which are enriched for the diffuse histological variant and mutations of RHOA or fusions involving RHO-family GTPase-activating proteins; and tumours with chromosomal instability, which show marked aneuploidy and focal amplification of receptor tyrosine kinases (see, e.g., Bass et al., Nature 513, 202-209 (11 Sep. 2014) may be targeted by one or more guide RNAs. Genes (such as RIT1 activating mutations, loss-of-function MGA mutations, MYC amplification, EGFR mutations, RBM10 mutations, NF1, MET, ERBB2 and RIT1 aberrations, exon skipping in MET mRNA, genes in the MAPK and PI(3) pathway)) involved in adenocarcinoma of the lung (see, e.g., Meyerson et al., Nature 511, 543-550 (31 Jul. 2014)) may be targeted by one or more guide RNAs. Genes involved in the phosphatidylinositol-3-OH kinase/AKT/mTOR pathway and targets (including ERBB2) in the RTK/MAPK pathway in urothelial carcinoma of the bladder (see, e.g., Weinstein et al., Nature 507, 315-322 (20 Mar. 2014)) may be targeted by one or more guide RNAs. Genes (such as genes encoding EGFR and PDGFRA, genes having TERT promoter mutations, genes responsible for a G-CIMP phenotype and MGMT DNA methylation) involved in somatic genomic alterations of glioblastoma tumors (GBMs) (see, e.g., Brennan et al., Cell, Volume 155, Issue 2, 10 Oct. 2013, Pages 462-477) may be targeted by one or more guide RNAs. Genes involved in the PI(3)K/AKT pathway, genes (such as genes encoding PBRM1, ARID1A, SMARCA4) involved in the SWI/SNF chromatin remodelling complex, genes (such as genes encoding AMPK and PTEN) involved in the TCA cycle, genes involved in the pentose phosphate pathway, genes involved in glutamine transport and genes encoding proteins such as acetyle-CoA carboxylase protein, altered promoter methylation of miR-21 (MIR21) and GRB10 (see, e.g., Linehan et al., Nature 499, 43-49 (4 Jul. 2013)) may be targeted by one or more guide RNAs. Genes having mutations in TP53 PTEN, CTNNB1, PIK3CA, ARID1A, KRAS SWI/SNF chromatin remodelling complex gene ARIDSB and POLE involved in endometrial carcinomas (see, e.g., Levine et al., Nature 497, 67-73 (2 May 2013)) may be targeted by one or more guide RNAs. Genes having mutations in FLT3, NPM1, KIT, CEBPA, TET2, DNMT3A, IDH1/2 involved in acute myeloid leukemia (AML) (see, e.g., Ley et al., N Engl J Med 2013; 368) may be targeted by one or more guide RNAs. Genes (such as TP53, PIK3CA, GATA3, GATA3, PIK3CA and MAP3K1 and genes having a HER2/phosphorylated HER2/EGFR/ phosphorylated EGFR signature within the HER2-enriched expression subtype) involved in primary breast cancers (see, e.g., Koboldt et al., Nature 490, 61-70 (4 Oct. 2012) may be targeted by one or more guide RNAs. Genes (such as TP53, HLA-A class I major histocompatibility gene, NFE2L2, KEAP1, squamous differentiation genes, phosphatidylinositol-3-OH kinase pathway genes, CDKN2A and RB1) involved in lung squamous cell carcinoma (see, e.g., Meyerson et al., Nature 489, 519-525 (27 Sep. 2012) may be targeted by one or more guide RNAs. Genes (such as MLH1, POLE, APC, TP53, SMAD4, PIK3CA, KRAS, ARID1A, SOX9, FAM123B, ERBB2, IGF2 and TCF7L1) involved in colorectal carcinoma (see, e.g., Kucherlapati et al., Nature 487, 330-337 (19 Jul. 2012)) may be targeted by one or more guide RNAs. Genes (such as BRCA1, BRCA2, RB1, CDK12, CCNE1) and genes involved in NOTCH and FOXM1 signalling involved in ovarian cancer (see, e.g., Spellman et al., Nature 474, 609-615 (30 Jun. 2011)) may be targeted by one or more guide RNAs. Genes having concerted hypermethylation at a large number of loci, indicating the existence of a glioma-CpG island methylator phenotype (G-CIMP) and IDH1 somatic mutations (see, e.g., Noushmehr et al., Cancer Cell, Volume 17, Issue 5, 18 May 2010, Pages 510-522) may be targeted by one or more guide RNAs. Genes (such as EGFR, NF1, and PDGFRA/IDH1) involved in glioblastoma multiforme (GBM) (see, e.g., Verhaak et al., Cancer Cell, Volume 17, Issue 1, 19 Jan. 2010, Pages 98-110) may be targeted by one or more guide RNAs. Genes (such as ERBB2, NF1, TP53, PIK3R1) and MGMT promoter methylation involved in glioblastomas (see, e.g., Chin et al., Nature 455, 1061-1068 (23 Oct. 2008)) and may be targeted by one or more guide RNAs.

The present invention encompasses targets exemplified in Lawrence et al. 2013 including, but not limited to, ABCB1, ABCD2, ACSM2B, ADAM18, ADAM2, ADAMTS12, ADAMTS16, ADAMTS20, ADCY2, ADCY8, ALPK2, ANKRD30A, ANKS1B, APBA2, APOBEC1, ASB17, ASB5, ASCL4, ASTN1, ATP10A, BAGE2, BAI3, BCHE, BCLAF1, BEND4, BMP5, C15orf2, C1orf173, C20orf26, C6, C6orf138, C6orf97, C8orf22, C8orf34, C9orf79, CADPS2, CALCR, CALN1, CBLN4, CCDC141, CCDC39, CCDC85A, CCT8L2, CD163, CD209, CD5L, CDH10, CDH12, CDH18, CDH8, CDH9, CDKN2A, CFHR4, CLEC3A, CLEC4C, CLRN2, CLSTN2, CLVS2, CNGB3, CNTN5, CNTNAP2, CNTNAP4, CNTNAP5, COL11A1, COL19A1, COL22A1, COLEC12, COX7B2, CPS1, CPXCR1, CPZ, CRB1, CSF2RA, CSMD1, CSMD3, CTNNA2, CTNND2, CUBN, CUL3, CYP11B1, CYP1A1, DACH2, DCAF12L1, DCAF4L2, DCUN1D1, DNAH11, DNAH5, DPP10, DPPA2, DPPA4, DSTN, ELTD1, EPB41L3, EPHA5, EPHA6, EPHB1, ESRRG, EYS, F13B, FAM123C, FAM135B, FAM159A, FAM47A, FAM47C, FAM58B, FAM5B, FAM5C, FAT1, FBXO22, FBXW7, FCAR, FLG, FLRT2, FMN2, FSCB, FSHR, FSTL5, FTHL17, FTMT, FYB, GABRA2, GABRB3, GABRG1, GABRG3, GALNT13, GAP43, GBA3, GFRAL, GLUD2, GLYATL1, GP2, GPCS, GPR174, GREM2, GRID2, GRIN2A, GRM3, GRMS, GRM8, GRXCR1, GUCY1A2, HAO1, HCN1, HDAC9, HEATR7B2, HEPH, HLA-A, HRNR, HSPB8, IFI44L, IL7R, INTS1, KCND2, KCNJ3, KCNN2, KDR, KEAP1, KIF2B, KLHL1, LEPROT, LILRA2, LPHN3, LRFNS, LRP1B, LRP2, LRRC4C, LRRC7, LRRK2, LRRTM1, LRRTM4, MAGEA6, MAGEB18, MAGEB2, MAGEB4, MAGEC1, MAGEC3, MCOLN3, MDGA2, MGC26647, MLL2, MMP16, MNDA, MS4A14, MS4A6E, MTNR1B, MUC16, MUC4, MYF5, MYH1, MYH2, MYH4, MYH8, MYT1L, NAV3, NCAM2, NDN, NDST4, NEUROD6, NFE2L2, NLGN1, NLRP13, NLRP4, NOTCH1, NOTCH2NL, NRK, NRXN1, NTM, NUCB2, OLFM3, OR10A4, OR10AG1, OR10G8, OR10G9, OR10Q1, OR11L1, OR14A16, OR14C36, OR1C1, OR1J4, OR2A5, OR2AK2, OR2B11, OR2B3, OR2G3, OR2G6, OR2L2, OR2L8, OR2M2, OR2M3, OR2M7, OR2T1, OR2T11, OR2T12, OR2T2, OR2T3, OR2T33, OR2T34, OR2T4, OR2T6, OR2T8, OR4A15, OR4A16, OR4C11, OR4C12, OR4C13, OR4C16, OR4C3, OR4C46, OR4C6, OR4D11, OR4D2, OR4D5, OR4F6, OR4K1, OR4K15, OR4K5, OR4M1, OR4M2, OR4N2, OR4N4, OR4P4, OR4Q3, OR4S2, OR51B2, OR51L1, OR51L1, OR51S1, OR52A5, OR52E2, OR52E6, OR52J3, OR56A1, OR56A4, OR5AC2, OR5AS1, OR5B12, OR5B2, OR5D14, OR5D16, OR5D18, OR5F1, OR5H14, OR5H6, OR5I1, OR5J2, OR5K1, OR5L1, OR5L2, OR5M11, OR5M9, OR5T1, OR5T3, OR5W2, OR6F1, OR6K2, OR6K3, OR6M1, OR6N1, OR8A1, OR8B2, OR8B4, OR8H1, OR8H2, OR8H3, OR812, OR8J1, OR8J3, OR8K3, OR9A2, OR9G9, ORCS1, ORCS3, PAPPA2, PARK2, PCDH10, PCDH11X, PCDH15, PCDHB10, PCLO, PDE1C, PDHA2, PDILT, PDYN, PEG3, PHACTR3, PIK3CA, PIK3CG, PKHD1, PKHD1L1, PLCH1, PNLIP, PNLIPRP3, POTEA, POTEE, POTEG, POTEH, PPFIA2, PPP1R3A, PRB1, PRDM9, PREX2, PRIM2, PRR23B, PRSS23, PSG2, PSG6, PTEN, PTPRT, PXDNL, PYHIN1, RB1, REG1A, REG1B, REG3A, REG3G, RELN, RGS7, RHAG, RIMS2, RNF144A, RP1, RPL10L, RSPO2, RSRC1, RTN1, RUNX1T1, RYR2, RYR3, SALL3, SCN1A, SCN7A, SERPINA4, SGCD, SI, SLC13A1, SLC17A8, SLC8A1, SLCO1B1, SLCO1B3, SLCO1C1, SLITRK3, SLITRK5, SPAG11A, SPANXN1, SPANXN2, SPATA8, SPHKAP, SPRYD5, SPTA1, ST8SIA6, STON1-GTF2A1L, SYCP1, TAF1L, TAS2R60, TBX18, TBX22, TDRD5, TECRL, TEX13A, TGIF2LX, THEMIS, THSD7A, THSD7B, TKTL2, TMEM132D, TNN, TNR, TP53, TPTE, TPTE2, TRAT1, TRDN, TRHDE, TRIM58, TRPA1, TSHZ3, TTN, TTPA, TYR, UBE2NL, UGT2B4, UGT3A2, UNC13C, UNC5D, USH2A, USP29, VN1R5, WDR17, WHSC1L1, XIRP2, ZBBX, ZC4H2, ZFHX4, ZFP42, ZIC1, ZNF208, ZNF230, ZNF257, ZNF33A, ZNF479, ZNF534, ZNF536, ZNF665, ZNF676, ZNF80, ZNF804A, ZNF804B, ZNF91, ZNF99 and/or ZSCAN5B which may be targeted by one or more guide RNAs.

Based upon genes significantly mutated in human cancer identified by The Cancer Genome Atlas (TCGA) or Cancer Cell Line Encyclopedia (CCLE) (see, e.g., Barretina et al., Nature. 2012 Mar. 28; 483(7391):603-7), bioinformatics may be utilized to identify genes of interest and to target by, for example, intersection with known pathways, ranked frequency of mutations or alterations and/or mutation-type based oncogene vs tumor suppressor genes for gain of function (GOF) and loss of function (LOF) studies Experimental modeling of cancer mutations in animals enables the study of the effects of specific mutagenic events, involving oncogenes and tumor suppressor genes, in tumor progression (Frese and Tuveson 2007; Jackson et al 2001; Ji et al 2007; Johnson et al. 2001). Due to the complexity of the cancer genome, single mutations rarely account for the totality of tumor evolution, whereby additional mutations almost always occur. (Kandoth et al. 2013). Models involving simultaneous introduction of multiple lesions in the same animal more closely recapitulate the genetic combinations in an evolving tumor, which are challenging due to exponential increase in the number of genetic crosses required to generate the desired genotype. Here, Applicants use Cas9-mediated genome editing in vivo to model the dynamics of multiple mutations in lung cancer in mice.

The CRISPR (clustered regularly interspaced short palindromic repeat)-associated endonuclease Cas9 from *Streptococcus pyogenes* (SpCas9, abbreviated as Cas9 throughout this paper) has been recently harnessed for genome editing by facilitating targeted DNA double strand breaks (DSBs) in mammalian cells (Cong et al. 2013; Mali et al. 2013). DSBs are subsequently repaired by the non-homologous end-joining (NHEJ) pathway to accumulate insertions and deletions (indels), or, in the presence of a repair template, by the homology directed repair (HDR) pathway to achieve precise sequence substitution. The targeting specificity of Cas9 is specified by RNAs to guide Cas9 comprise CRISPR RNA and transactivating (tracr) RNA (sometimes collectively referred to as a pair of CRISPR RNAs) or a single guide RNA (sgRNA) (see Deltcheva et al. 2011; Gasiunas et al. 2012; Jinek et al. 2012). A unique advantage of the Cas9 system is that the Cas9 enzyme can be combined with multiple sgRNAs to achieve efficient multiplex genome editing at multiple loci simultaneously (Cong et al. 2013; Wang et al. 2013), therefore making it possible to study multigenic processes such as the role of gene combinations in tumor evolution.

Fully realizing the potential of the Cas9 system in vivo will be challenging given that its large size (4.1 kb) will severely limit delivery options. The hydrodynamic delivery technique was applied to deliver Cas9 in vivo (Xue et al. 2012), but this technique is inefficient and only limited to hepatocytes within the mouse liver. Viral delivery enables targeting of more tissues, while the insertion is constrained by the packaging capacity, which will limit the number of sgRNAs, HDR donors, and other elements that will fit within the same vector as Cas9. For example, lentivirus was used to deliver Cas9 in vitro (Shalem et al. 2014) but this leaves little space for other elements. Lentiviruses are also prone to recombination if multiple repetitive elements are present (Dull et al. 1998). Adeno-associated viral (AAV) vectors are DNA-based and not prone to recombination, making the expression of multiple U6-sgRNA cassettes feasible. To facilitate the in vivo application of Cas9-mediated genome editing in tumor development, Applicants generated a Cre-conditional Cas9 mouse model, which facilitates rapid and efficient modeling of single and multigenic mutations in specific tissue and cell types of interest.

In this model, Cas9 is already present and dormant within the genome of all cells, which opens up a larger capacity for delivery of sgRNAs as well as other elements. Applicants combined this conditional Cas9 mouse with AAV vector-mediated expression of sgRNAs in the lung to study the combinatorial contribution of mutations during tumor evolution.

Here, Applicants chose to model lung cancer using a combination of the Kras oncogene and two tumor suppressor genes, p53 and Lkb1 (Stk11). Applicants chose this combination because, first, KRAS is the major oncogenic driver in human lung cancers (Pylayeva-Gupta et al. 2011: Weinberg 2007); second, p53 is the most-frequently mutated tumor suppressor gene in lung adenocarcinoma (TCGA-Network 2014; Weinberg 2007); and third, LKB1 is the second most-frequently mutated tumor suppressor gene in lung adenocarcinoma (TCGA-Network 2014) and a potent factor that modulates cancer cell growth and metabolism (Shakelford and Shaw, 2009). Moreover, both p53 and Lkb1 have been shown to modulate Kras-driven lung cancer progression by conventional Cre-LoxP targeting in transgenic mice (Jackson et al 2001; Ji et al 2007). In a recent large-cohort adenocarcinoma sequencing study by The Cancer Genome Atlas (TCGA), p53 (46%), KRAS (33%) and LKB1 (17%) stand out as the top three most frequently mutated genes (TCGA-Network 2014) and a potent factor that modulates cancer cell growth and metabolism (Shackelford and Shaw, 2009). Moreover, both p53 and Lkb1 have been shown to modulate Kras-driven lung cancer progression by conventional Cre-LoxP targeting in transgenic mice (Jackson et al., 2001; Ji et al., 2007). In a recent large-cohort adenocarcinoma sequencing study by The Cancer Genome Atlas (TCGA), p53 (46%), KRAS (33%) and KLB1 (17%) stand out as the top three most frequently mutated genes (TCGA-Network, 2014). To model the dynamics of mutations in these three genes, Applicants built a single-vector that is capable of generating $Kras^{G12D}$ mutations while simultaneously knocking out two tumor suppressors, p53 and Lkb1, in conditional Cas9 mice. Mice receiving this virus developed macroscopic tumors in the lung within two months. These tumors have a spectrum of grades I and II adenomas, to grades III and IV adenocarcinomas showing clear signs of angiogenesis, aneuploidy, and invasion. Dissection of the fast-growing tumors showed the majority of mutations being p53 and Lkb1 LOF mutations.

Results

Generation of a Rosa26-LSL-Cas9 Knock-in Transgenic Mouse

Figure 6:
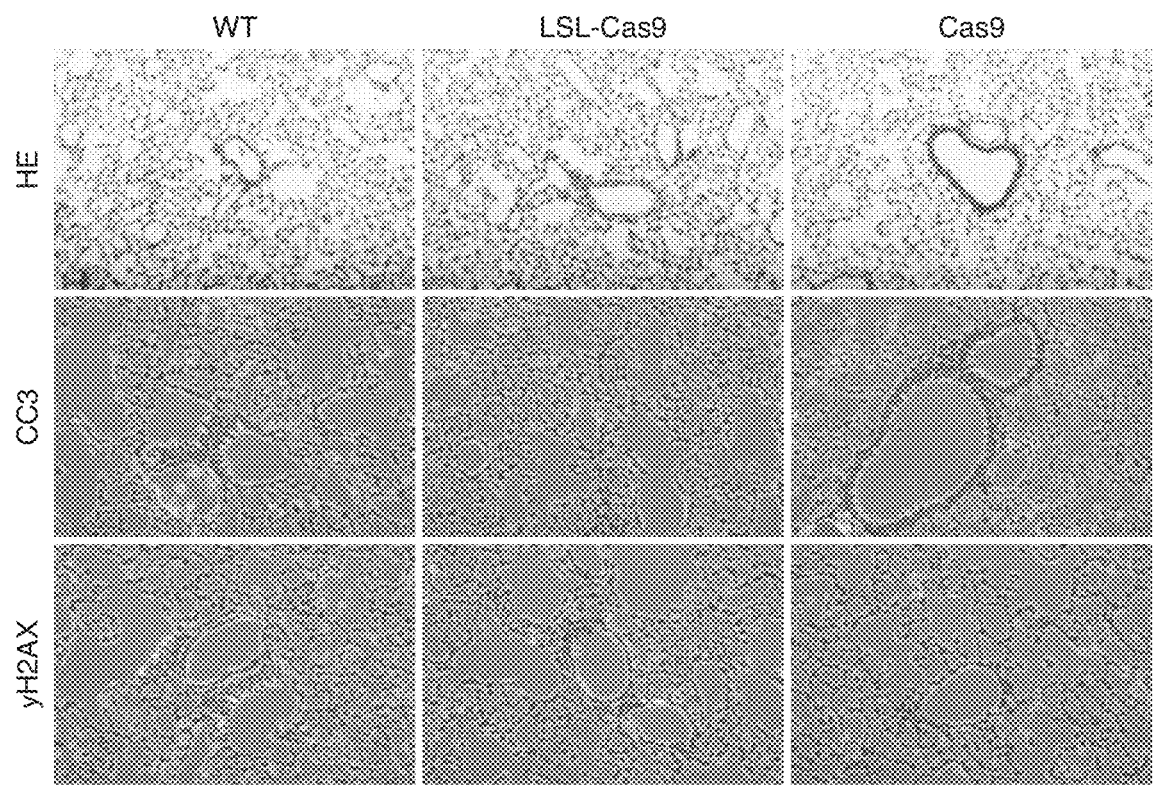
FIG. 6 shows toxicity analysis in constitutive Cas9 mouse tissue. HE and IHC images show no difference between wild-type and constitutively active R26C9-Cas9 mice suggesting that there is no toxicity inducing tumor formation in the absence of targeted sgRNAs.

In order to facilitate efficient and uniform expression of Cas9 in vivo, Applicants generated a transgenic mouse line with a conditional Cas9 transgene knocked into the Rosa26 locus (Rosa26-LSL-Cas9 mouse). To facilitate visualization of Cas9-expressing cells, the transgene consists of a 3×FLAG-tagged mammalian codon-optimized Cas9 from *Streptococcus pyogenes* linked via a self-cleavage linker P2A to an enhanced green fluorescent protein (EGFP). The transgene is driven by the ubiquitous CAG promoter and is interrupted by a Lox-Stop-polyA-Lox (LSL) cassette to render Cas9 expression inducible by the Cre recombinase (FIG. 1A). Crossing of the Rosa26-LSL-Cas9 mouse with a beta-actin-Cre mouse line derived constitutive Cas9 expressing lines (Rosa26-Cas9 mouse) (FIG. 1B-D). All progenies successfully bred for five generations and whole-body wide tissue analysis did not reveal any tumor formation, suggesting that constitutive Cas9 expression is well tolerated and, by itself, does not contribute to tumorigenesis. More specifically for this study, comparison of lung tissue from wild-type as well as the Rosa26-Cas9 mice did not reveal any increased levels of genome instability or cellular toxicity (FIG. 6).

AAV9 Mediates Efficient Transgene Expression in the Lung

Figure 7:
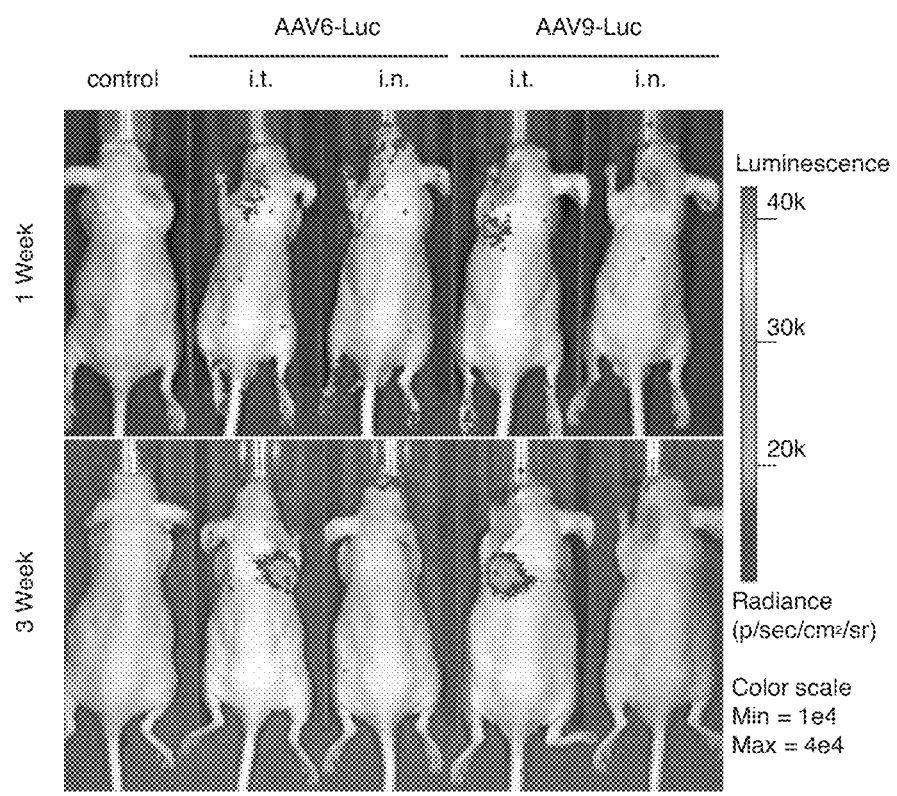
FIG. 7 shows AAV delivery optimization. Comparison of AAV serotypes and routes of delivery using live animal in vivo luciferase imaging. Using a constitutively active Firefly luciferase AAV virus nude mice were injected by the AAV serotype and route shown and imaged at one and three weeks.

AAV has been widely used as a gene delivery vehicle for transgene expression in the lung. It has also been shown by several studies that HDR efficiency is improved when the repair template is delivered in the form of AAV (Bell et al 2011; Limberis and Wilson 2006). To evaluate the efficacy of AAV-mediated gene delivery to the lung in mice, Applicants packaged a Firefly luciferase (Fluc) expression vector using two different serotypes of AAV (AAV6-Fluc and AAV9-Fluc) that have been shown previously to be capable of transducing the lung efficiently (Bell et al 2011; Halbert et al 2002; Limberis and Wilson 2006) and delivered the viruses using both intranasal (i.n.) and intratracheal (i.t.) methods (FIG. 2A). Using in vivo luminescence imaging, Applicants detected luciferase activity in the lung one week after i.t. delivery of AAV9-Fluc, but not for AAV6-Fluc. Both AAV6-Fluc and AAV9-Fluc showed positive signal in the lung by three weeks but AAV9 showed higher intensity (FIG. 2B and FIG. 7). Based on these data, Applicants chose i.t. delivery of AAV9 vectors for all subsequent in vivo studies.

A Single-Vector Mediates Knockout of p53, and Lkb1 and Targeted Mutation of Kras$^{G12D}$ In order to test the role of Kras, p53, and Lkb1 in tumor formation, Applicants designed multiple sgRNAs targeting early exons for each of the three mouse genes using a previously developed informatics tool (Hsu et al. 2013). To select an effective sgRNA for each gene, Applicants individually expressed each sgRNA as well as Cas9 in the cancer cell lines (N2a) and quantified the editing efficiency of each sgRNA using the SURVEYOR nuclease assay. Most of these sgRNAs are capable of inducing cleavage of specific targeted loci (FIG. 8A). Applicants chose one sgRNA for each of the three genes and then generated a single vector containing U6 expression cassettes for all three sgRNAs. Transient transfection of this single vector resulted in significant cleavage in all three genes (35% Kras, 44% p53, and 30% Lkb1) (FIG. 2C and FIG. 8B-C).

While p53 and Lkb1 mutations in patient tumors are often loss-of-function in nature, mutations in the Kras gene are often missense mutations that lead to gain-of-function (TCGA-Network 2014). To model a missense Kras mutation, Applicants designed an HDR donor template, which consists of an 800 basepair (bp) genomic sequence homologous to a region flanking the first exon of the mouse Kras gene. This HDR donor encodes (1) a glycine (G) to aspartate (D) mutation in the 12$^{th}$ amino acid position (G12D) resulting in the oncogenic Kras$^{G12D}$ mutation, (2) eleven synonymous single nucleotide changes for enhanced clarity for distinguishing between the donor and wild-type sequence, and (3) protospacer adjacent motif (PAM) mutations to prevent Cas9 cleavage of the donor. To simplify in vivo delivery, Applicants generated a single AAV vector integrating the HDR donor, the triple U6-sgRNA cassettes, as well as an expression cassette containing Cre recombinase and Renilla luciferase (AAV-sgKPL-HDR, FIG. 2C). The expression of luciferase enables simple and non-invasive monitoring of tumor expansion.

To test the efficacy of HDR-mediated missense mutation in Kras, Applicants used deep sequencing to assess the rate of G12D incorporation. As a result Applicants detected sequencing reads that identically matched the donor sequence, which included the G12D mutation and synonymous mutations, at 4% frequency in vitro (FIG. 9). Collectively, these data indicated that the single vector can stimulate HDR events to induce Kras$^{G12D}$ mutations as well as facilitate efficient editing of the p53 and Lkb1 genes in vitro.

The Single AAV9-sgKPL-HDR Vector Induces Indels and HDR in the Lung

Applicants packaged AAV-sgKPL-HDR using AAV9 and delivered i.t. into Rosa26-LSL-Cas9 mice. At four weeks post delivery, lungs were harvested from the AAV9-sgKPL-HDR transduced animals and control animals transduced with AAV9-sgLacZ (a non-specific sgRNA control), and characterized by Illumina sequencing (FIG. 2A). Applicants identified indels in p53 and Lkb1 at the predicted cutting site (FIG. 2D-E), with an average of 1.3% for each gene in the whole lung. A large fraction of these indels potentially disrupt the endogenous gene function because they are mostly out of frame (i.e. 3n+1 bp or 3n+2 bp in length) (FIG. 2D-E). This is an underestimate because some indels without frame-shifting lengths (i.e. 3n bp) are also inactivating mutations. Furthermore, Applicants detected Kras$^{G12D}$ HDR events in the genomes of the lung cells as indicated by the synonymous-SNP-barcoded G12D reads (FIG. 2F). The frequency of indels in p53, and Lkb1 and targeted Kras$^{G12D}$ mutations increase over time (FIG. 2G-H). These data suggested that delivery of AAV9-sgKPL-HDR into the lungs of Rosa26-LSL-Cas9 mice generate the Kras$^{G12D}$ mutation and putative LOF mutations in p53 and Lkb1, which increase with time.

The Single AAV9-sgKPL-HDR Vector Generates Tumors in the Lung of Rosa26-LSL-Cas9 Mice To investigate the phenotypic effect of delivery of the four-component vector, the animals were imaged by micro-computed tomography (μCT). Two months post transduction all (5/5=100%) AAV9-sgKPL-HDR treated animals developed nodules in the lung, while none (0/5=0%, fisher's exact test, one-tail, p=0.008) of the AAV9-sgLacZ treated animals showed detectable nodules (FIG. 3A-B). Quantification showed that the average total tumor burden at two months was approximately 33 mm$^3$ (FIG. 3C), which is close to 10% of the total lung volume (Mitzner et al 2001).

After sacrificing and dissecting the lungs of these animals, Applicants observed multiple tumor nodules in AAV9-sgKPL-HDR but not AAV9-sgLacZ treated mice (FIG. 3D). Moreover, certain lobes are dominated by one large tumor, while others have many tumors of various sizes (FIG. 3D-G). The sizes of these tumors significantly increased over time and ranged from 0.003 to 7.57 mm$^2$ in sectioned area (FIG. 3E). The total tumor area per lobe also significantly increased over time (FIG. 3H). The variation of tumor size distribution suggests dynamic tumor initiation and growth across lobes and animals, which is reminiscent of the complexity observed in human tumors (Herbst et al 2008).

Pathology of Tumors Generated by the AAV9-sgKPL-HDR Vector

Figure 4B:
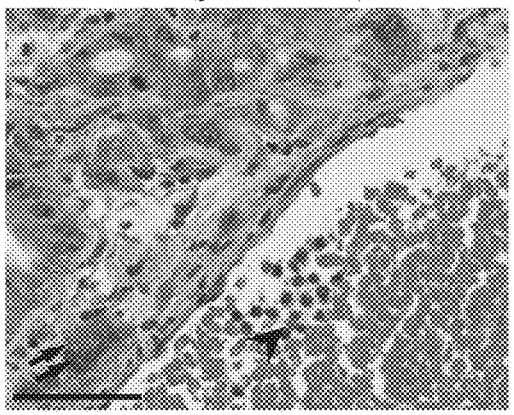
Figure 4C:
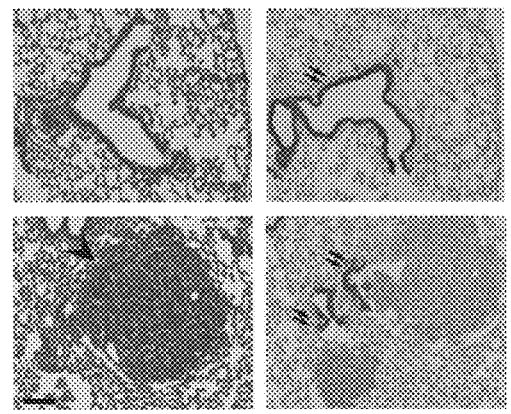
Figure 4D:
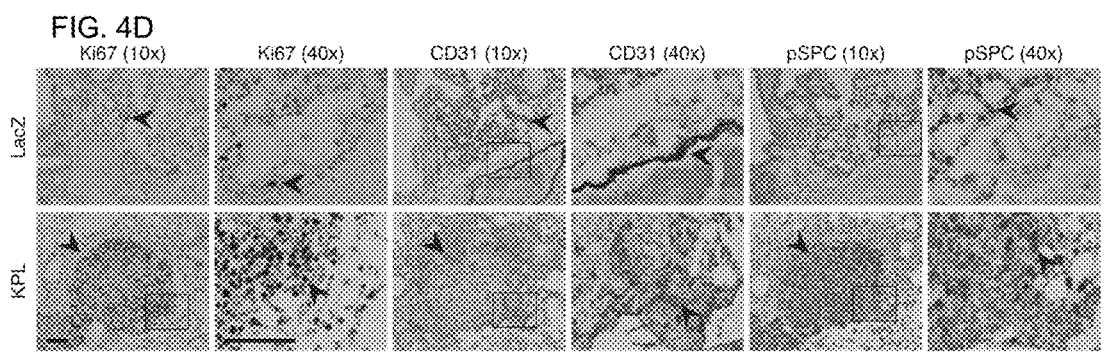
Figure 10:
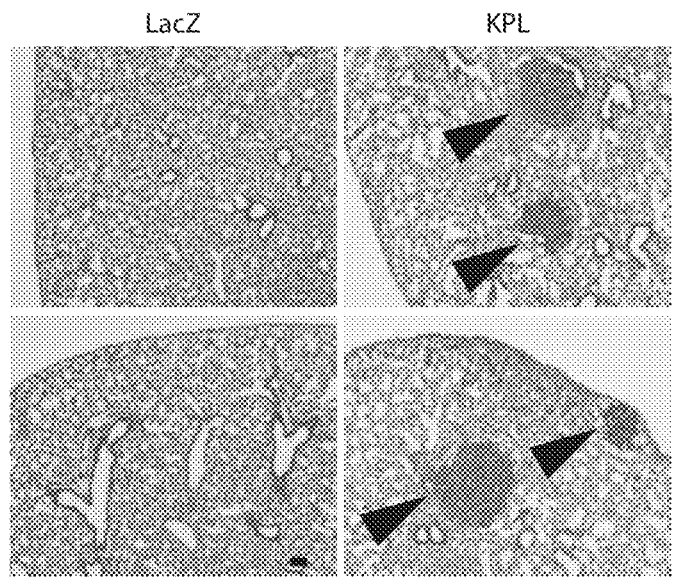
FIG. 10 shows tumor formation in the lungs of AAV9-sgKPL-HDR injected mice. HE staining of lung from AAV9-sgLacZ and AAV9-sgKPL-HDR injected mice after four weeks. Black arrowheads highlight tumors. Scale bar, 100 μm.

To understand the pathology of tumors formed by injection of the AAV9-sgKPL-HDR vector, Applicants performed hematoxylin and eosin (HE) staining and immunohistochemistry (IHC). Pathology showed that lungs of AAV9-sgKPL-HDR treated mice developed multiple grade I and grade II bronchial alveolar adenomas at one month (FIG. 10). In humans this tumor type generally arises from type II pneumocytes (also called alveolar type II cells) at the junction between bronchial and terminal bronchial (Park et al. 2012). These tumors progress to grade III lung adenocarcinomas in two months and occasionally became invasive grade IV adenocarcinomas (FIG. 4A-B). None of the AAV9-sgLacZ mice showed any tumors detectable by histology (FIG. 3D and FIG. 4A, t-test, one-tailed, p=0.004). Clara cell secretory protein (CCSP) staining shows that almost all tumors are adjacent to the clara cells of bronchials (FIG. 4C). In addition, most tumors (178/182=95.7%) stain positive for pro-surfactant C (pSPC), a marker for type II pneumocytes (FIG. 4D), suggesting that most of these tumors originated from this cell type. Many tumor cells also stain positive for Ki67, an indicator of active cell cycle (FIG. 4D), suggesting more rapid proliferation in these tumor cells compared to the rate of natural proliferation in the lung. All higher-grade (grades II to IV) tumors have embedded CD31-positive endothelial cells (FIG. 4D), suggesting these tumors induced angiogenesis. These data suggested that AAV9-sgKPL-HDR delivery generates a spectrum of tumors from bronchial alveolar adenomas to invasive adenocarcinomas in the lungs of Rosa26-LSL-Cas9 mice in less than two months.

Predominant Mutations in Fast-Growing Tumors

Figure 5A:
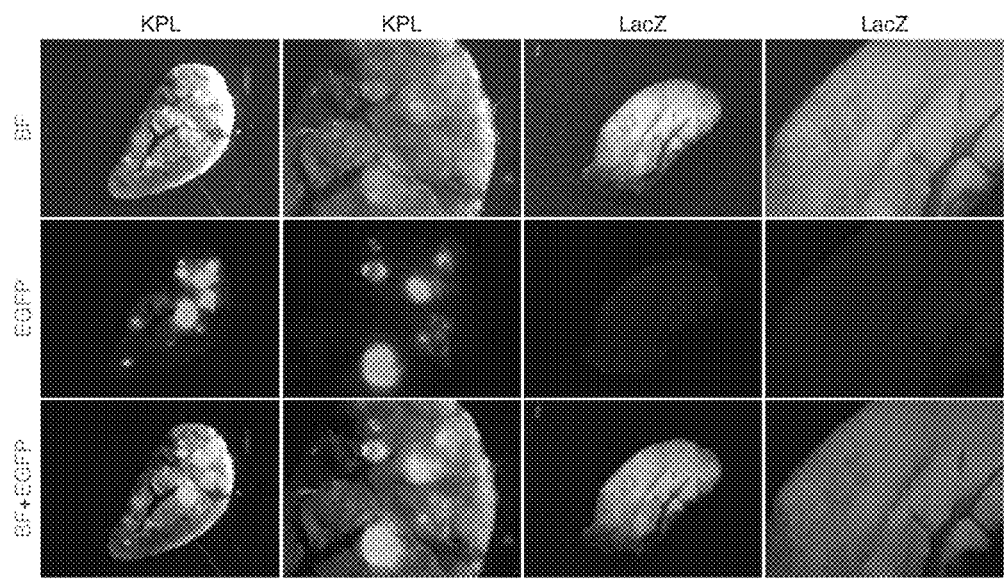
FIG. 5A-B show mutational analysis of individual tumors. (A) Representative stereotactic images showing EGFP+ tumors within the lung of an AAV9-sgKPL-HDR but not AAV9-sgLacZ injected mouse nine weeks post transduction; (B) Kras, p53 and Lkb1 mutational analysis of whole lung and individual tumors dissected from mice injected with AAV9-sgKras-HDR and AAV9-sgLacZ nine weeks post transduction. The data are plotted as percent HDR (Kras) and percent indel (p53 and Lkb1).
Figure 5B:
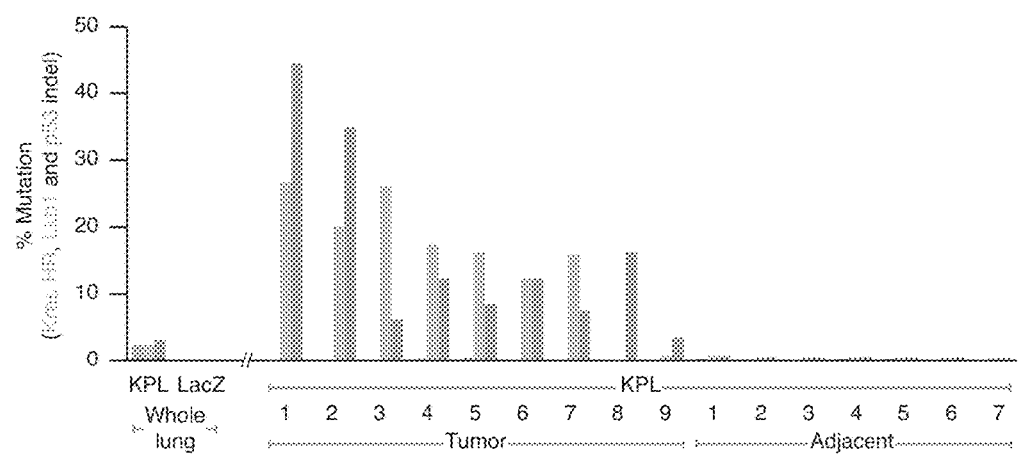

Applicants dissected the largest EGFP+ tumors and adjacent tissues without visible tumors from the lungs of AAV9-sgKPL-HDR treated mice (FIG. 5A), and performed captured sequencing of Kras, p53 and Lkb1 loci. Applicants detected $Kras^{G12D}$ mutations, and p53 and Lkb1 indels in dissected tumors with low background in adjacent tissues (FIG. 5B). The frequencies of p53 or Lkb1 indels in dissected tumors from AAV9-sgKPL-HDR treated animals are highly enriched over whole-lobe, adjacent tissues and AAV9-sgLacZ control, suggesting that p53 and/or Lkb1 LOF are driving the formation of these particular tumors. Interestingly, the frequency of $Kras^{G12D}$ mutations is lower in all dissected tumors compared to whole-lobe tissue (FIG. 5B). Moreover $Kras^{G12D}$ mutations are much lower than the frequencies of p53 and Lkb1 indels. The whole-lobe level shows 0.1% $Kras^{G12D}$ HDR at four weeks and 2% at nine weeks (FIG. 2H), suggesting that $Kras^{G12D}$ mutation frequency increases over time in whole tissue but is not enriched in the large tumors (FIG. 5B). Taken together these data suggest that the dissected tumors do not depend on oncogenic Kras for growth, whereby p53 and/or Lkb1 mutation-containing tumors outcompete $Kras^{G12D}$ containing tumors.

Discussion

Figure 11A:
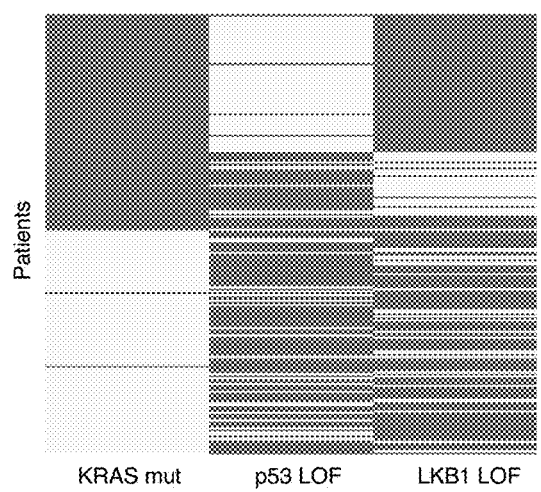
FIG. 11A-B shows co-occurrence of missense KRAS mutations, LOF TP53 mutations and LOF STK11 (LKB1) mutations in TCGA LUAD patients. (A) A co-mutation plot with data from 227 patients' lung adenocarcinomas exome sequencing from TCGA. Each row represents one patient and each mutation was shown as a red bars. Only missense KRAS mutations, LOF TP53 mutations and LOF STK11 (LKB1) mutations were include; (B) A clustering heatmap with data from 227 patients' lung adenocarcinomas exome sequencing from TCGA. Each row represents one patient and each mutation was shown as a red bar. Patients were clustered by status of missense KRAS mutations (K), LOF TP53 mutations (P) and LOF STK11 (LKB1) mutations (L). The clustering pattern shows subgroups of different combinations involving K, P and L.
Figure 11B:
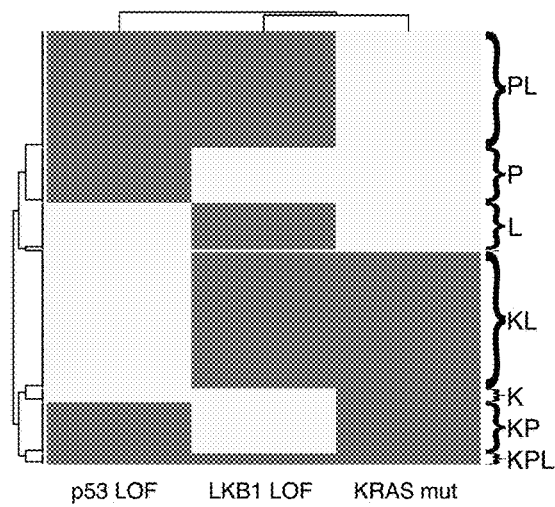

Tumor evolution is a complex biological process (Weinberg 2007). Mutations in the cancer genome often involve oncogenes, tumor suppressor genes, as well as cancer-associated genes with unknown roles (Lawrence et al 2013). In this study, Applicants developed a new method to model the competition of multiple mutations in lung cancer using a single vector in combination with conditional Cas9 mice. Delivery of this single vector using AAV9 generates targeted genetic lesions including the specific missense $Kras^{G12D}$ mutation as well as p53 and Lkb1 LOF mutations in whole lung and dissected tumors. The initial mutation frequency is on the order of 0.1~1% for these three loci in the whole lung of an animal. Because the mutation frequencies differ for each mutation, different cells must have different combinations of the three mutations. The fastest growing combination of mutations, p53 and Lkb1 lead to a rapid onset and early progression of lung cancer. Low initial frequency of multiple mosaic mutations might mimic the sporadic initial cellular mutations in a tumor during the course of evolution (Weinberg 2007). The heterogeneity of mutations is reminiscent of mosaicism of multiple mutations in the clinic, with different patients having different combinations (FIG. 11A-B).

The Rosa26-LSL-Cas9 mouse is a versatile platform for in vivo CRISPR-Cas9 mediated genome engineering beyond this initial study. Crossing with cell-type specific Cre drivers will enable the study of mutations within specific cell types, which enables rapid assessment of biological functions in well-defined contexts. Because Cas9 is stably expressed within all cells, genome editing requires only delivery of sgRNA, such as delivery by nanoparticles. Furthermore, traditional transgenic mice have fixed genetic mutations in the germline and throughout the body, while the Cas9 mouse enables introduction of mutations directly in virtually any somatic tissue. This may provide an efficient and flexible alternative to creating specific transgenic strains with single genetic lesions. The Cas9 mouse will be a valuable resource for the community.

Previously testing combinations of mutations in tumor suppressor genes and oncogenes required the time consuming construction of multiple mouse strains. The Rosa26-LSL-Cas9 mouse described here facilitates combinations of mutations to be tested much more rapidly. The Rosa26-LSL-Cas9 mouse is a mere example of how this approach is modular and can be readily re-designed to target other or additional oncogenes, tumor suppressor genes, and cancer-associated genes with known and unknown function. In particular, this platform provides a means for targeting multiple gene targets, simultaneously, to better define the role specific combinations of gene mutations has in the etiology of cancers. This platform provides an efficient means to rapidly model competition of, for example, multiple lung cancer mutations by inducing LOF tumor suppressor mutations and precise gain-of-function mutations, which opens new venues for studying the disease and testing therapeutics. This is in particular to cancers, including the following exemplary forms thereof: Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, and Urinary bladder cancer. As further explained in, for example, Ioannidis et al. J. Natl Cancer Inst 2010; 102: 846-858 and Lawrence et al., Nature 23 Jan. 2014; vol 505, 495-355 and supplementary tables 1-6 there are several genes known which are associated with specific cancers and these gene sequences are exemplary target sequences for performing the invention and establishing such cancer models. These genes and the respective cancers are summarized as follows:

Acute myeloid leukemia: FLT3, DNMT3A, NPM1, IDH2, IDH1, TET2, NRAS, RUNX1, WT1, U2AF1, TP53, KRAS, PTPN11, KIT, SMC3, STAG2, PHF6, RAD21, CEBPA, ASXL1, SFRS2, SMC1A, PAPD5, EZH2, PDSS2, XRA5, KDM6A.

Basal cell (skin) carcinoma: RHOU, *PADI4*, *PADI6*, RCC2, ARHGEF10L, KRT5, CDKN2A/B, Intergenic.

Bladder cancer: TP53, KDM6A, RB1, PIK3CA, ARID1A, MLL2, CDKN1A, ERCC2, STAG2, RXRA, TBC1D12, NFE2L2, C3orf70, ERBB3, ELF3, FBXW7, FGFR3, FOXQ1, CREBBP, HRAS, SNX25, TSC1, MGA, EZR, DDX5, MLL, RHOA, PHF6, MLL3, BCLAF1, TGFBR2, EPHA2, SETD2, CDKN2A.

Breast cancer: PIK3CA, TP53, GATA3, MAP3K1, PTEN, AKT1, CTCF, CBFB, MLL3, MAP2K4, RUNX1, CDH1, SF3B1, PIK3R1, ARID1A, NCOR1, KRAS, SPEN, RB1, MLL, ERBB2, TBL1XR1, CDKN1B, HIST1H3B, FOXA1, CASP8, MED23, TBX3, CUL4B, STAG2, MYB, RAB40A, EP300, FGFR2, GNPTAB, ERBB3, ACVR1B, FGFR2, MAP3K1, Intergenic, LSP1, TNCR9, LOC643714, ECHDC1, RNF146, C6orf97, SLC4A7, NEK10, COX11.

Carcinoid: CDKN1B.

Chronic lymphocytic leukemia: SF3B1, TP53, MYD88, XPO1, HIST1H1E, RPS15, RPS2, NRAS, DDX3X, SPEN, ATM, MED12, IDH1, SETDB1, JAK1.

Colorectal cancer: APC, TP53, FBXW7, SMAD4, NRAS, SMAD2, TCF7L2, BRAF, KRAS, PIK3CA, PCBP1, ARID1A, ACVR1B, ERBB3, CASP8, ELF3, TRIM23, CDC27, B2M, NTN4, AXIN2, SIRT4, GOT1, RBM10, BCLAF1, BCOR, MAP2K4, IDH2, PTEN, ERBB2, ARID2, CTNNB1, TRAF3, CNBD1, CD70, Intergenic, SMAD7, EIF3H, POU5FIP1, HsG57825, DQ515897, RHPN2, BMP4, CDH1.

Diffuse large B-cell lymphoma: TP53, MYD88, TNFRSF14, CD79B, MLL2, EZH2, CARD11, CREBBP, TNF, CD70, POU2F2, ITPKB, HLA-A, BRAF, GNA13, POU2AF1, HIST1H3B, KRAS, B2M, NOTCH1, PTEN, MAP2K1, ZNF471.

Endometrial cancer: PTEN, PIK3CA, PIK3R1, TP53, KRAS, FBXW7, CTCF, ARID1A, ARHGAP35, ZFHX3, FGFR2, CCND1, PPP2R1A, ING1, ZNF471, ERBB3, CTNNB1, BCOR, CUX1, SPOP, NRAS, FAT1, ARIDSB, CCDC6, ZNF620, AKT1, SLC1A3, EIF2S2, TCP11L2, SGK1, DIAPH1, KLHL8, SOX17, GNPTAB, SLC44A3, ADNP, POLE, TTLL9, SELP, CHD4, PPM1D, RSBN1L, MICALCL, SACS, ANK3, TBL1XR1, SOS1, DNER, MORC4, MYCN, TXNDC8, INPPL1, ZRANB3, TAP1, EP300, TPX2, CAP2, ALKBH6, CASP8, RASA1, MGA, PBRM1, ERBB2, MLL4, ATM, CDKN1B, RB1, NFE2L2, TP53BP1, COL5A1, FLT3, MTOR, TDRD10.

Esophageal cancer: ADH6, ADH1B, BRAP, ALDH2.

Esophageal adenocarcinoma: TP53, CDKN2A, FLG, SMARCA4, PIK3CA, SMARCB1, IL7R, COL5A1, SMAD4, KRAS, ARID1A, SETDB1, ERBB2, SACS, PIK3R1.

Glioblastoma multiforme: TP53, EGFR, PIK3R1, PIK3CA, IDH1, RB1, PTEN, NF1, STAG2, RPL5, SLC26A3, BRAF, MAP3K1, KEL, CD1D, CHD8, DDX5, MUC17, QKI, AZGP1, SETD2, NUP210L, SMC1A, BCOR, PTPN11, EZR.

Glioma: CDKN2A, CDKN2B, CCDC26, TERT, PHLDB1, RTEL1 (locus 1), CCDC26, RTEL1 (locus 2), Intergenic.

Head and neck cancer: TP53, CDKN2A, CASP8, FAT1, NFE2L2, NOTCH1, MLL2, NSD1, HRAS, EPHA2, PIK3CA, AJUBA, RAC1, ZNF750, RHOA, TGFBR2, PTEN, HLA-A, EP300, B2M, OTUD7A, HLA-B, CTCF, IPO7, RASA1, MAP4K3, RB1, KDM6A, SMAD4, ARID2, ASXL1, ARHGAP35, MLL3, NCOR1, PBRM1.

Kidney clear cell cancer: SETD2, BAP1, VHL, PBRM1, PTEN, KDM5C, TP53, MTOR, ARID1A, GUSB, RHEB, ATM, TCEB1, MPO, CCDC120, PIK3CA, EGFR, ARHGAP35, BRCA1, FGFR3, COL5A3.

Lung cancer: CHRNA3, CHRNA5, CHRNB4, PSMA4, LOC123688, CLPTM1L, BAT3, MSH5, TERT, TRNAA-UGC.

Lung adenocarcinoma: TP53, KEAP1, STK11, CDKN2A, KRAS, U2AF1, SMARCA4, EGFR, MET, NF1, RIT1, BRAF, PIK3CA, RBM10, ERBB2, ARID1A, ATM, SLC4A5, NBPF1, STX2, MAP2K1, RB1, FAT1, APC, MLL3, NRAS, SMAD4, CDKN1B, CTNNB1, ARHGAP35, ARID2, CDK12.

Lung squamous cell carcinoma: TP53, CDKN2A, MLL2, KEAP1, PIK3CA, NFE2L2, RB1, HRAS, HLA-A, ARID1A, FBXW7, PTEN, EP300, EGFR, ARHGAP35, RASA1, FGFR3, NF1, NSD1, ASXL1, STK11, FAT1, NOTCH1, ERPINB13.

Medulloblastoma: DDX3X, CTNNB1, TP53.

Melanoma: BRAF, NRAS, CDKN2A, TP53, BCLAF1, RAC1, PTEN, PPP6C, FRMD7, CDK4, STK19, ACO1, XIRP2, LCTL, OR52N1, ALPK2, WASF3, OR4A16, MYOCD, CTNNB1, ZNF750, KIT, MXRA5, ARID2, ANK3, RXRA, PIK3CA, NCOR1, CDC91L1, Intergenic, MC1R, TYR, MC1R.

Multiple myeloma: KRAS, NRAS, TP53, DIS3, BRAF, FAM46C, INTS12, TRAF3, PRDM1, IRF4, IDH1, FGFR3, PTPN11, EZR.

Nasopharyngeal cancer: GABBR1, HLA-A, HLA-F, HCG9.

Neuroblastoma: ALK, F1122536, F1144180 BARD1.

Ovarian cancer: TP53, BRCA1, RB1, CDK12, NF1, SMARCB1, KRAS, NRAS, CREBBP, ERBB2, Intergenic.

Prostate cancer: SPOP, TP53, ATM, MED12, FOXA1, COL5A1, Intergenic, TCF2, KLK3, SLC22A3, LMTK2, NUDT10, NUDT11, LOC340602, GSPT2, MAGED1, EHBP1, MSMB, THADA, ITGA6, PDLIM5, TET2, NKX3.1, IGF2, IGF2A, INS, TH, TTLL1, BIK, MCAT, PACSIN2.

Rhabdoid tumor: SMARCB1.

Testicular germ cell tumor: KITLG, SPRY4, BAK1, KITLG.

Thyroid cancer: FOXE1, NKX2-1.

Urinary bladder cancer: MYC, BC042052, PSAC.

Additionally, the current invention provides for the screening of known genes both in vitro and in vivo for the evaluation as to the possible association of such genes with cancers. This includes the introduction of known and unknown mutations into the genes to be evaluated to determine if such mutations and combinations thereof results in cancer. The results of such screenings are then available in turn as the basis for establishing further cancer models as defined in the current invention. This applies also to genes currently known to be associated with cancer (e.g. Lawrence et al. and Ioannidis et al.), as known and unknown mutations and combinations thereof, as provided in the current invention, may be introduced to the genome and evaluated to determine if such mutations and combinations thereof results in cancer. The results of such screenings are then available in turn as the basis for establishing the cancer models as defined in the current invention.

Experimental Procedures

Rosa26-LSL-Cas9 Knock-in Transgenic Mouse

The LSL-Cas9 mouse was made by knocking in a Cas9 transgene (CAG promoter, foxed 3×SV40 polyA signal, 3×FLAG, human codon optimized SpCas9, P2A ribosomal skip cleavage peptide, EGFP, Woodchuck Hepatitis Virus (WHP) Posttranscriptional Regulatory Element (WPRE), bovine growth hormone polyA) into the Rosa26 locus of R1S mESCs followed by selection (PGK promoter, Neomycin resistance, PGK polyA), screening for positive clones using a forward primer within the PGK polyA signal and outside the long homology arm (Forward primer: GCAGCCTCTGTTCCACATACAC (SEQ ID NO: 27), Reverse primer: ACCATTCTCAGTGGCTCAACAA (SEQ ID NO: 28), and finally injection of mouse embryonic stem cells (mESCs) into C57BL6/J blastocysts. The resulting mosaics were backcrossed to the C57BL6/J strain to generate founders that were backcrossed further to the C57B16/J strain where pups were used for experiments.

Vector Design

The single vector design was cloned utilizing ITRs from AAV2, human U6 promoter for noncoding sgRNA transcription, the short EFs promoter derived from EF1α, Renilla luciferase for in vivo luciferase imaging, P2A for peptide cleavage, Cre recombinase for recombination of LSL, a short polyA sequence, and an 800 bp Kras$^{G12D}$ homologous recombination donor template. SgRNAs were chosen using the CRISPRtool (crispr.mit.edu) to minimize potential off-target effects. SgRNA sequences and genomic primers are listed in Table 2.

In Vitro sgRNA Testing

In vitro testing of sgRNAs was performed by transient transfection of the AAV-sgRNA plasmid using Lipofectamine 2000 transfection reagent (Life Technologies) into the mouse cancer cell line N2a (ATCC). Each plasmid was cotransfected in equimolar amount with a plasmid expressing SpCas9. 72 hours post transfection genomic DNA was harvested by QuickExtract (Epicenter) and used as a PCR template.

SURVEYOR Nuclease Assay

PCR was performed using high fidelity polymerases (Thermo) and genomic DNA template from in vitro or in vivo experiments. PCRs were purified by QIAquick (Qiagen) and then processed by SURVEYOR assay (Transgenomics) as described by the manufacturer's protocol. SURVEYOR assay products were run out on a 4-12% PA-TBE gel (Life Technologies), stained using SYBR gold (Life Technologies), and imaged on a gel imager (Bio-Rad). Quantification was based on relative band intensities.

Illumina Sequencing

For Illumina sequencing, 20 cycles of genomic PCR was performed followed by library preparation using the Nextera XT DNA Sample Prep Kit (Illumina). Mixed barcoded library was sequenced on an Illumina MiSeq System.

Illumina Sequencing Analysis

Illumina sequencing reads were mapped to specific amplicons of Kras, p53 or Lkb1 as reference sequences using bwa (Li and Durbin 2000) with custom scripts. Insertions and deletions were called against reference using VarScan2 (Koboldt et al 2012). Indel length distribution, indel phase and donor allele frequencies were processed using custom scripts as described previously (Chen et al 2014). Briefly, indel phase was calculated as the length of insertions or deletions modulus 3. The rate of Kras$^{G12D}$ HDR was calculated as donor allele frequency based on the G12D mutations as well as the synonymous barcoded SNPs.

AAV Production and Purification

AAV6 and AAV9 were packaged and produced in HEK 293FT cells and chemically purified by chloroform. Briefly, HEK 293FT cells were transiently transfected with the vector of interest, AAV serotype plasmid (AAV6 or AAV9), and pDF6 using polyethyleneimine (PEI). 72 hours post transfection cells were dislodged and transferred to a conical tube in sterile DPBS. 1/10 volume of pure chloroform was added and the mixture was incubated at 37° C. and vigorously shaken for 1 hour. NaCl was added to a final concentration of 1 M and the mixture was shaken until dissolved and then pelleted at 20 k g at 4° C. for 15 minutes. The aqueous layer was discarded while the chloroform layer was transferred to another tube. PEG8000 was added to 10% (w/v) and shaken until dissolved. The mixture was incubated at 4° C. for 1 hour and then spun at 20 k g at 4° C. for 15 minutes. The supernatant was discarded and the pellet was resuspended in DPBS plus MgCl$_2$ and treated with Benzonase (Sigma) and incubated at 37° C. for 30 minutes. Chloroform (1:1 volume) was added, shaken, and spun down at 12 k g at 4 C for 15 min. The aqueous layer was isolated and passed through a 100 kDa MWCO (Millipore). The concentrated solution was washed with DPBS and the filtration process was repeated. The virus was titered by qPCR using custom Taqman assays (Life Technologies) targeted to Cre.

Animal Work Statement

All animal work were performed under the guidelines of Division of Comparative Medicine (DCM), with protocols (0411-040-14, 0911-098-11 and 0911-098-14) approved by Massachusetts Institute of Technology Committee for Animal Care (CAC), and were consistent with the Guide for Care and Use of Laboratory Animals, National Research Council, 1996 (institutional animal welfare assurance no. A-3125-01).

Virus Delivery

Intranasal and intratracheal delivery of adeno-associated virus were performed adapting a previously established protocol (DuPage et al 2009). Briefly, animals were anesthetized using isoflurane, and setup in a biosafety cabinet. For intranasal delivery, previously titrated virus solution in 50 μl sterile saline was pipetted directly into one nostril of the mouse. For intratracheal delivery, a gauge-24 catheter was inserted to the trachea and virus solution in 75 μl sterile saline was pipetted to the top of the catheter to allow animal to gradually breathe in the solution. A titer of $1 \times 10^{11}$ viral genome copies was administered to each mouse. Animals after the procedure were kept warm using a heat lamp for recovery.

μCT Imaging and Processing

μCT imaging was performed using standard imaging protocol with a μCT machine (GE Healthcare). Briefly, animals were anesthetized using isoflurane, and setup in the imaging bed with a nosecone providing constant isoflurane. A total of 720 views were acquired for each mouse using a soft-tissue-fast-scan setting. Raw image stacks were processed for lung reconstruction using the standard ROI tool (MicroView). Rendering and quantification were performed using render volume tool and measurement tool in MicroView. Tumor burden was calculated as the sum of the sizes in mm$^3$ from all detectable tumors per mouse, with 3-4 mice per group.

Histology

Mice were sacrificed by carbon dioxide asphyxiation. Lungs were dissected under a fluorescent stereoscope, fixed in 4% formaldehyde or 10% formalin overnight, embedded in paraffin, sectioned at 6 μm and stained with hematoxylin and eosin (HE) for pathology. For tumor size quantification, images were taken tiling the whole lobe, merged into a single lobe, and tumors were manually outlined as region-of-interest (ROI), and subsequently quantified using imageJ (Schneider et al 2012). Sections were de-waxed, rehydrated and stained using standard immunohistochemistry (IHC) protocols (Chen et al 2014). The following antibodies were used for IHC: anti-Ki67 (abcam ab16667, 1:100), anti-CCSP (Millipore, 1:500), anti-pSPC (Millipore AB3786, 1:500) and anti-CD31 (abcam, ab28364, 1:50). IHC was quantified 10 randomly chosen low-magnification fields per lobe with 3 mice per group using imageJ (Schneider et al 2012) and/or Cellprofiler.

TCGA Data Analysis

TCGA lung adenocarcinoma (LUAD) mutation data was downloaded from the TCGA data portal (tcga-data.nci.nih-.gov/tcga/). Mutation annotation format file of LUAD was re-processed to show KRAS coding missense mutation as well as TP53 and STK11 LOF mutations in 227 patients.

TABLE 2

List of sgRNAs and genomic PCR primers used in this study.

| Oligo | Sequence (5'→3') | SEQ ID NO: | |
|---|---|---|---|
| KRAS_sgRNA-1 | GCAGCGTTACCTCTATCGTA | 29 | sgRNA |
| KRAS_sgRNA-2 | TGAGTATGACCCTACGATAG | 30 | sgRNA |
| KRAS_sgRNA-3 | CTGAATTAGCTGTATCGTCA | 31 | sgRNA |
| KRAS_sgRNA-4 | GACTGAGTATAAACTTGTGG | 32 | sgRNA |
| KRAS_sgRNA-5 | GTGGTTGGAGCTGGTGGCGT | 33 | sgRNA |
| KRAS_sgRNA-6 | AAACTTGTGGTGGTTGGAGC | 34 | sgRNA |
| p53_sgRNA-1 | GTACCTCTCTTTGCGCTCCC | 35 | sgRNA |
| p53_sgRNA-2 | CCGGATAGTGGGAACCTTCT | 36 | sgRNA |
| p53_sgRNA-3 | TACCTCTCTTTGCGCTCCCT | 37 | sgRNA |
| p53_sgRNA-4 | TCTGTACGGCGGTCTCTCCC | 38 | sgRNA |
| p53_sgRNA-5 | CCCAGAAGGTTCCCACTATC | 39 | sgRNA |
| p53_sgRNA-6 | CTGTACGGCGGTCTCTCCCA | 40 | sgRNA |
| p53_sgRNA-7 | CCTCGAGCTCCCTCTGAGCC | 41 | sgRNA |
| p53_sgRNA-8 | GTGTAATAGCTCCTGCATGG | 42 | sgRNA |
| LKB1_sgRNA-1 | ACTCCGAGACCTTATGCCGC | 43 | sgRNA |
| LKB1_sgRNA-2 | AGCTTGGCGCGTTTGCGGCG | 44 | sgRNA |
| LKB1_sgRNA-3 | CTTGACCGCCCTGCGGCATA | 45 | sgRNA |
| LKB1_sgRNA-4 | GTGGCGGACCCCGAGCCGTT | 46 | sgRNA |
| LKB1_sgRNA-5 | CGTGGCGGACCCCGAGCCGT | 47 | sgRNA |
| LKB1_sgRNA-6 | CGATGAGCTTGGCGCGTTTG | 48 | sgRNA |
| Kras-F | TTTGTTGCCCTTTATTGCAGAA | 49 | Primer |
| Kras-R | ATGCAAATACAAAGCACGGATG | 50 | Primer |
| p53-1-6 F | TCTGTTTCCTCTTGGGCTTAGG | 51 | Primer |
| p53-1-6 R | AAAGACCTGGCAACCTGCTAAT | 52 | Primer |
| p53-7-F | CTGGCCGACTTCTTGGATACTT | 53 | Primer |
| p53-7-R | CAGACACCCAACACCATACCAT | 54 | Primer |
| p53-8-F | ATAGAGACGCTGAGTCCGGTTC | 55 | Primer |
| p53-8-R | CCTAAGCCCAAGAGGAAACAGA | 56 | Primer |
| Lkb1-F | GAGGTGACGCTCAGGGATAGAT | 57 | Primer |
| Lkb1-R | GTTGTGGAGGTCGTTCCTGTTT | 58 | Primer |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention is further described by the following numbered paragraphs:

1. A vector containing nucleic acid molecule(s), whereby in vivo and/or ex vivo in a eukaryotic cell containing or expressing or that is able to be induced to express or that conditionally expresses Cas9: the vector expresses and provides a plurality of RNAs to guide the Cas9 and optionally delivers donor templates, and a plurality of specific mutations or precise sequence substitutions in a plurality of target loci are introduced.

2. The vector of paragraph 1 wherein the cell contains Cas9 conditionally or inducibly and the vector expresses that which induces or gives rise to the condition of Cas9 expression and the cell containing Cas9.

3. The vector of paragraph 2 wherein the vector expresses Cre recombinase and Cre recombinase induces or gives rise to the condition of Cas9 expression and the cell containing Cas9.

4. The vector of any one of paragraphs 1-3 wherein the RNAs to guide Cas9 comprise CRISPR RNA and transactivating (tracr) RNA.

5. The vector of any one of paragraphs 1-3 wherein the RNAs to guide Cas9 comprise chimeric single guide RNA (sgRNA).

6. The vector of paragraph 5, wherein each sgRNA is driven by an independent U6 promoter.

7. The vector of any one of paragraphs 1-6, wherein the vector is an AAV.

8. The vector of paragraph 7, wherein the AAV is AAV9 or AAV6.

9. The vector of any one of paragraphs 6-8, wherein each of the sgRNAs targets a different genetic locus associated with a multigenic disease or disorder.

10. The vector of paragraph 9, wherein the multigenic disease or disorder is cancer.

11. The vector of paragraph 10, wherein the cancer is lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhadbdoid tumor, thyroid cancer, or urinary bladder cancer.

12. The vector of any one of paragraphs 6-8, wherein the sgRNAs target one or more tumor suppressor genes so as to introduce loss-of-function mutations.

13. The vector of paragraph 12, wherein the tumor suppressor genes are p53 and Lkb1.

14. The vector of any one of paragraphs 6-8, wherein the sgRNAs target one or more proto-oncogenes or oncogenes so as to introduce a gain-of-function mutation.

15. The vector of paragraph 14, wherein the proto-oncogenes or oncogenes is Kras.

16. The vector of any one of paragraphs 6-8, wherein the sgRNAs target
one or more of p53, Lkb1, or Kras; or
one or more of Kras, p53, Lkb1, CHRNA3, CHRNA5, CHRNB4, PSMA4, LOC123688, CLPTM1L, BAT3, MSH5, TERT, and TRNAA-UGC; or
one or more of TP53, KEAP1, STK11, CDKN2A, KRAS, U2AF1, SMARCA4, EGFR, MET, NF1, RIT1, BRAF, PIK3CA, RBM10, ERBB2, ARID1A, ATM, SLC4A5, NBPF1, STX2, MAP2K1, RB1, FAT1, APC, MLL3, NRAS, SMAD4, CDKN1B, CTNNB1, ARHGAP35, ARID2, and CDK12; or one or more of TP53, CDKN2A, MLL2, KEAP1, PIK3CA, NFE2L2, RB1, HRAS, HLA-A, ARID1A, FBXW7, PTEN, EP300, EGFR, ARHGAP35, RASA1, FGFR3, NF1, NSD1, ASXL1, STK11, FAT1, NOTCH1, and ERPINB13; or one or more of FLT3, DNMT3A, NPM1, IDH2, IDH1, TET2, NRAS, RUNX1, WT1, U2AF1, TP53, KRAS, PTPN11, KIT, SMC3, STAG2, PHF6, RAD21, CEBPA, ASXL1, SFRS2, SMC1A, PAPD5, EZH2, PDSS2, XRA5, and KDM6A; or one or more of RHOU, *PADI*4, *PADI*6, RCC2, ARHGEF10L, KRT5, and CDKN2A/B; or one or more of TP53, KDM6A, RB1, PIK3CA, ARID1A, MLL2, CDKN1A, ERCC2, STAG2, RXRA, TBC1D12, NFE2L2, C3orf70, ERBB3, ELF3, FBXW7, FGFR3, FOXQ1, CREBBP, HRAS, SNX25, TSC1, MGA, EZR, DDX5, MLL, RHOA, PHF6, MLL3, BCLAF1, TGFBR2, EPHA2, SETD2, and CDKN2A; or one or more of PIK3CA, TP53, GATA3, MAP3K1, PTEN, AKT1, CTCF, CBFB, MLL3, MAP2K4, RUNX1, CDH1, SF3B1, PIK3R1, ARID1A, NCOR1, KRAS, SPEN, RB1, MLL, ERBB2, TBL1XR1, CDKN1B, HIST1H3B, FOXA1, CASP8, MED23, TBX3, CUL4B, STAG2, MYB, RAB40A, EP300, FGFR2, GNPTAB, ERBB3, ACVR1B, FGFR2, MAP3K1, Intergenic, LSP1, TNCR9, LOC643714, ECHDC1, RNF146, C6orf97, SLC4A7, NEK10, and COX11; or CDKN1B;

or one or more of SF3B1, TP53, MYD88, XPO1, HIST1H1E, RPS15, RPS2, NRAS, DDX3X, SPEN, ATM, MED12, IDH1, SETDB1, and JAK1;

or one or more of APC, TP53, FBXW7, SMAD4, NRAS, SMAD2, TCF7L2, BRAF, KRAS, PIK3CA, PCBP1, ARID1A, ACVR1B, ERBB3, CASP8, ELF3, TRIM23, CDC27, B2M, NTN4, AXIN2, SIRT4, GOT1, RBM10, BCLAF1, BCOR, MAP2K4, IDH2, PTEN, ERBB2, ARID2, CTNNB1, TRAF3, CNBD1, CD70, Intergenic, SMAD7, EIF3H, POU5FIP1, HsG57825, DQ515897, RHPN2, BMP4, and CDH1; or one or more of TP53, MYD88, TNFRSF14, CD79B, MLL2, EZH2, CARD11, CREBBP, TNF, CD70, POU2F2, ITPKB, HLA-A, BRAF, GNA13, POU2AF1, HIST1H3B, KRAS, B2M, NOTCH1, PTEN, MAP2K1, and ZNF471; or one or more of PTEN, PIK3CA, PIK3R1, TP53, KRAS, FBXW7, CTCF, ARID1A, ARHGAP35, ZFHX3, FGFR2, CCND1, PPP2R1A, ING1, ZNF471, ERBB3, CTNNB1, BCOR, CUX1, SPOP, NRAS, FAT1, ARID5B, CCDC6, ZNF620, AKT1, SLC1A3, EIF2S2, TCP11L2, SGK1, DIAPH1, KLHL8, SOX17, GNPTAB, SLC44A3, ADNP, POLE, TTLL9, SELP, CHD4, PPM1D, RSBN1L, MICALCL, SACS, ANK3, TBL1XR1, SOS1, DNER, MORC4, MYCN, TXNDC8, INPPL1, ZRANB3, TAP1, EP300, TPX2, CAP2, ALKBH6, CASP8, RASA1, MGA, PBRM1, ERBB2, MLL4, ATM, CDKN1B, RB1, NFE2L2, TP53BP1, COL5A1, FLT3, MTOR, and TDRD10; or one or more of ADH6, ADH1B, BRAP, and ALDH2; or one or more of TP53, CDKN2A, FLG, SMARCA4, PIK3CA, SMARCB1, IL7R, COL5A1, SMAD4, KRAS, ARID1A, SETDB1, ERBB2, SACS, and PIK3R1; or one or more of TP53, EGFR, PIK3R1, PIK3CA, IDH1, RB1, PTEN, NF1, STAG2, RPL5, SLC26A3, BRAF, MAP3K1, KEL, CD1D, CHD8, DDX5, MUC17, QKI, AZGP1, SETD2, NUP210L, SMC1A, BCOR, PTPN11, and EZR; or one or more of CDKN2A, CDKN2B, CCDC26, TERT, PHLDB1, RTEL1 (locus 1), CCDC26, RTEL1 (locus 2), and intergenic; or one or more of TP53, CDKN2A, CASP8, FAT1, NFE2L2, NOTCH1, MLL2, NSD1, HRAS, EPHA2, PIK3CA, AJUBA, RAC1, ZNF750, RHOA, TGFBR2, PTEN, HLA-A, EP300, B2M, OTUD7A, HLA-B, CTCF, IPO7, RASA1, MAP4K3, RB1, KDM6A, SMAD4, ARID2, ASXL1, ARHGAP35, MLL3, NCOR1, and PBRM1; or one or more of SETD2, BAP1, VHL, PBRM1, PTEN, KDM5C, TP53, MTOR, ARID1A, GUSB, RHEB, ATM, TCEB1, MPO, CCDC120, PIK3CA, EGFR, ARHGAP35, BRCA1, FGFR3, and COL5A3; or one or more of DDX3X, CTNNB1, and TP53; or one or more of BRAF, NRAS, CDKN2A, TP53, BCLAF1, RAC1, PTEN, PPP6C, FRMD7, CDK4, STK19, ACO1, XIRP2, LCTL, OR52N1, ALPK2, WASF3, OR4A16, MYOCD, CTNNB1, ZNF750, KIT, MXRA5, ARID2, ANK3, RXRA, PIK3CA, NCOR1, CDC91L1, Intergenic, MC1R, TYR, and MC1R; or one or more of KRAS, NRAS, TP53, DIS3, BRAF, FAM46C, INTS12, TRAF3, PRDM1, IRF4, IDH1, FGFR3, PTPN11, and EZR; or one of GABBR1, HLA-A, HLA-F, and HCG9; or one or more of ALK, F1122536, F1144180, and BARD1; or one or more of TP53, BRCA1, RB1, CDK12, NF1, SMARCB1, KRAS, NRAS, CREBBP, ERBB2, and intergenic; or one or more of SPOP, TP53, ATM, MED12, FOXA1, COL5A1, Intergenic, TCF2, KLK3, SLC22A3, LMTK2, NUDT10, NUDT11, LOC340602, GSPT2, MAGED1, EHBP1, MSMB, THADA, ITGA6, PDLIM5, TET2, NKX3.1, IGF2, IGF2A, INS, TH, TTLL1, BIK, MCAT, and PACSIN2; or SMARCB1; or one or more of KITLG, SPRY4, BAK1, and KITLG; or one or more of FOXE1 and NKX2-1; or one or more of MYC, BC042052, and PSAC.

17. The vector of any one of paragraphs 1-16 wherein from 3 to 50 specific mutations or precise sequence substitutions in from 3 to 50 target loci are introduced.

18. The vector of any one of paragraphs 1-17 wherein the eukaryotic cell is a mammalian cell.

19. The vector of paragraph 18 wherein the eukaryotic cell is part of a non-human transgenic eukaryote having cells that express or that are able to be induced to express or that conditionally express Cas9.

20. The vector of paragraph 19 wherein the non-human transgenic eukaryote having cells that express or that are able to be induced to express or that conditionally express Cas9 is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.

21. The vector of paragraph 18 wherein the mammalian cell is a mouse cell.

22. The vector of paragraph 21 wherein the mouse cell is part of a transgenic mouse having cells that express or that are able to be induced to express or that conditionally express Cas9.

23. A method for introducing multiple mutations ex vivo in a tissue, organ or a cell line comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22.

24. The method of paragraph 23, wherein the method comprises deliveryeing to cells of the transgenic non-human mammal, and the transgenic non-human mammal is a transgenic mouse having cells that express or that are able to be induced to express or that conditionally express Cas9.

25. The method of paragraph 24, wherein transgenic mouse having cells that express Cas9 comprises a mouse that has had a Cas9 transgene knocked into the Rosa26 locus.

26. The method of paragraph 25, wherein the Cas9 transgene further comprises a Lox-Stop-polyA-Lox (LSL) cassette thereby rendering Cas9 expression inducible by Cre recombinase.

27. A method for modeling a genetic disease or cancer comprising introducing multiple mutations ex vivo in a tissue, organ or a cell line comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22, wherein the specific mutations or precise sequence substitutions are or have been correlated to the genetic disease or cancer.

28. The method of paragraph 27, wherein the method comprises delivering to cells of the transgenic non-human mammal the vector, and the transgenic non-human mammal is a transgenic mouse having cells that express or that are able to be induced to express or that conditionally express Cas9.

29. The method of paragraph 28, wherein transgenic mouse having cells that express Cas9 comprises a mouse that has had a Cas9 transgene knocked into the Rosa26 locus.

30. The method of paragraph 29, wherein the Cas9 transgene further comprises a Lox-Stop-polyA-Lox (LSL) cassette thereby rendering Cas9 expression inducible by Cre recombinase.

31. The method of any one of paragraphs 27-30, wherein the genetic disease or cancer is lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdboid tumor, thyroid cancer, or urinary bladder cancer.

32. An individualized or personalized treatment of a genetic disease in a subject in need of such treatment comprising:
  (a) introducing multiple mutations ex vivo in a tissue, organ or a cell line comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22, wherein the specific mutations or precise sequence substitutions are or have been correlated to the genetic disease;
  (b) testing treatment(s) for the genetic disease on the cells to which the vector has been delivered that have the specific mutations or precise sequence substitutions correlated to the genetic disease; and
  (c) treating the subject based on results from the testing of treatment(s) of step (b).

33. The method of paragraph 32 wherein the method comprises delivering to cells of the transgenic non-human mammal the vector, and the transgenic non-human mammal is a transgenic mouse having cells that express or that are able to be induced to express or that conditionally express Cas9, and the genetic disease is a cancer.

34. The method of paragraph 33 wherein the cancer is lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdboid tumor, thyroid cancer, or urinary bladder cancer.

35. A cancerous non-human transgenic eukaryote or mammal having cells that express or that are able to be induced to express or that conditionally express Cas9.

36. A cancerous non-human transgenic eukaryote or mammal having cells that express or that are able to be induced to express or that conditionally express Cas9, obtained or obtainable by or in a method of any one of paragraphs 23-34.

37. The cancerous non-human transgenic eukaryote or mammal of paragraph 35 or 36 is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.

38. A kit comprising one or more vectors as claimed in any one of paragraphs 1-22 and a tissue, organ or a cell line comprising Cas9-expressing eukaryotic cell(s) or cell(s) that are able to be induced to express or that conditionally express Cas9, or in vivo in a transgenic non-human eukaryote or mammal having cells that express or that are able to be induced to express or that conditionally express Cas9; and optionally instructions for using the vector(s) and the tissue, organ or cell(s) or the eukaryote or mammal.

39. The kit of paragraph 38 wherein the kit includes the instructions.

40. The kit of paragraph 39 wherein the instructions provide for performing a method of any one of paragraphs 23-34.

41. The kit of any one of paragraphs 38-40 wherein the kit includes a non-human transgenic eukaryote or mammal having cells that express or that are able to be induced to express or that conditionally express Cas9 that is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.

42. The kit of paragraph 41 wherein the kit includes a transgenic mouse having cells that express or that are able to be induced to express or that conditionally express Cas9.

REFERENCES

Bell, C. L., Vandenberghe, L. H., Bell, P., Limberis, M. P., Gao, G. P., Van Vliet, K., Agbandje-McKenna, M., and Wilson, J. M. (2011). The AAV9 receptor and its modification to improve in vivo lung gene transfer in mice. The Journal of clinical investigation 121, 2427-2435.

Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Dull, T., Zufferey, R., Kelly, M., Mandel, R. J., Nguyen, M., Trono, D., and Naldini, L. (1998). A third-generation lentivirus vector with a conditional packaging system. Journal of virology 72, 8463-8471.

DuPage, M., Dooley, A. L., and Jacks, T. (2009). Conditional mouse lung cancer models using adenoviral or lentiviral delivery of Cre recombinase. Nature protocols 4, 1064-1072.

Frese, K. K., and Tuveson, D. A. (2007). Maximizing mouse cancer models. Nature reviews Cancer 7, 645-658.

Garraway, L. A., and Lander, E. S. (2013). Lessons from the cancer genome. Cell 153, 17-37.

Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.

Govindan, R., Ding, L., Griffith, M., Subramanian, J., Dees, N. D., Kanchi, K. L., Maher, C. A., Fulton, R., Fulton, L., Wallis, J., et al. (2012). Genomic landscape of non-small cell lung cancer in smokers and never-smokers. Cell 150, 1121-1134.

Halbert, C. L., Allen, J. M., and Miller, A. D. (2002). Efficient mouse airway transduction following recombination between AAV vectors carrying parts of a larger gene. Nature biotechnology 20, 697-701.

Herbst, R. S., Heymach, J. V., and Lippman, S. M. (2008). Lung cancer. The New England journal of medicine 359, 1367-1380.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

Ioannidis John, P. A., Castaldi P., Evangelou E. A compendium of genome-wide associations for cancer: critical synopsis and reappraisal. J. Natl Cancer Inst 2010; 102: 846-858

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes & development 15, 3243-3248.

Ji, H., Ramsey, M. R., Hayes, D. N., Fan, C., McNamara, K., Kozlowski, P., Torrice, C., Wu, M. C., Shimamura, T., Perera, S. A., et al. (2007). LKB1 modulates lung cancer differentiation and metastasis. Nature 448, 807-810.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Johnson, L., Mercer, K., Greenbaum, D., Bronson, R. T., Crowley, D., Tuveson, D. A., and Jacks, T. (2001). Somatic activation of the K-ras oncogene causes early onset lung cancer in mice. Nature 410, 1111-1116.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Koboldt, D. C., Zhang, Q., Larson, D. E., Shen, D., McLellan, M. D., Lin, L., Miller, C. A., Mardis, E. R., Ding, L., and Wilson, R. K. (2012). VarScan 2: somatic mutation and copy number alteration discovery in cancer by exome sequencing. Genome research 22, 568-576.

Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Lawrence, M. S. Stojanov, P., Mermel, C. H., Robinson, J. T., Garraway, L. A., Golub, T. R, Meyerson, M., Gabriel, S. B., and Lander E. S. Discovery and saturation analysis of cancer genes across 21 tumour types. Nature 23 Jan. 2014; vol 505, 495-355 and supplementary tables 1-6.

Li, H., and Durbin, R. (2010). Fast and accurate long-read alignment with Burrows-Wheeler transform. Bioinformatics 26, 589-595.

Limberis, M. P., and Wilson, J. M. (2006). Adeno-associated virus serotype 9 vectors transduce murine alveolar and nasal epithelia and can be readministered. Proceedings of the National Academy of Sciences of the United States of America 103, 12993-12998.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Mitzner, W., Brown, R., and Lee, W. (2001). In vivo measurement of lung volumes in mice. Physiological genomics 4, 215-221.

Park, W. Y., Kim, M. H., Shin, D. H., Lee, J. H., Choi, K. U., Kim, J. Y., Park do, Y., Lee, C. H., and Sol, M. Y. (2012). Ciliated adenocarcinomas of the lung: a tumor of non-terminal respiratory unit origin. Modern pathology: an official journal of the United States and Canadian Academy of Pathology, Inc 25, 1265-1274.

Pylayeva-Gupta, Y., Grabocka, E., and Bar-Sagi, D. (2011). RAS oncogenes: weaving a tumorigenic web. Nature reviews Cancer 11, 761-774.

Schneider, C. A., Rasband, W. S., and Eliceiri, K. W. (2012). NIH Image to ImageJ: 25 years of image analysis. Nature methods 9, 671-675.

Shackelford, D. B., and Shaw, R. J. (2009). The LKB1-AMPK pathway: metabolism and growth control in tumour suppression. Nature reviews Cancer 9, 563-575.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

TCGA-Network (2014). Comprehensive molecular profiling of lung adenocarcinoma. Nature Published online 9 Jul. 2014.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Weinberg, R. A. (2007). The biology of cancer (New York, Garland Science).

Xue, W., Chen, S., Yin, H., Tammela, T., Papagiannakopoulos, T., Joshi, N. S., Cai, W., Yang, G., Bronson, R., Crowley, D. G., et al. (2014). CRISPR-mediated direct mutation of cancer genes in the mouse liver. Nature.

What is claimed is:

1. A method comprising:
   (a) delivering a vector expressing a plurality of RNAs to guide Cas9 to a plurality of target loci into a non-human mammal having cells that express or that are able to be induced to express or that conditionally express Cas9, thereby introducing 3 or more mutations in the plurality of target loci in the non-human mammal and causing a genetic disorder in the non-human mammal,
   wherein the vector comprises (i) a donor polynucleotide, (ii) coding sequences for the plurality of RNAs, (iii) a coding sequence for a Cre recombinase, and (iv) a reporter gene; and
   (b) identifying, among the introduced 3 or more mutations, a combination of mutations that results in the genetic disorder.

2. The method of claim 1, wherein the method comprises delivering to cells of the non-human mammal the vector, and the non-human mammal is a mouse having cells that express or that are able to be induced to express or that conditionally express Cas9.

3. The method of claim 2, wherein the mouse having cells that express Cas9 comprises a mouse that has had a Cas9 transgene knocked into the Rosa26 locus, wherein the Cas9 transgene further comprises a Lox-Stop-polyA-Lox (LSL) cassette thereby rendering Cas9 expression inducible by Cre recombinase.

4. The method of claim 1, wherein one or more of the plurality of mutations are or have been correlated to a genetic disease or cancer.

5. The method of claim 4, further comprising modeling the genetic disease or cancer.

6. The method of claim 4, further comprising testing treatment(s) for the genetic disease on the cells to which the vector has been delivered in a subject.

7. The method of claim 6, further comprising treating the subject based on results from the testing of treatment(s).

8. The method of claim 4, wherein the genetic disease or cancer is lung cancer, lung adenocarcinoma, lung squamous cell carcinoma, acute myeloid leukemia, skin basal cell carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, or urinary bladder cancer.

9. The method of claim 1, wherein the plurality of mutations comprise specific mutations or precise sequence substitutions in the plurality of targeted loci.

10. The method of claim 1, wherein the 3 or more mutations comprise at least one loss-of-function mutation and at least one gain-of-function mutation.

11. The method of claim 1, wherein the vector is an adeno-associated virus vector.

* * * * *

UNITED STATES PATENT AND TRADEMARK OFFICE
CERTIFICATE OF CORRECTION

Page 1 of 2

PATENT NO. : 11,124,796 B2
APPLICATION NO. : 15/467888
DATED : September 21, 2021
INVENTOR(S) : Phillip A. Sharp et al.

It is certified that error appears in the above-identified patent and that said Letters Patent is hereby corrected as shown below:

On the Title Page

On the page 3, in Column 2, item (56) under "Other Publications", Line 4, after "Humans:" delete "20, 1995, 404-410.".

On the page 3, in Column 2, item (56) under "Other Publications", Line 46, delete "herbst," and insert -- Herbst, --.

On the page 3, in Column 2, item (56) under "Other Publications", Line 49, delete "hermonat," and insert -- Hermonat, --.

In the Specification

In Column 1, Line 58, delete "47627992078 SL.txt" and insert -- 47627992078_SL.txt --.

In Column 1, Line 59, delete "114,990" and insert -- 115,008 --.

In Column 53, Line 38, delete "$T_m$." and insert -- $T_m$, --.

In Column 56, Line 42, delete "PositvelyH" and insert -- Positively H --.

In Column 56, Line 44, delete "NegativelyE" and insert -- Negatively E --.

In Column 67, Line 14, delete "ARIDSB" and insert -- ARID5B --.

In Column 67, Line 60, delete "ASBS," and insert -- ASB5, --.

In Column 68, Line 13, delete "GPCS," and insert -- GPC5, --.

In Column 68, Line 14, delete "GRMS," and insert -- GRM5, --.

Signed and Sealed this
Twenty-sixth Day of April, 2022

Katherine Kelly Vidal
*Director of the United States Patent and Trademark Office*

In Column 68, Line 18, delete "LRFNS," and insert -- LRFN5, --.

In Column 68, Line 35, delete "OR51L1," and insert -- OR51I1, --.

In Column 75, Line 25, delete "ARIDSB," and insert -- ARID5B, --.

SEQUENCE LISTING

<160> NUMBER OF SEQ ID NOS: 150

<210> SEQ ID NO 1
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 1
nnnnnnnnnn nnnnnnnnnn gtttttgtac tctcaagatt tagaaataaa tcttgcagaa    60
gctacaaaga taaggcttca tgccgaaatc aacaccctgt cattttatgg cagggtgttt   120
tcgttattta attttt                                                   137

<210> SEQ ID NO 2
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 2
nnnnnnnnnn nnnnnnnnnn gtttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 3
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 3
nnnnnnnnnn nnnnnnnnnn gtttttgtac tctcagaaat gcagaagcta caaagataag    60
gcttcatgcc gaaatcaaca ccctgtcatt ttatggcagg gtgtttttt                110

<210> SEQ ID NO 4
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn gttttagagc tagaaatagc aagttaaaat aaggctagtc    60
cgttatcaac ttgaaaaagt ggcaccgagt cggtgctttt tt    102

<210> SEQ ID NO 5
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gttttagagc tagaaatagc aagttaaaat aaggctagtc    60
cgttatcaac ttgaaaaagt gttttttt    88

<210> SEQ ID NO 6
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttagagc tagaaatagc aagttaaaat aaggctagtc    60
cgttatcatt tttttt    76

<210> SEQ ID NO 7
<211> LENGTH: 20
<212> TYPE: DNA
<213> ORGANISM: Homo sapiens

<400> SEQUENCE: 7
gagtccgagc agaagaagaa    20

<210> SEQ ID NO 8
<211> LENGTH: 20
<212> TYPE: DNA
<213> ORGANISM: Homo sapiens

<400> SEQUENCE: 8
gagtcctagc aggagaagaa    20

<210> SEQ ID NO 9
<211> LENGTH: 20
<212> TYPE: DNA
<213> ORGANISM: Homo sapiens

<400> SEQUENCE: 9
gagtctaagc agaagaagaa    20

<210> SEQ ID NO 10

```
<211> LENGTH: 7
<212> TYPE: PRT
<213> ORGANISM: Simian virus 40

<400> SEQUENCE: 10

Pro Lys Lys Lys Arg Lys Val
1               5

<210> SEQ ID NO 11
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 11

Lys Arg Pro Ala Ala Thr Lys Lys Ala Gly Gln Ala Lys Lys Lys Lys
1               5                   10                  15

<210> SEQ ID NO 12
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 12

Pro Ala Ala Lys Arg Val Lys Leu Asp
1               5

<210> SEQ ID NO 13
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 13

Arg Gln Arg Arg Asn Glu Leu Lys Arg Ser Pro
1               5                   10

<210> SEQ ID NO 14
<211> LENGTH: 38
<212> TYPE: PRT
<213> ORGANISM: Homo sapiens

<400> SEQUENCE: 14

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35

<210> SEQ ID NO 15
<211> LENGTH: 42
<212> TYPE: PRT
<213> ORGANISM: Unknown
<220> FEATURE:
<221> NAME/KEY: source
<223> OTHER INFORMATION: /note="Description of Unknown:
```

IBB domain from importin-alpha sequence"

<400> SEQUENCE: 15

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 16
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 16

Val Ser Arg Lys Arg Pro Arg Pro
1               5

<210> SEQ ID NO 17
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 17

Pro Pro Lys Lys Ala Arg Glu Asp
1               5

<210> SEQ ID NO 18
<211> LENGTH: 8
<212> TYPE: PRT
<213> ORGANISM: Homo sapiens

<400> SEQUENCE: 18

Pro Gln Pro Lys Lys Lys Pro Leu
1               5

<210> SEQ ID NO 19
<211> LENGTH: 12
<212> TYPE: PRT
<213> ORGANISM: Mus musculus

<400> SEQUENCE: 19

Ser Ala Leu Ile Lys Lys Lys Lys Lys Met Ala Pro
1               5                   10

<210> SEQ ID NO 20
<211> LENGTH: 5
<212> TYPE: PRT
<213> ORGANISM: Influenza virus

<400> SEQUENCE: 20

Asp Arg Leu Arg Arg
1               5

<210> SEQ ID NO 21
<211> LENGTH: 7

```
<212> TYPE: PRT
<213> ORGANISM: Influenza virus

<400> SEQUENCE: 21

Pro Lys Gln Lys Lys Arg Lys
1               5

<210> SEQ ID NO 22
<211> LENGTH: 10
<212> TYPE: PRT
<213> ORGANISM: Hepatitis delta virus

<400> SEQUENCE: 22

Arg Lys Leu Lys Lys Lys Ile Lys Lys Leu
1               5                   10

<210> SEQ ID NO 23
<211> LENGTH: 10
<212> TYPE: PRT
<213> ORGANISM: Mus musculus

<400> SEQUENCE: 23

Arg Glu Lys Lys Lys Phe Leu Lys Arg Arg
1               5                   10

<210> SEQ ID NO 24
<211> LENGTH: 20
<212> TYPE: PRT
<213> ORGANISM: Homo sapiens

<400> SEQUENCE: 24

Lys Arg Lys Gly Asp Glu Val Asp Gly Val Asp Glu Val Ala Lys Lys
1               5                   10                  15

Lys Ser Lys Lys
            20

<210> SEQ ID NO 25
<211> LENGTH: 17
<212> TYPE: PRT
<213> ORGANISM: Homo sapiens

<400> SEQUENCE: 25

Arg Lys Cys Leu Gln Ala Gly Met Asn Leu Glu Ala Arg Lys Thr Lys
1               5                   10                  15

Lys

<210> SEQ ID NO 26
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
guuuuagagc ua                                                          12

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 27
gcagcctctg ttccacatac ac                                           22

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
accattctca gtggctcaac aa                                           22

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
gcagcgttac ctctatcgta                                              20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
tgagtatgac cctacgatag                                              20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ctgaattagc tgtatcgtca                                              20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gactgagtat aaacttgtgg                                              20

<210> SEQ ID NO 33
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gtggttggag ctggtggcgt                                                    20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
aaacttgtgg tggttggagc                                                    20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
gtacctctct ttgcgctccc                                                    20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ccggatagtg ggaaccttct                                                    20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
tacctctctt tgcgctccct                                                    20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
```
tctgtacggc ggtctctccc                                           20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cccagaaggt tcccactatc                                           20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
ctgtacggcg gtctctccca                                           20

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cctcgagctc cctctgagcc                                           20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gtgtaatagc tcctgcatgg                                           20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
actccgagac cttatgccgc                                           20

<210> SEQ ID NO 44
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 44
agcttggcgc gtttgcggcg                                              20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cttgaccgcc ctgcggcata                                              20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gtggcggacc ccgagccgtt                                              20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
cgtggcggac cccgagccgt                                              20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cgatgagctt ggcgcgtttg                                              20

<210> SEQ ID NO 49
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
tttgttgccc tttattgcag aa                                           22

<210> SEQ ID NO 50
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
atgcaaatac aaagcacgga tg                                            22

<210> SEQ ID NO 51
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tctgtttcct cttgggctta gg                                            22

<210> SEQ ID NO 52
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
aaagacctgg caacctgcta at                                            22

<210> SEQ ID NO 53
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
ctggccgact tcttggatac tt                                            22

<210> SEQ ID NO 54
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
cagacaccca acaccatacc at                                            22

<210> SEQ ID NO 55
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
```

-continued

```
atagagacgc tgagtccggt tc                                              22
```

<210> SEQ ID NO 56
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56

```
cctaagccca agaggaaaca ga                                              22
```

<210> SEQ ID NO 57
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57

```
gaggtgacgc tcagggatag at                                              22
```

<210> SEQ ID NO 58
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58

```
gttgtggagg tcgttcctgt tt                                              22
```

<210> SEQ ID NO 59
<211> LENGTH: 34
<212> TYPE: DNA
<213> ORGANISM: Mus musculus

<400> SEQUENCE: 59

```
tgtgtaatag ctcctgcatg gggggcatga accg                                 34
```

<210> SEQ ID NO 60
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60

```
tgtgtaatag gggcatgaac cg                                              22
```

<210> SEQ ID NO 61
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 61
tgtgtaatag cttgaaccg                                              19

<210> SEQ ID NO 62
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
tgtgtaatag ctcctggggg catgaaccg                                   29

<210> SEQ ID NO 63
<211> LENGTH: 34
<212> TYPE: DNA
<213> ORGANISM: Mus musculus

<400> SEQUENCE: 63
gactccgaga ccttatgccg cagggcggtc aaga                             34

<210> SEQ ID NO 64
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gactccgaga cagggcggtc aaga                                        24

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gactccgaga cggcggtcaa ga                                          22

<210> SEQ ID NO 66
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gactccgaga ccttatcgca gggcggtcaa ga                               32

<210> SEQ ID NO 67
<211> LENGTH: 11
<212> TYPE: PRT
<213> ORGANISM: Mus musculus

<400> SEQUENCE: 67

Val Val Gly Ala Gly Gly Val Gly Lys Ser Ala
```

-continued

```
<210> SEQ ID NO 68
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 68 gtg gtt gga gct ggt ggc gta ggc aag agc gcc                        33
Val Val Gly Ala Gly Gly Val Gly Lys Ser Ala
1               5                   10

<210> SEQ ID NO 69
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 69 gtc gtg ggc gcg gac ggc gtg ggc aag agc gct                        33
Val Val Gly Ala Asp Gly Val Gly Lys Ser Ala
1               5                   10

<210> SEQ ID NO 70
<211> LENGTH: 11
<212> TYPE: PRT
<213> ORGANISM: Mus musculus

<400> SEQUENCE: 70

Val Val Gly Ala Asp Gly Val Gly Lys Ser Ala
1               5                   10

<210> SEQ ID NO 71
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gtcgtgggcg ccgacggcgt gggcaagagc                                   30

<210> SEQ ID NO 72
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gtcgtgggcg ccgacggcgt gggcaagagc gc                                32

<210> SEQ ID NO 73
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 73
gtgggcgccg acggcgtggg caagagcgct         30

<210> SEQ ID NO 74
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
gcagcgttac ctctatcgta ggg         23

<210> SEQ ID NO 75
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
tgagtatgac cctacgatag agg         23

<210> SEQ ID NO 76
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ctgaattagc tgtatcgtca agg         23

<210> SEQ ID NO 77
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
gactgagtat aaacttgtgg tgg         23

<210> SEQ ID NO 78
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gtggttggag ctggtggcgt agg         23

<210> SEQ ID NO 79
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
aaacttgtgg tggttggagc tgg                                           23

<210> SEQ ID NO 80
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gtacctctct ttgcgctccc tgg                                           23

<210> SEQ ID NO 81
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ccggatagtg ggaaccttct ggg                                           23

<210> SEQ ID NO 82
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
tacctctctt tgcgctccct ggg                                           23

<210> SEQ ID NO 83
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
tctgtacggc ggtctctccc agg                                           23

<210> SEQ ID NO 84
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
```

```
cccagaaggt tcccactatc cgg                                              23
```

<210> SEQ ID NO 85
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85

```
ctgtacggcg gtctctccca ggg                                              23
```

<210> SEQ ID NO 86
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86

```
cctcgagctc cctctgagcc agg                                              23
```

<210> SEQ ID NO 87
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87

```
gtgtaatagc tcctgcatgg ggg                                              23
```

<210> SEQ ID NO 88
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88

```
actccgagac cttatgccgc agg                                              23
```

<210> SEQ ID NO 89
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89

```
agcttggcgc gtttgcggcg cgg                                              23
```

<210> SEQ ID NO 90
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 90
cttgaccgcc ctgcggcata agg                                              23

<210> SEQ ID NO 91
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
gtggcggacc ccgagccgtt ggg                                              23

<210> SEQ ID NO 92
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
cgtggcggac cccgagccgt tgg                                              23

<210> SEQ ID NO 93
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
cgatgagctt ggcgcgtttg cgg                                              23

<210> SEQ ID NO 94
<211> LENGTH: 39
<212> TYPE: DNA
<213> ORGANISM: Mus musculus

<400> SEQUENCE: 94
gtggtggttg gagctggtgg cgtaggcaag agcgccttg                             39

<210> SEQ ID NO 95
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gtggtcgtgg gcgccgacgg cgtgggcaag agcgctttg                             39

<210> SEQ ID NO 96
<211> LENGTH: 27
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 96
gccgacggcg tgggcaagag cgctttg                                            27

<210> SEQ ID NO 97
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gtggtggttg gagctggtgg cgtaggcaag agcgccttg                               39

<210> SEQ ID NO 98
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
tggtggttgg agctggtggc gtaggcaaga gcgccttg                                38

<210> SEQ ID NO 99
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
tggagctggt ggcgtaggca agagcgcctt g                                       31

<210> SEQ ID NO 100
<211> LENGTH: 20602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (3015)..(3015)
<223> OTHER INFORMATION: a, c, t, g, unknown or other
<220> FEATURE:
<221> NAME/KEY: modified_base
<222> LOCATION: (3041)..(3041)
<223> OTHER INFORMATION: a, c, t, g, unknown or other

<400> SEQUENCE: 100
caggccctcc gagcgtggtg gagccgttct gtgagacagc cgggtacgag tcgtgacgct        60
ggaaggggca agcgggtggt gggcaggaat gcggtccgcc ctgcagcaac cggagggga       120 gggagaaggg agcggaaaag tctccaccgg acgcggccat ggctcggggg gggggggca       180 gcggaggagc gcttccggcc gacgtctcgt cgctgattgg cttcttttcc tcccgccgtg      240
tgtgaaaaca caaatggcgt gttttggttg gcgtaaggcg cctgtcagtt aacggcagcc      300
```

```
ggagtgcgca gccgccggca gcctcgctct gcccactggg tggggcggga ggtaggtggg     360
gtgaggcgag ctggacgtgc gggcgcggtc ggcctctggc ggggcggggg aggggaggga     420
gggtcagcga aagtagctcg cgcgcgagcg gccgcccacc ctccccttcc tctggggag      480 tcgttttacc cgccgccggc cgggcctcgt cgtctgattg gctctcgggg cccagaaaac     540
tggcccttgc cattggctcg tgttcgtgca agttgagtcc atccgccggc cagcggggc      600 ggcgaggagg cgctcccagg ttccggccct cccctcggcc ccgcgccgca gagtctggcc     660
gcgcgcccct gccgcaacgtg gcaggaagcg cgcgctgggg gcggggacgg gcagtagggc    720
tgagcggctg cggggcgggt gcaagcacgt ttccgacttg agttgcctca agagggggcgt    780 gctgagccag acctccatcg cgcactccgg ggagtggagg aaggagcga gggctcagtt      840 gggctgttt  ggaggcagga agcacttgct ctcccaaagt cgctctgagt tgttatcagt     900
aagggagctg cagtggagta ggcggggaga aggccgcacc cttctccgga ggggggaggg    960
gagtgttgca atacctttct gggagttctc tgctgcctcc tggcttctga ggaccgccct    1020
gggcctggga gaatcccttc cccctcttcc ctcgtgatct gcaactccag tctttctagc    1080
cttaattaac cgtttaaaca attctgcagg aatctagtta ttaatagtaa tcaattacgg    1140
ggtcattagt tcatagccca tatatggagt tccgcgttac ataacttacg gtaaatggcc    1200
cgcctggctg accgcccaac gacccccgcc cattgacgtc aataatgacg tatgttccca    1260
tagtaacgcc aatagggact ttccattgac gtcaatgggt ggagtattta cggtaaactg    1320
cccacttggc agtacatcaa gtgtatcata tgccaagtac gccccctatt gacgtcaatg    1380
acggtaaatg gcccgcctgg cattatgccc agtacatgac cttatgggac tttcctactt    1440
ggcagtacat ctacgtatta gtcatcgcta ttaccatggt cgaggtgagc ccacgttct     1500 gcttcactct ccccatctcc ccccctccc caccccaat tttgtattta tttattttt      1560 aattattttg tgcagcgatg ggggcggggg ggggggggg gcgcgcgcca ggcggggcgg     1620
ggcggggcga ggggcggggc ggggcgaggc ggagaggtgc ggcggcagcc aatcagagcg    1680
gcgcgctccg aaagtttcct tttatggcga ggcggcggcg gcggcggccc tataaaaagc    1740
gaagcgcgcg gcgggcggaa gtcgctgcgc gctgccttcg ccccgtgccc cgctccgccg    1800
ccgcctcgcg ccgcccgccc cggctctgac tgaccgcgtt actcccacag gtgagcgggc    1860
gggacggccc ttctcctccg ggctgtaatt agcgcttggt ttaatgacgg cttgtttctt    1920
ttctgtggct gcgtgaaagc cttgagggc tccgggaggg ccctttgtgc gggggagcg     1980 gctcgggggg tgcgtgcgtg tgtgtgtgcg tggggagcgc gcgtgcggc tccgcgctgc    2040 ccggcggctg tgagcgctgc gggcgcggcg cggggctttg tgcgctccgc agtgtgcgcg    2100
aggggagcgc ggccggggc ggtgccccgc ggtgcggggg gggctgcgag gggaacaaag    2160
gctgcgtgcg gggtgtgtgc gtggggggt gagcagggg tgtgggcgcg tcggtcgggc     2220 tgcaacccc  cctgcacccc cctccccgag ttgctgagca cggccggct tcgggtgcgg    2280 ggctccgtac ggggcgtggc gcggggctcg ccgtgccggg cgggggtgg cggcaggtgg    2340 gggtgccggg cggggcgggg ccgcctcggg ccggggaggg ctcggggag  gggcgcggcg    2400 gcccccggag cgccggcggc tgtcgaggcg cggcgagccg cagccattgc cttttatggt    2460
aatcgtgcga gagggcgcag ggacttcctt tgtcccaaat ctgtgcggag ccgaaatctg    2520
ggaggcgccg ccgcacccc  tctagcgggc gcggggcgaa gcggtgcggc gccggcagga    2580
aggaaatggg cggggagggc cttcgtgcgt cgccgcgccg ccgtccccctt ctccctctcc    2640
```

```
agcctcgggg ctgtccgcgg ggggacggct gccttcgggg gggacggggc agggcgggt    2700 tcggcttctg gcgtgtgacc ggcggctcta gagcctctgc taaccatgtt catgccttct    2760 tcttttcct acagctcctg ggcaacgtgc tggttattgt gctgtctcat cattttggca    2820
aagaattgat ttgataccgc gggccctaag aagttcctat tctctagaaa gtataggaac    2880
ttcgtcgaca tttaaatcat ttaaatataa cttcgtataa tgtatgctat acgaagttat    2940
tcgcgatgaa taaatgaaag cttgcagatc tgcgactcta gaggatctgc gactctagag    3000
gatcataatc agccntacca cattttgtag aggttttact ngctttaaaa aacctcccac    3060
acctccccct gaacctgaaa cataaaatga atgcaattgt tgttgttaac ttgtttattg    3120
cagcttataa tggttacaaa taaagcaata gcatcacaaa tttcacaaat aaagcatttt    3180
tttcactgca ttctagttgt ggtttgtcca aactcatcaa tgtatcttat catgtctgga    3240
tctgcgactc tagaggatca taatcagcca taccacattt gtagaggttt tacttgcttt    3300
aaaaaacctc ccacacctcc ccctgaacct gaaacataaa atgaatgcaa ttgttgttgt    3360
taacttgttt attgcagctt ataatggtta caaataaagc aatagcatca caaatttcac    3420
aaataaagca ttttttcac tgcattctag ttgtggtttg tccaaactca tcaatgtatc    3480
ttatcatgtc tggatctgcg actctagagg atcataatca gccataccac atttgtagag    3540
gttttacttg ctttaaaaaa cctcccacac ctcccctga acctgaaaca taaaatgaat    3600
gcaattgttg ttgttaactt gtttattgca gcttataatg gttacaaata aagcaatagc    3660
atcacaaatt tcacaaataa agcattttt tcactgcatt ctagttgtgg tttgtccaaa    3720
ctcatcaatg tatcttatca tgtctggatc cccatcaagc tgatccggaa cccttaatat    3780
aacttcgtat aatgtatgct atacgaagtt attaggtccc tcgacctgca gcccaagcta    3840
gatcgaattc ggccggcctt cgaacacgtg ccaccatgga ctataaggac cacgacggag    3900
actacaagga tcatgatatt gattacaaag acgatgacga taagatggcc ccaaagaaga    3960
agcggaaggt cggtatccac ggagtcccag cagccgacaa gaagtacagc atcggcctgg    4020
acatcggcac caactctgtg ggctgggccg tgatcaccga cgagtacaag gtgcccagca    4080
agaaattcaa ggtgctgggc aacaccgacc ggcacagcat caagaagaac ctgatcggag    4140
ccctgctgtt cgacagcggc gaaacagccg aggccacccg gctgaagaga accgccagaa    4200
gaagatacac cagacggaag aaccggatct gctatctgca agagatcttc agcaacgaga    4260
tggccaaggt ggacgacagc ttcttccaca gactggaaga gtccttcctg gtggaagagg    4320
ataagaagca cgagcggcac cccatcttcg gcaacatcgt ggacgaggtg gcctaccacg    4380
agaagtaccc caccatctac cacctgagaa agaaactggt ggacagcacc gacaaggccg    4440
acctgcggct gatctatctg gccctggccc acatgatcaa gttccggggc cacttcctga    4500
tcgagggcga cctgaacccc gacaacagcg acgtggacaa gctgttcatc cagctggtgc    4560
agacctacaa ccagctgttc gaggaaaacc ccatcaacgc cagcggcgtg gacgccaagg    4620
ccatcctgtc tgccagactg agcaagagca cggctggaa aaatctgatc gcccagctgc    4680
ccggcgagaa gaagaatggc ctgttcggaa acctgattgc cctgagcctg ggcctgaccc    4740
ccaacttcaa gagcaacttc gacctggccg aggatgccaa actgcagctg agcaaggaca    4800
cctacgacga cgacctggac aacctgctgg cccagatcgg cgaccagtac gccgacctgt    4860
ttctggccgc caagaacctg tccgacgcca tcctgctgag cgacatcctg agagtgaaca    4920
ccgagatcac caaggccccc ctgagcgcct ctatgatcaa gagatacgac gagcaccacc    4980
aggacctgac cctgctgaaa gctctcgtgc ggcagcagct gcctgagaag tacaaagaga    5040
```

```
ttttcttcga ccagagcaag aacggctacg ccggctacat tgacggcgga gccagccagg    5100
aagagttcta caagttcatc aagcccatcc tggaaaagat ggacggcacc gaggaactgc    5160
tcgtgaagct gaacagagag gacctgctgc ggaagcagcg gaccttcgac aacggcagca    5220
tcccccacca gatccacctg ggagagctgc acgccattct gcggcggcag gaagattttt    5280
acccattcct gaaggacaac cgggaaaaga tcgagaagat cctgaccttc cgcatcccct    5340
actacgtggg ccctctggcc aggggaaaca gcagattcgc ctggatgacc agaaagagcg    5400
aggaaaccat cacccccctgg aacttcgagg aagtggtgga caagggcgct tccgcccaga    5460
gcttcatcga gcggatgacc aacttcgata agaacctgcc caacgagaag gtgctgccca    5520
agcacagcct gctgtacgag tacttcaccg tgtataacga gctgaccaaa gtgaaatacg    5580
tgaccgaggg aatgagaaag cccgccttcc tgagcggcga gcagaaaaag gccatcgtgg    5640
acctgctgtt caagaccaac cggaaagtga ccgtgaagca gctgaaagag gactacttca    5700
agaaaatcga gtgcttcgac tccgtggaaa tctccggcgt ggaagatcgg ttcaacgcct    5760
ccctgggcac ataccacgat ctgctgaaaa ttatcaagga caaggacttc ctggacaatg    5820
aggaaaacga ggacattctg gaagatatcg tgctgaccct gacactgttt gaggacagag    5880
agatgatcga ggaacggctg aaaacctatg cccacctgtt cgacgacaaa gtgatgaagc    5940
agctgaagcg gcggagatac accggctggg gcaggctgag ccggaagctg atcaacggca    6000
tccgggacaa gcagtccggc aagacaatcc tggatttcct gaagtccgac ggcttcgcca    6060
acagaaactt catgcagctg atccacgacg acagcctgac cttttaaagag gacatccaga    6120 aagcccaggt gtccggccag ggcgatagcc tgcacgagca cattgccaat ctggccggca    6180
gccccgccat taagaagggc atcctgcaga cagtgaaggt ggtggacgag ctcgtgaaag    6240
tgatgggccg gcacaagccc gagaacatcg tgatcgaaat ggccagagag aaccagacca    6300
cccagaaggg acagaagaac agccgcgaga gaatgaagcg gatcgaagag ggcatcaaag    6360
agctgggcag ccagatcctg aaagaacacc ccgtggaaaa cacccagctg cagaacgaga    6420
agctgtacct gtactacctg cagaatgggc gggatatgta cgtggaccag gaactggaca    6480
tcaaccggct gtccgactac gatgtggacc atatcgtgcc tcagagcttt ctgaaggacg    6540
actccatcga caacaaggtg ctgaccagaa gcgacaagaa ccggggcaag agcgacaacg    6600
tgccctccga agaggtcgtg aagaagatga agaactactg gcggcagctg ctgaacgcca    6660
agctgattac ccagagaaag ttcgacaatc tgaccaaggc cgagagaggc ggcctgagcg    6720
aactggataa ggccggcttc atcaagagac agctggtgga aacccggcag atcacaaagc    6780
acgtggcaca gatcctggac tcccggatga acactaagta cgacgagaat gacaagctga    6840
tccgggaagt gaaagtgatc accctgaagt ccaagctggt gtccgatttc cggaaggatt    6900
tccagtttta caaagtgcgc gagatcaaca actaccacca cgcccacgac gcctacctga    6960
acgccgtcgt gggaaccgcc ctgatcaaaa agtaccctaa gctggaaagc gagttcgtgt    7020
acggcgacta caaggtgtac gacgtgcgga agatgatcgc caagagcgag caggaaatcg    7080
gcaaggctac cgccaagtac ttcttctaca gcaacatcat gaacttttt aagaccgaga    7140 ttaccctggc caacggcgag atccggaagc ggcctctgat cgagacaaac ggcgaaaccg    7200
gggagatcgt gtgggataag gcccgggatt tgccaccgt gcggaaagtg ctgagcatgc    7260
cccaagtgaa tatcgtgaaa aagaccgagg tgcagacagg cggcttcagc aaagagtcta    7320
tcctgcccaa gaggaacagc gataagctga tcgccagaaa gaaggactgg gaccctaaga    7380
```

-continued

```
agtacggcgg cttcgacagc cccaccgtgg cctattctgt gctggtggtg gccaaagtgg   7440
aaaagggcaa gtccaagaaa ctgaagagtg tgaaagagct gctggggatc accatcatgg   7500
aaagaagcag cttcgagaag aatcccatcg actttctgga agccaagggc tacaaagaag   7560
tgaaaaagga cctgatcatc aagctgccta agtactccct gttcgagctg aaaacggcc    7620 ggaagagaat gctggcctct gccggcgaac tgcagaaggg aaacgaactg ccctgccct    7680 ccaaatatgt gaacttcctg tacctggcca gccactatga aagctgaag gctcccccg     7740 aggataatga gcagaaacag ctgtttgtgg aacagcacaa gcactacctg gacgagatca   7800
tcgagcagat cagcgagttc tccaagagag tgatcctggc cgacgctaat ctggacaaag   7860
tgctgtccgc ctacaacaag caccgggata agcccatcag agagcaggcc gagaatatca   7920
tccacctgtt taccctgacc aatctgggag cccctgccgc cttcaagtac tttgacacca   7980
ccatcgaccg gaagaggtac accagcacca agaggtgct ggacgccacc ctgatccacc    8040
agagcatcac cggcctgtac gagacacgga tcgacctgtc tcagctggga ggcgacaaaa   8100
ggccggcggc cacgaaaaag gccggccagg caaaaaagaa aaaggaagc ggagccacta    8160 acttctccct gttgaaacaa gcaggggatg tcgaagagaa tcccgggcca gtgagcaagg   8220
gcgaggagct gttcaccggg gtggtgccca tcctggtcga gctggacggc gacgtaaacg   8280
gccacaagtt cagcgtgtcc ggcgagggcg agggcgatgc cacctacggc aagctgaccc   8340
tgaagttcat ctgcaccacc ggcaagctgc ccgtgccctg gcccaccctc gtgaccaccc   8400
tgacctacgg cgtgcagtgc ttcagccgct accccgacca catgaagcag cacgacttct   8460
tcaagtccgc catgcccgaa ggctacgtcc aggagcgcac catcttcttc aaggacgacg   8520
gcaactacaa gacccgcgcc gaggtgaagt tcgagggcga caccctggtg aaccgcatcg   8580
agctgaaggg catcgacttc aaggaggacg gcaacatcct ggggcacaag ctggagtaca   8640
actacaacag ccacaacgtc tatatcatgg ccgacaagca gaagaacggc atcaaggtga   8700
acttcaagat ccgccacaac atcgaggacg gcagcgtgca gctcgccgac cactaccagc   8760
agaacacccc catcggcgac ggccccgtgc tgctgcccga caaccactac ctgagcaccc   8820
agtccgccct gagcaaagac cccaacgaga gcgcgatca catggtcctg ctggagttcg    8880
tgaccgccgc cgggatcact ctcggcatgg acgagctgta caagtaaacg cgtatgcatg   8940
gccggccctg caggaattcg atatcaagct tatcgataat caacctctgg attacaaaat   9000
ttgtgaaaga ttgactggta ttcttaacta tgttgctcct tttacgctat gtggatacgc   9060
tgctttaatg ccttttgtatc atgctattgc ttcccgtatg gctttcattt tctcctcctt   9120
gtataaatcc tggttgctgt ctctttatga ggagttgtgg cccgttgtca ggcaacgtgg   9180
cgtggtgtgc actgtgtttg ctgacgcaac ccccactggt tggggcattg ccaccacctg   9240
tcagctcctt tccgggactt tcgctttccc cctccctatt gccacggcgg aactcatcgc   9300
cgcctgcctt gcccgctgct ggacagggc tcggctgttg ggcactgaca attccgtggt   9360
gttgtcgggg aaatcatcgt cctttccttg gctgctcgcc tgtgttgcca cctggattct   9420
gcgcgggacg tccttctgct acgtcccttc ggccctcaat ccagcggacc ttccttcccg   9480
cggcctgctg ccggctctgc ggcctcttcc gcgtcttcgc cttcgccctc agacgagtcg   9540
gatctccctt tgggccgcct ccccgcatcg ataccgtcga cctcgacctc gactgtgcct   9600
tctagttgcc agccatctgt tgtttgcccc tccccgtgc cttccttgac cctggaaggt    9660
gccactccca ctgtcctttc ctaataaaat gaggaaattg catcgcattg tctgagtagg   9720
tgtcattcta ttctgggggg tggggtgggg caggacagca agggggagga ttgggaagac   9780
```

```
aatggcaggc atgctgggga actagtggtg ccagggcgtg cccttgggct ccccgggcgc   9840
ggcggccgca tcgaattcta ccgggtaggg gaggcgcttt ccccaaggca gtctggagca   9900
tgcgctttag cagccccgct gggcacttgg cgctacacaa gtggcctctg gcctcgcaca   9960
cattccacat ccaccggtag cgccaaccg gctccgttct ttggtggccc cttcgcgcca   10020
ccttctactc ctcccctagt caggaagttc cccccgccc cgcagctcgc gtcgtgcagg   10080
acgtgacaaa tggaagtagc acgtctcact agtctcgtgc agatggacag caccgctgag   10140
caatggaagc gggtaggcct ttggggcagc ggccaatagc agctttgctc cttcgctttc   10200
tgggctcaga ggctgggaag gggtgggtcc ggggcgggc tcagggcgg gctcaggggc   10260 ggggcgggcg cccgaaggtc ctccggaggc ccggcattct gcacgcttca aaagcgcacg   10320
tctgccgcgc tgttctcctc ttcctcatct ccgggccttt cgacctgcaa tcgccgctag   10380
cgaagttcct attctctaga aagtatagga acttcgccac catgggatcg gccattgaac   10440
aagatggatt gcacgcaggt tctccggccg cttgggtgga gaggctattc ggctatgact   10500
gggcacaaca gacaatcggc tgctctgatg ccgccgtgtt ccggctgtca gcgcaggggc   10560
gcccggttct ttttgtcaag accgacctgt ccggtgccct gaatgaactg caggacgagg   10620
cagcgcggct atcgtggctg gccacgacgg gcgttccttg cgcagctgtg ctcgacgttg   10680
tcactgaagc gggaagggac tggctgctat tgggcgaagt gccggggcag gatctcctgt   10740
catctcacct tgctcctgcc gagaaagtat ccatcatggc tgatgcaatg cggcggctgc   10800
atacgcttga tccggctacc tgcccattcg accaccaagc gaaacatcgc atcgagcgag   10860
cacgtactcg gatggaagcc ggtcttgtcg atcaggatga tctggacgaa gagcatcagg   10920
ggctcgcgcc agccgaactg ttcgccaggc tcaaggcgcg catgcccgac ggcgatgatc   10980
tcgtcgtgac ccatggcgat gcctgcttgc cgaatatcat ggtggaaaat ggccgctttt   11040
ctggattcat cgactgtggc cggctgggtg tggcggaccg ctatcaggac atagcgttgg   11100
ctacccgtga tattgctgaa gagcttggcg gcgaatgggc tgaccgcttc ctcgtgcttt   11160
acggtatcgc cgctcccgat tcgcagcgca tcgccttcta tcgccttctt gacgagttct   11220
tctgagggga tccgctgtaa gtctgcagaa attgatgatc tattaaacaa taaagatgtc   11280
cactaaaatg gaagtttttc ctgtcatact ttgttaagaa gggtgagaac agagtaccta   11340
cattttgaat ggaaggattg gagctacggg ggtgggggtg gggtgggatt agataaatgc   11400 ctgctctttta ctgaaggctc tttactattg ctttatgata atgtttcata gttggatatc   11460
ataatttaaa caagcaaaac caaattaagg gccagctcat tcctcccact catgatctat   11520
agatctatag atctctcgtg ggatcattgt ttttctcttg attcccactt tgtggttcta   11580
agtactgtgg tttccaaatg tgtcagtttc atagcctgaa gaacgagatc agcagcctct   11640
gttccacata cacttcattc tcagtattgt tttgccaagt tctaattcca tcagaaagct   11700
tgcagaagat ctccccaact ggggtaacct ttgagttctc tcagttgggg gggcgcgccg   11760
gctagaagat gggcgggagt cttctgggca ggcttaaagg ctaacctggt gtgtgggcgt   11820
tgtcctgcag gggaattgaa caggtgtaaa attggaggga caagacttcc cacagatttt   11880
cggttttgtc gggaagtttt ttaatagggg caaataagga aaatgggagg ataggtagtc   11940 atctgggggtt ttatgcagca aaactacagg ttattattgc ttgtgatccg cctcggagta   12000
ttttccatcg aggtagatta aagacatgct caccccgagtt ttatactctc ctgcttgaga   12060
tccttactac agtatgaaat tacagtgtcg cgagttagac tatgtaagca gaattttaat   12120
```

```
cattttaaa gagcccagta cttcatatcc atttctcccg ctccttctgc agccttatca    12180
aaaggtattt tagaacactc attttagccc cattttcatt tattatactg gcttatccaa    12240
cccctagaca gagcattggc attttccctt tcctgatctt agaagtctga tgactcatga    12300
aaccagacag attagttaca tacaccacaa atcgaggctg tagctgggggc ctcaacactg    12360 cagttcttt ataactcctt agtacacttt ttgttgatcc tttgccttga tccttaattt    12420
tcagtgtcta tcacctctcc cgtcaggtgg tgttccacat ttgggcctat tctcagtcca    12480
gggagtttta caacaataga tgtattgaga atccaaccta aagcttaact ttccactccc    12540
atgaatgcct ctctccttt tctccattta taaactgagc tattaaccat taatggtttc    12600
caggtggatg tctcctcccc caatattacc tgatgtatct tacatattgc caggctgata    12660
ttttaagaca ttaaaaggta tatttcatta ttgagccaca tggtattgat tactgcttac    12720
taaaattttg tcattgtaca catctgtaaa aggtggttcc ttttggaatg caaagttcag    12780
gtgtttgttg tctttcctga cctaaggtct tgtgagcttg tatttttct atttaagcag    12840 tgctttctct tggactggct tgactcatgg cattctacac gttattgctg gtctaaatgt    12900
gattttgcca agcttcttca ggacctataa ttttgcttga cttgtagcca aacacaagta    12960
aaatgattaa gcaacaaatg tatttgtgaa gcttggtttt taggttgttg tgttgtgtgt    13020
gcttgtgctc tataataata ctatccaggg gctggagagg tggctcggag ttcaagagca    13080
cagactgctc ttccagaagt cctgagttca attcccagca accacatggt ggctcacaac    13140
catctgtaat gggatctgat gccctcttct ggtgtgtctg aagaccacaa gtgtattcac    13200
attaaataaa taaatcctcc ttcttcttct ttttttttt tttaaagaga atactgtctc    13260
cagtagaatt tactgaagta atgaaatact ttgtgtttgt tccaatatgg tagccaataa    13320
tcaaattact ctttaagcac tggaaatgtt accaaggaac taattttat ttgaagtgta    13380 actgtggaca gaggagccat aactgcagac ttgtgggata cagaagacca atgcagactt    13440
taatgtcttt tctcttacac taagcaataa agaaataaaa attgaacttc tagtatccta    13500
tttgtttaaa ctgctagctt tacttaactt ttgtgcttca tctatacaaa gctgaaagct    13560
aagtctgcag ccattactaa acatgaaagc aagtaatgat aattttggat ttcaaaaatg    13620
tagggccaga gtttagccag ccagtggtgg tgcttgcctt tatgcctta atcccagcac    13680 tctggaggca gagacaggca gatctctgag tttgagccca gcctggtcta cacatcaagt    13740
tctatctagg atagccagga atacacacag aaaccctgtt ggggaggggg gctctgagat    13800
ttcataaaat tataattgaa gcattcccta atgagccact atggatgtgg ctaaatccgt    13860
ctacctttct gatgagattt gggtattatt ttttctgtct ctgctgttgg ttgggtcttt    13920
tgacactgtg ggcttttcttt aaagcctcct tcctgccatg tggtctcttg tttgctacta    13980
acttcccatg gcttaaatgg catggctttt tgccttctaa gggcagctgc tgagatttgc    14040
agcctgattt ccagggtggg gttgggaaat cttttcaaaca ctaaaattgt cctttaattt    14100 ttttttaaa aaatgggtta tataataaac ctcataaaat agttatgagg agtgaggtgg    14160
actaatatta aatgagtccc tcccctataa aagagctatt aaggcttttt gtcttatact    14220 taacttttt tttaaatgtg gtatctttag aaccaagggt cttagagttt tagtatacag    14280
aaactgttgc atcgcttaat cagattttct agtttcaaat ccagagaatc caaattcttc    14340
acagccaaag tcaaattaag aatttctgac ttttaatgtt aatttgctta ctgtgaatat    14400
aaaaatgata gcttttcctg aggcagggtc tcactgtga tctctgcctg atctgcaaca    14460
agatatgtag actaaagttc tgcctgcttt tgtctcctga atactaaggt taaaatgtag    14520
```

```
taatactttt ggaacttgca ggtcagattc ttttataggg dacacactaa gggagcttgg   14580
gtgatagttg gtaaatgtgt ttaagtgatg aaaacttgaa ttattatcac cgcaacctac   14640
tttttaaaaa aaaaagccag gcctgttaga gcatgcttaa gggatccta ggacttgctg    14700 agcacacaag agtagttact tggcaggctc ctggtgagag catatttcaa aaaacaaggc   14760
agacaaccaa gaaactacag ttaaggttac ctgtctttaa accatctgca tatacacagg   14820
gatattaaaa tattccaaat aatatttcat tcaagttttc ccccatcaaa ttgggacatg   14880
gatttctccg gtgaataggc agagttggaa actaaacaaa tgttggtttt gtgatttgtg   14940
aaattgtttt caagtgatag ttaaagccca tgagatacag aacaaagctg ctatttcgag   15000
gtctcttggt ttatactcag aagcacttct ttgggtttcc ctgcactatc ctgatcatgt   15060
gctaggccta ccttaggctg attgttgttc aaataaactt aagttcctg tcaggtgatg    15120 tcatatgatt tcatatatca aggcaaaaca tgttatatat gttaaacatt tgtacttaat   15180
gtgaaagtta ggtctttgtg ggtttgattt ttaattttca aaacctgagc taaataagtc   15240 attttttacat gtcttacatt tggtggaatt gtataattgt ggtttgcagg caagactctc  15300
tgacctagta accctaccta tagagcactt tgctgggtca caagtctagg agtcaagcat   15360
ttcaccttga agttgagacg ttttgttagt gtatactagt ttatatgttg gaggacatgt   15420
ttatccagaa gatattcagg actatttttg actgggctaa ggaattgatt ctgattagca   15480
ctgttagtga gcattgagtg gcctttaggc ttgaattgga gtcacttgta tatctcaaat   15540
aatgctggcc tttttaaaa gcccttgttc tttatcaccc tgttttctac ataattttg    15600 ttcaaagaaa tacttgtttg gatctccttt tgacaacaat agcatgtttt caagccatat   15660 ttttttttcct tttttttttt tttttggtt tttcgagaca gggtttctct gtatagccct   15720
ggctgtcctg gaactcactt tgtagaccag gctggcctcg aactcagaaa tccgcctgcc   15780
tctgcctcct gagtgccggg attaaaggcg tgcaccacca cgcctggcta agttggatat   15840
tttgttatat aactataacc aatactaact ccactgggtg gattttttaat tcagtcagta   15900 gtcttaagtg gtctttattg gcccttcatt aaaatctact gttcactcta acagaggctg   15960
ttggtactag tggcacttaa gcaacttcct acgatatac tagcagatta agggtcaggg   16020
atagaaacta gtctagcgtt ttgtatacct accagcttta tactaccttg ttctgataga   16080
aatatttcag gacatctagc ttatcgatac cgtcgacggt atcgataagc ttgatatcga   16140
attctaccgg gtaggggagg cgcttttccc aaggcagtct ggagcatgcg ctttagcagc   16200
cccgctgggc acttggcgct acacaagtgg cctctggcct cgcacacatt ccacatccac   16260
cggtaggcgc caaccggctc cgttctttgg tggcccttc gcgccacctt ctactcctcc    16320
cctagtcagg aagttccccc ccgccccgca gctcgcgtcg tgcaggacgt gacaaatgga   16380
agtagcacgt ctcactagtc tcgtgcagat ggacagcacc gctgagcaat ggaagcgggt   16440
aggcctttgg ggcagcggcc aatagcagct ttgctcctc gctttctggg ctcagaggct    16500
gggaaggggt gggtccgggg gcgggctcag gggcgggctc aggggcgggg cggcgcccg    16560 aaggtcctcc ggaggcccgg cattctgcac gcttcaaaag cgcacgtctg ccgcgctgtt   16620
ctcctcttcc tcatctccgg gcctttcgac ctgcaggtcc tcgccatgga tcctgatgat   16680
gttgttgatt cttctaaatc ttttgtgatg gaaaactttt cttcgtacca cgggactaaa   16740
cctggttatg tagattccat tcaaaaaggt atacaaaagc caaatctgg tacacaagga    16800 aattatgacg atgattggaa agggttttat agtaccgaca taaatacga cgctgcggga   16860
```

-continued

```
tactctgtag ataatgaaaa cccgctctct ggaaaagctg gaggcgtggt caaagtgacg    16920
tatccaggac tgacgaaggt tctcgcacta aaagtggata atgccgaaac tattaagaaa    16980
gagttaggtt taagtctcac tgaaccgttg atggagcaag tcggaacgga agagtttatc    17040
aaaaggttcg gtgatggtgc ttcgcgtgta gtgctcagcc ttcccttcgc tgaggggagt    17100
tctagcgttg aatatattaa taactgggaa caggcgaaag cgttaagcgt agaacttgag    17160
attaattttg aaacccgtgg aaaacgtggc caagatgcga tgtatgagta tatggctcaa    17220
gcctgtgcag gaaatcgtgt caggcgatct ctttgtgaag gaaccttact tctgtggtgt    17280
gacataattg gacaaactac ctacagagat ttaaagctct aaggtaaata taaaattttt    17340
aagtgtataa tgtgttaaac tactgattct aattgtttgt gtattttaga ttccaaccta    17400
tggaactgat gaatgggagc agtggtggaa tgcagatcct agagctcgct gatcagcctc    17460
gactgtgcct tctagttgcc agccatctgt tgtttgcccc tcccccgtgc cttccttgac    17520
cctggaaggt gccactccca ctgtcctttc ctaataaaat gaggaaattg catcgcattg    17580
tctgagtagg tgtcattcta ttctgggggg tggggtgggg caggacagca agggggagga    17640
ttgggaagac aatagcaggc atgctgggga tgcggtgggc tctatggctt ctgaggcgga    17700
aagaaccagc tggggctcga gggggcccg gtacccagct tttgttccct ttagtgaggg    17760
ttaattgcgc gcttggcgta atcatggtca tagctgtttc ctgtgtgaaa ttgttatccg    17820
ctcacaattc cacacaacat acgagccgga agcataaagt gtaaagcctg gggtgcctaa    17880
tgagtgagct aactcacatt aattgcgttg cgctcactgc ccgctttcca gtcgggaaac    17940
ctgtcgtgcc agctgcatta atgaatcggc caacgcgcgg ggagaggcgg tttgcgtatt    18000
gggcgctctt ccgcttcctc gctcactgac tcgctgcgct cggtcgttcg gctgcggcga    18060
gcggtatcag ctcactcaaa ggcggtaata cggttatcca cagaatcagg ggataacgca    18120
ggaaagaaca tgtgagcaaa aggccagcaa aaggccagga accgtaaaaa ggccgcgttg    18180
ctggcgtttt tccataggct ccgcccccct gacgagcatc acaaaaatcg acgctcaagt    18240
cagaggtggc gaaacccgac aggactataa agataccagg cgtttccccc tggaagctcc    18300
ctcgtgcgct ctcctgttcc gaccctgccg cttaccggat acctgtccgc ctttctccct    18360
tcgggaagcg tggcgctttc tcatagctca cgctgtaggt atctcagttc ggtgtaggtc    18420
gttcgctcca agctgggctg tgtgcacgaa ccccccgttc agcccgaccg ctgcgcctta    18480
tccggtaact atcgtcttga gtccaacccg gtaagacacg acttatcgcc actggcagca    18540
gccactggta acaggattag cagagcgagg tatgtaggcg gtgctacaga gttcttgaag    18600
tggtggccta actacggcta cactagaagg acagtatttg gtatctgcgc tctgctgaag    18660
ccagttacct tcggaaaaag agttggtagc tcttgatccg gcaaacaaac caccgctggt    18720
agcggtggtt tttttgtttg caagcagcag attacgcgca gaaaaaaagg atctcaagaa    18780
gatcctttga tcttttctac ggggtctgac gctcagtgga acgaaaactc acgttaaggg    18840
attttggtca tgagattatc aaaaaggatc ttcacctaga tccttttaaa ttaaaaatga    18900
agttttaaat caatctaaag tatatatgag taaacttggt ctgacagtgg agctccaatt    18960
cgccctatag tgagtcgtat tacgcgcgct cactggccgt cgttttacaa cgtcgtgact    19020
gggaaaaccc tggcgttacc caacttaatc gccttgcagc acatccccct ttcgccagct    19080
ggcgtaatag cgaagaggcc cgcaccgatc gcccttccca acagttgcgc agcctgaatg    19140
gcgaatggga cgcgccctgt agcggcgcat taagcgcggc gggtgtggtg gttacgcgca    19200
gcgtgaccgc tacacttgcc agcgccctag cgcccgctcc tttcgctttc ttcccttcct    19260
```

```
ttctcgccac gttcgccggc ttteceegte aagetetaaa tegggggete cetttagggt      19320 tecgatttag tgetttacgg cacetegace ccaaaaaact tgattagggt gatggttcac      19380
gtagtgggcc atcgccctga tagacggttt ttcgccettt gacgttggag tccacgttct      19440
ttaatagtgg actcttgttc caaactggaa caacactcaa ccctatctcg gtctattctt      19500
ttgatttata agggattttg ccgatttcgg cctattggtt aaaaaatgag ctgatttaac      19560
aaaaatttaa cgcgaatttt aacaaaatat taacgcttac aatttaggtg gcacttttcg      19620
gggaaatgtg cgcggaaccc ctatttgttt attttctaa atacattcaa atatgtatcc       19680
gctcatgaga caataaccct gataaatgct tcaataatat tgaaaaagga agagtatgag      19740
tattcaacat ttccgtgtcg cccttattcc cttttttgcg gcattttgcc ttcctgtttt      19800
tgctcaccca gaaacgctgg tgaaagtaaa agatgctgaa gatcagttgg gtgcacgagt      19860
gggttacatc gaactggatc tcaacagcgg taagatcctt gagagttttc gccccgaaga     19920
acgttttcca atgatgagca cttttaaagt tctgctatgt ggcgcggtat tatcccgtat      19980
tgacgccggg caagagcaac tcggtcgccg catacactat tctcagaatg acttggttga     20040
gtactcacca gtcacagaaa agcatcttac ggatggcatg acagtaagag aattatgcag     20100
tgctgccata accatgagtg ataacactgc ggccaactta cttctgacaa cgatcggagg     20160
accgaaggag ctaaccgctt ttttgcacaa catgggggat catgtaactc gccttgatcg     20220
ttgggaaccg gagctgaatg aagccatacc aaacgacgag cgtgacacca cgatgcctgt     20280
agcaatggca acaacgttgc gcaaactatt aactggcgaa ctacttactc tagcttcccg     20340
gcaacaatta atagactgga tggaggcgga taaagttgca ggaccacttc tgcgctcggc     20400
ccttccggct ggctggttta ttgctgataa atctggagcc ggtgagcgtg ggtctcgcgg     20460
tatcattgca gcactggggc cagatggtaa gccctcccgt atcgtagtta tctacacgac     20520
ggggagtcag gcaactatgg atgaacgaaa tagacagatc gctgagatag gtgcctcact     20580
gattaagcat tggtaaccgc gg                                              20602
```

<210> SEQ ID NO 101
<211> LENGTH: 1079
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

```
caggccctcc gagcgtggtg gagccgttct gtgagacagc cgggtacgag tcgtgacgct        60
ggaaggggca agcgggtggt gggcaggaat gcggtccgcc ctgcagcaac cggaggggga       120
gggagaaggg agcggaaaag tctccaccgg acgcggccat ggctcggggg ggggggggca       180
gcggaggagc gcttccggcc gacgtctcgt cgctgattgg cttcttttcc tcccgccgtg       240
tgtgaaaaca caaatggcgt gttttggttg gcgtaaggcg cctgtcagtt aacggcagcc       300
ggagtgcgca gccgccggca gcctcgctct gcccactggg tggggcggga ggtaggtggg       360
gtgaggcgag ctggacgtgc gggcgcggtc ggcctctggc ggggcggggg aggggaggga      420
gggtcagcga agtagctcg cgcgcgagcg gccgcccacc ctccccttcc tctgggggag        480
tcgttttacc cgccgccggc cgggcctcgt cgtctgattg gctctcgggg cccagaaaac       540
tggcccttgc cattggctcg tgttcgtgca agttgagtcc atccgccggc cagcgggggc       600
```

| | |
|---|---|
| ggcgaggagg cgctcccagg ttccggccct ccctcggcc ccgcgccgca gagtctggcc | 660 |
| gcgcgcccct gcgcaacgtg gcaggaagcg cgcgctgggg gcggggacgg gcagtagggc | 720 |
| tgagcggctg cggggcgggt gcaagcacgt ttccgacttg agttgcctca agaggggcgt | 780 |
| gctgagccag acctccatcg cgcactccgg ggagtggagg gaaggagcga gggctcagtt | 840 |
| gggctgtttt ggaggcagga agcacttgct ctcccaaagt cgctctgagt tgttatcagt | 900 |
| aagggagctg cagtggagta ggcggggaga aggccgcacc cttctccgga gggggaggg | 960 |
| gagtgttgca ataccttct gggagttctc tgctgcctcc tggcttctga ggaccgccct | 1020 |
| gggcctggga gaatcccttc ccctcttcc ctcgtgatct gcaactccag tctttctag | 1079 |

<210> SEQ ID NO 102
<211> LENGTH: 1733
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102

| | |
|---|---|
| ccgtttaaac aattctgcag gaatctagtt attaatagta atcaattacg gggtcattag | 60 |
| ttcatagccc atatatggag ttccgcgtta cataacttac ggtaaatggc ccgcctggct | 120 |
| gaccgcccaa cgacccccgc ccattgacgt caataatgac gtatgttccc atagtaacgc | 180 |
| caatagggac tttccattga cgtcaatggg tggagtattt acggtaaact gcccacttgg | 240 |
| cagtacatca agtgtatcat atgccaagta cgccccctat tgacgtcaat gacggtaaat | 300 |
| ggcccgcctg gcattatgcc cagtacatga ccttatggga ctttcctact tggcagtaca | 360 |
| tctacgtatt agtcatcgct attaccatgg tcgaggtgag ccccacgttc tgcttcactc | 420 |
| tccccatctc cccccctcc ccaccccaa ttttgtattt atttattttt taattatttt | 480 |
| gtgcagcgat gggggcgggg ggggggggg ggcgcgcgcc aggcggggcg gggcggggcg | 540 |
| aggggcgggg cggggcgagg cggagaggtg cggcggcagc caatcagagc ggcgcgctcc | 600 |
| gaaagtttcc ttttatggcg aggcggcggc ggcggcggcc ctataaaaag cgaagcgcgc | 660 |
| ggcgggcgga agtcgctgcg cgctgccttc gccccgtgcc ccgctccgcc gccgcctcgc | 720 |
| gccgcccgcc ccggctctga ctgaccgcgt tactcccaca ggtgagcggg cgggacggcc | 780 |
| cttctcctcc gggctgtaat tagcgcttgg tttaatgacg cttgtttct tttctgtggc | 840 |
| tgcgtgaaag ccttgagggg ctccggggag gcccttttgtg cgggggagc ggctcggggg | 900 |
| gtgcgtgcgt gtgtgtgtgc gtggggagcg ccgcgtgcgg ctccgcgctg cccggcggct | 960 |
| gtgagcgctg cgggcgcggc gcggggcttt gtgcgctccg cagtgtgcgc gaggggagcg | 1020 |
| cggccggggg cggtgcccg cggtgcgggg ggggctgcga ggggaacaaa ggctgcgtgc | 1080 |
| ggggtgtgtg cgtgggggg tgagcagggg gtgtgggcgc gtcggtcggg ctgcaacccc | 1140 |
| ccctgcaccc ccctccccga gttgctgagc acggcccggc ttcgggtgcg gggctccgta | 1200 |
| cggggcgtgg cgcggggctc gccgtgccgg gcggggggtg gcggcaggtg ggggtgccgg | 1260 |
| gcggggcggg gccgcctcgg gccggggagg gctcggggga ggggcgcggc ggccccggga | 1320 |
| gcgccggcgg ctgtcgaggc gcggcgagcc gcagccattg cctttatgg taatcgtgcg | 1380 |
| agagggcgca gggacttcct ttgtcccaaa tctgtgcgga gccgaaatct gggaggcgcc | 1440 |
| gccgcacccc ctctagcggg cgcggggcga agcggtgcgg cgccggcagg aaggaaatgg | 1500 |
| gcggggaggg ccttcgtgcg tcgccgcgcc gccgtccccc tctccctctc cagcctcggg | 1560 |

```
gctgtccgcg gggggacggc tgccttcggg ggggacgggg cagggcgggg ttcggcttct   1620
ggcgtgtgac cggcggctct agagcctctg ctaaccatgt tcatgccttc ttcttttttcc  1680 tacagctcct gggcaacgtg ctggttattg tgctgtctca tcattttggc aaa          1733
```

<210> SEQ ID NO 103
<211> LENGTH: 906
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other

<400> SEQUENCE: 103

```
ataacttcgt ataatgtatg ctatacgaag ttattcgcga tgaataaatg aaagcttgca    60
gatctgcgac tctagaggat ctgcgactct agaggatcat aatcagccnt accacatttt   120
gtagaggttt tactngcttt aaaaaacctc ccacacctcc ccctgaacct gaaacataaa   180
atgaatgcaa ttgttgttgt taacttgttt attgcagctt ataatggtta caaataaagc   240
aatagcatca caaatttcac aaataaagca ttttttttcac tgcattctag ttgtggtttg   300
tccaaactca tcaatgtatc ttatcatgtc tggatctgcg actctagagg atcataatca   360
gccataccac atttgtagag gttttacttg cttttaaaaaa cctcccacac ctcccccctga   420 acctgaaaca taaaatgaat gcaattgttg ttgttaactt gtttattgca gcttataatg   480
gttacaaata aagcaatagc atcacaaatt tcacaaataa agcatttttt tcactgcatt   540
ctagttgtgg tttgtccaaa ctcatcaatg tatcttatca tgtctggatc tgcgactcta   600
gaggatcata tcagccata ccacatttgt agaggtttta cttgctttaa aaaacctccc   660
acacctcccc ctgaacctga acataaaat gaatgcaatt gttgttgtta acttgtttat   720
tgcagcttat aatggttaca ataaagcaa tagcatcaca aatttcacaa ataaagcatt   780 ttttcactg cattctagtt gtggtttgtc caaactcatc aatgtatctt atcatgtctg   840
gatccccatc aagctgatcc ggaaccctta atataacttc gtataatgta tgctatacga   900
agttat                                                             906
```

<210> SEQ ID NO 104
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104

```
gactataagg accacgacgg agactacaag gatcatgata ttgattacaa agacgatgac    60
gataag                                                              66
```

<210> SEQ ID NO 105
<211> LENGTH: 51
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
atggccccaa agaagaagcg gaaggtcggt atccacggag tcccagcagc c            51

<210> SEQ ID NO 106
<211> LENGTH: 4101
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
gacaagaagt acagcatcgg cctggacatc ggcaccaact ctgtgggctg ggccgtgatc       60
accgacgagt acaaggtgcc cagcaagaaa ttcaaggtgc tgggcaacac cgaccggcac      120
agcatcaaga gaacctgat cggagccctg ctgttcgaca cggcgaaac agccgaggcc       180 acccggctga gagaaccgc cagaagaaga taccaccagac ggaagaaccg gatctgctat      240
ctgcaagaga tcttcagcaa cgagatggcc aaggtggacg acagcttctt ccacagactg      300
gaagagtcct cctggtgga agaggataag aagcacgagc ggcacccat cttcggcaac      360 atcgtggacg aggtggccta ccacgagaag taccccacca tctaccacct gagaaagaaa      420
ctggtggaca gcaccgacaa ggccgacctg cggctgatct atctggccct ggcccacatg      480
atcaagttcc ggggccactt cctgatcgag ggcgacctga ccccgacaa cagcgacgtg      540 gacaagctgt tcatccagct ggtgcagacc tacaaccagc tgttcgagga aaaccccatc      600
aacgccagcg gcgtggacgc caaggccatc ctgtctgcca gactgagcaa gagcagacgg      660
ctggaaaatc tgatcgccca gctgcccggc gagaagaaga tggcctgtt cggaaacctg      720 attgccctga gcctgggcct gacccccaac ttcaagagca cttcgacct ggccgaggat      780 gccaaactgc agctgagcaa ggacacctac gacgacgacc tggacaacct gctggcccag      840
atcggcgacc agtacgccga cctgtttctg gccgccaaga acctgtccga cgccatcctg      900
ctgagcgaca tcctgagagt gaacaccgag atcaccaagg cccccctgag cgcctctatg      960
atcaagagat acgacgagca ccaccaggac ctgaccctgc tgaaagctct cgtgcggcag     1020
cagctgcctg agaagtacaa agagattttc ttcgaccaga gcaagaacgg ctacgccggc     1080
tacattgacg gcggagccag ccaggaagag ttctacaagt tcatcaagcc catcctggaa     1140
aagatggacg gcaccgagga actgctcgtg aagctgaaca gagaggacct gctgcggaag     1200
cagcggacct tcgacaacgg cagcatcccc caccagatcc acctgggaga gctgcacgcc     1260
attctgcggc ggcaggaaga tttttaccca ttcctgaagg acaaccggga aaagatcgag     1320
aagatcctga ccttccgcat cccctactac gtgggccctc tggccagggg aaacagcaga     1380
ttcgcctgga tgaccagaaa gagcgaggaa accatcaccc cctggaactt cgaggaagtg     1440
gtggacaagg gcgcttccgc ccagagcttc atcgagcgga tgaccaactt cgataagaac     1500
ctgcccaacg agaaggtgct gcccaagcac agcctgctgt acgagtactt caccgtgtat     1560
aacgagctga ccaaagtgaa atacgtgacc gagggaatga gaaagcccgc cttcctgagc     1620
ggcgagcaga aaaaggccat cgtggacctg ctgttcaaga ccaaccggaa agtgaccgtg     1680
aagcagctga aagaggacta cttcaagaaa atcgagtgct tcgactccgt ggaaatctcc     1740
```

```
ggcgtggaag atcggttcaa cgcctccctg ggcacatacc acgatctgct gaaaattatc      1800
aaggacaagg acttcctgga caatgaggaa acgaggaca ttctggaaga tatcgtgctg       1860
accctgacac tgtttgagga cagagagatg atcgaggaac ggctgaaaac ctatgcccac      1920 ctgttcgacac acaaagtgat gaagcagctg aagcggcgga gatacaccgg ctggggcagg    1980
ctgagccgga agctgatcaa cggcatccgg gacaagcagt ccggcaagac aatcctggat     2040
ttcctgaagt ccgacggctt cgccaacaga aacttcatgc agctgatcca cgacgacagc     2100 ctgacctttta agaggacat ccagaaagcc caggtgtccg gccagggcga tagcctgcac     2160
gagcacattg ccaatctggc cggcagcccc gccattaaga agggcatcct gcagacagtg     2220
aaggtggtgg acgagctcgt gaaagtgatg ggccggcaca gcccgagaa catcgtgatc      2280 gaaatggcca gagagaacca gaccacccag aagggacaga agaacagccg cgagagaatg    2340
aagcggatcg aagagggcat caaagagctg ggcagccaga tcctgaaaga cacccccgtg    2400
gaaaacaccc agctgcagaa cgagaagctg tacctgtact acctgcagaa tgggcgggat    2460
atgtacgtgg accaggaact ggacatcaac cggctgtccg actacgatgt ggaccatatc    2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac    2640
tactggcggc agctgctgaa cgccaagctg attacccaga aaagttcga caatctgacc     2700 aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcacccc tgaagtccaag    2880 ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg   3060
atcgccaaga gcgagcagga aatcggcaag gctaccgcca gtacttctt ctacagcaac     3120 atcatgaact tttcaagac cgagattacc ctggccaacg cgagatccg gaagcggcct     3180 ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc     3360 agaaagaagg actgggaccc taagaagtac ggcggcttcg acagccccac cgtggcctat    3420
tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctgacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
```
ctgtctcagc tgggaggcga c                                                4101

<210> SEQ ID NO 107
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
aaaaggccgg cggccacgaa aaaggccggc caggcaaaaa agaaaaag                      48

<210> SEQ ID NO 108
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ggaagcggag ccactaactt ctccctgttg aaacaagcag gggatgtcga agagaatccc         60
gggcca                                                                   66

<210> SEQ ID NO 109
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
gtgagcaagg gcgaggagct gttcaccggg gtggtgccca tcctggtcga gctggacggc         60
gacgtaaacg gccacaagtt cagcgtgtcc ggcgagggcg agggcgatgc cacctacggc        120
aagctgaccc tgaagttcat ctgcaccacc ggcaagctgc ccgtgccctg gcccaccctc        180
gtgaccaccc tgacctacgg cgtgcagtgc ttcagccgct accccgacca catgaagcag        240
cacgacttct tcaagtccgc catgcccgaa ggctacgtcc aggagcgcac catcttcttc        300
aaggacgacg gcaactacaa gacccgcgcc gaggtgaagt tcgagggcga caccctggtg        360
aaccgcatcg agctgaaggg catcgacttc aaggaggacg gcaacatcct ggggcacaag        420
ctggagtaca actacaacag ccacaacgtc tatatcatgg ccgacaagca gaagaacggc        480
atcaaggtga acttcaagat ccgccacaac atcgaggacg gcagcgtgca gctcgccgac        540
cactaccagc agaacacccc catcggcgac ggccccgtgc tgctgcccga caaccactac        600
ctgagcaccc agtccgccct gagcaaagac cccaacgaga agcgcgatca catggtcctg        660
ctggagttcg tgaccgccgc cgggatcact ctcggcatgg acgagctgta caag              714

<210> SEQ ID NO 110
<211> LENGTH: 597
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110

-continued

```
cgataatcaa cctctggatt acaaaatttg tgaaagattg actggtattc ttaactatgt    60
tgctcctttt acgctatgtg gatacgctgc tttaatgcct ttgtatcatg ctattgcttc   120
ccgtatggct ttcattttct cctccttgta taaatcctgg ttgctgtctc tttatgagga   180
gttgtggccc gttgtcaggc aacgtggcgt ggtgtgcact gtgtttgctg acgcaacccc   240
cactggttgg ggcattgcca ccacctgtca gctcctttcc gggactttcg ctttccccct   300
ccctattgcc acggcggaac tcatcgccgc ctgccttgcc cgctgctgga caggggctcg   360
gctgttgggc actgacaatt ccgtggtgtt gtcggggaaa tcatcgtcct tccttggct    420 gctcgcctgt gttgccacct ggattctgcg cgggacgtcc ttctgctacg tcccttcggc   480
cctcaatcca gcggaccttc cttcccgcgg cctgctgccg gctctgcggc ctcttccgcg   540
tcttcgcctt cgccctcaga cgagtcggat ctccctttgg gccgcctccc cgcatcg      597
```

<210> SEQ ID NO 111
<211> LENGTH: 216
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111

```
cgacctcgac ctcgactgtg ccttctagtt gccagccatc tgttgtttgc ccctcccccg    60
tgccttcctt gaccctggaa ggtgccactc ccactgtcct ttcctaataa aatgaggaaa   120
ttgcatcgca ttgtctgagt aggtgtcatt ctattctggg gggtggggtg gggcaggaca   180
gcaaggggga ggattgggaa gacaatggca ggcatg                              216
```

<210> SEQ ID NO 112
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112

```
aattctaccg ggtaggggag gcgcttttcc caaggcagtc tggagcatgc gctttagcag    60
ccccgctggg cacttggcgc tacacaagtg gcctctggcc tcgcacacat tccacatcca   120
ccggtaggcg ccaaccggct ccgttctttg gtggcccctt cgcgccacct tctactcctc   180
ccctagtcag gaagttcccc cccgccccgc agctcgcgtc gtgcaggacg tgacaaatgg   240
aagtagcacg tctcactagt ctcgtgcaga tggacagcac cgctgagcaa tggaagcggg   300
taggcctttg gggcagcggc caatagcagc tttgctcctt cgctttctgg gctcagaggc   360
tgggaagggg tgggtccggg ggcggggctca gggggcgggct cagggggcggg gcgggcgccc   420 gaaggtcctc cggaggcccg gcattctgca cgcttcaaaa gcgcacgtct gccgcgctgt   480
tctcctcttc ctcatctccg ggcctttcga                                     510
```

<210> SEQ ID NO 113
<211> LENGTH: 804
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 113

```
atgggatcgg ccattgaaca agatggattg cacgcaggtt ctccggccgc ttgggtggag      60
aggctattcg gctatgactg ggcacaacag acaatcggct gctctgatgc cgccgtgttc     120
cggctgtcag cgcaggggcg cccggttctt tttgtcaaga ccgacctgtc cggtgccctg     180
aatgaactgc aggacgaggc agcgcggcta tcgtggctgg ccacgacggg cgttccttgc     240
gcagctgtgc tcgacgttgt cactgaagcg ggaagggact ggctgctatt gggcgaagtg     300
ccggggcagg atctcctgtc atctcacctt gctcctgccg agaaagtatc catcatggct     360
gatgcaatgc ggcggctgca tacgcttgat ccggctacct gcccattcga ccaccaagcg     420
aaacatcgca tcgagcgagc acgtactcgg atggaagccg tcttgtcga tcaggatgat      480
ctggacgaag agcatcaggg gctcgcgcca gccgaactgt tcgccaggct caaggcgcgc     540
atgcccgacg gcgatgatct cgtcgtgacc catggcgatg cctgcttgcc gaatatcatg     600
gtggaaaatg gccgcttttc tggattcatc gactgtggcc ggctgggtgt ggcggaccgc     660
tatcaggaca tagcgttggc tacccgtgat attgctgaag agcttggcgg cgaatgggct     720
gaccgcttcc tcgtgcttta cggtatcgcc gctcccgatt cgcagcgcat cgccttctat     780
cgccttcttg acgagttctt ctga                                             804
```

<210> SEQ ID NO 114
<211> LENGTH: 465
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 114

```
ctgtaagtct gcagaaattg atgatctatt aaacaataaa gatgtccact aaaatggaag      60
ttttttcctgt catactttgt taagaagggt gagaacagag tacctacatt tgaatggaa     120
ggattggagc tacggggtg ggggtggggt gggattagat aaatgcctgc tctttactga     180
aggctcttta ctattgcttt atgataatgt ttcatagttg gatatcataa tttaaacaag     240
caaaaccaaa ttaagggcca gctcattcct cccactcatg atctatagat ctatagatct     300
ctcgtgggat cattgttttt ctcttgattc ccactttgtg gttctaagta ctgtggtttc     360
caaatgtgtc agtttcatag cctgaagaac gagatcagca gcctctgttc cacatacact     420
tcattctcag tattgttttg ccaagttcta attccatcag aaagc                      465
```

<210> SEQ ID NO 115
<211> LENGTH: 4336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 115

```
agatgggcgg gagtcttctg gcaggcttta aggctaacc tggtgtgtgg gcgttgtcct       60
gcaggggaat tgaacaggtg taaaattgga gggacaagac ttcccacaga tttcggttt      120
tgtcgggaag ttttttaata ggggcaaata aggaaatgg gaggataggt agtcatctgg      180
ggttttatgc agcaaaacta caggttatta ttgcttgtga tccgcctcgg agtattttcc      240
```

```
atcgaggtag attaaagaca tgctcacccg agttttatac tctcctgctt gagatcctta    300
ctacagtatg aaattacagt gtcgcgagtt agactatgta agcagaattt taatcatttt    360
taaagagccc agtacttcat atccatttct cccgctcctt ctgcagcctt atcaaaaggt    420
attttagaac actcatttta gccccatttt catttattat actggcttat ccaacccta    480 gacagagcat tggcattttc cctttcctga tcttagaagt ctgatgactc atgaaaccag    540
acagattagt tacatacacc acaaatcgag gctgtagctg gggcctcaac actgcagttc    600
ttttataact ccttagtaca cttttgttg atcctttgcc ttgatcctta attttcagtg    660
tctatcacct ctcccgtcag gtggtgttcc acatttgggc ctattctcag tccagggagt    720
tttacaacaa tagatgtatt gagaatccaa cctaaagctt aactttccac tcccatgaat    780
gcctctctcc tttttctcca tttataaact gagctattaa ccattaatgg tttccaggtg    840
gatgtctcct cccccaatat tacctgatgt atcttacata ttgccaggct gatattttaa    900
gacattaaaa ggtatatttc attattgagc cacatggtat tgattactgc ttactaaaat    960
tttgtcattg tacacatctg taaaaggtgg ttccttttgg aatgcaaagt tcaggtgttt   1020
gttgtctttc ctgacctaag gtcttgtgag cttgtatttt ttctatttaa gcagtgcttt   1080
ctcttggact ggcttgactc atggcattct acacgttatt gctggtctaa atgtgatttt   1140
gccaagcttc ttcaggacct ataattttgc ttgacttgta gccaaacaca agtaaaatga   1200
ttaagcaaca aatgtatttg tgaagcttgg ttttaggtt gttgtgttgt gtgtgcttgt   1260
gctctataat aatactatcc aggggctgga gaggtggctc ggagttcaag agcacagact   1320
gctcttccag aagtcctgag ttcaattccc agcaaccaca tggtggctca caaccatctg   1380
taatgggatc tgatgccctc ttctggtgtg tctgaagacc acaagtgtat tcacattaaa   1440
taaataaatc ctccttcttc ttcttttttt tttttttaaa gagaatactg tctccagtag   1500
aatttactga agtaatgaaa actttgtgt ttgttccaat atggtagcca ataatcaaat   1560
tactctttaa gcactggaaa tgttaccaag gaactaattt ttatttgaag tgtaactgtg   1620
gacagaggag ccataactgc agacttgtgg gatacagaag accaatgcag actttaatgt   1680
cttttctctt acactaagca ataaagaaat aaaaattgaa cttctagtat cctatttgtt   1740
taaactgcta gctttactta acttttgtgc ttcatctata caaagctgaa agctaagtct   1800
gcagccatta ctaaacatga aagcaagtaa tgataatttt ggattcaaa aatgtagggc   1860 cagagtttag ccagccagtg gtggtgcttg cctttatgcc tttaatccca gcactctgga   1920
ggcagagaca ggcagatctc tgagtttgag cccagcctgg tctacacatc aagttctatc   1980
taggatagcc aggaatacac acagaaaccc tgttggggag gggggctctg agatttcata   2040
aaattataat tgaagcattc cctaatgagc cactatggat gtggctaaat ccgtctacct   2100
ttctgatgag atttgggtat tatttttct gtctctgctg ttggttgggt cttttgacac   2160
tgtgggcttt ctttaaagcc tccttcctgc catgtggtct cttgtttgct actaacttcc   2220
catggcttaa atggcatggc ttttgccctt ctaagggcag ctgctgagat ttgcagcctg   2280
atttccaggg tggggttggg aaatctttca aacactaaaa ttgtcctta atttttttt   2340 taaaaaatgg gttatataat aaacctcata aaatagttat gaggagtgag gtggactaat   2400
attaaatgag tccctcccct ataaagagc tattaaggct ttttgtctta tacttaactt   2460 ttttttaaa tgtggtatct ttagaaccaa gggtcttaga gttttagtat acagaaactg   2520
ttgcatcgct taatcagatt ttctagtttc aaatccagag aatccaaatt cttcacagcc   2580
```

| | |
|---|---|
| aaagtcaaat taagaatttc tgactttaa tgttaatttg cttactgtga atataaaaat | 2640 |
| gatagctttt cctgaggcag ggtctcacta tgtatctctg cctgatctgc aacaagatat | 2700 |
| gtagactaaa gttctgcctg cttttgtctc ctgaatacta aggttaaaat gtagtaatac | 2760 |
| ttttggaact tgcaggtcag attcttttat aggggacaca ctaagggagc ttgggtgata | 2820 |
| gttggtaaat gtgtttaagt gatgaaaact tgaattatta tcaccgcaac ctactttta | 2880 |
| aaaaaaaaag ccaggcctgt tagagcatgc ttaagggatc cctaggactt gctgagcaca | 2940 |
| caagagtagt tacttggcag gctcctggtg agagcatatt tcaaaaaaca aggcagacaa | 3000 |
| ccaagaaact acagttaagg ttacctgtct ttaaaccatc tgcatataca cagggatatt | 3060 |
| aaaatattcc aaataatatt tcattcaagt tttcccccat caaattggga catggatttc | 3120 |
| tccggtgaat aggcagagtt ggaaactaaa caaatgttgg ttttgtgatt tgtgaaattg | 3180 |
| ttttcaagtg atagttaaag cccatgagat acagaacaaa gctgctattt cgaggtctct | 3240 |
| tggtttatac tcagaagcac ttctttgggt ttccctgcac tatcctgatc atgtgctagg | 3300 |
| cctaccttag gctgattgtt gttcaaataa acttaagttt cctgtcaggt gatgtcatat | 3360 |
| gatttcatat atcaaggcaa aacatgttat atatgttaaa catttgtact taatgtgaaa | 3420 |
| gttaggtctt tgtgggtttg attttaatt ttcaaaacct gagctaaata agtcattttt | 3480 |
| acatgtctta catttggtgg aattgtataa ttgtggtttg caggcaagac tctctgacct | 3540 |
| agtaaccta cctatagagc actttgctgg gtcacaagtc taggagtcaa gcatttcacc | 3600 |
| ttgaagttga gacgttttgt tagtgtatac tagtttatat gttggaggac atgtttatcc | 3660 |
| agaagatatt caggactatt tttgactggg ctaaggaatt gattctgatt agcactgtta | 3720 |
| gtgagcattg agtggccttt aggcttgaat tggagtcact tgtatatctc aaataatgct | 3780 |
| ggcctttttt aaaagccctt gttctttatc accctgtttt ctacataatt tttgttcaaa | 3840 |
| gaaatacttg tttggatctc cttttgacaa caatagcatg ttttcaagcc atatttttt | 3900 |
| tcctttttt tttttttt ggttttcga cagggttc tctgtatag ccctggctgt | 3960 |
| cctggaactc actttgtaga ccaggctggc ctcgaactca gaaatccgcc tgcctctgcc | 4020 |
| tcctgagtgc cgggattaaa ggcgtgcacc accacgcctg gctaagttgg atattttgtt | 4080 |
| atataactat aaccaatact aactccactg ggtggatttt taattcagtc agtagtctta | 4140 |
| agtggtcttt attggcccctt cattaaaatc tactgttcac tctaacagag gctgttggta | 4200 |
| ctagtggcac ttaagcaact tcctacggat atactagcag attaagggtc agggatagaa | 4260 |
| actagtctag cgttttgtat acctaccagc tttatactac cttgttctga tagaaatatt | 4320 |
| tcaggacatc tagctt | 4336 |

<210> SEQ ID NO 116
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116

| | |
|---|---|
| aattctaccg ggtaggggag gcgcttttcc caaggcagtc tggagcatgc gctttagcag | 60 |
| ccccgctggg cacttggcgc tacacaagtg gcctctggcc tcgcacacat tccacatcca | 120 |
| ccggtaggcg ccaaccggct ccgttctttg gtggcccctt cgcgccacct tctactcctc | 180 |
| ccctagtcag gaagttcccc cccgccccgc agctcgcgtc gtgcaggacg tgacaaatgg | 240 |

```
aagtagcacg tctcactagt ctcgtgcaga tggacagcac cgctgagcaa tggaagcggg    300
taggcctttg gggcagcggc caatagcagc tttgctcctt cgctttctgg gctcagaggc    360
tgggaagggg tgggtccggg ggcgggctca ggggcgggct caggggcggg gcgggcgccc    420
gaaggtcctc cggaggcccg gcattctgca cgcttcaaaa gcgcacgtct gccgcgctgt    480
tctcctcttc ctcatctccg ggcctttcga                                     510

<210> SEQ ID NO 117
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
atggatcctg atgatgttgt tgattcttct aaatcttttg tgatggaaaa ctttcttcg     60 taccacggga ctaaacctgg ttatgtagat tccattcaaa aaggtataca aaagccaaaa   120
tctggtacac aaggaaatta tgacgatgat tggaaagggt tttatagtac cgacaataaa   180
tacgacgctg cgggatactc tgtagataat gaaaacccgc tctctggaaa agctggaggc   240
gtggtcaaag tgacgtatcc aggactgacg aaggttctcg cactaaaagt ggataatgcc   300
gaaactatta agaaagagtt aggtttaagt ctcactgaac cgttgatgga gcaagtcgga   360
acggaagagt ttatcaaaag gttcggtgat ggtgcttcgc gtgtagtgct cagccttccc   420
ttcgctgagg ggagttctag cgttgaatat attaataact gggaacaggc gaaagcgtta   480
agcgtagaac ttgagattaa ttttgaaacc cgtggaaaac gtggccaaga tgcgatgtat   540
gagtatatgg ctcaagcctg tgcaggaaat cgtgtcaggc gatctctttg tgaaggaacc   600
ttacttctgt ggtgtgacat aattggacaa actacctaca gagatttaaa gctctaa      657

<210> SEQ ID NO 118
<211> LENGTH: 204
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118
cgactgtgcc ttctagttgc cagccatctg ttgtttgccc ctccccgtg ccttccttga     60 ccctggaagg tgccactccc actgtccttt cctaataaaa tgaggaaatt gcatcgcatt   120
gtctgagtag gtgtcattct attctggggg gtggggtggg gcaggacagc aagggggagg   180
attgggaaga caatagcagg catg                                           204

<210> SEQ ID NO 119
<211> LENGTH: 7189
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119
cctgcaggca gctgcgcgct cgctcgctca ctgaggccgc ccgggcaaag cccgggcgtc     60
```

-continued

```
gggcgacctt tggtcgcccg gcctcagtga gcgagcgagc gcgcagagag ggagtggcca      120
actccatcac taggggttcc tgcggccgca cgcgtgaggg cctatttccc atgattcctt      180
catatttgca tatacgatac aaggctgtta gagagataat tggaattaat ttgactgtaa      240
acacaaagat attagtacaa aatacgtgac gtagaaagta ataatttctt gggtagtttg      300
cagttttaaa attatgtttt aaaatggact atcatatgct taccgtaact tgaaagtatt      360
tcgatttctt ggctttatat atcttgtgga aaggacgaaa caccgcagcg ttacctctat      420
cgtagtttta gagctagaaa tagcaagtta aaataaggct agtccgttat caacttgaaa      480
aagtggcacc gagtcggtgc ttttttggat ccgagggcct atttcccatg attccttcat      540
atttgcatat acgatacaag gctgttagag agataattgg aattaatttg actgtaaaca      600
caaagatatt agtacaaaat acgtgacgta gaaagtaata atttcttggg tagtttgcag      660
ttttaaaatt atgttttaaa atggactatc atatgcttac cgtaacttga agtatttcg       720 atttcttggc tttatatatc ttgtggaaag gacgaaacac cgtgtaatag ctcctgcatg      780
ggttttagag ctagaaatag caagttaaaa taaggctagt ccgttatcaa cttgaaaaag      840
tggcaccgag tcggtgcttt ttttctagaa gagggcctat ttcccatgat tccttcatat      900
ttgcatatac gatacaaggc tgttagagag ataattggaa ttaatttgac tgtaaacaca      960
aagatattag tacaaaatac gtgacgtaga aagtaataat ttcttgggta gtttgcagtt     1020
ttaaaattat gttttaaaat ggactatcat atgcttaccg taacttgaaa gtatttcgat     1080
ttcttggctt tatatatctt gtggaaagga cgaaacacca ctccgagacc ttatgccgcg     1140
ttttagagct agaaatagca agttaaaata aggctagtcc gttatcaact tgaaaaagtg     1200
gcaccgagtc ggtgcttttt tggtaccagg tcttgaaagg agtgggaatt ggctccggtg     1260
cccgtcagtg gcagagcgc acatcgccca cagtccccga gaagtggggg ggaggggtcg     1320
gcaattgaac cggtgcctag agaaggtggc gcggggtaaa ctgggaaagt gatgtcgtgt     1380
actggctccg ccttttttccc gagggtgggg gagaaccgta tataagtgca gtagtcgccg     1440
tgaacgttct ttttcgcaac gggtttgccg ccagaacaca ggcgtacggc caccatgact     1500
tcgaaagttt atgatccaga acaaaggaaa cggatgataa ctggtccgca gtggtgggcc     1560
agatgtaaac aaatgaatgt tcttgattca tttattaatt attatgattc agaaaaacat     1620
gcagaaaatg ctgttatttt tttacatggt aacgcggcct cttcttattt atggcgacat     1680
gttgtgccac atattgagcc agtagcgcgg tgtattatac cagaccttat tggtatgggc     1740
aaatcaggca atctggtaa tggttcttat aggttacttg atcattacaa atatcttact     1800
gcatggtttg aacttcttaa tttaccaaag aagatcattt ttgtcggcca tgattggggt     1860
gcttgtttgg catttcatta tagctatgag catcaagata agatcaaagc aatagttcac     1920
gctgaaagtg tagtagatgt gattgaatca tgggatgaat ggcctgatat tgaagaagat     1980
attgcgttga tcaaatctga agaaggagaa aaaatggttt tggagaataa cttcttcgtg     2040
gaaaccatgt tgccatcaaa aatcatgaga aagttagaac cagaagaatt tgcagcatat     2100
cttgaaccat tcaaagagaa aggtgaagtt cgtcgtccaa cattatcatg gcctcgtgaa     2160
atcccgttag taaaaggtgg taaacctgac gttgtacaaa ttgttaggaa ttataatgct     2220
tatctacgtg caagtgatga tttaccaaaa atgtttattg aatcggaccc aggattcttt     2280
tccaatgcta ttgttgaagg tgccaagaag tttcctaata ctgaatttgt caaagtaaaa     2340
ggtcttcatt tttcgcaaga agatgcacct gatgaaatgg gaaaatatat caaatcgttc     2400
gttgagcgag ttctcaaaaa tgaacaagct agcggaagcg gagccactaa cttctccctg     2460
```

```
ttgaaacaag caggggatgt cgaagagaat cccgggccac ccaagaagaa gaggaaggtg   2520
tccaatctcc tgactgttca ccagaacctc cctgcgctgc cagtagatgc cactagcgat   2580
gaggtcagga aaaatctcat ggatatgttt agggatagac aggcgttttc tgaacacacc   2640
tggaaaatgc tgcttagcgt gtgccgatcc tgggcagcct ggtgtaagct gaacaatcgc   2700
aaatggttcc ccgccgagcc ggaggacgtg cgcgattacc tgctgtatct ccaggcaaga   2760
gggctggctg tcaagactat ccagcagcac ttgggccaac tgaatatgct gcatcgacgc   2820
agcgggctcc cccggcctag cgattcaaac gcagtctccc ttgttatgag gagaattaga   2880
aaggaaaacg tagatgcggg tgagagggct aagcaggctc tcgcttttga gcggactgat   2940
ttcgaccagg tcagatccct gatggagaac agcgatcggt gccaggacat caggaacctc   3000
gcatttctgg gaattgcata taacacactt ctgcgcatag ctgagatcgc ccggatcaga   3060
gtgaaagaca tcagtcgaac ggacggcggc cggatgctta ttcatattgg acgcacaaag   3120
acattggtca gcaccgctgg cgttgaaaag gccttgtccc tgggcgtaac gaagctggtg   3180
gaaagatgga tctcagtgtc cggcgtggct gacgacccta ataattactt gttctgtcga   3240
gtgagaaaaa acgagtcgc cgcgccctct gccaccagcc aattgagtac acgggccctt   3300
gaagggatct tgaggcaac ccaccgactc atatacgagg ccaaggatga cagtggccag   3360
aggtatctcg cctggtcagg tcattctgct agggtggggg ccgcacgaga catggcgcgg   3420
gcaggagtct ccataccaga gattatgcaa gctggaggtt ggacaaatgt gaacatcgtt   3480
atgaactata tccgcaatct tgactctgaa accggggcca tggtgagact gctcgaagat   3540
ggtgactacc catacgatgt tccagattac gcttaaagcg ctaataaaag atctttattt   3600
tcattagatc tgtgtgttgg ttttttgtgt aagctttggc tccaacacag atgttcttag   3660
gctacctaac ttctaacttt taatatccag tcaacaaaga ataccgcaag ggtaggtgtt   3720
gggatagctg tcgacaagct catgcgggtg tgtccacagg gtatagcgta ctatgcagaa   3780
tatttgtact gagtgaagtc atgatacatt cctttgagag ccattagctg ctacaaaaca   3840
gtaatctggc tgtttagatc aacaagctaa atgatagaag atgaaagtac tggtttccat   3900
gtatttttat taagtgttga tgagaaagtt gtaagtgact tacaggttac tctgtacatc   3960
tgtagtcact gaattcggaa tatcttagag ttttacacac aaaggtgagt gttaaaatat   4020
tgataaagtt tttgataatc ttgtgtgaga catgttctaa tttagttgta ttttattatt   4080
tttattgtaa ggcctgctga aaatgactga gtataaactt gtggtcgtgg gcgccgacgg   4140
cgtgggcaag agcgctttga cgatacagct aattcagaat cactttgtgg atgagtatga   4200
tccaaccatc gaggtaacgc tgctctacag tctgcgtgcg cttgtaaagg acggcagcca   4260
gccgctttga aaaagatatc attttttatat ttattagaaa attatattga agttatttc   4320 agttatatgt gatgtccttt agttccaagg ctttaaactg ggtgttaggg aaccataggt   4380
gcaagaaagt ccacttctca tgagagctca ccacagagaa agaaagtcca cttctcaggt   4440
aaccacgtgc ggaccgagcg gccgcaggaa cccctagtga tggagttggc cactccctct   4500
ctgcgcgctc gctcgctcac tgaggccggg cgaccaaagg tcgcccgacg cccgggcttt   4560
gcccgggcgg cctcagtgag cgagcgagcg cgcagctgcc tgcaggtatt ttctccttac   4620
gcatctgtgc ggtatttcac accgcatacg tcaaagcaac catagtacgc gccctgtagc   4680
ggcgcattaa gcgcggcggg tgtggtggtt acgcgcagcg tgaccgctac acttgccagc   4740
gccctagcgc ccgctccttt cgctttcttc ccttcctttc tcgccacgtt cgccggcttt   4800
```

```
ccccgtcaag ctctaaatcg ggggctccct ttagggttcc gatttagtgc tttacggcac    4860
ctcgacccca aaaaacttga tttgggtgat ggttcacgta gtgggccatc gccctgatag    4920
acggtttttc gccctttgac gttggagtcc acgttcttta atagtggact cttgttccaa    4980
actggaacaa cactcaaccc tatctcgggc tattctttttg atttataagg gattttgccg    5040
atttcggcct attggttaaa aaatgagctg atttaacaaa aatttaacgc gaattttaac    5100
aaaatattaa cgtttacaat tttatggtgc actctcagta caatctgctc tgatgccgca    5160
tagttaagcc agccccgaca cccgccaaca cccgctgacg cgccctgacg ggcttgtctg    5220
ctcccggcat ccgcttacag acaagctgtg accgtctccg ggagctgcat gtgtcagagg    5280
ttttcaccgt catcaccgaa acgcgcgaga cgaaagggcc tcgtgatacg cctattttta    5340
taggttaatg tcatgataat aatggtttct tagacgtcag gtggcacttt tcggggaaat    5400
gtgcgcggaa cccctatttg tttatttttc taaatacatt caaatatgta tccgctcatg    5460
agacaataac cctgataaat gcttcaataa tattgaaaaa ggaagagtat gagtattcaa    5520
catttccgtg tcgcccttat tcccttttttt gcggcatttt gccttcctgt ttttgctcac    5580
ccagaaacgc tggtgaaagt aaaagatgct gaagatcagt tgggtgcacg agtgggttac    5640
atcgaactgg atctcaacag cggtaagatc cttgagagtt ttcgccccga agaacgtttt    5700
ccaatgatga gcacttttaa agttctgcta tgtggcgcgg tattatcccg tattgacgcc    5760
gggcaagagc aactcggtcg ccgcatacac tattctcaga atgacttggt tgagtactca    5820
ccagtcacag aaaagcatct tacggatggc atgacagtaa gagaattatg cagtgctgcc    5880
ataaccatga gtgataacac tgcggccaac ttacttctga caacgatcgg aggaccgaag    5940
gagctaaccg cttttttgca acatgggg gatcatgtaa ctcgccttga tcgttgggaa    6000
ccggagctga atgaagccat accaaacgac gagcgtgaca ccacgatgcc tgtagcaatg    6060
gcaacaacgt tgcgcaaact attaactggc gaactactta ctctagcttc ccggcaacaa    6120
ttaatagact ggatggaggc ggataaagtt gcaggaccac ttctgcgctc ggcccttccg    6180
gctggctggt ttattgctga taaatctgga gccggtgagc gtgggtctcg cggtatcatt    6240
gcagcactgg ggccagatgg taagccctcc cgtatcgtag ttatctacac gacggggagt    6300
caggcaacta tggatgaacg aaatagacag atcgctgaga taggtgcctc actgattaag    6360
cattggtaac tgtcagacca agtttactca tatatacttt agattgattt aaaacttcat    6420
ttttaattta aaaggatcta ggtgaagatc cttttttgata atctcatgac caaaatccct    6480
taacgtgagt tttcgttcca ctgagcgtca gaccccgtag aaaagatcaa aggatcttct    6540
tgagatcctt ttttttctgcg cgtaatctgc tgcttgcaaa caaaaaaacc accgctacca    6600
gcggtggttt gtttgccgga tcaagagcta ccaactcttt ttccgaaggt aactggcttc    6660
agcagagcgc agataccaaa tactgtcctt ctagtgtagc cgtagttagg ccaccacttc    6720
aagaactctg tagcaccgcc tacatacctc gctctgctaa tcctgttacc agtggctgct    6780
gccagtggcg ataagtcgtg tcttaccggg ttggactcaa gacgatagtt accggataag    6840
gcgcagcggt cgggctgaac ggggggttcg tgcacacagc ccagcttgga gcgaacgacc    6900
tacaccgaac tgagatacct acagcgtgag ctatgagaaa gcgccacgct tcccgaaggg    6960
agaaaggcgg acaggtatcc ggtaagcggc agggtcggaa caggagagcg cacgagggag    7020
cttccagggg gaaacgcctg gtatctttat agtcctgtcg ggtttcgcca cctctgactt    7080
gagcgtcgat ttttgtgatg ctcgtcaggg gggcggagcc tatggaaaaa cgccagcaac    7140
gcggcctttt tacggttcct ggccttttgc tggccttttg ctcacatgt                7189
```

<210> SEQ ID NO 120
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc t                                            141

<210> SEQ ID NO 121
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                           249

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gcagcgttac ctctatcgta                                                20

<210> SEQ ID NO 123
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gttttagagc tagaaatagc aagttaaaat aaggctagtc cgttatcaac ttgaaaaagt    60
ggcaccgagt cggtgctttt tt                                             82

<210> SEQ ID NO 124
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 124

| | | |
|---|---|---|
| gagggcctat tcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacacc | 249 |

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125

| | |
|---|---|
| gtgtaatagc tcctgcatgg | 20 |

<210> SEQ ID NO 126
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126

| | |
|---|---|
| gttttagagc tagaaatagc aagttaaaat aaggctagtc cgttatcaac ttgaaaaagt | 60 |
| ggcaccgagt cggtgctttt tt | 82 |

<210> SEQ ID NO 127
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127

| | |
|---|---|
| gagggcctat tcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacacc | 249 |

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128

| | |
|---|---|
| actccgagac cttatgccgc | 20 |

<210> SEQ ID NO 129
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
gttttagagc tagaaatagc aagttaaaat aaggctagtc cgttatcaac ttgaaaaagt    60
ggcaccgagt cggtgctttt tt    82

<210> SEQ ID NO 130
<211> LENGTH: 255
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
aggtcttgaa aggagtggga attggctccg gtgcccgtca gtgggcagag cgcacatcgc    60
ccacagtccc cgagaagttg gggggagggg tcggcaattg aaccggtgcc tagagaaggt    120
ggcgcggggt aaactgggaa agtgatgtcg tgtactggct ccgccttttt cccgagggtg    180
ggggagaacc gtatataagt gcagtagtcg ccgtgaacgt tctttttcgc aacgggtttg    240
ccgccagaac acagg    255

<210> SEQ ID NO 131
<211> LENGTH: 933
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131
atgacttcga aagtttatga tccagaacaa aggaaacgga tgataactgg tccgcagtgg    60
tgggccagat gtaaacaaat gaatgttctt gattcattta ttaattatta tgattcagaa    120
aaacatgcag aaaatgctgt tatttttttta catggtaacg cggcctcttc ttatttatgg    180
cgacatgttg tgccacatat tgagccagta gcgcggtgta ttataccaga ccttattggt    240
atgggcaaat caggcaaatc tggtaatggt tcttataggt tacttgatca ttacaaatat    300
cttactgcat ggtttgaact tcttaattta ccaaagaaga tcattttttgt cggccatgat    360 tggggtgctt gtttggcatt tcattatagc tatgagcatc aagataagat caaagcaata    420
gttcacgctg aaagtgtagt agatgtgatt gaatcatggg atgaatggcc tgatattgaa    480
gaagatattg cgttgatcaa atctgaagaa ggagaaaaaa tggttttgga gaataacttc    540
ttcgtggaaa ccatgttgcc atcaaaaatc atgagaaagt tagaaccaga agaatttgca    600
gcatatcttg aaccattcaa agagaaaggt gaagttcgtc gtccaacatt atcatggcct    660
cgtgaaatcc cgttagtaaa aggtggtaaa cctgacgttg tacaaattgt taggaattat    720
aatgcttatc tacgtgcaag tgatgattta ccaaaaaatgt ttattgaatc ggacccagga    780
ttcttttcca atgctattgt tgaaggtgcc aagaagtttc ctaatactga atttgtcaaa    840

```
gtaaaaggtc ttcattttc gcaagaagat gcacctgatg aaatgggaaa atatatcaaa        900
tcgttcgttg agcgagttct caaaaatgaa caa                                    933
```

<210> SEQ ID NO 132
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132

```
ggaagcggag ccactaactt ctccctgttg aaacaagcag gggatgtcga agagaatccc        60
gggcca                                                                  66
```

<210> SEQ ID NO 133
<211> LENGTH: 1047
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

```
cccaagaaga agaggaaggt gtccaatctc ctgactgttc accagaacct ccctgcgctg        60
ccagtagatg ccactagcga tgaggtcagg aaaaatctca tggatatgtt tagggataga      120
caggcgtttt ctgaacacac ctggaaaatg ctgcttagcg tgtgccgatc ctgggcagcc      180
tggtgtaagc tgaacaatcg caaatggttc cccgccgagc cggaggacgt gcgcgattac      240
ctgctgtatc tccaggcaag agggctggct gtcaagacta ccagcagca cttgggccaa       300 ctgaatatgc tgcatcgacg cagcgggctc ccccggccta gcgattcaaa cgcagtctcc      360
cttgttatga ggagaattag aaaggaaaac gtagatgcgg gtgagagggc taagcaggct      420
ctcgcttttg agcggactga tttcgaccag gtcagatccc tgatggagaa cagcgatcgg      480
tgccaggaca tcaggaacct cgcatttctg ggaattgcat ataacacact tctgcgcata      540
gctgagatcg cccggatcag agtgaaagac atcagtcgaa cggacggcgg ccggatgctt      600
attcatattg gacgcacaaa gacattggtc agcaccgctg gcgttgaaaa ggccttgtcc      660
ctgggcgtaa cgaagctggt ggaaagatgg atctcagtgt ccggcgtggc tgacgaccct      720
aataattact tgttctgtcg agtgagaaaa aacggagtcg ccgcgccctc tgccaccagc      780
caattgagta cacgggccct tgaagggatc tttgaggcaa cccaccgact catatacgga      840
gccaaggatg acagtggcca gaggtatctc gcctggtcag gtcattctgc tagggtgggg      900
gccgcacgag acatggcgcg ggcaggagtc tccataccag agattatgca agctggaggt      960
tggacaaatg tgaacatcgt tatgaactat atccgcaatc ttgactctga aaccggggcc     1020
atggtgagac tgctcgaaga tggtgac                                         1047
```

<210> SEQ ID NO 134
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134

```
tacccatacg atgttccaga ttacgct                                           27
```

<210> SEQ ID NO 135
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135

```
aataaaagat ctttattttc attagatctg tgtgttggtt ttttgtgt                    48
```

<210> SEQ ID NO 136
<211> LENGTH: 800
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136

```
ggctccaaca cagatgttct taggctacct aacttctaac ttttaatatc cagtcaacaa       60
agaataccgc aagggtaggt gttgggatag ctgtcgacaa gctcatgcgg gtgtgtccac      120
agggtatagc gtactatgca gaatatttgt actgagtgaa gtcatgatac attcctttga      180
gagccattag ctgctacaaa acagtaatct ggctgtttag atcaacaagc taaatgatag      240
aagatgaaag tactggtttc catgtatttt tattaagtgt tgatgagaaa gttgtaagtg      300
acttacaggt tactctgtac atctgtagtc actgaattcg gaatatctta gagttttaca      360
cacaaaggtg agtgttaaaa tattgataaa gttttttgata atcttgtgtg agacatgttc    420
taatttagtt gtatttattt atttttattg taaggcctgc tgaaaatgac tgagtataaa      480
cttgtggtcg tgggcgccga cggcgtgggc aagagcgctt tgacgataca gctaattcag      540
aatcactttg tggatgagta tgatccaacc atcgaggtaa cgctgctcta cagtctgcgt      600
gcgcttgtaa aggacggcag ccagccgctt tgaaaaagat atcattttta tatttattag      660
aaaattatat tgaaagttat ttcagttata tgtgatgtcc tttagttcca aggctttaaa      720
ctgggtgtta gggaaccata ggtgcaagaa agtccacttc tcatgagagc tcaccacaga      780
gaaagaaagt ccacttctca                                                  800
```

<210> SEQ ID NO 137
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137

```
aggaacccct agtgatggag ttggccactc cctctctgcg cgctcgctcg ctcactgagg       60
ccgggcgacc aaaggtcgcc cgacgcccgg gctttgcccg ggcggcctca gtgagcgagc      120
gagcgcgcag ctgcctgcag g                                                141
```

<210> SEQ ID NO 138
<211> LENGTH: 6475
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccgca cgcgtgaggg cctatttccc atgattcctt   180
catatttgca tatacgatac aaggctgtta gagagataat tggaattaat ttgactgtaa   240
acacaaagat attagtacaa atacgtgacg gtagaaagta ataatttctt gggtagtttg   300
cagttttaaa attatgtttt aaaatggact atcatatgct taccgtaact gaaaagtatt   360
tcgatttctt ggctttatat atcttgtgga aaggacgaaa caccgtgcga atacgcccac   420
gcgatgtttt agagctagaa atagcaagtt aaaataaggc tagtccgtta tcaacttgaa   480
aaagtggcac cgagtcggtg cttttttggt accaggtctt gaaaggagtg ggaattggct   540
ccggtgcccg tcagtgggca gagcgcacat cgcccacagt ccccgagaag ttgggggggag   600
gggtcggcaa ttgaaccggt gcctagaaga ggtggcgcgg ggtaaactgg gaaagtgatg   660
tcgtgtactg gctccgcctt tttcccgagg gtgggggaga accgtatata agtgcagtag   720
tcgccgtgaa cgttctttttt cgcaacgggt ttgccgccag aacacaggcg tacggccacc   780
atgacttcga agtttatga tccagaacaa aggaaacgga tgataactgg tccgcagtgg   840
tgggccagat gtaaacaaat gaatgttctt gattcattta ttaattatta tgattcagaa   900
aaacatgcag aaaatgctgt tattttttta catggtaacg cggcctcttc ttatttatgg   960
cgacatgttg tgccacatat tgagccagta gcgcggtgta ttataccaga ccttattggt  1020
atgggcaaat caggcaaatc tggtaatggt tcttataggt tacttgatca ttacaaatat  1080
cttactgcat ggtttgaact tcttaattta ccaaagaaga tcattttttgt cggccatgat  1140
tggggtgctt gttttggcatt tcattatagc tatgagcatc aagataagat caaagcaata  1200
gttcacgctg aaagtgtagt agatgtgatt gaatcatggg atgaatgcc tgatattgaa  1260
gaagatattg cgttgatcaa atctgaagaa ggagaaaaaa tggttttgga gaataacttc  1320
ttcgtggaaa ccatgttgcc atcaaaaatc atgagaaagt tagaaccaga gaatttgca  1380
gcatatcttg aaccattcaa agagaaaggt gaagttcgtc gtccaacatt atcatggcct  1440
cgtgaaatcc cgttagtaaa aggtggtaaa cctgacgttg tacaaattgt taggaattat  1500
aatgcttatc tacgtgcaag tgatgattta ccaaaaatgt ttattgaatc ggacccagga  1560
ttcttttcca atgctattgt tgaaggtgcc aagaagtttc ctaatactga atttgtcaaa  1620
gtaaaaggtc ttcattttc gcaagaagat gcacctgatg aaatgggaaa atatatcaaa  1680
tcgttcgttg agcgagttct caaaaatgaa caagctagcg gaagcggagc cactaacttc  1740
tccctgttga acaagcagg ggatgtcgaa gagaatcccg gccacccaa gaagaagagg  1800
aaggtgtcca atctcctgac tgttcaccag aacctccctg cgctgccagt agatgccact  1860
agcgatgagg tcaggaaaaa tctcatggat atgtttaggg atagacaggc gttttctgaa  1920
cacacctgga aaatgctgct tagcgtgtgc cgatcctggg cagcctggtg taagctgaac  1980
aatcgcaaat ggttccccgc cgagccggag gacgtgcgcg attacctgct gtatctccag  2040
gcaagagggc tggctgtcaa gactatccag cagcacttgg gccaactgaa tatgctgcat  2100
cgacgcagcg ggctcccccg gcctagcgat tcaaacgcag tctcccttgt tatgaggaga  2160
```

```
attagaaagg aaaacgtaga tgcgggtgag agggctaagc aggctctcgc ttttgagcgg   2220
actgatttcg accaggtcag atccctgatg gagaacagcg atcggtgcca ggacatcagg   2280
aacctcgcat ttctgggaat tgcatataac acacttctgc gcatagctga gatcgcccgg   2340
atcagagtga aagacatcag tcgaacggac ggcggccgga tgcttattca tattggacgc   2400
acaaagacat tggtcagcac cgctggcgtt gaaaaggcct tgtccctggg cgtaacgaag   2460
ctggtggaaa gatggatctc agtgtccggc gtggctgacg accctaataa ttacttgttc   2520
tgtcgagtga gaaaaaacgg agtcgccgcg ccctctgcca ccagccaatt gagtacacgg   2580
gcccttgaag ggatctttga ggcaacccac cgactcatat acggagccaa ggatgacagt   2640
ggccagaggt atctcgcctg gtcaggtcat tctgctaggg tgggggccgc acgagacatg   2700
gcgcgggcag gagtctccat accagagatt atgcaagctg gaggttggac aaatgtgaac   2760
atcgttatga actatatccg caatcttgac tctgaaaccg gggccatggt gagactgctc   2820
gaagatggtg actacccata cgatgttcca gattacgctt aaagcgctaa taaaagatct   2880
ttattttcat tagatctgtg tgttggtttt tgtgtaagc tttggctcca acacagatgt    2940
tcttaggcta cctaacttct aacttttaat atccagtcaa caagaatac cgcaagggta    3000 ggtgttggga tagctgtcga caagctcatg cgggtgtgtc cacagggtat agcgtactat   3060
gcagaatatt tgtactgagt gaagtcatga tacattcctt tgagagccat tagctgctac   3120
aaaacagtaa tctggctgtt tagatcaaca agctaaatga tagaagatga aagtactggt   3180
ttccatgtat ttttattaag tgttgatgag aaagttgtaa gtgacttaca ggttactctg   3240
tacatctgta gtcactgaat tcggaatatc ttagagtttt acacacaaag gtgagtgtta   3300
aaatattgat aaagtttttg ataatcttgt gtgagacatg ttctaattta gttgtatttt    3360 attatttta ttgtaaggcc tgctgaaaat gactgagtat aaacttgtgg tcgtgggcgc     3420
cgacggcgtg ggcaagagcg ctttgacgat acagctaatt cagaatcact tgtggatga    3480 gtatgatcca accatcgagg taacgctgct ctacagtctg cgtgcgcttg taaaggacgg   3540
cagccagccg cttgaaaaa gatatcattt ttatatttat tagaaaatta tattgaaagt    3600
tatttcagtt atatgtgatg tcctttagtt ccaaggcttt aaactgggtg ttagggaacc   3660
ataggtgcaa gaaagtccac ttctcatgag agctcaccac agagaaagaa agtccacttc   3720
tcaggtaacc acgtgcggac cgagcggccg caggaacccc tagtgatgga gttggccact   3780
ccctctctgc gcgctcgctc gctcactgag gccgggcgac caaaggtcgc ccgacgcccg   3840
ggctttgccc gggcggcctc agtgagcgag cgagcgcgca gctgcctgca ggtattttct   3900
ccttacgcat ctgtgcggta tttcacaccg catacgtcaa agcaaccata gtacgcgccc   3960
tgtagcggcg cattaagcgc ggcgggtgtg tggttacgc gcagcgtgac cgctacactt    4020
gccagcgccc tagcgcccgc tcctttcgct ttcttccctt cctttctcgc cacgttcgcc   4080
ggctttcccc gtcaagctct aaatcggggg ctccctttag ggttccgatt tagtgcttta   4140
cggcacctcg accccaaaaa acttgatttg ggtgatggtt cacgtagtgg gccatcgccc   4200
tgatagacgg ttttctcgcc tttgacgttg gagtccacgt tctttaatag tggactcttg   4260
ttccaaactg gaacaacact caaccctatc tcggctatt cttttgattt ataagggatt    4320
ttgccgattt cggcctattg gttaaaaaat gagctgattt aacaaaaatt taacgcgaat   4380
tttaacaaaa tattaacgtt tacaatttta tggtgcactc tcagtacaat ctgctctgat   4440
gccgcatagt taagccagcc ccgacacccg ccaacacccg ctgacgcgcc ctgacgggct   4500
```

```
tgtctgctcc cggcatccgc ttacagacaa gctgtgaccg tctccgggag ctgcatgtgt    4560
cagaggtttt caccgtcatc accgaaacgc gcgagacgaa agggcctcgt gatacgccta    4620 ttttttatagg ttaatgtcat gataataatg gtttcttaga cgtcaggtgg cacttttcgg   4680
ggaaatgtgc gcggaacccc tatttgttta tttttctaaa tacattcaaa tatgtatccg    4740
ctcatgagac aataaccctg ataaatgctt caataatatt gaaaaggaa gagtatgagt     4800 attcaacatt tccgtgtcgc ccttattccc ttttttgcgg catttttgcct tcctgttttt   4860 gctcacccag aaacgctggt gaaagtaaaa gatgctgaag atcagttggg tgcacgagtg    4920
ggttacatcg aactggatct caacagcggt aagatccttg agagttttcg ccccgaagaa    4980
cgttttccaa tgatgagcac ttttaaagtt ctgctatgtg gcgcggtatt atcccgtatt    5040
gacgccgggc aagagcaact cggtcgccgc atacactatt ctcagaatga cttggttgag    5100
tactcaccag tcacagaaaa gcatcttacg gatggcatga cagtaagaga attatgcagt    5160
gctgccataa ccatgagtga taacactgcg gccaacttac ttctgacaac gatcggagga   5220
ccgaaggagc taaccgcttt tttgcacaac atggggatc atgtaactcg ccttgatcgt     5280
tgggaaccgg agctgaatga agccatacca aacgacgagc gtgacaccac gatgcctgta   5340
gcaatggcaa caacgttgcg caaactatta actggcgaac tacttactct agcttcccgg   5400
caacaattaa tagactggat ggaggcggat aaagttgcag gaccacttct gcgctcggcc   5460
cttccggctg gctggtttat tgctgataaa tctggagccg gtgagcgtgg gtctcgcggt    5520
atcattgcag cactggggcc agatggtaag ccctcccgta tcgtagttat ctacacgacg   5580
gggagtcagg caactatgga tgaacgaaat agacagatcg ctgagatagg tgcctcactg   5640
attaagcatt ggtaactgtc agaccaagtt tactcatata ctttagat tgatttaaaa      5700 cttcatttt aatttaaaag gatctaggtg aagatccttt ttgataatct catgaccaaa     5760
atcccttaac gtgagttttc gttccactga gcgtcagacc ccgtagaaaa gatcaaagga    5820
tcttcttgag atccttttt tctgcgcgta atctgctgct tgcaaacaaa aaaaccaccg     5880
ctaccagcgg tggtttgttt gccggatcaa gagctaccaa ctctttttcc gaaggtaact    5940
ggcttcagca gagcgcagat accaaatact gtccttctag tgtagccgta gttaggccac   6000
cacttcaaga actctgtagc accgcctaca tacctcgctc tgctaatcct gttaccagtg    6060
gctgctgcca gtggcgataa gtcgtgtctt accgggttgg actcaagacg atagttaccg    6120
gataaggcgc agcggtcggg ctgaacgggg ggttcgtgca cacagcccag cttggagcga    6180
acgacctaca ccgaactgag atacctacag cgtgagctat gagaaagcgc cacgcttccc    6240
gaagggagaa aggcggacag gtatccggta agcggcaggg tcggaacagg agagcgcacg    6300
agggagcttc caggggggaaa cgcctggtat ctttatagtc ctgtcgggtt tcgccacctc   6360
tgacttgagc gtcgattttt gtgatgctcg tcagggggc ggagcctatg gaaaaacgcc     6420
agcaacgcgg cctttttacg gttcctggcc ttttgctggc cttttgctca catgt         6475
```

<210> SEQ ID NO 139
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
cctgcaggca gctgcgcgct cgctcgctca ctgaggccgc ccgggcaaag cccgggcgtc    60
```

```
gggcgacctt tggtcgcccg gcctcagtga gcgagcgagc gcgcagagag ggagtggcca    120
actccatcac tagggttcc t                                               141

<210> SEQ ID NO 140
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
gagggcctat ttcccatgat tccttcatat ttgcatatac gatacaaggc tgttagagag    60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacacc                                                            249

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
tgcgaatacg cccacgcgat                                                20

<210> SEQ ID NO 142
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
gttttagagc tagaaatagc aagttaaaat aaggctagtc cgttatcaac ttgaaaaagt    60
ggcaccgagt cggtgctttt tt                                             82

<210> SEQ ID NO 143
<211> LENGTH: 255
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 143
aggtcttgaa aggagtggga attggctccg gtgcccgtca gtgggcagag cgcacatcgc    60
ccacagtccc cgagaagttg gggggagggg tcggcaattg aaccggtgcc tagagaaggt    120
ggcgcggggt aaactgggaa agtgatgtcg tgtactggct ccgccttttt cccgagggtg    180
ggggagaacc gtatataagt gcagtagtcg ccgtgaacgt tcttttttcgc aacgggtttg    240 ccgccagaac acagg                                                     255
```

<210> SEQ ID NO 144
<211> LENGTH: 933
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
atgacttcga aagtttatga tccagaacaa aggaaacgga tgataactgg tccgcagtgg      60
tgggccagat gtaaacaaat gaatgttctt gattcattta ttaattatta tgattcagaa     120
aaacatgcag aaaatgctgt tattttttta catggtaacg cggcctcttc ttatttatgg     180
cgacatgttg tgccacatat tgagccagta gcgcggtgta ttataccaga ccttattggt     240
atgggcaaat caggcaaatc tggtaatggt tcttataggt tacttgatca ttacaaatat     300
cttactgcat ggtttgaact tcttaattta ccaaagaaga tcattttttgt cggccatgat     360
tggggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
ttcgtggaaa ccatgttgcc atcaaaaatc atgagaaagt tagaaccaga gaatttgca      600
gcatatcttg aaccattcaa agagaaaggt gaagttcgtc gtccaacatt atcatggcct     660
cgtgaaatcc cgttagtaaa aggtggtaaa cctgacgttg tacaaattgt taggaattat     720
aatgcttatc tacgtgcaag tgatgattta ccaaaaatgt ttattgaatc ggacccagga     780
ttcttttcca atgctattgt tgaaggtgcc aagaagtttc ctaatactga atttgtcaaa     840
gtaaaaggtc ttcattttc gcaagaagat gcacctgatg aaatgggaaa atatatcaaa     900
tcgttcgttg agcgagttct caaaaatgaa caa                                  933
```

<210> SEQ ID NO 145
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145

```
ggaagcggag ccactaactt ctccctgttg aaacaagcag gggatgtcga agagaatccc     60
gggcca                                                                66
```

<210> SEQ ID NO 146
<211> LENGTH: 1047
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 146

```
cccaagaaga agaggaaggt gtccaatctc ctgactgttc accagaacct ccctgcgctg     60
ccagtagatg ccactagcga tgaggtcagg aaaaatctca tggatatgtt tagggataga    120
caggcgtttt ctgaacacac ctggaaaatg ctgcttagcg tgtgccgatc ctgggcagcc    180
tggtgtaagc tgaacaatcg caaatggttc cccgccgagc cggaggacgt gcgcgattac    240
```

-continued

```
ctgctgtatc tccaggcaag agggctggct gtcaagacta tccagcagca cttgggccaa    300
ctgaatatgc tgcatcgacg cagcgggctc ccccggccta cgattcaaa cgcagtctcc    360 cttgttatga ggagaattag aaaggaaaac gtagatgcgg gtgagagggc taagcaggct    420
ctcgcttttg agcggactga tttcgaccag gtcagatccc tgatggagaa cagcgatcgg    480
tgccaggaca tcaggaacct cgcatttctg ggaattgcat ataacacact tctgcgcata    540
gctgagatcg cccggatcag agtgaaagac atcagtcgaa cggacggcgg ccggatgctt    600
attcatattg gacgcacaaa gacattggtc agcaccgctg gcgttgaaaa ggccttgtcc    660
ctgggcgtaa cgaagctggt ggaaagatgg atctcagtgt ccggcgtggc tgacgaccct    720
aataattact tgttctgtcg agtgagaaaa acggagtcg ccgcgccctc tgccaccagc    780
caattgagta cacgggccct tgaagggatc tttgaggcaa cccaccgact catatacgga    840
gccaaggatg acagtggcca gaggtatctc gcctggtcag gtcattctgc tagggtgggg    900
gccgcacgag acatggcgcg ggcaggagtc tccataccag agattatgca agctggaggt    960
tggacaaatg tgaacatcgt tatgaactat atccgcaatc ttgactctga aaccgggggcc   1020 atggtgagac tgctcgaaga tggtgac                                       1047
```

<210> SEQ ID NO 147
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147

```
tacccatacg atgttccaga ttacgct                                         27
```

<210> SEQ ID NO 148
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148

```
aataaaagat ctttatttc attagatctg tgtgttggtt ttttgtgt                  48
```

<210> SEQ ID NO 149
<211> LENGTH: 800
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 149

```
ggctccaaca cagatgttct taggctacct aacttctaac ttttaatatc cagtcaacaa     60
agaataccgc aagggtaggt gttgggatag ctgtcgacaa gctcatgcgg gtgtgtccac    120
agggtatagc gtactatgca gaatatttgt actgagtgaa gtcatgatac attcctttga    180
gagccattag ctgctacaaa acagtaatct ggctgtttag atcaacaagc taatgatag     240 aagatgaaag tactggtttc catgtatttt tattaagtgt tgatgagaaa gttgtaagtg    300
```

```
acttacaggt tactctgtac atctgtagtc actgaattcg gaatatctta gagttttaca        360
cacaaaggtg agtgttaaaa tattgataaa gttttttgata atcttgtgtg agacatgttc       420
taatttagtt gtattttatt atttttattg taaggcctgc tgaaaatgac tgagtataaa        480
cttgtggtcg tgggcgccga cggcgtgggc aagagcgctt tgacgataca gctaattcag        540
aatcactttg tggatgagta tgatccaacc atcgaggtaa cgctgctcta cagtctgcgt        600
gcgcttgtaa aggacggcag ccagccgctt tgaaaaagat atcattttta tatttattag        660
aaaattatat tgaaagttat ttcagttata tgtgatgtcc tttagttcca aggctttaaa        720
ctgggtgtta gggaaccata ggtgcaagaa agtccacttc tcatgagagc tcaccacaga        780
gaaagaaagt ccacttctca                                                    800

<210> SEQ ID NO 150
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
aggaacccct agtgatggag ttggccactc cctctctgcg cgctcgctcg ctcactgagg         60
ccgggcgacc aaaggtcgcc cgacgcccgg gctttgcccg ggcggcctca gtgagcgagc        120
gagcgcgcag ctgcctgcag g                                                  141
```